US008754107B2

(12) United States Patent
George et al.

(10) Patent No.: US 8,754,107 B2
(45) Date of Patent: Jun. 17, 2014

(54) AMINOPYRROLIDINES AS CHEMOKINE RECEPTOR ANTAGONISTS

(75) Inventors: Dawn M. George, Charlton, MA (US); Richard W. Dixon, Jefferson, MA (US); Michael Friedman, Newton, MA (US); Adrian D. Hobson, Shrewsbury, MA (US); Biqin Li, Northborough, MA (US); Lu Wang, Northborough, MA (US); Xiaoyun Wu, Westborough, MA (US); Neil Wishart, Jefferson, MA (US)

(73) Assignee: AbbVie Inc., North Chicago, IL (US)

( * ) Notice: Subject to any disclaimer, the term of this patent is extended or adjusted under 35 U.S.C. 154(b) by 495 days.

(21) Appl. No.: 11/985,724

(22) Filed: Nov. 16, 2007

(65) Prior Publication Data

US 2008/0176883 A1    Jul. 24, 2008

Related U.S. Application Data

(60) Provisional application No. 60/859,804, filed on Nov. 17, 2006.

(51) Int. Cl.
| | |
|---|---|
| A61K 31/553 | (2006.01) |
| A61K 31/55 | (2006.01) |
| A61K 31/5377 | (2006.01) |
| A61K 31/506 | (2006.01) |
| A61K 31/517 | (2006.01) |
| A61K 31/4709 | (2006.01) |
| A61K 31/4545 | (2006.01) |
| A61K 31/454 | (2006.01) |
| A61K 31/4747 | (2006.01) |
| A61K 31/438 | (2006.01) |
| A61K 31/437 | (2006.01) |
| C07D 487/04 | (2006.01) |
| C07D 487/10 | (2006.01) |
| C07D 487/14 | (2006.01) |
| C07D 471/10 | (2006.01) |
| C07D 471/04 | (2006.01) |
| C07D 417/14 | (2006.01) |
| C07D 413/14 | (2006.01) |
| C07D 401/14 | (2006.01) |
| C07D 401/04 | (2006.01) |

(52) U.S. Cl.
CPC ............ *A61K 31/454* (2013.01); *A61K 31/553* (2013.01); *A61K 31/55* (2013.01); *A61K 31/5377* (2013.01); *A61K 31/506* (2013.01); *A61K 31/517* (2013.01); *A61K 31/4709* (2013.01); *A61K 31/4545* (2013.01); *A61K 31/4747* (2013.01); *A61K 31/438* (2013.01); *A61K 31/437* (2013.01); *C07D 487/04* (2013.01); *C07D 487/10* (2013.01); *C07D 487/14* (2013.01); *C07D 471/10* (2013.01); *C07D 471/04* (2013.01); *C07D 417/14* (2013.01); *C07D 413/14* (2013.01); *C07D 401/14* (2013.01); *C07D 401/04* (2013.01)

USPC . 514/326; 514/211.15; 514/278; 514/266.22; 514/266.2; 514/318; 514/292; 514/235.5; 514/217.08; 540/544; 540/602; 544/293; 544/230; 544/130; 546/17; 546/208; 546/210; 546/200; 546/87

(58) Field of Classification Search
CPC . A61K 31/553; A61K 31/55; A61K 31/5377; A61K 31/506; A61K 31/517; A61K 31/4709; A61K 31/4545; A61K 31/454; A61K 31/4747; A61K 31/438; A61K 31/437; C07D 487/04; C07D 487/10; C07D 487/14; C07D 471/10; C07D 471/04; C07D 417/14; C07D 413/14; C07D 401/14; C07D 401/04
USPC ............ 544/284, 293, 230, 130; 546/208, 17, 546/210, 200, 87; 514/211.15, 278, 326, 514/266.22, 266.2, 318, 292, 235.5, 514/217.08; 540/544, 602
See application file for complete search history.

(56) References Cited

U.S. PATENT DOCUMENTS

| | | | |
|---|---|---|---|
| 3,320,124 | A | 5/1967 | Waletzky et al. |
| 4,176,116 | A | 11/1979 | Hassall et al. |

(Continued)

FOREIGN PATENT DOCUMENTS

| | | |
|---|---|---|
| WO | WO96/09294 A1 | 3/1996 |
| WO | WO97/29131 A1 | 8/1997 |

(Continued)

OTHER PUBLICATIONS

Yokochi et al. Journal of interferon and Cytokine Research 2001, 21, 389-398.*

(Continued)

*Primary Examiner* — Joseph Kosack
*Assistant Examiner* — Matthew Coughlin

(57) ABSTRACT

The present invention is directed to novel aminopyrrolidines of formula I

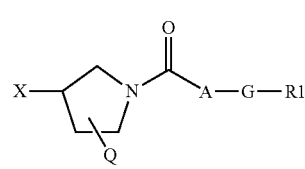

pharmaceutically acceptable salts thereof, metabolites thereof, isomers thereof, stereoisomers thereof or pro-drugs thereof, wherein the variables are as defined herein. The compounds of formula (I) are useful as chemokine receptor antagonists and as such would be useful in treating certain conditions and diseases, especially inflammatory conditions and diseases and proliferative disorders and conditions, for example, cancers.

17 Claims, No Drawings

(56) References Cited

U.S. PATENT DOCUMENTS

| | | | |
|---|---|---|---|
| 4,277,395 A | | 7/1981 | Bey et al. |
| 4,719,200 A | | 1/1988 | Eguchi et al. |
| 4,880,780 A | | 11/1989 | Trainor et al. |
| 4,923,890 A | | 5/1990 | Trainor et al. |
| 5,164,371 A | | 11/1992 | Edwards et al. |
| 5,296,591 A | | 3/1994 | Hemmi et al. |
| 5,449,787 A | * | 9/1995 | Miyashita et al. ......... 548/362.5 |
| 5,478,811 A | | 12/1995 | Peet et al. |
| 5,698,523 A | | 12/1997 | Peet et al. |
| 5,739,157 A | | 4/1998 | Pegg et al. |
| 5,756,763 A | | 5/1998 | Takeuchi et al. |
| 5,948,886 A | | 9/1999 | Peet et al. |
| 6,090,382 A | | 7/2000 | Salfeld et al. |
| 6,525,070 B2 | * | 2/2003 | Rigby et al. ................. 514/316 |
| 6,531,474 B1 | | 3/2003 | Wannamaker et al. |
| 2002/0013278 A1 | | 1/2002 | Wannamaker et al. |
| 2002/0151534 A1 | | 10/2002 | Ries et al. |
| 2003/0119899 A1 | | 6/2003 | Wannamaker et al. |
| 2004/0048848 A1 | * | 3/2004 | Pissarnitski et al. ..... 514/217.05 |
| 2004/0063720 A1 | * | 4/2004 | Bilodeau et al. ......... 514/252.18 |
| 2004/0132745 A1 | | 7/2004 | Bertinato et al. |
| 2005/0192302 A1 | | 9/2005 | Xue et al. |
| 2005/0209162 A1 | | 9/2005 | Roy et al. |
| 2005/0209254 A1 | | 9/2005 | Wang et al. |
| 2005/0233974 A1 | | 10/2005 | Randle et al. |
| 2006/0020016 A1 | | 1/2006 | Tanoury et al. |
| 2006/0073013 A1 | | 4/2006 | Emigholz et al. |
| 2007/0191335 A1 | | 8/2007 | Lemoine et al. |

FOREIGN PATENT DOCUMENTS

| | | | |
|---|---|---|---|
| WO | 03041641 A2 | | 5/2003 |
| WO | 03093231 A2 | | 11/2003 |
| WO | WO 2004/050024 | | 6/2004 |
| WO | WO 2004/050613 | | 6/2004 |
| WO | WO 2004/056799 A2 | * | 7/2004 |
| WO | 2004096798 A2 | | 11/2004 |
| WO | WO2005/014537 A2 | | 2/2005 |
| WO | WO2005/044264 A1 | | 5/2005 |
| WO | WO 2005/051922 | | 6/2005 |
| WO | WO 2005/053665 | | 6/2005 |
| WO | WO 2005/060665 | | 7/2005 |
| WO | 2005080371 A1 | | 9/2005 |
| WO | WO 2005/090334 | | 9/2005 |
| WO | WO 2006/067401 | | 6/2006 |
| WO | 2006071958 A1 | | 7/2006 |
| WO | WO2006/092731 A1 | | 9/2006 |
| WO | WO2008004096 A1 | * | 1/2008 |

OTHER PUBLICATIONS

Corruble et al., J. Org. Chem. 1998, 63, 8266-8275.*
McCombie et al. "Piperazine-based CCR5 antagonist as HIV-1 inhibitors. III: synthesis, antiviral and pharmacokinetic profiles of symmetrical heteroaryl carboxamides" Bioorganic & Medicinal Chemistry Letters; 2003, vol. 13, No. 3; 1355-1371.
Bazan, et al., Nature, 385:640-644 (1997).
Ben-Barruch, et al., J. Biol. Chem., 270:22123-22128 (1995).
Campbell, et al., J. Cell. Biol., 141:1053-1059 (1998).
Chaudhuri, et al., J. Biol. Chem., 269:7835-7838 (1994).
Dairaghi, et al., J. Biol. Chem., 274:21569-21574 (1999).
Deng, et al., Nature, 381:661-666 (1996).
Fingl et al., 1975, in "The Pharmacological Basis of Therapeutics", Ch. 1 p. 1.
Gennaro, A.R., "Remington's Pharmaceutical Sciences," Mack Publishing Co., Easton, Pa., 1985.
Greaves, et al., J. Exp. Med., 186:837-844 (1997).
Greene, T. W. and Wuts, P. G. M. Protective Groups in Organic Synthesis, 3rd Edition, 1999, Wiley-Interscience, New York.
Harriman, J., et al. Tetr. Lett., 41 (2000) 8853-8856.
Horuk, Trends Pharm. Sci., 15:159-165 (1994).
Imai, et al., J. Biol. Chem., 273:1764-1768 (1998).
Kelner, et al., Science, 266:1395-1399 (1994).
Murphy, Rev. Immun., 12:593-633 (1994).
Neote, et al., Cell, 72:415-425 (1993).
Nibbs, et al., J. Biol. Chem., 272:32078-32083 (1997).
Ponath, et al., J. Exp. Med., 183:2437-2448 (1996).
Samson, et al., Biochemistry, 35:3362-3367 (1996).
Schall, Cytokine, 3:165-183 (1991).
Schall, et al., Curr. Opin. Immunol., 6:865-873 (1994).
Smith, A.B., et al., J. Am. Chem. Soc., 113(6)2071-2092 (1991).
Zaballos, et al., J. Immunol., 162:5671-5675 (1999).
Katritzky, et al., "General Synthesis of Unsymmetrical Tetrasubstituted Oxamides via 1,1'-(1,2-Dioxoethane-1,2-diyi)bis-1H-benzotriazole," Synthesis, 2, 1998, pp. 153-156.

* cited by examiner

AMINOPYRROLIDINES AS CHEMOKINE RECEPTOR ANTAGONISTS

CROSS REFERENCE TO RELATED APPLICATION

This application claims the benefit of priority to U.S. Provisional Application No. 60/859,804, filed on Nov. 17, 2006. The contents of the priority document are incorporated by reference herein.

BACKGROUND OF THE INVENTION

Chemokines are chemotactic cytokines that are released by a wide variety of cells to attract leukocytes, as illustrated by macrophages, T cells, B cells, eosinophils, basophils, and neutrophils to and from sites of inflammation or within specific compartments, as illustrated by lymph nodes (reviewed in Schall, *Cytokine*, 3:165-183 (1991), Schall, et al., *Curr. Opin. Immunol.*, 6:865-873 (1994) and Murphy, *Rev. Immun.*, 12:593-633 (1994)). In addition to stimulating chemotaxis, other changes can be selectively induced by chemokines in responsive cells, including changes in cell shape, transient rises in the concentration of intracellular free calcium ions ($[Ca^{2+}]$), granule exocytosis, integrin upregulation, formation of bioactive lipids (e.g., leukotrienes), and respiratory burst, associated with leukocyte activation. Thus, the chemokines are early modulators of inflammatory response, effecting inflammatory mediator release, chemotaxis and extravasation to sites of infection or inflammation.

There are four classes of chemokines, CXC ($\alpha$), CC ($\beta$), C ($\gamma$), and $CX_3C$ ($\delta$), depending on whether the first two cysteines are separated by a single amino acid (C—X—C), are adjacent (C—C), have a missing cysteine pair (C), or are separated by three amino acids ($CX_3C$). The $\alpha$-chemokines, such as interleukin-8 (IL-8), melanoma growth stimulatory activity protein (MGSA), and stromal cell derived factor 1 (SDF-1) are chemotactic primarily for neutrophils and lymphocytes, whereas $\beta$-chemokines, such as RANTES, MIP-1$\alpha$, MIP-11, monocyte chemotactic protein-1 (MCP-1), MCP-2, MCP-3, and eotaxin are chemotactic for macrophages, T-cells, eosinophils and basophils (Deng, et al., *Nature*, 381:661-666 (1996)). The C chemokine lymphotactin shows specificity for lymphocytes (Kelner, et al., *Science*, 266: 1395-1399 (1994)) while the $CX_3C$ chemokine fractalkine shows specificity for lymphocytes and monocytes (Bazan, et al., *Nature*, 385:640-644 (1997)).

Chemokines bind to specific cell-surface receptors belonging to the family of G-protein-coupled seven-transmembrane-domain proteins (reviewed in Horuk, *Trends Pharm. Sci.*, 15:159-165 (1994)) termed "chemokine receptors." On binding their cognate ligands, chemokine receptors transduce an intracellular signal through the associated heterotrimeric G protein, resulting in a rapid increase in intracellular calcium concentration. There are at least twelve human chemokine receptors that bind or respond to $\beta$-chemokines with the following characteristic pattern: CCR1 (or "CKR-1" or "CC-CKR-1") MIP-1$\alpha$, MIP-1$\beta$, MCP-3, RANTES (Ben-Barruch, et al., *J. Biol. Chem.*, 270:22123-22128 (1995); Neote, et al., *Cell*, 72:415-425 (1993)); CCR2A and CCR2B (or "CKR-2A"/"CKR-2A" or "CC-CKR-2A"/"CC-CKR2A") MCP-1, MCP-2, MCP-3, MCP-4; CCR3 (or "CKR-3" or "CC-CKR-3") eotaxin, RANTES, MCP; (Ponath, et al., *J. Exp. Med.*, 183:2437-2448 (1996)); CCR4 (or "CKR4" or "CC-CKR4") TARC, MDC (Imai, et al., *J. Biol. Chem.*, 273: 1764-1768 (1998)); CCR5 (or "CKR-5" or "CC-CKR-5") MIP-1$\alpha$, RANTES, MIP-1$\beta$; (Sanson, et al., *Biochemistry*, 35:3362-3367 (1996)); CCR6 MIP-3$\alpha$ (Greaves, et al., *J. Exp. Med.*, 186:837-844 (1997)); CCR7 MIP-3$\beta$ and 6Ckine (Campbell, et al., *J. Cell. Biol.*, 141:1053-1059 (1998)); CCR8 I-309, HHV8 vMIP-I, HHV-8 vMIP-II, MCV vMCC-1 (Dairaghi, et al., *J. Biol. Chem.*, 274:21569-21574 (1999)); CCR9 TECK (Zaballos, et al., *J. Immunol.*, 162: 5671-5675 (1999)), D6 MIP-1 beta, RANTES, and MCP-3 (Nibbs, et al., *J. Biol. Chem.*, 272:32078-32083 (1997)), and the Duffy blood-group antigen RANTES, MCP-1 (Chaudhun, et al., *J. Biol. Chem.*, 269:7835-7838 (1994)).

Chemokine receptors, such as CCR1, CCR2, CCR3, CCR4, CCR5, CCR6, CCR7, CCR8, CCR9, CXCR1, CXCR2, CXCR3, CXCR4, CXCR5, $CX_3CR1$, and XCR1 have been implicated as being important mediators of inflammatory and immunoregulatory disorders and diseases, including asthma and allergic diseases, as well as autoimmune pathologies such as rheumatoid arthritis and atherosclerosis.

The CCR2 chemokine receptor is expressed primarily in monocytes and activated T lymphocytes, and its functional activity can be measured by cytosolic calcium elevation or chemotaxis. CCR2 exists in two isoforms, CCR2A and CCR2B. These two isoforms are alternatively spliced variants of a single MCP-1 receptor gene and differ only in the carboxyl-terminal tails. The chromosomal location of the CCR2 gene is localized to 3p21. Ligands that have been identified that are selective and of high affinity are the CC chemokines, MCP-1, MCP-2, MCP-3 and MCP4.

The highly selective expression of CCR2 makes it an ideal target for intervention to interrupt inappropriate monocyte and T cell trafficking. The clinical indications for such intervention are in inflammatory diseases and T-cell mediated autoimmune diseases such as multiple sclerosis, rheumatoid arthritis, asthma, allergy, chronic obstructive pulmonary disease, atherosclerosis, restinosis, type I and type II diabetes, metabolic syndrome and neuropathic pain. Ectopic expression of MCP-1 and CCR2 in certain tumors indicate that selective antagonists of CCR2 will have value in tumor immunotherapy, particularly attenuation of metastasis.

In view of the clinical importance of CCR2, the identification of compounds that modulate CCR2 function represents an attractive avenue into the development of new therapeutic agents. Such compounds are provided herein

SUMMARY OF INVENTION

The present invention is directed to a compound of formula (I),

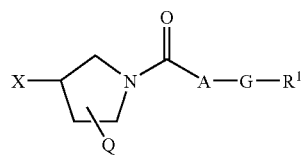

pharmaceutically acceptable salts thereof, metabolites thereof, isomers thereof, stereoisomers thereof or pro-drugs thereof, wherein X is —N(R²)—Y—Z; or
X is
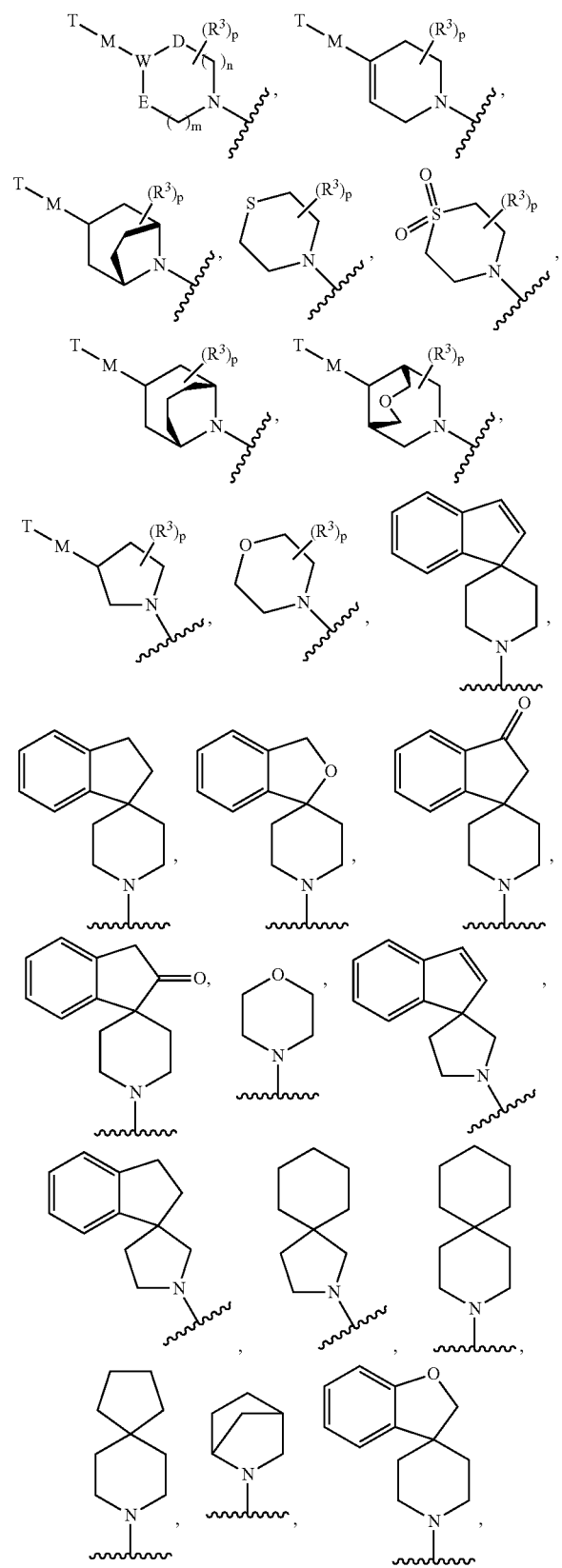
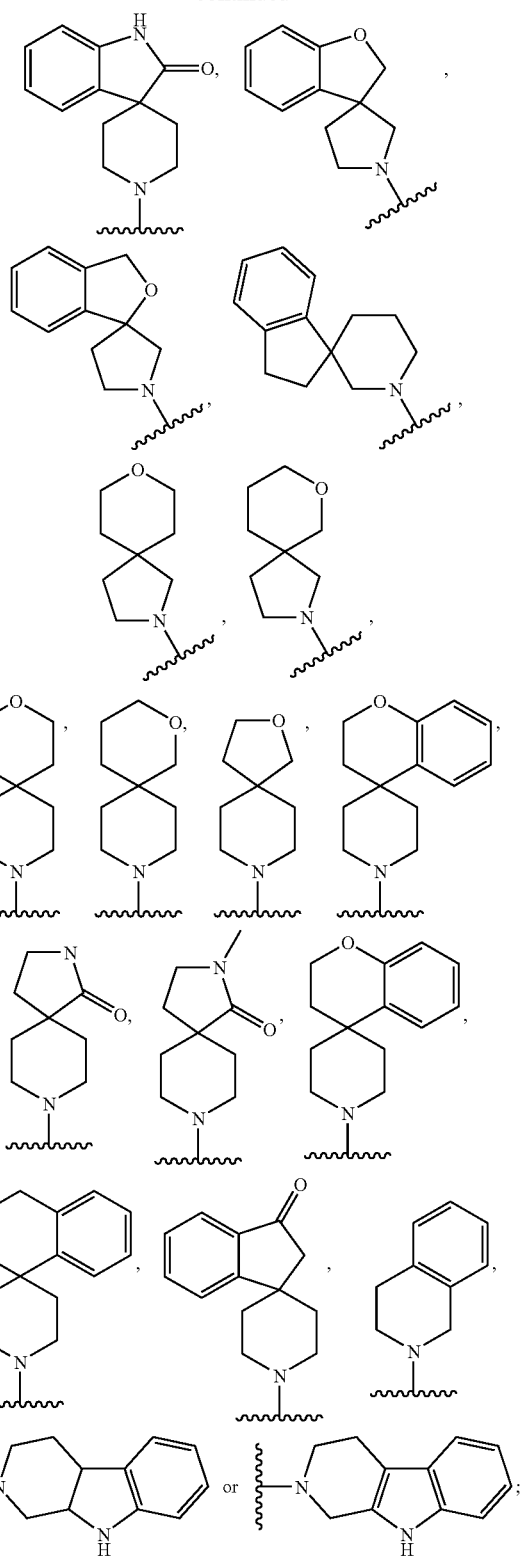
-continued
optionally substituted with one or more substituents selected from the group consisting of (C₁-C₅)alkyl, —O(C₁-C₃)alkyl, CN, Cl, F, CF₃ and OH;
Y is a bond or C(O) or is selected from the optionally substituted group consisting of (C₁-C₆)alkyl, (C₁-C₄)alkyl-heterocyclyl, $(C_1-C_4)$alkyl-heteroaryl, heterocyclyl, heteroaryl, aryl, $(C_1-C_4)$alkyl-C(O), $(C_1-C_4)$alkyl-C(O)N(R$^2$) and $(C_1-C_4)$alkyl-N(R$^2$)C(O);

wherein when Y is $(C_1-C_4)$alkyl-heterocyclyl, $(C_1-C_4)$alkyl-C(O)N(R$^2$) or $(C_1-C_4)$alkyl-N(R$^2$)C(O) it is the alkyl portion of the moiety that is attached to the nitrogen;

Z is H or Z is selected from the optionally substituted group consisting of —$(C_1-C_5)$alkyl, —$(C_1-C_3)$alkyl-aryl, —$(C_1-C_3)$alkyl-heteroaryl, —$(C_1-C_3)$alkyl-diphenyl, —$(C_3-C_6)$cycloalkyl, heterocyclyl, —$(C_1-C_4)$alkyl-heterocyclyl, —O—$(C_1-C_5)$alkyl, aryl and heteroaryl;

D is O, N, S(O)$_y$, C(O) or C(R$^5$)$_2$;
E is O, N, S(O)$_y$, C(O) or C(R$^5$)$_2$;
W is C(R$^4$) or N;
M is a bond, O or C(O); or
M is selected from the optionally substituted group consisting of —$(C_1-C_4)$alkyl, C(O)N(R$^2$), —N(R$^2$)C(O), —N(R$^2$), -aryl, -heterocyclyl and -heteroaryl; or
M is selected from the optionally substituted group consisting of —$(C_1-C_4)$alkyl-heterocyclyl, —$(C_1-C_4)$alkyl—C(O), —$(C_1-C_4)$alkyl-C(O)N(R$^2$), —$(C_1-C_4)$alkyl-C(O)O, —$(C_1-C_4)$alkyl-N(R$^2$)C(O)O, —$(C_1-C_4)$)alkyl-N(R$^2$)C(O) and —CH$_2$—NH—C(O) wherein the alkyl portion of the moiety is connected to W;

T is H or NH$_2$ or T is selected from the optionally substituted group consisting of $(C_1-C_5)$alkyl, $(C_1-C_5)$alkoxy, —$(C_1-C_3)$alkyl-aryl, —$(C_1-C_3)$alkyl-heteroaryl, —$(C_1-C_3)$alkyl-diphenyl, heterocyclyl, —$(C_1-C_4)$alkyl-heterocyclyl, aryl and heteroaryl;

A is selected from the group consisting of a bond, O and optionally substituted $(C_1-C_5)$alkyl;

G is selected from the group consisting of a bond, N(R$^2$), C(O), —C(O)—N(R$^2$)—$(C_1-C_4)$alkyl, —$(C_1-C_4)$alkyl-N(R$^2$)—C(O), —$(C_1-C_4)$alkyl-N(R$^2$), N(R$^2$)—$(C_1-C_4)$alkyl, N(R$^2$)—CH(R$^2$)—C(O), C(O)—CH(R$^4$)—N(R$^2$), optionally substituted —$(C_1-C_4)$alkyl, $(C_2)$alkenyl, —$(C_1-C_4)$alkyl-N(R$^2$)S(O)$_x$—, —S(O)$_x$N(R$^2$)—$(C_1-C_4)$alkyl, —N(R$^2$)S(O)$_x$, —S(O)$_x$N(R$^2$), —N(R$^2$)CON(R$^2$), —N(R$^2$)C(O), C(O)N(R$^2$), —NH-optionally substituted heteroaryl, optionally substituted heteroaryl and optionally substituted phenyl;

Q is H or is selected from the optionally substituted group consisting of $(C_1-C_5)$alkyl, $(C_3-C_7)$cycloalkyl, —O—$(C_1-C_4)$alkyl, —O—$(C_3-C_7)$cycloalkyl and —$(C_1-C_3)$alkyl-O—$(C_1-C_3)$alkyl;

R$^1$ is selected from the optionally substituted group consisting of amino, aryl, adamantanyl, diphenyl($C_1-C_2$)alkyl, heteroaryl, heterocyclyl, $(C_1-C_6)$alkyl, —O—$(C_1-C_4)$alkyl, —O—CH$_2$-phenyl, and $(C_3-C_6)$cycloalkyl;

R$^2$ is independently selected from the optionally substituted group consisting of H, $(C_1-C_4)$alkyl and $(C_3-C_5)$cycloalkyl;

R$^3$ is independently H, OH, CN, F, CF$_3$, C(O)N(R$^2$)$_2$, N(R$^2$)$_2$, or oxo; or
R$^3$ is independently selected from the optionally substituted group consisting of $(C_1-C_3)$alkyl, $(C_3-C_7)$cycloalkyl, —O—$(C_1-C_3)$alkyl, $(C_1-C_3)$alkyl-O—$(C_1-C_3)$alkyl, —$(C_1-C_3)$alkyl-C(O)—O—$(C_1-C_3)$alkyl, aryl, —O-aryl, heteroaryl, heterocyclyl, —$(C_1-C_3)$alkyl-aryl, —N(R$^2$)aryl, —O-aryl, —C(O)—O—$(C_1-C_3)$alkyl, —NH-phenyl and phenyl;

R$^5$ is H or OH or R$^5$ is independently selected from the optionally substituted group consisting of $(C_1-C_4)$alkyl, $(C_3-C_5)$cycloalkyl, —O—$(C_1-C_4)$alkyl and —O—$(C_3-C_7)$cycloalkyl;

R$^4$ is H, OH, CN or F or R$^4$ is selected from the optionally substituted group consisting of —O—$(C_1-C_3)$alkyl, —O—$(C_3-C_7)$cycloalkyl, aryl and heteroaryl;

m and n are independently 0, 1, or 2; and
p is 1 or 2;
x is 1 or 2;
y is 0, 1 or 2;
provided that D and E are not O or N at the same time; and
provided that when W is N, D is not N or O and E is not N or O.

In a preferred embodiment, embodiment 2,
X is —N(R$^2$)—Y—Z; or
X is

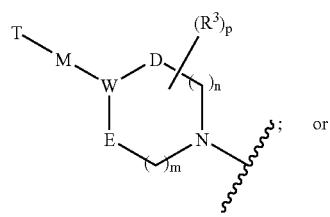

X is:

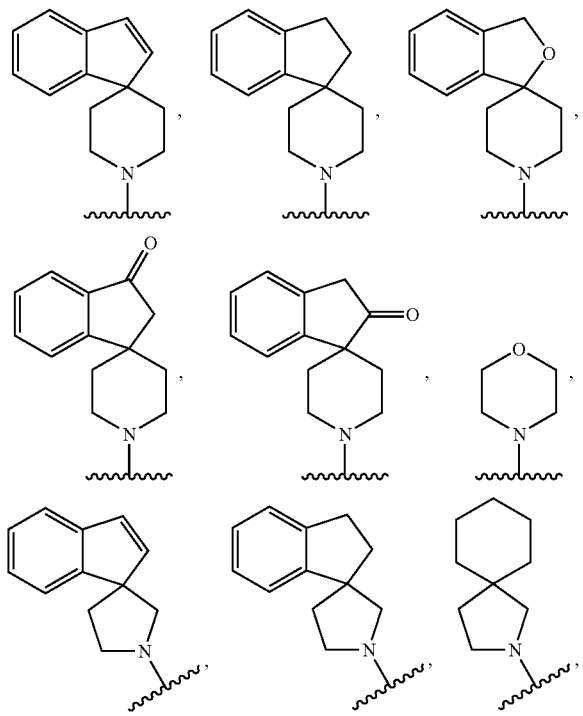

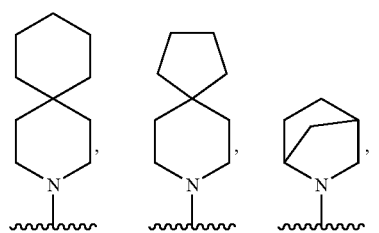

-continued

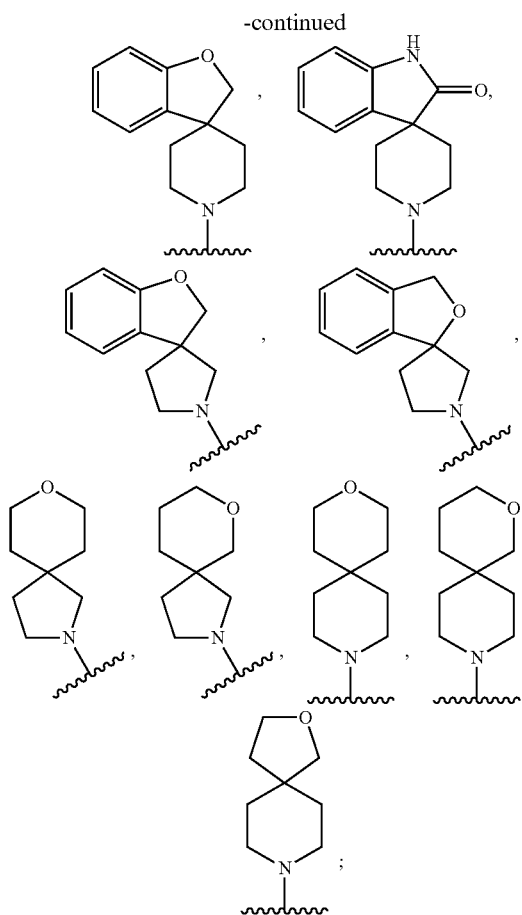

optionally substituted with one or more substituents selected from the group consisting of $(C_1-C_5)$alkyl, $-O(C_1-C_3)$alkyl, CN, Cl, F, $CF_3$ and OH;

Y is a bond or is selected from the optionally substituted group consisting of $(C_1-C_6)$alkyl, $(C_1-C_4)$alkyl-heterocyclyl, $(C_1-C_4)$alkyl-heteroaryl, heterocyclyl, heteroaryl, aryl, $(C_1-C_4)$alkyl-C(O), $(C_1-C_4)$alkyl-C(O)N(R$^2$) and $(C_1-C_4)$alkyl-N(R$^2$)C(O);

wherein when Y is $(C_1-C_4)$alkyl-heterocyclyl, $(C_1-C_4)$alkyl-C(O)N(R$^2$) or $(C_1-C_4)$alkyl-N(R$^2$)C(O) it is the alkyl portion of the moiety that is attached to the nitrogen;

Z is H or Z is selected from the optionally substituted group consisting of $-(C_1-C_5)$alkyl, $-(C_1-C_3)$alkyl-aryl, $-(C_1-C_3)$alkyl-heteroaryl, $-(C_1-C_3)$alkyl-diphenyl, $-(C_3-C_6)$cycloalkyl, heterocyclyl, $-(C_1-C_4)$alkyl-heterocyclyl, aryl and heteroaryl;

D is O, N, S(O)$_y$, C(O) or C(R$^5$)$_2$;
E is O, N, S(O)$_y$, C(O) or C(R$^5$)$_2$;
W is C(R$^4$) or N;
M is a bond, O or C(O); or
M is selected from the optionally substituted group consisting of $-(C_1-C_4)$alkyl, $-C(O)N(R^2)$, $-N(R^2)C(O)$, $-N(R^2)$, -aryl, -heterocyclyl and -heteroaryl; or
M is selected from the optionally substituted group consisting of $-(C_1-C_4)$alkyl-heterocyclyl, $-(C_1-C_4)$alkyl-C(O)$, $-(C_1-C_4)$alkyl-C(O)N(R$^2$)$, $-(C_1-C_4)$alkyl-C(O)O, $-(C_1-C_4)$alkyl-N(R$^2$)C(O)O, $-(C_1-C_4)$alkyl-N(R$^2$)C(O) and $-CH_2-NH-C(O)$ wherein the alkyl portion of the moiety is connected to W;

T is H or T is selected from the optionally substituted group consisting of $(C_1-C_5)$alkyl, $(C_1-C_5)$alkoxy, $-(C_1-C_3)$alkyl-aryl, $-(C_1-C_3)$alkyl-heteroaryl, $-(C_1-C_3)$alkyl-diphenyl, heterocyclyl, $-(C_1-C_4)$alkyl-heterocyclyl, aryl and heteroaryl;

A is selected from the group consisting of a bond, O and optionally substituted $(C_1-C_5)$alkyl;

G is selected from the group consisting of a bond, N(R$^2$), C(O), $-C(O)-N(R^2)-(C_1-C_4)$alkyl, $-(C_1-C_4)$alkyl-N(R$^2$)$-$C(O), $-(C_1-C_4)$alkyl-N(R$^2$), N(R$^2$)$-(C_1-C_4)$alkyl, N(R$^2$)$-$CH(R$^2$)$-$C(O), C(O)$-$CH(R$^4$)$-$N(R$^2$), optionally substituted $-(C_1-C_4)$alkyl, $(C_2)$alkenyl, $-(C_1-C_4)$alkyl-N(R$^2$)S(O)$_x$—, $-S(O)_xN(R^2)-(C_1-C_4)$alkyl, $-N(R^2)S(O)_x$—, $-S(O)$, N(R$^2$), $-N(R^2)CON(R^2)$, $-N(R^2)C(O), C(O)N(R^2)$, $-$NH-optionally substituted heteroaryl, optionally substituted heteroaryl and optionally substituted phenyl;

Q is H or is selected from the optionally substituted group consisting of $(C_1-C_5)$alkyl, $(C_3-C_7)$cycloalkyl, $-O-(C_1-C_4)$alkyl, $-O-(C_3-C_7)$cycloalkyl and $-(C_1-C_3)$alkyl-O-$(C_1-C_3)$alkyl;

R$^1$ is selected from the optionally substituted group consisting of amino, aryl, adamantanyl, diphenyl(C$_1$-C$_2$)alkyl, heteroaryl, heterocyclyl, $(C_1-C_6)$alkyl and $(C_3-C_6)$cycloalkyl;

R$^2$ is independently selected from the optionally substituted group consisting of H, $(C_1-C_4)$alkyl and $(C_3-C_5)$cycloalkyl;

R$^3$ is H, OH, CN, F, CF$_3$, C(O)N(R$^2$)$_2$, N(R$^2$)$_2$, or R$^3$ is selected from the optionally substituted group consisting of $(C_1-C_3)$alkyl, $(C_3-C_7)$cycloalkyl, $-O-(C_1-C_3)$alkyl, $(C_1-C_3)$alkyl-O-$(C_1-C_3)$alkyl, $-(C_1-C_3)$alkyl-C(O)-O-$(C_1-C_3)$alkyl, aryl, $-O$-aryl, heteroaryl, heterocyclyl, $-(C_1-C_3)$alkyl-aryl, $-N(R^2)$aryl, $-O$-aryl, $-C(O)-O-(C_1-C_3)$alkyl, $-NH$-phenyl and phenyl;

R$^5$ is H or OH or R$^5$ is independently selected from the optionally substituted group consisting of $(C_1-C_4)$alkyl, $(C_3-C_5)$cycloalkyl, $-O-(C_1-C_4)$alkyl and $-O-(C_3-C_7)$cycloalkyl;

R$^4$ is H, OH, CN or F or R$^4$ is selected from the optionally substituted group consisting of $-O-(C_1-C_3)$alkyl, $-O-(C_3-C_7)$cycloalkyl, aryl and heteroaryl;

m and n are independently 0, 1, or 2; and p is 1 or 2;

x is 1 or 2;

y is 0, 1 or 2;

provided that D and E are not O or N at the same time; and provided that when W is N, D is not N or O and E is not N or O.

In a preferred embodiment of embodiment 2, referred to as embodiment 3, X is $-N(R^2)-Y-Z$,

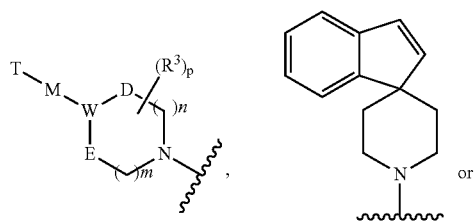

-continued

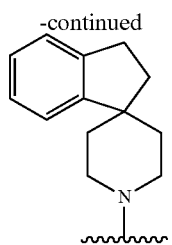

optionally substituted with one or more substituents selected from the group consisting of (C₁-C₅)alkyl, —O(C₁-C₃)alkyl, CN, Cl, F, CF₃ and OH.

In a preferred embodiment of any of the foregoing embodiments, referred to as embodiment 4, Y is selected from the group consisting of a bond, optionally substituted (C₁-C₆) alkyl, optionally substituted piperidinyl, optionally substituted —CH₂-pyrimidinyl, optionally substituted indanyl, optionally substituted tetrahydrofuranyl and optionally substituted tetrahydropyranyl;

Z is selected from the optionally substituted group consisting of (C₁-C₄)alkyl, cyclohexyl, 2,3-dihydrobenzofuranyl, benzo[1,3]dioxolyl, 1,3-dihydrobenzoimidazol-2-one, benzothiazolyl, benzo[b]thiophenyl, chromanyl, indanyl, indolyl, morpholinyl, naphthyl, phenyl, piperazinyl, piperidinyl, pyrazinyl, pyrazolyl, pyridinyl, pyrimidinyl, quinolinyl, 4,5,6,7-tetrahydrobenzofuranyl, tetrahydrofuranyl, 5,6,7,8-tetrahydroquinolinyl, 5,6,7,8-tetrahydronaphthyl, tetrahydropyranyl, tetrahydrothienyl, tetrahydrothienyl 1,1-dioxide, tetrahydrothiopyranyl, tetrahydrothiopyranyl 1,1-dioxide, —CH₂-benzofuranyl, —CH₂-phenyl, —CH₂-pyridinyl, —(C₂)alkyl-diphenyl, —CH₂-tetrahydropyranyl;

D is C(R⁵)₂;
E is C(R⁵)₂;
M is a bond, O, C(O), optionally substituted pyrrolidinyl, optionally substituted (C₁-C₄)alkyl, —CH₂—NH—C(O) or (C₁)alkyl-C(O)O; wherein the alkyl portion of the moiety is connected to W;

T is H or NH₂ or is selected from the optionally substituted group consisting of (C₁-C₄)alkyl, benzothiazolyl, benzo[b]thiophenyl, 1H-benzotriazolyl, decahydroisoquinolinyl, imidazolyl, indanyl, indenyl, indolyl, 1H-pyrrolo[2,3-b]pyridinyl, 1,2,3,4-tetrahydroisoquinolinyl, morpholinyl phenyl, pyrazolyl, pyridazinyl, pyridinyl, pyrimidinyl, pyrrolidinyl, tetrazolyl, [1,2,3]triazolyl and [1,2,4]triazolyl, A is a bond or (C₁-C₅)alkyl;
G is a bond, N(R²), C(O), phenyl, pyridinyl or 5,6,7,8-tetrahydro[1,6]naphthyridinyl, (C₁-C₂)alkyl, (C₂)alkenyl or N(R²)—C(O), N(H)—(C₁)alkyl-C(O), wherein the nitrogen is attached to A; or
G is N(R²)—(C₁-C₂)alkyl, N(H)—(C₂)alkyl (C₁)alkyl-NH—S(O)₂, (C₁)alkyl-NH—C(O) wherein the alkyl portion of the moiety is attached to A;

Q is H, methyl, isopropyl or cyclopropyl;
R¹ is selected from the optionally substituted group consisting of adamantanyl, benzo[1,3]dioxolyl, benzimidazolyl, diphenyl(C₁-C₂)alkyl, fluorenyl, furanyl, indanyl, indolyl, isoquinolinyl, isoxazolyl, naphthyl, oxazolyl, phenyl, piperidinyl, pyrazolyl, pyridinyl, dihydropyrazolo[1,5-a]pyrimidinyl, pyrazolo[1,5-a]pyrimidinyl, quinolinyl, quinazolinyl, 1,2,3,4-tetrahydroisoquinolinyl and 5,6,7,8-tetrahydro[1,6]naphthyridinyl, R² is H or (C₁)alkyl;
R³ is H, OH, F, CH₃, OCH₃, CF₃, CN, —CH₂—O—CH₃, —CH₂—C(O)—O—CH₃, —C(O)—OCH₃, —NH-phenyl, —O-phenyl, indolyl, optionally substituted phenyl, phenoxy or C(O)NH₂;

R⁴ is H, CN or OH;
m is 0 or 1; and
n is 1.

In a preferred embodiment of any of the foregoing embodiments, referred to as embodiment 5, Y is selected from the group consisting of a bond, optionally substituted (C₁-C₆) alkyl, optionally substituted piperidinyl and optionally substituted —CH₂-pyrimidinyl and optionally substituted indanyl;

Z is selected from the optionally substituted group consisting of (C₁-C₄)alkyl, cyclohexyl, 2,3-dihydrobenzofuranyl, benzo[1,3]dioxolyl, benzo[b]thiophenyl, chromanyl, indanyl, indolyl, morpholinyl, naphthyl, phenyl, piperidinyl, pyrazinyl, pyrazolyl, pyridinyl, pyrimidinyl, quinolinyl, 4,5,6,7-tetrahydrobenzofuranyl, 5,6,7,8-tetrahydroquinolinyl, 5,6,7,8-tetrahydronaphthyl, tetrahydropyranyl, —CH₂-benzofuranyl, —CH₂-phenyl, —CH₂-pyridinyl, —(C₂)alkyl-diphenyl, —CH₂-tetrahydropyranyl;

D is C(R⁵)₂;
E is C(R⁵)₂;
M is a bond, O, C(O), optionally substituted (C₁-C₄)alkyl, —CH₂—NH—C(O) or (C₁)alkyl-C(O)O; wherein the alkyl portion of the moiety is connected to W;

T is H or is selected from the optionally substituted group consisting of (C₁-C₄)alkyl, benzo[b]thiophenyl, decahydroisoquinolinyl, imidazolyl, indanyl, indenyl, indolyl, 1,2,3,4-tetrahydroisoquinolinyl, morpholinyl phenyl, pyridinyl and pyrrolidinyl;

A is a bond or (C₁-C₅)alkyl);
G is a bond, N(R²), C(O), phenyl, pyridinyl or 5,6,7,8-tetrahydro[1,6]naphthyridinyl, (C₁-C₂)alkyl, (C₂)alkenyl or N(R²)—C(O), N(H)—(C₁)alkyl-C(O), wherein the nitrogen is attached to A; or
G is N(R²)—(C₁-C₂)alkyl, N(H)—(C₂)alkyl (C₁)alkyl-NH—S(O)₂, (C₁)alkyl-NH—C(O) wherein the alkyl portion of the moiety is attached to A;

Q is H or isopropyl;
R¹ is selected from the optionally substituted group consisting of adamantanyl, benzo[1,3]dioxolyl, diphenyl(C₁-C₂) alkyl, fluorenyl, indanyl, indolyl, isoxazolyl, naphthyl, phenyl, piperidinyl, pyridinyl, quinazolinyl, 1,2,3,4-tetrahydroisoquinolinyl and 5,6,7,8-tetrahydro[1,6] naphthyridinyl, R² is H or (C₁)alkyl;
R³ is H, OH, F, CH₃, OCH₃, CF₃, CN, —CH₂—O—CH₃, —CH₂—C(O)—O—CH₃, —C(O)—OCH₃, —NH-phenyl, indolyl, optionally substituted phenyl, phenoxy or C(O)NH₂;

R⁴ is H, CN or OH;
m is 0 or 1; and
n is 1.

In a preferred embodiment of any of the foregoing embodiments, referred to as embodiment 6, Y is a bond, or is selected from the optionally substituted group consisting of (C₁-C₄) alkyl and indanyl;

Z is selected from the optionally substituted group consisting of (C₁-C₄)alkyl, benzo[b]thiophenyl, indolyl, naphthyl, phenyl and tetrahydropyranyl; is a bond, C(O), 0, optionally substituted (C₁-C₄)alkyl, —CH₂—NH—C(O) or (C₁)alkyl-C(O)O;

T is H or is selected from the optionally substituted group consisting of (C₁-C₄)alkyl, benzo[b]thiophenyl, decahydroisoquinolinyl, imidazolyl, indanyl, indenyl, indolyl, phenyl, pyridinyl and pyrrolidinyl;

G is a bond, CH₂, N(R²), N(R²)—CH₂ or N(R²)—C(O) wherein the N is attached to A;

R¹ is selected from the optionally substituted group consisting of benzo[1,3]dioxolyl, diphenyl(C₁-C₂)alkyl, indanyl, naphthyl, phenyl, piperidinyl, pyridinyl, quinazolinyl, 1,2,3,4-tetrahydroisoquinolinyl, and 5,6,7,8-tetrahydro[1,6]naphthyridinyl; and R³ is H, OH, F, CH₃, OCH₃, CF₃, —CH₂—O—CH₃, —CH₂—C(O)—O—CH₃, —C(O)—OCH₃, —NH-phenyl, phenyl, phenoxy or C(O)NH₂.

In a preferred embodiment of any of the foregoing embodiments, referred to as embodiment 7, Z is selected from the optionally substituted group consisting of (C₁-C₂)alkyl, indolyl, benzo[1,3]dioxolyl, phenyl and tetrahydropyranyl;

M is a bond, C(O), optionally substituted (C₁-C₄)alkyl, —CH₂—NH—C(O) or (C₁)alkyl-C(O)O;

T is H or is selected from the optionally substituted group consisting of (C₁-C₂)alkyl, —O—(C₁-C₄)alkyl, decahydroisoquinolinyl, imidazolyl, indanyl, indenyl, phenyl, pyridinyl and pyrrolidinyl;

G is a bond, CH₂, N(H), C(O), N(H)CH₂ or N(R²)—C(O) wherein the N is attached to A;

R¹ is selected from the optionally substituted group consisting of benzo[1,3]dioxolyl, indanyl, diphenylalkyl, naphthyl, phenyl, piperidinyl, quinazolinyl, 1,2,3,4-tetrahydroisoquinolinyl, 5,6,7,8-tetrahydroquinolinyl and 5,6,7,8-tetrahydro[1,6]naphthyridinyl; and W is CH or N.

In a preferred embodiment of any of the foregoing embodiments, referred to as embodiment 8, D is C(R⁵);

E is C(R⁵);

M is a bond, C(O), (C₁-C₂)alkyl or (C₁)alkyl-C(O)O;

T is H or is selected from the optionally substituted group consisting of (C₁-C₂)alkyl, decahydroisoquinolinyl, imidazolyl, indanyl, indenyl, indolyl, phenyl and pyridinyl;

G is a bond, N(H), C(O), NH—CH₂ or N(H)—CO wherein the N is attached to A;

Q is H;

R¹ is selected from the optionally substituted group consisting of 5,6,7,8-tetrahydro[1,6]naphthyridinyl, diphenylalkyl, naphthyl, phenyl, piperidinyl and quinazolinyl;

R³ is H, OH, CH₃, —CH₂—O—CH₃, —CH₂—C(O)—O—CH₃, —C(O)—OCH₃ or —NH-phenyl; and m is 1.

In a preferred embodiment of any of the foregoing embodiments, referred to as embodiment 9, Y is (C₁-C₄)alkyl;

Z is selected from the optionally substituted group consisting of benzo[1,3]dioxolyl and phenyl;

M is bond or (C₁)alkyl;

T is H or is selected from the optionally substituted group consisting of (C₁-C₂)alkyl, imidazolyl, indanyl, indenyl, indolyl, phenyl and pyridinyl;

R¹ is selected from the optionally substituted group consisting of 5,6,7,8-tetrahydro[1,6]naphthyridinyl, diphenylalkyl, naphthyl, phenyl, piperidinyl and quinazolinyl; and R² is H.

In a preferred embodiment of any of the foregoing embodiments, referred to as embodiment 10, W is CH or N;

M is a bond;

T is H or is selected from the optionally substituted group consisting of imidazolyl, indanyl, indenyl, phenyl and pyridinyl;

R³ is H, OH or CH₃;

m is 1; and n is 1.

In a preferred embodiment of any of the foregoing embodiments, referred to as embodiment 11, T is H or is selected from the optionally substituted group consisting of indanyl, indenyl and phenyl;

A is a bond or CH₂;

G is NH, NH—CH₂, or NH—C(O) wherein the N is attached to A;

R¹ is selected from the optionally substituted group consisting of 5,6,7,8-tetrahydro[1,6]naphthyridinyl, phenyl, piperidinyl and quinazolinyl; and R⁵ is H or CH₃.

In a preferred embodiment of any of the foregoing embodiments, referred to as embodiment 12, Y is CH₂;

Z is phenyl optionally substituted with one or more CH₃;

E is CH₂;

W is CH;

T is H or is selected from the optionally substituted group consisting of indanyl, indenyl and phenyl and is optionally substituted with one or more substituents selected from the group consisting of Cl, F, OH CN, CH₃ and OCH₃;

A is CH₂;

D is CH₂; and

R¹ is selected from the optionally substituted group consisting of phenyl and quinazolinyl; wherein R¹ is optionally substituted with one or more substitutents selected from the group consisting of Cl, F, CH₃ and CF₃.

In a preferred embodiment of any of the foregoing embodiments, referred to as embodiment 13, X is

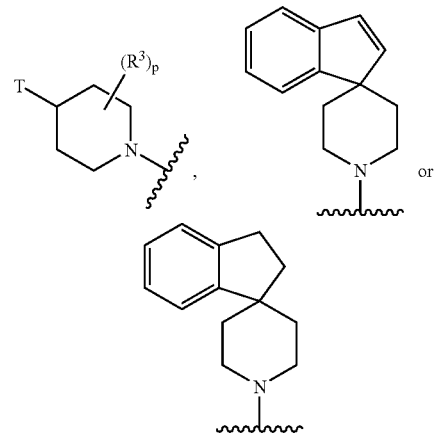

optionally substituted with one or more substituents selected from the group consisting of (C₁-C₅)alkyl, —O(C₁-C₃)alkyl, CN, Cl, F, CF₃ and OH.

In a preferred embodiment of any of the foregoing embodiments, referred to as embodiment 14, G is NH or —NH—C(O) wherein the N is attached to A;

R¹ is phenyl or quinazolinyl and R¹ is optionally substituted with one or more Cl;

R³ is H, OH or CH₃; and p is 1.

In a preferred embodiment of any of the foregoing embodiments, referred to as embodiment 15, the compound is

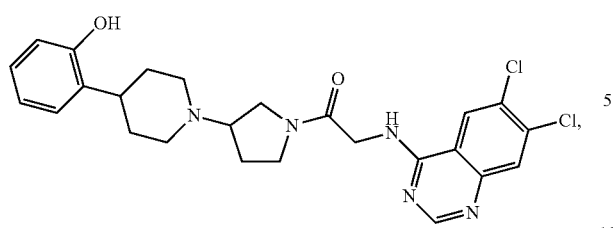

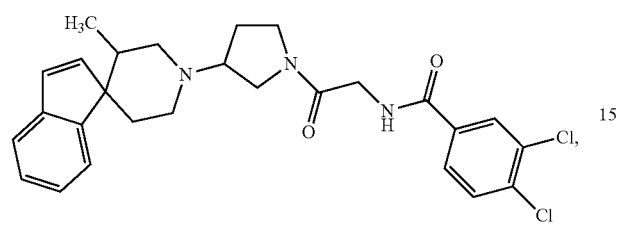

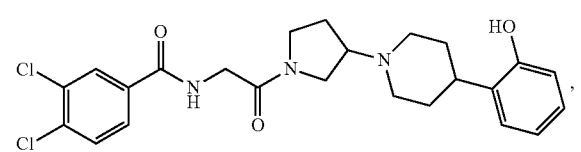

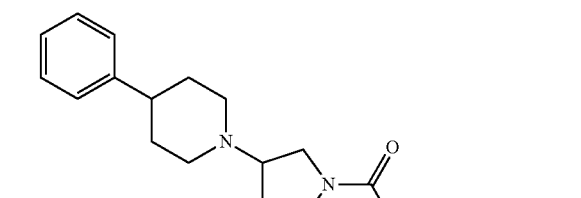

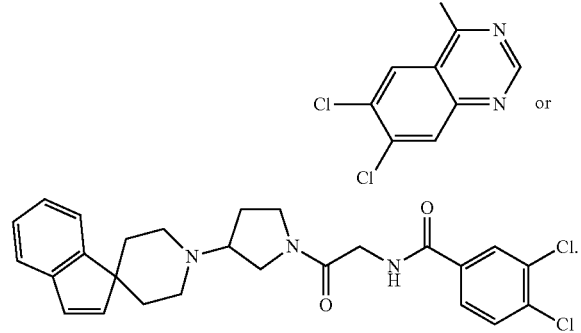

In another embodiment, referred to as embodiment 16, the invention provides a method of treating a $CCR^2$ dependent disease or condition comprising administering a therapeutically effective amount of a compound of formula I

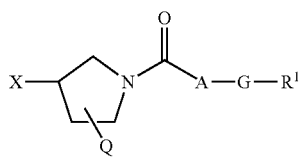

I pharmaceutically acceptable salts thereof, metabolites thereof, isomers thereof, stereoisomers thereof or pro-drugs thereof, wherein X is —$N(R^2)$—Y—Z; or X is

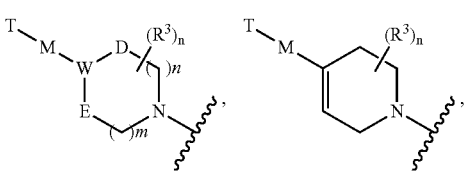

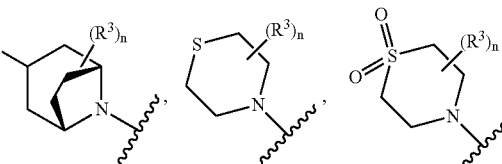

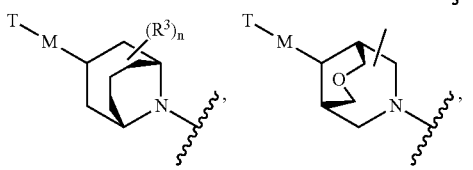

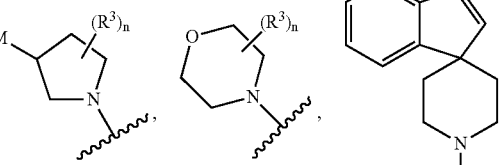

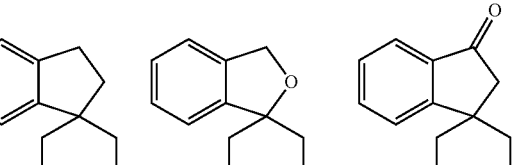

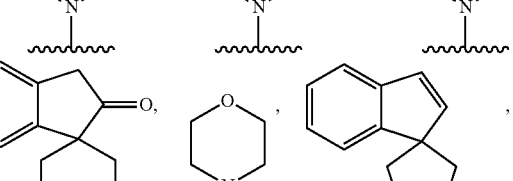

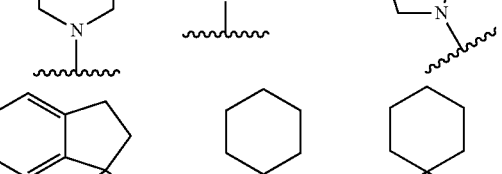

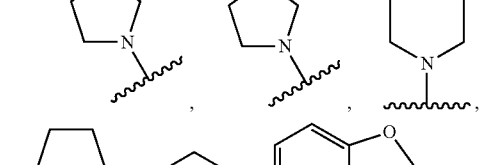

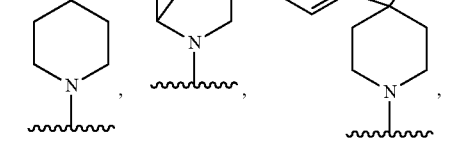

-continued

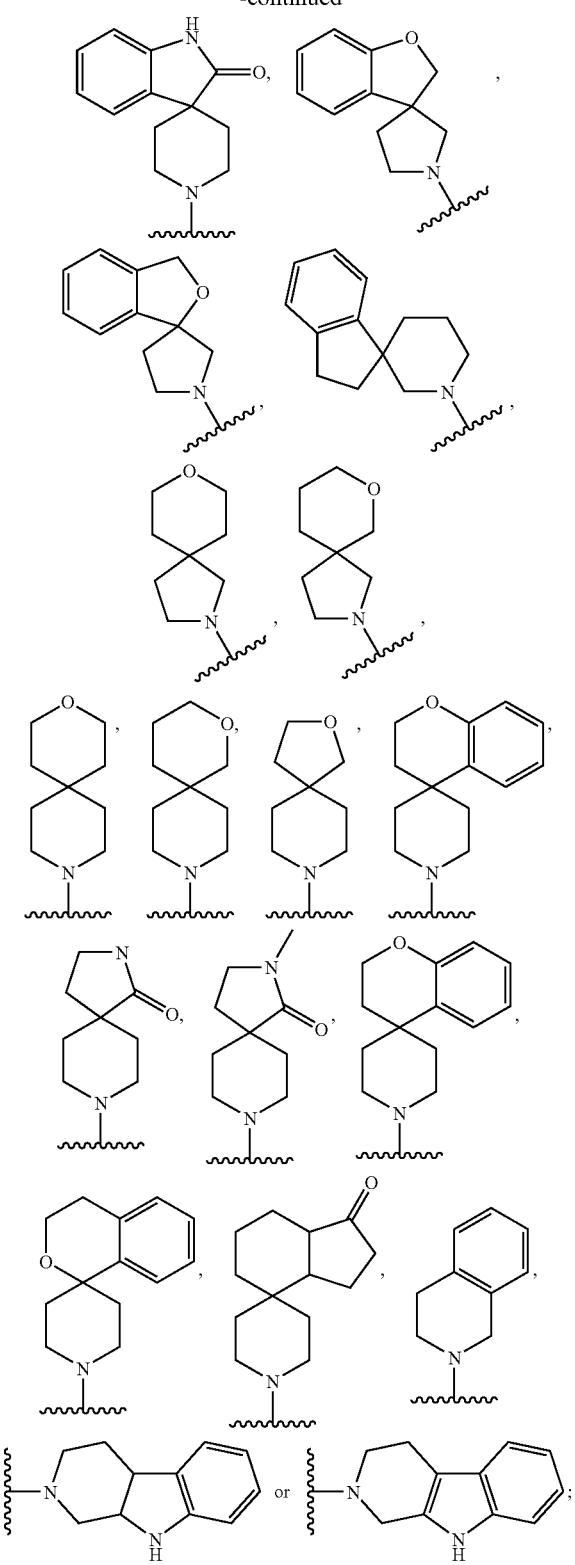

optionally substituted with one or more substituents selected from the group consisting of $(C_1-C_5)$alkyl, —O$(C_1-C_3)$alkyl, CN, Cl, F, $CF_3$ and OH;

Y is a bond or C(O) or is selected from the optionally substituted group consisting of $(C_1-C_6)$alkyl, $(C_1-C_4)$alkyl-heterocyclyl, $(C_1-C_4)$alkyl-heteroaryl, heterocyclyl, heteroaryl, aryl, $(C_1-C_4)$alkyl-C(O), $(C_1-C_4)$alkyl-C(O)N($R^2$) and $(C_1-C_4)$alkyl-N($R^2$)C(O);

wherein when Y is $(C_1-C_4)$alkyl-heterocyclyl, $(C_1-C_4)$alkyl-C(O)N($R^2$) or $(C_1-C_4)$alkyl-N($R^2$)C(O) it is the alkyl portion of the moiety that is attached to the nitrogen;

Z is H or Z is selected from the optionally substituted group consisting of —$(C_1-C_5)$alkyl, —$(C_1-C_3)$alkyl-aryl, —$(C_1-C_3)$alkyl-heteroaryl, —$(C_1-C_3)$alkyl-diphenyl, —$(C_3-C_6)$cycloalkyl, heterocyclyl, —$(C_1-C_4)$alkyl-heterocyclyl, —O—$(C_1-C_5)$alkyl, aryl and heteroaryl;

D is O, N, S(O)$_y$, C(O) or C($R^5$)$_2$;
E is O, N, S(O)$_y$, C(O) or C($R^5$)$_2$;
W is C($R^4$) or N;
M is a bond, O or C(O); or
M is selected from the optionally substituted group consisting of —$(C_1-C_4)$alkyl, —C(O)N($R^2$), —N($R^2$)C(O), —N($R^2$), -aryl, -heterocyclyl and -heteroaryl; or
M is selected from the optionally substituted group consisting of —$(C_1-C_4)$alkyl-heterocyclyl, —$(C_1-C_4)$alkyl-C(O), —$(C_1-C_4)$alkyl-C(O)N($R^2$), —$(C_1-C_4)$alkyl-C(O)O, —$(C_1-C_4)$alkyl-N($R^2$)C(O)O, —$(C_1-C_4)$)alkyl-N($R^2$)C(O) and —$CH_2$—NH—C(O) wherein the alkyl portion of the moiety is connected to W;

T is H or $NH_2$ or T is selected from the optionally substituted group consisting of $(C_1-C_5)$alkyl, $(C_1-C_5)$alkoxy, —$(C_1-C_3)$alkyl-aryl, —$(C_1-C_3)$alkyl-heteroaryl, —$(C_1-C_3)$alkyl-diphenyl, heterocyclyl, —$(C_1-C_4)$alkyl-heterocyclyl, aryl and heteroaryl;

A is selected from the group consisting of a bond, O and optionally substituted $(C_1-C_5)$alkyl;

G is selected from the group consisting of a bond, N($R^2$), C(O), —C(O)—N($R^2$)—$(C_1-C_4)$alkyl, —$(C_1-C_4)$alkyl-N($R^2$)—C(O), —$(C_1-C_4)$alkyl-N($R^2$), N($R^2$)—$(C_1-C_4)$alkyl, N($R^2$)—CH($R^2$)—C(O), C(O)—CH($R^4$)—N($R^2$), optionally substituted —$(C_1-C_4)$alkyl, $(C_2)$alkenyl, —$(C_1-C_4)$alkyl-N($R^2$)S(O)$_x$—, —S(O)$_x$N($R^2$)—$(C_1-C_4)$alkyl, —N($R^2$)S(O)$_x$, —S(O), N($R^2$), —N($R^2$)CON($R^2$), —N($R^2$)C(O), C(O)N($R^2$), —NH-optionally substituted heteroaryl, optionally substituted heteroaryl and optionally substituted phenyl;

Q is H or is selected from the optionally substituted group consisting of $(C_1-C_5)$alkyl, $(C_3-C_7)$cycloalkyl, —O—$(C_1-C_4)$alkyl, —O—$(C_3-C_7)$cycloalkyl and —$(C_1-C_3)$alkyl-O—$(C_1-C_3)$alkyl;

$R^1$ is selected from the optionally substituted group consisting of amino, aryl, adamantanyl, diphenyl$(C_1-C_2)$alkyl, heteroaryl, heterocyclyl, $(C_1-C_6)$alkyl, —O—$(C_1-C_4)$alkyl, —O—$CH_2$-phenyl, and $(C_3-C_6)$cycloalkyl;

$R^2$ is independently selected from the optionally substituted group consisting of H, $(C_1-C_4)$alkyl and $(C_3-C_5)$cycloalkyl;

$R^3$ is independently H, OH, CN, F, $CF_3$, C(O)N($R^2$)$_2$, N($R^2$)$_2$, and oxo or $R^3$ is independently selected from the optionally substituted group consisting of $(C_1-C_3)$alkyl, $(C_3-C_7)$cycloalkyl, —O—$(C_1-C_3)$alkyl, $(C_1-C_3)$alkyl-O—$(C_1-C_3)$alkyl, —$(C_1-C_3)$alkyl-C(O)—O—$(C_1-C_3)$alkyl, aryl, —O-aryl, heteroaryl, heterocyclyl, —$(C_1-C_3)$alkyl-aryl, —N($R^2$)aryl, —O-aryl, —C(O)—O—$(C_1-C_3)$alkyl, —NH-phenyl and phenyl;

$R^5$ is H or OH or $R^5$ is independently selected from the optionally substituted group consisting of $(C_1-C_4)$alkyl, $(C_3-C_5)$cycloalkyl, —O—$(C_1-C_4)$alkyl and —O—$(C_3-C_7)$cycloalkyl;

$R^4$ is H, OH, CN or F or $R^4$ is selected from the optionally substituted group consisting of —O—$(C_1-C_3)$alkyl, —O—$(C_3-C_7)$cycloalkyl, aryl and heteroaryl;

m and n are independently 0, 1, or 2; and p is 1 or 2;

x is 1 or 2;

y is 0, 1 or 2;

provided that D and E are not O or N at the same time; and provided that when W is N, D is not N or O and E is not N or O.

In another embodiment, referred to as embodiment 17, the invention provides a method of treating disease wherein the disease is an autoimmune disease.

In another embodiment, referred to as embodiment 18, the invention provides a method of treating an autoimmune disease wherein the autoimmune disease is rheumatoid arthritis, osteoarthritis, asthma, chronic obstructive pulmonary disease (COPD), sepsis, psoriasis, psoriatic arthritis, inflammatory bowel disease, Crohn's disease, lupus, multiple sclerosis, juvenile chronic arthritis, Lyme arthritis, reactive arthritis, septic arthritis, spondyloarthropathy or systemic lupus erythematosus.

In another embodiment, referred to as embodiment 19, the invention provides a method of treating multiple sclerosis.

In another embodiment, referred to as embodiment 20, the invention provides a pharmaceutical composition comprising a compound of formula I

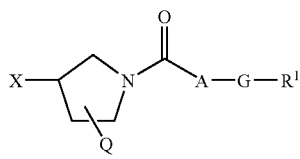

I pharmaceutically acceptable salts thereof, metabolites thereof, isomers thereof, stereoisomers thereof or pro-drugs thereof, wherein X is —N($R^2$)—Y—Z; or X is

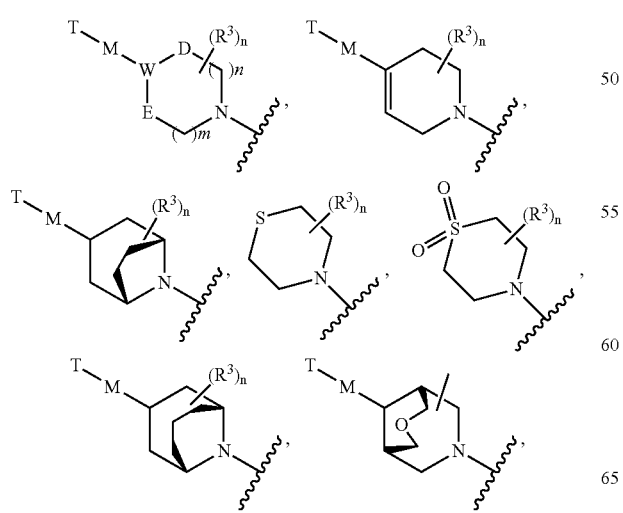

-continued

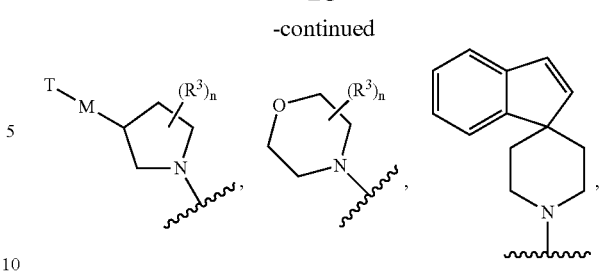

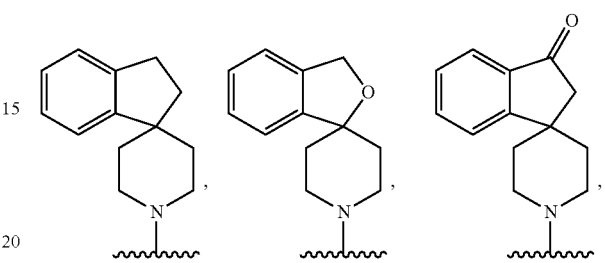

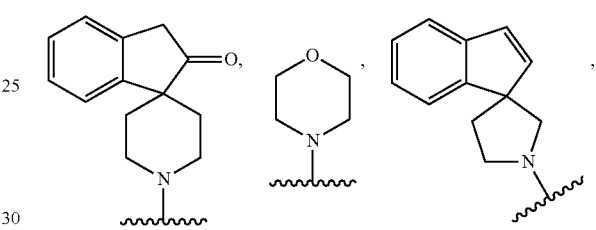

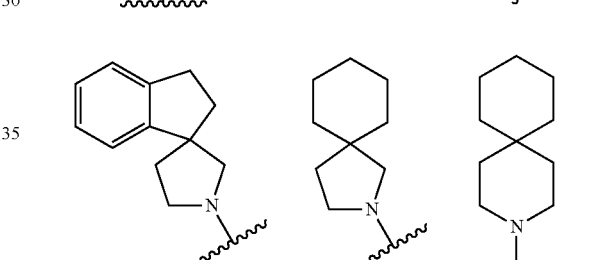

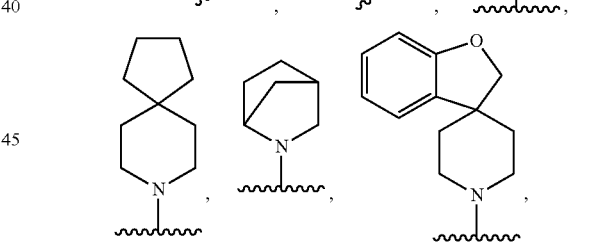

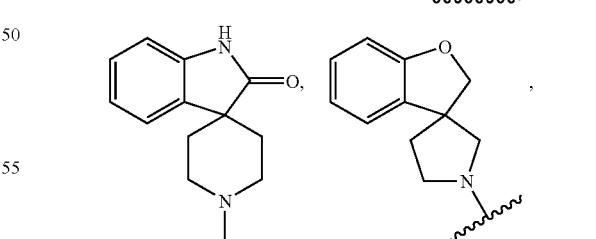

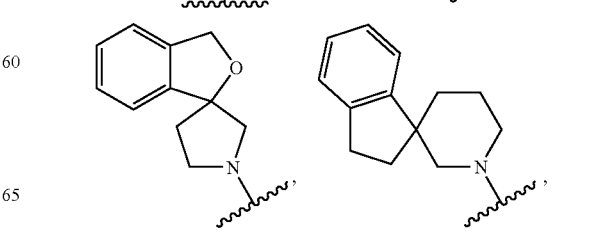

-continued

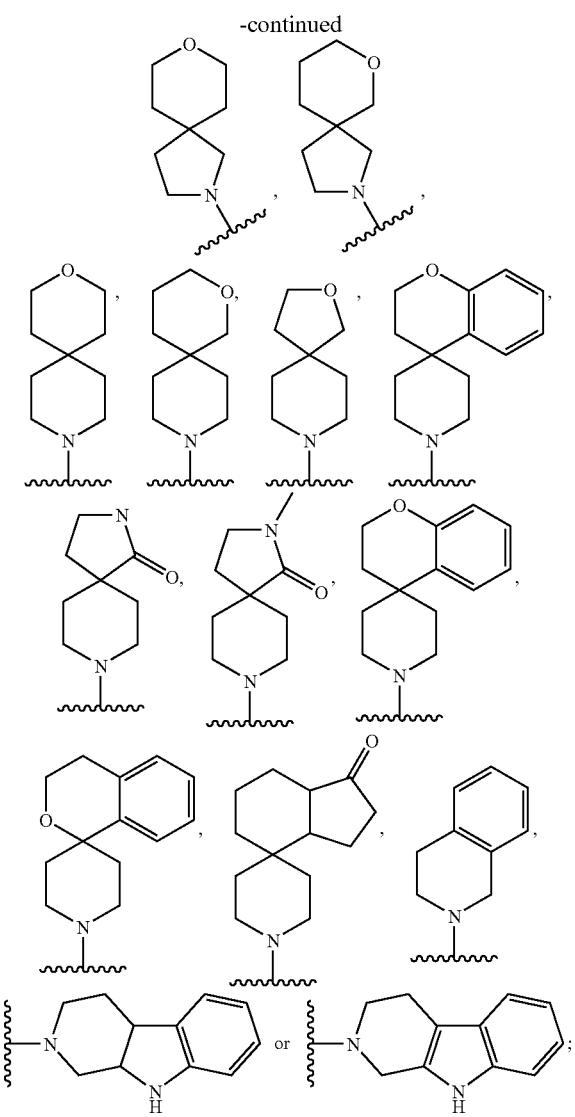

optionally substituted with one or more substituents selected from the group consisting of (C₁-C₅)alkyl, —O(C₁-C₃)alkyl, CN, Cl, F, CF₃ and OH;

Y is a bond or C(O) or is selected from the optionally substituted group consisting of (C₁-C₆)alkyl, (C₁-C₄)alkyl-heterocyclyl, (C₁-C₄)alkyl-heteroaryl, heterocyclyl, heteroaryl, aryl, (C₁-C₄)alkyl-C(O), (C₁-C₄)alkyl-C(O)N(R²) and (C₁-C₄)alkyl-N(R²)C(O);

wherein when Y is (C₁-C₄)alkyl-heterocyclyl, (C₁-C₄)alkyl-C(O)N(R²) or (C₁-C₄)alkyl-N(R²)C(O) it is the alkyl portion of the moiety that is attached to the nitrogen;

Z is H or Z is selected from the optionally substituted group consisting of —(C₁-C₅)alkyl, —(C₁-C₃)alkyl-aryl, —(C₁-C₃)alkyl-heteroaryl, —(C₁-C₃)alkyl-diphenyl, —(C₃-C₆)cycloalkyl, heterocyclyl, —(C₁-C₄)alkyl-heterocyclyl, —O—(C₁-C₅)alkyl, aryl and heteroaryl;

D is O, N, S(O)ᵧ, C(O) or C(R⁵)₂;
E is O, N, S(O)ᵧ, C(O) or C(R⁵)₂;
W is C(R⁴) or N;
M is a bond, O or C(O); or
M is selected from the optionally substituted group consisting of —(C₁-C₄)alkyl, —C(O)N(R²), —N(R²)C(O), —N(R²), -aryl, -heterocyclyl and -heteroaryl; or M is selected from the optionally substituted group consisting of —(C₁-C₄)alkyl-heterocyclyl, —(C₁-C₄)alkyl-C(O), —(C₁-C₄)alkyl-C(O)N(R²), —(C₁-C₄)alkyl-C(O)O, —(C₁-C₄)alkyl-N(R²)C(O)O, (C₁-C₄))alkyl-N(R²)C(O) and —CH₂—NH—C(O) wherein the alkyl portion of the moiety is connected to W;

T is H or NH₂ or T is selected from the optionally substituted group consisting of (C₁-C₅)alkyl, (C₁-C₅)alkoxy, —(C₁-C₃)alkyl-aryl, —(C₁-C₃)alkyl-heteroaryl, —(C₁-C₃)alkyl-diphenyl, heterocyclyl, —(C₁-C₄)alkyl-heterocyclyl, aryl and heteroaryl;

A is selected from the group consisting of a bond, O and optionally substituted (C₁-C₅)alkyl;

G is selected from the group consisting of a bond, N(R²), C(O), —C(O)—N(R²)—(C₁-C₄)alkyl, —(C₁-C₄)alkyl-N(R²)—C(O), —(C₁-C₄)alkyl-N(R²), N(R²)—(C₁-C₄)alkyl, N(R²)—CH(R²)—C(O), C(O)—CH(R⁴)—N(R²), optionally substituted —(C₁-C₄)alkyl, (C₂)alkenyl, —(C₁-C₄)alkyl-N(R²)S(O)), —S(O)ₓN(R²)—(C₁-C₄)alkyl, —N(R²)S(O)ₓ—, —S(O), N(R²), —N(R²)CON(R²), —N(R²)C(O), C(O)N(R²), —NH-optionally substituted heteroaryl, optionally substituted heteroaryl and optionally substituted phenyl;

Q is H or is selected from the optionally substituted group consisting of (C₁-C₅)alkyl, (C₃-C₇)cycloalkyl, —O—(C₁-C₄)alkyl, —O—(C₃-C₇)cycloalkyl and —(C₁-C₃)alkyl-O—(C₁-C₃)alkyl;

R¹ is selected from the optionally substituted group consisting of amino, aryl, adamantanyl, diphenyl(C₁-C₂)alkyl, heteroaryl, heterocyclyl, (C₁-C₆)alkyl, —O—(C₁-C₄)alkyl, —O—CH₂-phenyl, and (C₃-C₆)cycloalkyl;

R² is independently selected from the optionally substituted group consisting of H, (C₁-C₄)alkyl and (C₃-C₅)cycloalkyl;

R³ is independently H, OH, CN, F, CF₃, C(O)N(R²)₂, N(R²)₂, and oxo or R³ is independently selected from the optionally substituted group consisting of (C₁-C₃)alkyl, (C₃-C₇)cycloalkyl, —O—(C₁-C₃)alkyl, (C₁-C₃)alkyl-O—(C₁-C₃)alkyl, —(C₁-C₃)alkyl-C(O)—O—(C₁-C₃)alkyl, aryl, —O-aryl, heteroaryl, heterocyclyl, —(C₁-C₃)alkyl-aryl, —N(R²)aryl, —O-aryl, —C(O)—O—(C₁-C₃)alkyl, —NH-phenyl and phenyl;

R⁵ is H or OH or R⁵ is independently selected from the optionally substituted group consisting of (C₁-C₄)alkyl, (C₃-C₅)cycloalkyl, —O—(C₁-C₄)alkyl and —O—(C₃-C₇)cycloalkyl;

R⁴ is H, OH, CN or F or R⁴ is selected from the optionally substituted group consisting of —O—(C₁-C₃)alkyl, —O—(C₃-C₇)cycloalkyl, aryl and heteroaryl;

m and n are independently 0, 1, or 2; and
p is 1 or 2;
x is 1 or 2;
y is 0, 1 or 2;
provided that D and E are not O or N at the same time; and
provided that when W is N, D is not N or O and E is not N or O.
and a pharmaceutically acceptable carrier or excipient.

DETAILED DESCRIPTION OF THE INVENTION

In a related aspect the invention provides a method for antagonizing CCR2 in a human subject suffering from a disorder in which CCR2 activity is detrimental, comprising administering to the human subject a compound of Formula (I) such that CCR2 activity in the human subject is inhibited and treatment is achieved.

Many autoimmune diseases and disease associated with chronic inflammation, as well as acute responses, have been linked to activation of CCR2. The present compounds are useful in the treatment of inflammatory disorders including, but not limited to rheumatoid arthritis, osteoarthritis, asthma, chronic obstructive pulmonary disease (COPD), sepsis, psoriasis, psoriatic arthritis, inflammatory bowel disease, Crohn's disease, lupus, multiple sclerosis, juvenile chronic arthritis, Lyme arthritis, reactive arthritis, septic arthritis, spondyloarthropathy and systemic lupus erythematosus.

The compounds of the invention are also useful in the treatment of cardiovascular disorders, such as acute myocardial infarction, acute coronary syndrome, chronic heart failure, coronary artery disease, atherosclerosis, viral myocarditis, cardiac allograft rejection, and sepsis-associated cardiac dysfunction. Furthermore, the compounds of the present invention are also useful for the treatment of central nervous system disorders such as meningococcal meningitis, Alzheimer's disease and Parkinson's disease.

The compounds of the invention are also useful in the treatment of an ocular condition, a cancer, a solid tumor, a sarcoma, fibrosarcoma, osteoma, melanoma, retinoblastoma, a rhabdomyosarcoma, glioblastoma, neuroblastoma, teratocarcinoma, an cancers such as lung, breast, stomach, bladder, colon, pancreas, ovarian, prostate and rectal cancer and hematopoietic malignancies (leukemia and lymphoma), Kaposi's sarcoma, Hodgkin's disease, lymphoma, myeloma, leukaemia, malignant ascites, hematopoietic cancers Crow-Fukase (POEMS) syndrome, a diabetic condition such as insulin-dependent diabetes mellitus glaucoma, diabetic retinopathy or microangiopathy, sickle cell anaemia, chronic inflammation, synovitis, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, vascular occlusion, carotid obstructive disease, ulcerative colitis, inflammatory bowel disease, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, sporadic, polyglandular deficiency type I and polyglandular deficiency type II, Schmidt's syndrome, adult (acute) respiratory distress syndrome, alopecia, alopecia greata, seronegative arthropathy, arthropathy, Reiter's disease, psoriatic arthropathy, ulcerative colitic arthropathy, enteropathic synovitis, chlamydia, yersinia and salmonella associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, insulin resistance, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), neuropathic pain, metabolic syndrome, Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer Helicobacter related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, or age-related macular degeneration. In addition, these compounds can be used as active agents against hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Compounds of formula (I) of the invention can be used alone or in combination with another therapeutic agent to treat such diseases, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

For example, in the treatment or prevention of inflammation, the present compounds may be used in conjunction or combination with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextromethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists, (b) steroids such as beclomethasone, methylprednisolone, betamethasone, prednisone, dexamethasone, and hydrocortisone; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as beta.2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib (Celebrex®) and rofecoxib (Vioxx®); (h) inhibitors of phosphodiesterase type IV (PDE-IV); (i) gold compounds such as auranofin and aurothioglucose, (j) inhibitors of phosphodiesterase type IV (PDE-IV); (k) other antagonists of the chemokine receptors, especially CCR1, CCR2, CCR3, CCR5, CCR6, CCR8 and CCR10; (l) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (m) anti-diabetic agents such as insulin, sulfonylureas, biguanides (metformin), α-glucosidase inhibitors (acarbose) and glitazones (troglitazone and pioglitazone); (n) preparations of interferon beta (interferon β-1α; interferon β-1b); (o) etanercept (Enbrel®), (p) antibody therapies such as orthoclone (OKT3), daclizumab (Zenapax®), infliximab (Remicade®), basiliximab (Simulect®) and anti-CD40 ligand antibodies (e.g., MRP-1); and (q) other compounds such as 5-aminosalicylic acid and prodrugs thereof, hydroxychloroquine, D-penicillamine, antimetabolites such as azathioprene and 6-mercaptopurine, and cytotoxic cancer chemotherapeutic agents. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Immunosuppressants within the scope of the present invention further include, but are not limited to, leflunomide, RAD001, ERL080, FTY720, CTLA4, antibody therapies such as orthoclone (OKT3), daclizumab (Zenapax®) and basiliximab (Simulect®), and antithymocyte globulins such as thymoglobulins.

In particularly preferred embodiments, the present methods are directed to the treatment or prevention of multiple sclerosis using a compound of the invention either alone or in combination with a second therapeutic agent selected from betaseron, avonex, azathioprene (Imurek®, Imuran®), capoxone, prednisolone and cyclophosphamide. When used in combination, the practitioner can administer a combination of the therapeutic agents, or administration can be sequential.

In still other particularly preferred embodiments, the present methods are directed to the treatment or prevention of rheumatoid arthritis, wherein the compound of the invention is administered either alone or in combination with a second therapeutic agent selected from the group consisting of methotrexate, sulfasalazine, hydroxychloroquine, cyclosporine A, D-penicillamine, infliximab (Remicade®), etanercept (Enbrel®), adalimumab (Humira®), auranofin and aurothioglucose.

In yet other particularly preferred embodiments, the present methods are directed to the treatment or prevention of an organ transplant condition wherein the compound of the invention is used alone or in combination with a second therapeutic agent selected from the group consisting of cyclosporine A, FK-506, rapamycin, mycophenolate, prednisolone, azathioprene, cyclophosphamide and an antilymphocyte globulin.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the CCR2 antagonists of this invention. Non-limiting examples of therapeutic agents for rheumatoid arthritis with which a compound of formula (I) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. S/T kinase inhibitors of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (HUMIRA™), (PCT Publication No. WO 97/29131), CA2 (REMICADE™), CDP 571, and soluble p55 or p75 TNF receptors, derivatives, thereof, (p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and L-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of formula (I) of the invention may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sL-1RI, sL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-L-12, Anti-IL15, BIRB-796, SCIO-469, VX-702, AMG-548, VX-740, Roflumilast, IC-485, CDC-801, and Mesopram. Preferred combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of formula (I) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors;

mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. IRAK, NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of formula (I) can be combined include the following: TNF antagonists, for example, anti-TNF antibodies, D2E7 (HUMIRA™), (U.S. Pat. No. 6,090,382) CA2 (REMICADE™), CDP 571, TNFR-Ig constructs, (p75TNFRIgG (ENBREL™) and p55TNFRIgG (LENERCEPT™)) inhibitors and PDE4 inhibitors. A compound of formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors 6-mercaptopurines; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen Idec); anti-α4 antibody (Tysabri®; Biogen Idec); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; clabribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of formula (I) may also be combined with agents such as methotrexate, cyclosporine, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

Preferred examples of therapeutic agents for multiple sclerosis in which a compound of formula (I) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of formula (I) may also be combined with agents, such as alemtuzumab, dronabinol, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for angina with which a compound of formula (I) of the invention can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil HCl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril and bisoprolol fumarate.

Non-limiting examples of therapeutic agents for ankylosing spondylitis with which a compound of formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, etanercept, and infliximab.

Non-limiting examples of therapeutic agents for asthma with which a compound of formula (I) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone and metaproterenol sulfate.

Non-limiting examples of therapeutic agents for COPD with which a compound of formula (I) can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for HCV with which a compound of formula (I) can be combined include the following: Interferon-alpha-2a, Interferon-alpha-2b, Interferon-alpha con1, Interferon-alpha-n1, pegylated interferon-alpha-2a, pegylated interferon-alpha-2b, ribavirin, peginterferon alfa-2b+ribavirin, ursodeoxycholic acid, glycyrrhizic acid, thymalfasin, Maxamine, VX497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of formula (I) can be combined include the following: prednisone, azathioprine, albuterol, colchicine, albuterol sulfate, digoxin, gamma interferon, methylprednisolone sod succ, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for myocardial infarction with which a compound of formula (I) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril HCl/mag carb, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, and sulfasalazine.

Non-limiting examples of therapeutic agents for psoriatic arthritis with which a compound of formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept and efalizumab.

Non-limiting examples of therapeutic agents for restenosis with which a compound of formula (I) can be combined include the following: sirolimus, paclitaxel, everolimus, tacrolimus, ABT-578, and acetaminophen.

Non-limiting examples of therapeutic agents for sciatica with which a compound of formula (I) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol hcl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene napsylate/apap, asa/oxycod/oxycodone ter, ibuprofen/hydrocodone bit, tramadol HCl, etodolac, propoxyphene HCl, amitriptyline HCl, carisoprodoucodeine phos/asa, morphine sulfate, multivitamins, naproxen sodium, orphenadrine citrate, and temazepam.

Preferred examples of therapeutic agents for SLE (Lupus) with which a compound of formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (HUMIRA™), (U.S. Pat. No. 6,090,382) CA2 (REMICADE™), CDP 571, TNFR-Ig constructs, (p75TNFRIgG (ENBREL™) and p55TNFRIgG (LENERCEPT™)).

In this invention, the following definitions are applicable:

A "therapeutically effective amount" is an amount of a compound of Formula I or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Physiologically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphonic acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of formula I which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of formula I and their salts may exist in more than one crystal form and the present invention includes each crystal form and mixtures thereof.

Certain compounds of formula I and their salts may also exist in the form of solvates, for example hydrates, and the present invention includes each solvate and mixtures thereof.

Certain compounds of formula I may contain one or more chiral centers, and exist in different optically active forms. When compounds of formula I contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of formula I contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of formula I and mixtures thereof.

Certain compounds of formula I may exist in different tautomeric forms or as different geometric isomers, and the present invention includes each tautomer and/or geometric isomer of compounds of formula I and mixtures thereof.

Certain compounds of formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of formula I and mixtures thereof.

Certain compounds of formula I may exist in zwitterionic form and the present invention includes each zwitterionic form of compounds of formula I and mixtures thereof.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —($CH_2$)C(O)H or a moiety that contains a carboxylic acid) wherein the free hydrogen is replaced by ($C_1$-$C_4$)alkyl, ($C_2$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino($C_2$-$C_3$)alkyl.

Other exemplary pro-drugs release an alcohol of Formula I wherein the free hydrogen of the hydroxyl substituent (e.g., $R^1$ contains hydroxyl) is replaced by ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylamino-methyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, P(O)(OH)$_2$, —P(O)(O($C_1$-$C_6$)alkyl)$_2$ or glycosyl (the radical resulting from detachment of the hydroxyl of the hemiacetal of a carbohydrate).

The term "heterocyclic" or "heterocyclyl", as used herein, include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo[b]thienyl, benzimidazolyl, benzofuranyl, benzoxazolyl, benzothiazolyl, benzothiadiazolyl, benzoxadiazolyl, furanyl, imidazolyl, imidazopyridyl, indolyl, indolinyl, indazolyls, isoindolinyl, isoxazolyl, isothiazolyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl or tropanyl.

When the term "substituted heterocyclic" (or heterocyclyl) or "substituted heteroaryl" is used, what is meant is that the heterocyclic group is substituted with one or more substituents that can be made by one of ordinary skill in the art and results in a molecule that is a CCR2 antagonist. For purposes of exemplification, which should not be construed as limiting the scope of this invention, preferred substituents for the heterocycle of this invention are each independently selected from the optionally substituted group consisting of alkenyl, alkoxy, alkoxyalkoxy, alkoxyalkyl, alkoxycarbonyl, alkoxycarbonylheterocycloalkoxy, alkyl, alkylcarbonyl, alkylester, alkyl-O—C(O)—, alkyl-heterocyclyl, alkyl-cycloalkyl, alkyl-nitrile, alkynyl, amido groups, amino, aminoalkyl, aminocarbonyl, carbonitrile, carbonylalkoxy, carboxamido, $CF_3$, CN, —C(O)OH, —C(O)H, —C(O)—C($CH_3$)$_3$, —OH, —C(O)O-alkyl, —C(O)O-cycloalkyl, —C(O)O-heterocyclyl, —C(O)-alkyl, —C(O)-cycloalkyl, —C(O)-heterocyclyl, cycloalkyl, dialkylaminoalkoxy, dialkylaminocarbonylalkoxy, dialkylaminocarbonyl, halogen, heterocyclyl, a heterocycloalkyl group, heterocyclyloxy, hydroxy, hydroxyalkyl, nitro, $OCF_3$, oxo, phenyl, —$SO_2CH_3$, —$SO_2CR_3$, tetrazolyl, thienylalkoxy, trifluoromethylcarbonylamino, trifluoromethylsulfonamido, heterocyclylalkoxy, heterocyclyl-S(O)$_p$, cycloalkyl-S(O)$_p$, alkyl-S—, heterocyclyl-S, heterocycloalkyl, cycloalkylalkyl, heterocyclothio, cycloalkylthio, —$Z^{105}$—C(O)N(R)$_2$, —$Z^{105}$—N(R)—C(O)—$Z^{200}$, —$Z^{105}$—N(R)—S(O)$_{200}$, —$Z^{105}$—N(R)—C(O)—N(R)—$Z^{200}$, —N(R)—C(O)R, —N(R)—C(O)OR, OR—C(O)-heterocyclyl-OR, $R_c$ and —$CH_2OR_c$;

wherein $R_3$ is $C_1$-$C_4$ alkyl, $C_3$-$C_6$ cycloalkyl or phenyl;

wherein p is 0, 1 or 2;

where $R_c$ for each occurrence is independently hydrogen, optionally substituted alkyl, optionally substituted aryl, —($C_1$-$C_6$)—$NR_dR_e$, -E-($CH_2$)$_t$—$NR_dR_e$, -E-($CH_2$)$_t$—O-alkyl, -E-($CH_2$), —S-alkyl, or -E-($CH_2$)$_t$—OH;

wherein t is an integer from about 1 to about 6;

$Z^{105}$ for each occurrence is independently a covalent bond, alkyl, alkenyl or alkynyl; and $Z^{200}$ for each occurrence is independently selected from an optionally substituted group selected from the group consisting of alkyl, alkenyl, alkynyl, phenyl, alkyl-phenyl, alkenyl-phenyl or alkynyl-phenyl;

E is a direct bond, O, S, S(O), S(O)$_2$, or $NR_f$, wherein $R_f$ is H or alkyl and $R_d$ and $R_e$ are independently H, alkyl, alkanoyl or $SO_2$-alkyl; or $R_d$, $R_e$ and the nitrogen atom to which they are attached together to form a five- or six-membered heterocyclic ring.

An "heterocycloalkyl" group, as used herein, is a heterocyclic group that is linked to a compound by an aliphatic group having from one to about eight carbon atoms. For example, a preferred heterocycloalkyl group is a morpholinomethyl group.

As used herein, "aliphatic" or "an aliphatic group" or notations such as "($C_0$-$C_8$)" include straight chained or branched hydrocarbons which are completely saturated or which contain one or more units of unsaturation, and, thus, includes alkyl, alkenyl, alkynyl and hydrocarbons comprising a mixture of single, double and triple bonds. When the group is a $C_0$ it means that the moiety is not present or in other words, it is a bond. As used herein, "alkyl" means $C_1$-$C_8$ and includes straight chained or branched hydrocarbons, which are completely saturated. Preferred alkyls are methyl, ethyl, propyl, butyl, pentyl, hexyl and isomers thereof. As used herein, "alkenyl" and "alkynyl" means $C_2$-$C_8$ and includes straight chained or branched hydrocarbons which contain one or more units of unsaturation, one or more double bonds for alkenyl and one or more triple bonds for alkynyl.

As used herein, aromatic groups (or aryl groups) include aromatic carbocyclic ring systems (e.g. phenyl and cyclopentyldienyl) and fused polycyclic aromatic ring systems (e.g. naphthyl, biphenylenyl and 1,2,3,4-tetrahydronaphthyl).

As used herein, cycloalkyl means $C_3$-$C_{12}$ monocyclic or multicyclic (e.g., bicyclic, tricyclic, etc.) hydrocarbons that is completely saturated or has one or more unsaturated bonds but does not amount to an aromatic group. Preferred examples of a cycloalkyl group are cyclopropyl, cyclobutyl, cyclopentyl, cyclopentenyl, cyclohexyl and cyclohexenyl.

As used herein, amido group means —NHC(=O)—.

As used herein, acyloxy groups are —OC(O)R.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: alkenyl groups, alkoxy group (which itself can be substituted, such as —O—$C_1$-$C_6$-alkyl-OR, —O—$C_1$-$C_6$-alkyl-N(R)$_2$, and $OCF_3$), alkoxyalkoxy, alkoxycarbonyl, alkoxycarbonylpiperidinyl-alkoxy, alkyl groups (which itself can also be substituted, such as —$C_1$-$C_6$-alkyl-OR, —$C_1$-$C_6$-alkyl-N(R)$_2$, and —$CF_3$), alkylamino, alkylcarbonyl, alkylester, alkylnitrile, alkylsulfonyl, amino, aminoalkoxy, $CF_3$, COH, COOH, CN, cycloalkyl, dialkylamino, dialkylaminoalkoxy, dialkylaminocarbonyl, dialkylaminocarbonylalkoxy, dialkylaminosulfonyl, esters (—C(O)—OR, where R is groups such as alkyl, heterocycloalkyl (which can be substituted), heterocyclyl, etc., which can be substituted), halogen or halo group (F, Cl, Br, I), hydroxy, morpholinoalkoxy, morpholinoalkyl, nitro, oxo, $OCF_3$, optionally substituted phenyl, $S(O)_2CH_3$, $S(O)_2CF_3$, and sulfonyl, N-alkylamino or N,N-dialkylamino (in which the alkyl groups can also be substituted).

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given CCR2 activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit CCR2 signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1). In the treatment of crises, the administration of an acute bolus or an infusion approaching the MTD may be required to obtain a rapid response.

Dosage amount and interval may be adjusted individually to provide plasma levels of the active moiety which are sufficient to maintain the CCR2 modulating effects, or minimal effective concentration (MEC). The MEC will vary for each compound but can be estimated from in vitro data; e.g. the concentration necessary to achieve 50-90% inhibition of CCR2 using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

| Parts by weight | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoletins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deletrious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of formula I as a medicament.

A further aspect of the present invention provides the use of a compound of formula I or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of formula I to a mammal, particularly a human being, in need thereof.

Enzyme Assays

Assays for Screening Compounds of Formula (I)

The in vitro potency of compounds in antagonizing CCR2 discussed herein or described in the art may be determined by the procedures detailed below.

Inhibition of MCP-1 Binding to hCCR2 or mCCR2

Radioligand binding assays were performed in CHO cells expressing either human CCR2B and the $G\alpha_{16}$ coupling protein or murine CCR2 and the $G\alpha_{16}$ coupling protein. All compounds were dissolved in DMSO and assays run at a final DMSO concentration of 1% (v/v). [$^{125}$I]-labeled human and murine MCP-1 was purchased from PerkinElmer. Unlabled human and murine MCP-1 were purchased from Peprotech. Assays with cells expressing human CCR2B were performed with human MCP-1, while assays with cells expressing murine CCR2 were performed with murine MCP-1.

Compounds are serially diluted in DMSO before diluting into assay buffer (25 mM HEPES, pH 7.4, 5 mM $MgCl_2$, 1 mM $CaCl_2$, 0.5% BSA) with cryo preserved CHO cells expressing either human CCR2B and the $G\alpha_{16}$ coupling protein or murine CCR2 and the $G\alpha_{16}$ coupling protein ($50\times10^3$/well) and [$^{125}$I]-MCP-1 (50 μM for human CCR2, 100 μM for murine CCR2). The reaction was incubated at room temperature for 90 minutes before transferring to GF/C filter plates (PerkinElmer) pre-treated with 0.3% polyethyleneimine for 2 hours at 4° C. The filter plates are washed six times with ice cold wash buffer (25 mM HEPES, pH 7.4, 5 mM $MgCl_2$, 1 mM $CaCl_2$, 500 mM NaCl) and dried before adding 50 ul/well Microscint to each well. Plates are counted on Packard Topcount scintillation counter where background binding is determined 100 nM MCP-1 and control total binding determined by addition of DMSO in place of the test compound. The radioactivity values (cpm) were used to calculate the percent inhibition at a given compound concentration and the data fit to a sigmoidal curve in a semi-log plot to determine $IC_{50}$ values.

Inhibition of MCP-1-Induced Intracellular Calcium Release in Cells Expressing hCCR2 or mCCR2

Calcium flux assays were performed in CHO cells expressing either human CCR2B and the $G\alpha_{16}$ coupling protein or murine CCR2 and the $G\alpha_{16}$ coupling protein. All compounds were dissolved in DMSO and assays run at a final DMSO concentration of 1% (v/v). Human and murine MCP-1 were purchased from Peprotech and used at a final assay concentration of 10 nM. Assays with cells expressing human CCR2B were performed with human MCP-1, while assays with cells expressing murine CCR2 were performed with murine MCP-1.

Briefly, cells were cultured overnight in a microtiter plate at 40,000 per well. The next day, the resultant adherent cells were incubated in assay buffer (20 mM HEPES pH 7.4, 0.1% bovine serum albumin, and 2.5 mM Probenocid in Hank's Buffered Saline Solution) containing 5 μg/ml μM Fluo-4 dye (Molecular Probes) at room temperature for 60 min. The dye-containing assay buffer was removed and replace by assay buffer without dye. Calcium flux assays were performed on a FLIPR Tetra instrument (Molecular Devices) by adding compound to the cells followed by addition of MCP-1 and measuring the change in fluorescence as a function of time. Maximal and minimal values for fluorescence were determined using 100 nM MCP-1 and buffer addition, respectively. Fluorescence values were used to calculate the percent inhibition at a given compound concentration and the data fit to a sigmoidal curve in a semi-log plot to determine $IC_{50}$ values.

Compounds of the invention may be prepared using the synthetic scheme illustrated in Scheme A. Starting materials are commercially available or may be prepared by the procedures described herein or by procedures that would be well known to one skilled in the art of organic chemistry. The variables used in the Scheme are as defined herein or as in the claims. General procedures are noted in parentheses.

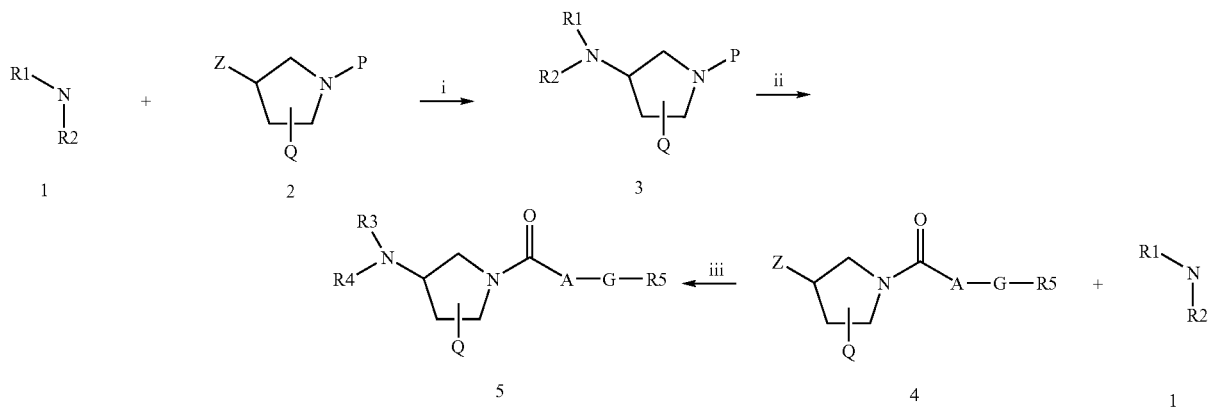

Scheme A

A method for preparing aminopyrrolidine compounds of the invention is illustrated in Scheme A. In Scheme 1, step i, a suitably substituted amine 1 is reacted with an optionally substituted N-protected pyrrolidinone or N-protected methanesulfonic acid pyrrolidinyl ester 2 by reductive amination or mesylate displacement. The reductive amination reaction is typically conducted in an organic solvent (such as 1,2-dichloroethane) at room temperature with sodium triacetoxyborohydride and acetic acid. The mesylate displacement reaction is typically conducted in an organic solvent (such as acetonitrile or DMF) at or below reflux (such as 80° C.) with sodium iodide and potassium carbonate. The product 3 is typically isolated from the reaction mixture by flash silica gel chromatography. Deprotection of compound 3 to yield an unprotected amine can be performed using conditions such as those described in Greene, T. W. and Wuts, P. G. M. *Protective Groups in Organic Synthesis,* 3rd Edition, 1999, Wiley-Interscience, New York. For example, a protecting group such as a t-butoxycarbonyl group can be removed from a protected amine to yield the unprotected amine. The deprotected compound is then reacted with an acyl chloride, carboxylic acid, imidazolium urea, or benzotriazolyl ethanedione to produce 5 as shown in step ii. For the reaction with an acyl chloride, the reaction is generally conducted in an organic solvent (such as dichloromethane) with a base (such as triethylamine) at room temperature. For the reaction with a carboxylic acid, the reaction is typically carried out in an organic solvent (such as dichloromethane) with EDC and triethylamine. For the reaction with an imidazolium urea, the reaction is generally conducted in an organic solvent (such as acetonitrile) with a base (such as triethylamine) at room temperature. For the reaction with a benzotriazolyl ethanedione, the reaction is typically accomplished in an organic solvent (such as THF) with a base (such as sodium hydride) at room temperature. The products 5 can then be isolated and purified using standard techniques (such as crystallization, flash column chromatography, or reverse-phase liquid chromatography). Compounds 5 can also be synthesized by the reaction of a suitably substituted amine with an optionally N-acylated pyrrolidine by reductive amination or mesylate displacement, step iii, utilizing chemistry similar to that described above.

ABBREVIATIONS

Boc tert-Butoxycarbonyl
n-BuLi n-Butyllithium
CDI 1,1'-Carbonyldiimidazole
DCC 1,3-Dicyclohexylcarbodiimide
DCE Dichloroethane
DCM Dichloromethane
DIEA N,N-Diisopropylethylamine
DMF N,N-Dimethylformamide
DMA N,N-Dimethylacetamide
DME 1,2-Dimethoxyethane
DMSO Dimethyl sulfoxide
EDC 1-(3-Dimethylaminopropyl)-3-ethylcarbodiimide
$Et_3N$ Triethylamine
$Et_2O$ Diethyl ether
EtOAc Ethyl acetate
EtOH Ethanol
HCl Hydrochloric acid
HOAc Acetic acid
HOBT 1-Hydroxybenzotriazole
HPLC High Pressure Liquid Chromatography
m-CPBA 3-Chloroperoxybenzoic acid
MeCN Acetonitrile
MeOH Methanol
$MgSO_4$ Magnesium sulfate
MP-carbonate Polymer bound tetraalkylammonium carbonate
i-PrOH 2-Propanol
n-PrOH 1-Propanol
Pd/C Palladium on carbon
PS-carbodiimide N-Cyclohexylcarbodiimide-N'-propyloxymethyl polystyrene
RP Reverse Phase
$R_t$ Retention time
TFA Trifluoroacetic acid
THF Tetrahydrofuran
XANTPHOS 9,9-Dimethyl-4,5-bis(diphenylphosphino)xanthene Synthetic Details Analytical data are included either in the illustrations of the general procedures or in the tables of examples. Unless otherwise stated, all $^1H$ or $^{13}C$ NMR data were collected on a Varian Mercury Plus 400 MHz instrument; chemical shifts are quoted in parts per million (ppm). High pressure liquid chromatography (HPLC) analytical data are either detailed within the experimental or referenced to the table of HPLC conditions, using the lower case method letter, in Table 1.

TABLE 1

List of HPLC methods

| Method | HPLC Conditions<br>Unless indicated otherwise mobile phase A was 10 mM ammonium acetate, mobile phase B was HPLC grade acetonitrile. |
|---|---|
| a | 5-95% B over 3.7 min with a hold at 95% B for 1 min (1.3 mL/min flow rate). 4.6 × 50 mm Waters Atlantis dC18 column (5 μm particles). Detection methods are diode array (DAD) and evaporative light scattering (ELSD) detection as well as pos/neg electrospray ionization. |
| b | 5-60% B over 1.5 min then 60-95% B to 2.5 min with a hold at 95% B for 1.2 min (1.3 mL/min flow rate). 4.6 × 30 mm Vydac Genesis C8 column (4 μm particles). Detection methods are diode array (DAD) and evaporative light scattering (ELSD) detection as well as pos/neg electrospray ionization. |
| c | 5-60% B over 1.5 min then 60-95% B over 2.5 min with a hold at 95% B for 1.2 min (1.3 mL/min flow rate). 4.6 × 50 mm Zorbax XDB C8 column (5 μm particles). Detection methods are diode array (DAD) and evaporative light scattering (ELSD) detection as well as pos/neg electrospray ionization. |
| d | 30-95% B over 2.0 min with a hold at 95% B for 5.7 min (1.3 mL/min flow rate). 4.6 × 30 mm Vydac Genesis C8 column (4 μm particles). Detection methods are diode array (DAD) and evaporative light scattering (ELSD) detection as well as pos/neg electrospray ionization. |
| e | 5-95% B in 3.7 min with a hold at 95% B for 1 min (1.3 mL/min flow rate). 4.6 × 50 mm Waters Atlantis dC18 column (5 μm particles). Detection methods are diode array (DAD) and evaporative light scattering (ELSD) detection as well as pos/neg atmospheric pressure chemical ionization (APCI) |
| f | 5-60% B in 1.5 min then 60-95% B to 2.5 min with a hold at 95% B for 1.2 min (1.3 mL/min flow rate). 4.6 × 30 mm Vydac Genesis C8 column (4 μm particles). Detection methods are diode array (DAD) and evaporative light scattering (ELSD) detection as well as pos/neg atmospheric pressure chemical ionization (APCI). |

GENERAL PROCEDURES AND EXAMPLES

The general synthetic schemes that were utilized to construct the majority of compounds disclosed in this application are described below in Schemes 1-12.

Scheme 1. General synthetic route to pyrrolidine ureas (General procedure A, B, C or D)

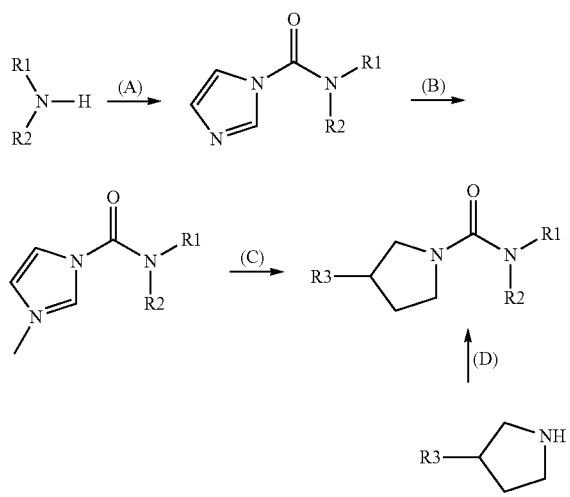

Scheme 2. General synthetic route to acylpyrrolidines (General procedure E, F, G)

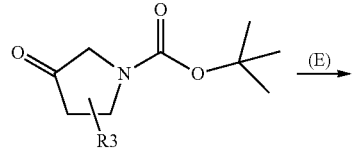

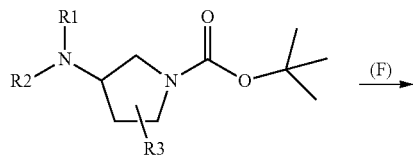

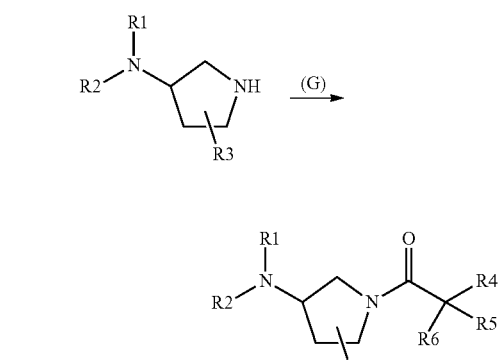

Scheme 3. General synthetic route to acylpyrrolidines (General procedure Q, L, G)

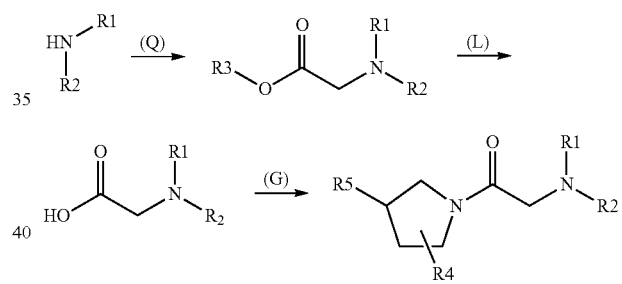

Scheme 4. General synthetic route to amino acylpyrrolidines (General procedure H, I, J, E)

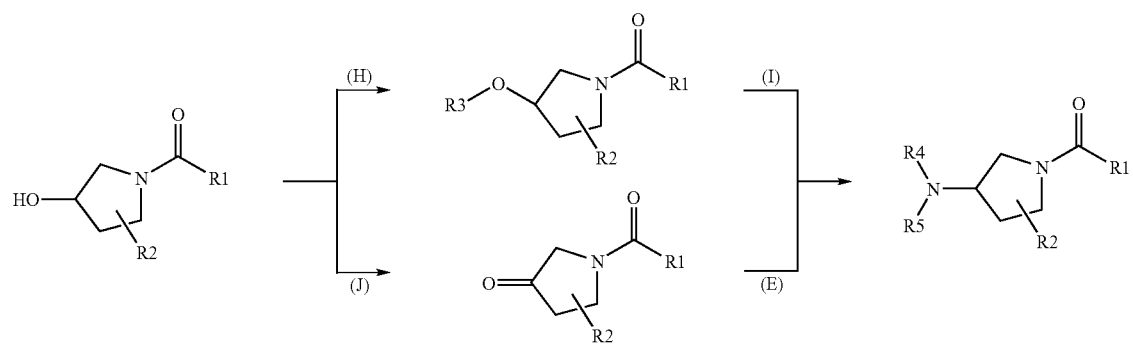

Scheme 5. General synthetic route to acylpyrrolidines (General procedure T, Q)

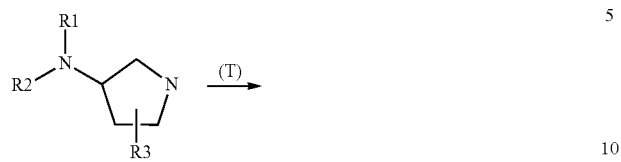

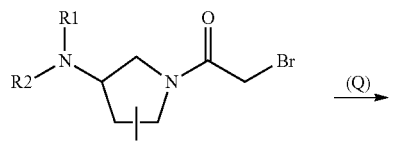

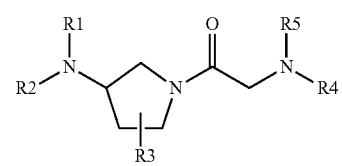

Scheme 6. General synthetic route to pyrrolidine amides (General procedure F, G, K, M)

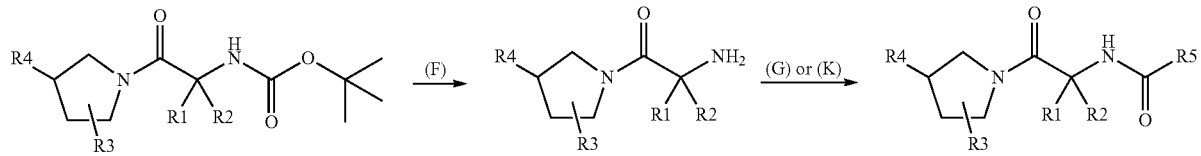

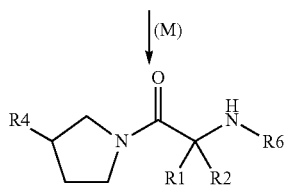

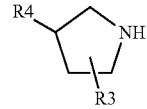

Scheme 7. General synthetic route to aryl piperidine pyrrolidines (General procedure O, P, E, I)

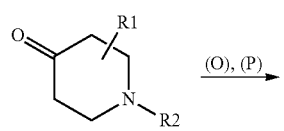

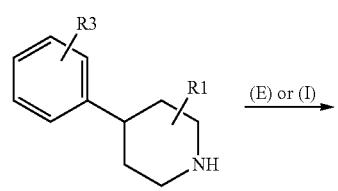

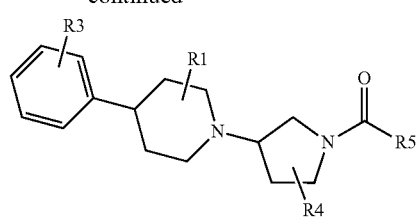

Scheme 8. General synthetic route to hydroxyaryl piperidine pyrrolidines (General procedure N)

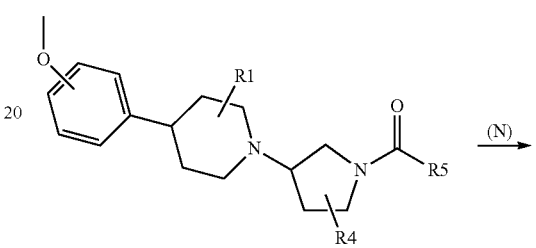

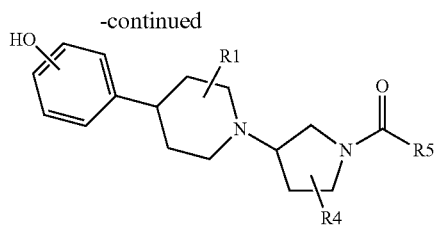

Scheme 9. General synthetic route to pyrrolidine oxamide (General procedure R, S)

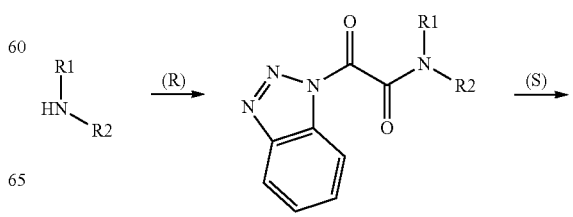

49
-continued
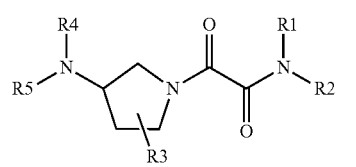
Scheme 10. General synthetic route to amino acylpyrrolidines (General procedure G, F, E)
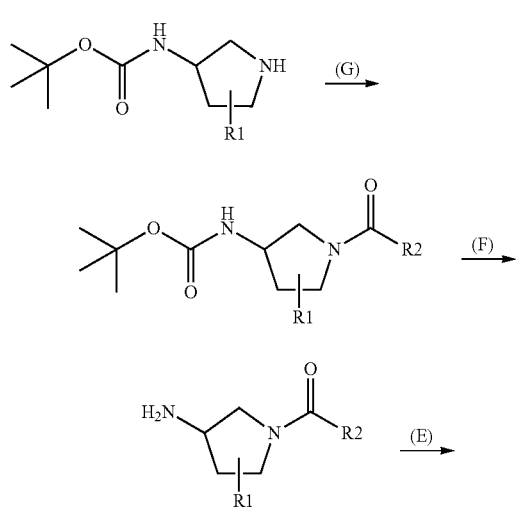
50
-continued
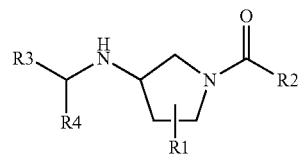
Scheme 11. General synthetic route to substituted piperidines (General procedure U, V, F)
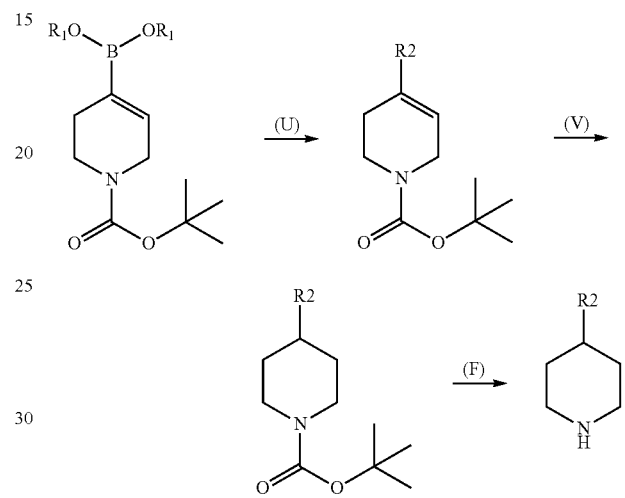
Scheme 12. General synthetic route to 2-substituted-3-aminopyrrolidines (General procedure W, X, Y, Z, AA)
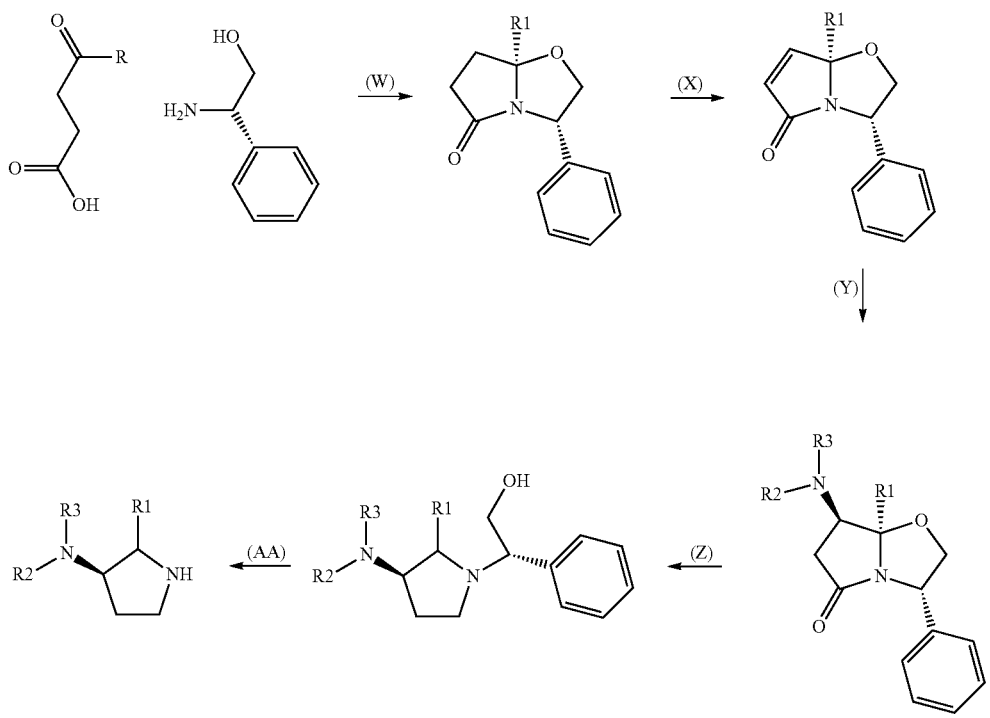

LIST OF GENERAL PROCEDURES

General Procedure A: Addition of an amine to carbonyl diimidazole.
General Procedure B: Methylation of an imidazole urea.
General Procedure C: Formation of an urea from an imidazolium urea.
General Procedure D: Formation of an urea from an isocyanate.
General Procedure E: Formation of an amine by reductive amination.
General Procedure F: Deprotection of a Boc-amine.
General Procedure G: Formation of an amide by peptide coupling.
General Procedure H: Formation of a mesylate from an alcohol.
General Procedure I: Formation of an amine by mesylate displacement.
General Procedure J: Oxidation of an alcohol to a ketone.
General Procedure K: Formation of an amide by acid chloride acylation.
General Procedure L: Hydrolysis of an ester to a carboxylic acid.
General Procedure M: Amine displacement of a heterocyclic halide.
General Procedure N: Demethylation of a methoxy group to a phenol.
General Procedure O: Formation of an aryl piperidinol.
General Procedure P: Dehydration and hydrogenation of an aryl piperidinol.
General Procedure Q: Alkylation of an amine or amide with an alkyl halide.
General Procedure R: Addition of an amine to a bis-benzotriazolyl ethanedione.
General Procedure S: Formation of an oxamide from a benzotriazolyl ethanedione.
General Procedure T: Formation of an α-bromo amide.
General Procedure U: Suzuki coupling of a halide with a boronate ester or boronic acid.
General Procedure V: Hydrogenation to reduce a double bond in a tetrahydropyridine.
General Procedure W: Formation of a saturated chiral bicyclic lactam.
General Procedure X: Formation of an unsaturated chiral bicyclic lactam.
General Procedure Y: Michael addition of an amine to a bicyclic lactam.
General Procedure Z: Reduction and ring opening of a bicyclic lactam.
General Procedure AA: Removal of benzyl group by hydrogenation.

Intermediates:

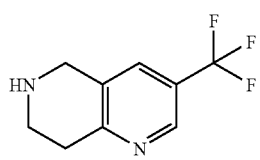

3-Trifluoromethyl-5,6,7,8-tetrahydro-[1,6]naphthyridine was prepared via the route detailed in WO2005/044264.

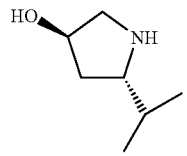

(3R,5S)-5-Isopropyl-pyrrolidin-3-ol was prepared via the route described in WO2005/060665.

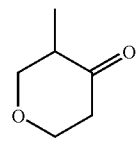

3-Methyl-tetrahydro-pyran-4-one was prepared via the route detailed in J. Am. Chem. Soc. 1991, 113, 2071-2092.

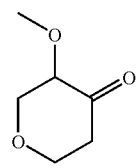

3-Methoxy-tetrahydro-pyran-4-one was prepared via the route detailed in WO2005/014537.

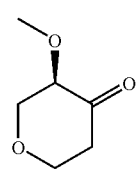

(R)-3-Methoxy-tetrahydro-pyran-4-one was prepared via the route detailed in WO 2005/044264.

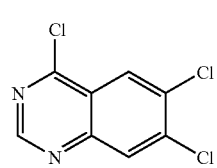 [SMILES: Clc1cc2ncnc(Cl)c2cc1Cl]

4,6,7-Trichloroquinazoline was prepared via the route detailed in WO 1996/09294A1.

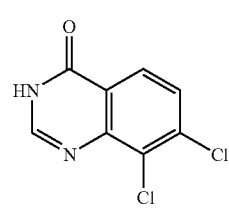 [SMILES: O=c1[nH]cnc2c(Cl)c(Cl)ccc12]

7,8-Dichloro-3H-quinazolin-4-one was prepared via the route detailed in US 1967/3320124.

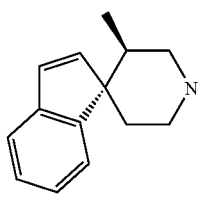

(1R,3'R)-3'-methylspiro[indene-1,4'-piperidine] was prepared via the route detailed in US 2006/073013 A1.

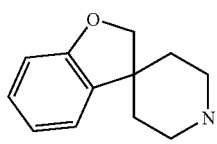 [SMILES: c1ccc2c(c1)OCC21CCNCC1]

2H-spiro[benzofuran-3,4'-piperidine] was prepared via the route detailed in WO 2006092731 A1.

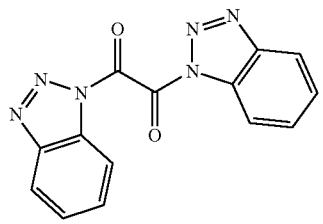 [SMILES: O=C(C(=O)n1nnc2ccccc21)n1nnc2ccccc21]

1,2-Bis-benzotriazol-1-yl-ethane-1,2-dione was prepared via the route detailed in Synthesis 1998 153.

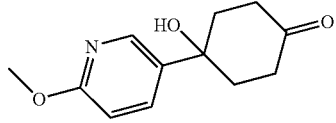 [SMILES: COc1ccc(C2(O)CCC(=O)CC2)cn1]

4-Hydroxy-4-(6-methoxypyridin-3-yl)cyclohexanone was prepared via the route detailed in WO2004/050024.

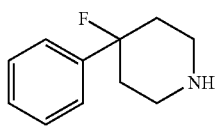 [SMILES: FC1(c2ccccc2)CCNCC1]

4-Fluoro-4-phenylpiperidine was synthesized according to the procedure described for the synthesis of 4-(4-chlorophenyl)-4-fluoropiperidine in J. Harriman et al. *Tetr. Lett.*, 41 (2000) 8853-8856.

The general procedure letter codes constitute a synthetic route to the final product. A worked example of how the route is determined is given below using the synthesis of Example #2.3 as a non-limiting illustration. Example #2.3 (6,7-dichloro-3,4-dihydro-1H-isoquinolin-2-yl)-[3-(4-phenyl-piperidin-1-yl)-pyrrolidin-1-yl]-methanone was prepared from 3-(6,7-dichloro-3,4-dihydro-1H-isoquinoline-2-carbonyl)-1-methyl-3H-imidazol-1-ium iodide and 4-phenyl-1-pyrrolidin-3-yl-piperidine using general procedure C, as represented in the following synthetic scheme.

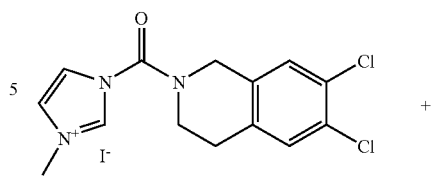

Precursor 1 to example #2.3

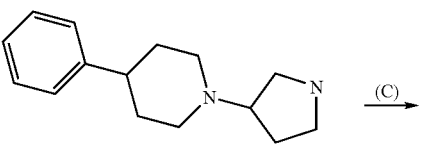

Precursor 2 to example #2.3

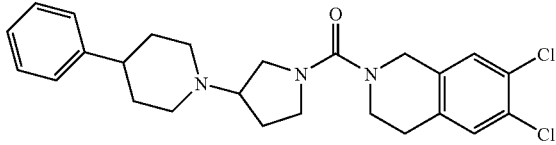 [SMILES: O=C(N1CCc2cc(Cl)c(Cl)cc2C1)N1CCC(N2CCC(c3ccccc3)CC2)C1]

Example #2.3

The precursor 1 to example #2.3, 3-(6,7-Dichloro-3,4-dihydro-1H-isoquinoline-2-carbonyl)-1-methyl-3H-imidazol-1-ium iodide was prepared via the noted reaction sequence: (A, B) which translates to the following synthetic scheme:

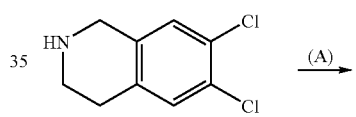

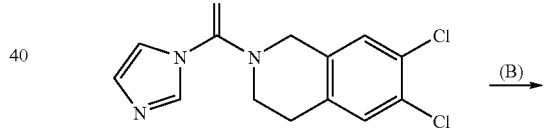

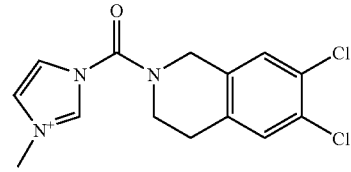

The precursor 2 to example #2.3, 4-phenyl-1-pyrrolidin-3-yl-piperidine was prepared via the noted reaction sequence: (E, F) which translates to the following synthetic scheme:

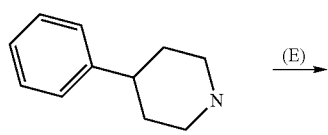

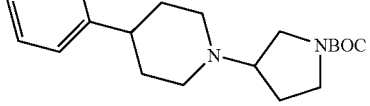

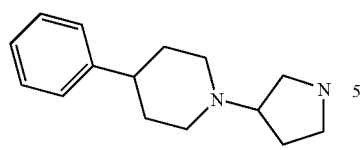

General Procedure A: Addition of an Amine to Carbonyl Diimidazole.

A mixture of CDI (preferably 1 equivalent) and an amine (1 to 3 equivalents, preferably 1 equivalent) in an organic solvent (preferably THF) is stirred at about 20-100° C. (preferably about 20° C.) for about 0.5-60 hours (preferably about 16 hours). The reaction mixture is concentrated in vacuo then dissolved in DCM, washed with water, and dried in vacuo. The residue can then be further purified by crystallization or chromatography.

Illustration of General Procedure A

Preparation #1: Imidazol-1-yl-(3-trifluoromethyl-7, 8-dihydro-5H-[1,6]naphthyridin-6-yl)-methanone

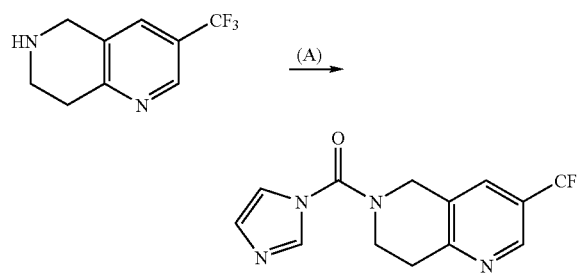

To a suspension of CDI (0.949 g, 5.86 mmol) in THF (10 mL) was added 3-trifluoromethyl-5,6,7,8-tetrahydro-[1,6]naphthyridine (0.988 g, 4.88 mmol) and the reaction mixture was heated at about 60° C. for about 16 h. The reaction mixture was cooled at ambient temperature and concentrated in vacuo to afford a light orange solid. The residue was dissolved in DCM (10 mL), washed with water (2×10 mL), and the organic portion was separated, dried over MgSO₄, filtered, and concentrated in vacuo to give imidazol-1-yl-(3-trifluoromethyl-7,8-dihydro-5H-[1,6]naphthyridin-6-yl)-methanone (1.28 g, 88%) as a yellow solid which was used in subsequent reactions without further purification. RP-HPLC (Table 1, Method d) $R_t$ 2.10 min; m/z: (M+H)⁺ 297.

Illustration of General Procedure A

Preparation #2: [1-(Imidazole-1-carbonyl)-pyrrolidin-3-yl]-carbamic acid tert-butyl ester

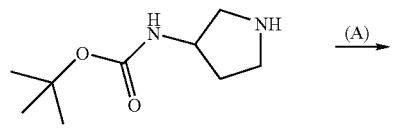

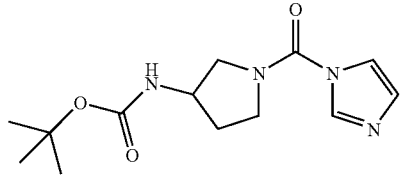

To a suspension of CDI (3.8 g, 20.5 mmol) in THF (40 mL) was added pyrrolidin-3-yl-carbamic acid tert-butyl ester (3.99 g, 20.5 mmol) and the reaction mixture was heated at about 55-60° C. for about 4 h. The reaction mixture was cooled at ambient temperature and concentrated in vacuo to afford an yellow oil. The residue was dissolved in DCM (40 mL), washed with water (2×30 mL), and the organic portion was separated, dried over MgSO₄, filtered, and concentrated in vacuo to give [1-(imidazole-1-carbonyl)-pyrrolidin-3-yl]-carbamic acid tert-butyl ester (5.06 g, 88%) as a yellow oil which was used in subsequent reactions without further purification. RP-HPLC (Table 1, Method d) $R_t$ 2.08 min; m/z: (M+H)⁺ 281.

General Procedure B: Methylation of an imidazole urea.

To a mixture of an imidazole urea (preferably 1 equivalent) in an organic solvent (preferably MeCN) is added methyl iodide (1 to 20 equivalents, preferably 4 equivalents) and the reaction mixture is stirred at about 20-100° C. (preferably about 20° C.) for about 0.5-60 hours (preferably about 2 hours). Additional methyl iodide (about 1 to 10 equivalents, preferably 2 equivalents) is added and stirring resumed for about 0.5-60 hours (preferably about 16 hours). The reaction mixture is concentrated in vacuo to give the product that is used without further purification.

Illustration of General Procedure B

Preparation #3: 1-Methyl-3-(3-trifluoromethyl-7,8-dihydro-5H-[1,6]naphthyridine-6-carbonyl)-3H-imidazol-1-ium iodide

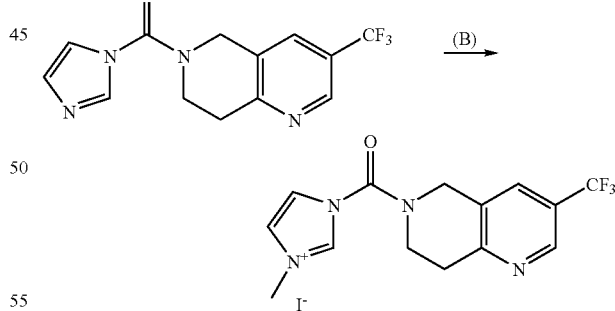

To a suspension of imidazol-1-yl-(3-trifluoromethyl-7,8-dihydro-5H-[1,6]naphthyridin-6-yl)-methanone (preparation #1) (1.28 g, 4.32 mmol) in MeCN (10 mL) was added methyl iodide (1.1 mL, 17 mmol) and the reaction mixture was stirred at ambient temperature for about 2 h. Additional methyl iodide (0.5 mL, 8 mol) was added and stirring resumed for about 16 h. The reaction mixture was concentrated in vacuo to afford 1-methyl-3-(3-trifluoromethyl-7,8-dihydro-5H-[1,6]naphthyridine-6-carbonyl)-3H-imidazol-1-ium iodide (1.89 g, 100%) as an orange solid which was used in subsequent reactions without further purification. RP-HPLC (Table 1, Method d) R$_t$ 1.77 min; m/z: (M+H)$^+$ 311.

Illustration of General Procedure B

Preparation #4: 3-(3-tert-Butoxycarbonylamino-pyrrolidine-1-carbonyl)-1-methyl-3H-imidazol-1-ium iodide

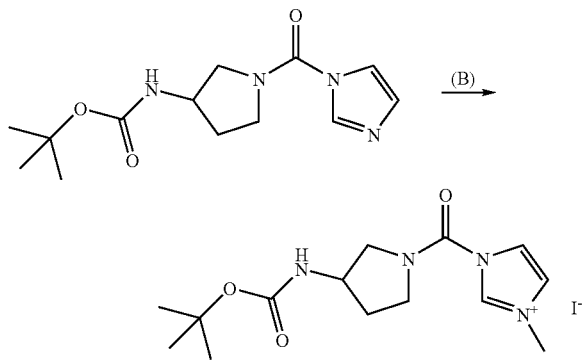

To a suspension of [1-(imidazole-1-carbonyl)-pyrrolidin-3-yl]-carbamic acid tert-butyl ester (preparation #2) (5.1 g, 18 mmol) in MeCN (50 mL) was added methyl iodide (4.5 mL, 73 mmol) and the reaction mixture was stirred at ambient temperature for about 1.5 h. Additional methyl iodide (2.0 mL, 32 mol) was added and stirring resumed for about 16 h. The reaction mixture was concentrated in vacuo to afford 3-(3-tert-butoxycarbonylamino-pyrrolidine-1-carbonyl)-1-methyl-3H-imidazol-1-ium iodide (1.89 g, 100%) as an orange solid which was used in subsequent reactions without further purification. RP-HPLC (Table 1, Method d) R$_t$ 1.77 min; m/z: (M+H)$^+$ 295.

General Procedure C: Formation of an Urea from an Imidazolium Urea.

To a mixture of an imidazolium urea (preferably 1 equivalent) in an organic solvent (preferably DCM) is added an amine (1 to 3 equivalents, preferably 1 equivalent) and an organic base (preferably Et$_3$N; 1 to 3 equivalents, preferably 1 equivalent) and the reaction mixture is stirred at about 20-100° C. (preferably about 20° C.) for about 0.5-60 hours (preferably about 0.5 hours). The reaction mixture is concentrated in vacuo and the residue can then be further purified by crystallization or chromatography.

Illustration of General Procedure C

EXAMPLE #1

(3-Hydroxy-pyrrolidin-1-yl)-(3-trifluoromethyl-7,8-dihydro-5H-[1,6]naphthyridin-6-yl)-methanone

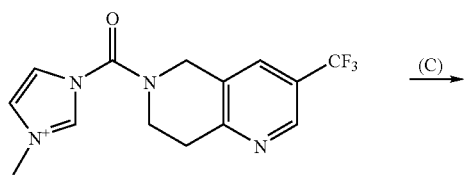

-continued

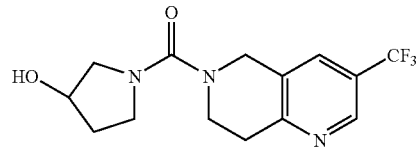

To a solution of 1-methyl-3-(3-trifluoromethyl-7,8-dihydro-5H-[1,6]naphthyridine-6-carbonyl)-3H-imidazol-1-ium iodide (preparation #3) (0.046 g, 0.10 mmol) in DCM (1 mL) was added pyrrolidin-3-ol (0.009 g, 0.10 mmol) and Et$_3$N (0.014 mL, 0.10 mmol) and the reaction mixture was shaken at ambient temperature for about 30 min. The reaction mixture was dried in vacuo (Genevac®) and the residue purified by RP-HPLC (10% acetonitrile/0.05M aqueous ammonium acetate, buffered to pH 4.5 for 3 min., 10% to 65% acetonitrile/0.05M aqueous ammonium acetate over 6 min at 22.5 mL/min with 2.5 mL/min. acetonitrile at-column dilution; APCI positive mode detection; Xterra prep. MS C18. 19×50 mm column) to afford (3-hydroxy-pyrrolidin-1-yl)-(3-trifluoromethyl-7,8-dihydro-5H-[1,6]naphthyridin-6-yl)-methanone (0.011 g, 33%). RP-HPLC (Table 1, Method a) R$_t$ 1.72 min; m/z: (M+H)$^+$ 316.

Illustration of General Procedure C

Preparation #5: [1-(3-Trifluoromethyl-7,8-dihydro-5H-[1,6]naphthyridine-6-carbonyl)-pyrrolidin-3-yl]-carbamic acid tert-butyl ester

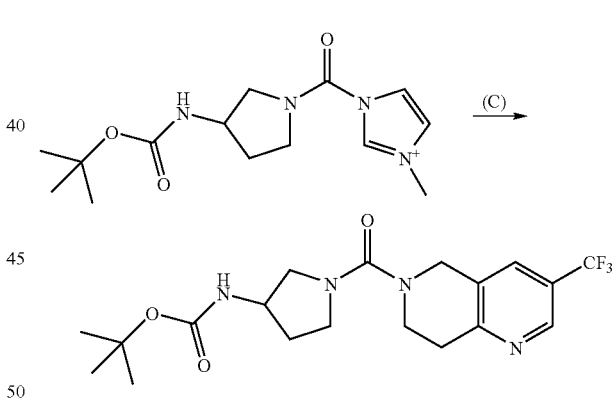

To a solution of 3-(3-tert-butoxycarbonylamino-pyrrolidine-1-carbonyl)-1-methyl-3H-imidazol-1-ium iodide (preparation #4) (7.81 g, 18.5 mmol) in DCM (70 mL) was added 3-trifluoromethyl-5,6,7,8-tetrahydro-[1,6]naphthyridine (3.74 g, 18.5 mmol) and Et$_3$N (2.6 mL, 18.5 mmol) and the reaction mixture was stirred at ambient temperature for about 16 h. Additional Et$_3$N (1.5 mL, 10.7 mmol) was added and the reaction mixture was stirred at ambient temperature for about 16 h. The reaction mixture was concentrated in vacuo and the residue was purified by flash chromatography on silica gel using 5% MeOH/DCM as the mobile phase to give [1-(3-trifluoromethyl-7,8-dihydro-5H-[1,6]naphthyridine-6-carbonyl)-pyrrolidin-3-yl]-carbamic acid tert-butyl ester (4.91 g, 64%). RP-HPLC (Table 1, Method a) R$_t$ 2.37 min; m/z: (M+H)$^+$ 415.

TABLE 2

Examples synthesized using general procedure C

| Starting Material | Amine | Product | Ex. # | HPLC R$_t$ (Method) | m/z or $^1$H NMR (d6 DMSO, 400 MHz) |
|---|---|---|---|---|---|
| 1-Methyl-3-(3-trifluoromethyl-7,8-dihydro-5H-[1,6]naphthyridine-6-carbonyl)-3H-imidazol-1-ium iodide (A, B) | 4-Phenyl-1-pyrrolidin-3-yl-piperidine (E, F) | | 2.1 | 1.96 min (a) | (M + H)$^+$ 459 |
| 1-Methyl-3-(3-trifluoromethyl-7,8-dihydro-5H-[1,6]naphthyridine-6-carbonyl)-3H-imidazol-1-ium iodide (A, B) | Methyl-pyrrolidin-3-yl-(tetrahydro-pyran-4-yl)-amine (E, F) | | 2.2 | 1.54 min (a) | (M + H)$^+$ 413 |
| 3-(6,7-Dichloro-3,4-dihydro-1H-iso-quinoline-2-carbonyl)-1-methyl-3H-imidazol-1-ium iodide (A, B) | 4-Phenyl-1-pyrrolidin-3-yl-piperidine (E, F) | | 2.3 | 2.01 min (b) | (M + H)$^+$ 458 |
| 1-Methyl-3-(3-trifluoromethyl-7,8-dihydro-5H-[1,6]naphthyridine-6-carbonyl)-3H-imidazol-1-ium iodide (A, B) | (1R,3'R)-3'-Methyl-1'-(pyrrolidin-3-yl) spiro[indene-1,4'-piperidine] (E, F) | | 2.4 | 1.92 min (b) | (M + H)$^+$ 497 |
| 3-(3,5-Bis-trifluoromethyl-benzyl-carbamoyl)-1-methyl-3H-imidazol-1-ium iodide (A, B) | (1R,3'R)-3'-Methyl-1'-(pyrrolidin-3-yl) spiro[indene-1,4'-piperidine] (E, F) | Chiral | 2.5 | 2.29 min (b) | (M + H)$^+$ 538 |
| 3-(3,5-Bis-trifluoromethyl-benzyl-carbamoyl)-1-methyl-3H-imidazol-1-ium iodide (A, B) | 4-Phenyl-1-pyrrolidin-3-yl-piperidine (E, F) | | 2.6 | 2.02 min (a) | (M + H)$^+$ 500 |
| 1-Methyl-3-(3-trifluoromethyl-7,8-dihydro-5H-[1,6]naphthyridine-6-carbonyl)-3H-imidazol-1-ium iodide (A, B) | 1-((3R)-2-cyclopropyl-pyrrolidin-3-yl)-4-(2-methoxy-phenyl)-piperidine (Preparation [#27]) | | 2.7 | 2.23 min. (a) | (M + H)$^+$ 529 |

TABLE 2-continued

Examples synthesized using general procedure C

| Starting Material | Amine | Product | Ex. # | HPLC $R_t$ (Method) | m/z or $^1$H NMR (d6 DMSO, 400 MHz) |
|---|---|---|---|---|---|
| 1-Methyl-3-(3-trifluoromethyl-7,8-dihydro-5H-[1,6]naphthyridine-6-carbonyl)-3H-imidazol-1-ium iodide (A, B) | 1-((3R)-2-methyl-pyrrolidin-3-yl)-4-(2-methoxy-phenyl)piperidine (Y, Z, AA) | 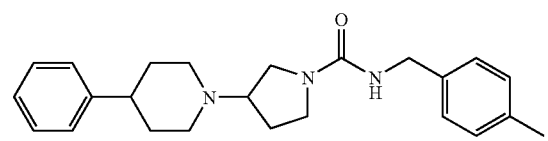 | 2.8 | 1.75 min. (a) | (M + H)$^+$ 503 |

General Procedure D: Formation of an Urea from an Isocyanate.

To a mixture of an amine (preferably 1 equivalent) and triethylamine (24 equivalents, preferably 4 equivalents) in an organic solvent (preferably DCM) is added an isocyanate (preferably 1 equivalent) and the reaction mixture is stirred at about 20-100° C. (preferably about 20° C.) for about 0.5-60 hours (preferably about 16 hours). The reaction mixture is concentrated in vacuo and the residue can then be further purified by chromatography or crystallization.

Illustration of General Procedure D

EXAMPLE #2

3-(4-Phenyl-piperidin-1-yl)-pyrrolidine-1-carboxylic acid 4-methyl-benzylamide

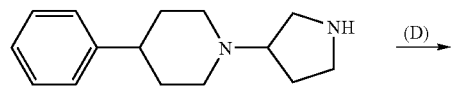

To a solution of 4-phenyl-1-pyrrolidin-3-yl-piperidine dihydrochloride (preparation #7) (0.050 g, 0.165 mmol) and triethylamine (0.092 mL, 0.66 mmol) in dichloromethane (1 mL) was added 1-isocyanatomethyl-4-methyl-benzene (0.024 g, 0.165 mmol) and the reaction mixture was stirred at ambient temperature for about 16 h. The reaction mixture was concentrated in vacuo and the residue was purified by flash chromatography on silica gel using 5% MeOH/EtOAc as the mobile phase to give 3-(4-phenyl-piperidin-1-yl)-pyrrolidine-1-carboxylic acid 4-methyl-benzylamide (0.042 g, 68%). RP-HPLC (Table 1, Method b) $R_t$ 1.72 min; m/z: (M+H)$^+$ 378.

TABLE 3

Examples synthesized using general procedure D

| Amine | Isocyanate | Product | Ex. # | HPLC $R_t$ (Method) | m/z or $^1$H NMR (d6 DMSO, 400 MHz) |
|---|---|---|---|---|---|
| 4-Phenyl-1-pyrrolidin-3-yl-piperidine, dihydrochloride (E, F) | 1-Iso-cyanatomethyl-4-methyl-benzene | | 3.1 | 1.72 min (b) | (M + H)$^+$ 378 |
| 4-Phenyl-1-pyrrolidin-3-yl-piperidine, dihydrochloride (E, F) | Isocyanato-methyl-benzene | | 3.2 | 2.06 min (a) | (M + H)$^+$ 364 |

TABLE 3-continued

Examples synthesized using general procedure D

| Amine | Isocyanate | Product | Ex. # | HPLC R$_t$ (Method) | m/z or $^1$H NMR (d6 DMSO, 400 MHz) |
|---|---|---|---|---|---|
| 4-Phenyl-1-pyrrolidin-3-yl-piperidine, dihydrochloride (E, F) | 1-Chloro-4-iso-cyanatomethyl-benzene | | 3.3 | 2.20 min (a) | (M + H)$^+$ 398 |
| 4-Phenyl-1-pyrrolidin-3-yl-piperidine, dihydrochloride (E, F) | 1-Chloro-2-iso-cyanatomethyl-benzene | | 3.4 | 2.16 min (a) | (M + H)$^+$ 398 |
| 4-Phenyl-1-pyrrolidin-3-yl-piperidine, dihydrochloride (E, F) | 2,2,2-Trifluoro-1-(4-iso-cyanatomethyl-piperidin-1-yl)-ethanone | | 3.5 | 1.99 min (a) | (M + H)$^+$ 453 |
| 4-Phenyl-1-pyrrolidin-3-yl-piperidine, dihydrochloride (E, F) | 1-Isocyanato-adamantane | | 3.6 | 2.46 min (a) | (M + H)$^+$ 408 |
| 4-Phenyl-1-pyrrolidin-3-yl-piperidine, dihydrochloride (E, F) | 4-Isocyanato-5-methyl-3-phenyl-isoxazole | | 3.7 | 2.07 min (a) | (M + H)$^+$ 431 |
| 4-Phenyl-1-pyrrolidin-3-yl-piperidine, dihydrochloride (E, F) | Isocyanato-benzene | | 3.8 | 2.04 min (a) | (M + H)$^+$ 350 |

TABLE 3-continued

Examples synthesized using general procedure D

| Amine | Isocyanate | Product | Ex. # | HPLC R$_t$ (Method) | m/z or $^1$H NMR (d6 DMSO, 400 MHz) |
|---|---|---|---|---|---|
| 4-Phenyl-1-pyrrolidin-3-yl-piperidine, dihydrochloride (E, F) | 1,2-Dichloro-4-isocyanato-benzene | | 3.9 | 2.39 min (a) | (M + H)$^+$ 418 |
| 4-Phenyl-1-pyrrolidin-3-yl-piperidine, dihydrochloride (E, F) | 2,4-Dichloro-1-isocyanato-methyl-benzene | | 3.10 | 2.30 min (a) | (M + H)$^+$ 432 |
| 4-Phenyl-1-pyrrolidin-3-yl-piperidine, dihydrochloride (E, F) | 9-Isocyanato-9H-fluorene | | 3.11 | 2.36 min (a) | (M + H)$^+$ 438 |
| 4-Phenyl-1-pyrrolidin-3-yl-piperidine, dihydrochloride (E, F) | 1-Isocyanato-methyl-2-methoxy-benzene | | 3.12 | 2.09 min (a) | (M + H)$^+$ 394 |
| 4-Phenyl-1-pyrrolidin-3-yl-piperidine, dihydrochloride (E, F) | (isocyanato-methylene)di-benzene | | 3.13 | 2.30 min (b) | (M + H)$^+$ 440 |
| 4-Phenyl-1-pyrrolidin-3-yl-piperidine, dihydrochloride (E, F) | 2,2,2-Trifluoro-1-(3-iso-cyanato-piperidin-1-yl)-ethanone | | 3.14 | 2.00 min | (M + H)$^+$ |

TABLE 3-continued

Examples synthesized using general procedure D

| Amine | Isocyanate | Product | Ex. # | HPLC R$_t$ (Method) | m/z or $^1$H NMR (d6 DMSO, 400 MHz) |
|---|---|---|---|---|---|
| 4-Phenyl-1-pyrrolidin-3-yl-piperidine, dihydrochloride (E, F) | 4-Isocyanato-3,5-dimethyl-isoxazole | | 3.15 | 2.20 min (b) | (M + H)$^+$ 369 |
| 4-Phenyl-1-pyrrolidin-3-yl-piperidine, dihydrochloride (E, F) | 1,3-Dichloro-5-isocyanato-benzene | | 3.16 | 2.50 min (b) | (M + H)$^+$ 418 |
| 4-Phenyl-1-pyrrolidin-3-yl-piperidine, dihydrochloride (E, F) | 1-Isocyanato-3,5-bis-trifluoromethyl-benzene | | 3.17 | 2.60 min (b) | (M + H)$^+$ 486 |
| 4-Phenyl-1-pyrrolidin-3-yl-piperidine, dihydrochloride (E, F) | ((S)-1-Isocyanato-ethyl)-benzene | | 3.18 | 2.10 min (b) | (M + H)$^+$ 378 |
| 4-Phenyl-1-pyrrolidin-3-yl-piperidine, dihydrochloride (E, F) | 1-((R)-1-Isocyanato-ethyl)-naphthalene | | 3.19 | 2.30 min (b) | (M + H)$^+$ 428 |
| 4-Phenyl-1-pyrrolidin-3-yl-piperidine, dihydrochloride (E, F) | ((R)-1-Isocyanato-ethyl)-benzene | | 3.20 | 2.10 min (b) | (M + H)$^+$ 378 |

TABLE 3-continued

Examples synthesized using general procedure D

| Amine | Isocyanate | Product | Ex. # | HPLC $R_t$ (Method) | m/z or $^1$H NMR (d6 DMSO, 400 MHz) |
|---|---|---|---|---|---|
| 4-Phenyl-1-pyrrolidin-3-yl-piperidine, dihydrochloride (E, F) | 1-((S)-1-Isocyanato-ethyl)-naphthalene | (structure) | 3.21 | 2.30 min (b) | (M + H)$^+$ 428 |
| 4-Phenyl-1-pyrrolidin-3-yl-piperidine, dihydrochloride (E, F) | 1-Fluoro-4-isocyanato-methyl-benzene | (structure) | 3.22 | 2.10 min (b) | (M + H)$^+$ 382 |
| 4-Phenyl-1-pyrrolidin-3-yl-piperidine, dihydrochloride (E, F) | 1-Fluoro-2-isocyanato-methyl-benzene | (structure) | 3.23 | 2.10 min (b) | (M + H)$^+$ 382 |

General Procedure E: Formation of an Amine by Reductive Amination.

To a mixture of an aldehyde or ketone (preferably 1 equivalent) in an organic solvent (preferably MeOH) is added a borohydride reagent (preferably NaBH(OAc)$_3$ or MP-cyanoborohydride; 1 to 10 equivalents, preferably 3 equivalents) and with or without an acid (preferably with an acid, preferably HOAc; 1 to 5 equivalents, preferably 1 equivalent) and the reaction mixture is stirred at about 20-100° C. (preferably about 20° C.) for about 0.5 to 60 hours (preferably about 16 hours). The reaction mixture is filtered and the filtrate concentrated in vacuo. The residue can then be further purified by crystallization or chromatography.

Illustration of General Procedure E

Preparation #6: 3-(4-Phenyl-piperidin-1-yl)-pyrrolidine-1-carboxylic acid tert-butyl ester

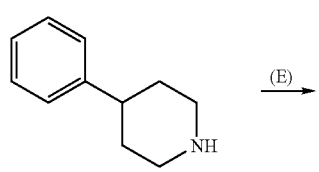

To a suspension of 4-phenylpiperidine (2.12 g, 13.1 mmol) and 3-oxo-pyrrolidine-1-carboxylic acid tert-butyl ester (2.43 g, 13.1 mmol) in MeOH (60 mL) was added NaBH(OAc)$_3$ (8.32 g, 39.3 mmol) and the reaction mixture was stirred at ambient temperature for about 16 h. The reaction mixture was concentrated in vacuo. The residue was dissolved in DCM (50 mL) and stirred with saturated aqueous NaHCO$_3$ (50 mL) for about 1 h. The organic portion was separated, dried over MgSO$_4$, filtered, and concentrated in vacuo to give 3-(4-phenyl-piperidin-1-yl)-pyrrolidine-1-carboxylic acid tert-butyl ester (4.3 g,) as a yellow oil which was used in subsequent reactions without further purification. RP-HPLC (Table 1, Method d) R$_t$ 2.73 min; m/z: (M+H)$^+$ 331.

TABLE 4

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| (3-Amino-pyrrolidin-1-yl)-(3-trifluoro-methyl-7,8-dihydro-5H-[1,6]naphthyridin-6-yl)-methanone (A, B, C, F) | 2,4-Dimethyl-benzaldehyde | | 4.1 | 1.92 min (a) | (M + H)$^+$ 433 |
| Methyl-(tetrahydro-pyran-4-yl)-amine | (S)-5-Isopropyl-1-(3-trifluoro-methyl-7,8-dihydro-5H-[1,6]naphthyridine-6-carbonyl)-pyrrolidin-3-one (A, B, C, J) | | 4.2 | 1.74 min (a) | (M + H)$^+$ 455 |
| 4-Phenyl-1-pyrrolidin-3-yl-piperidine (E, F) | (S)-5-Isopropyl-1-(3-trifluoro-methyl-7,8-dihydro-5H-[1,6]naphthyridine-6-carbonyl)-pyrrolidin-3-one (A, B, C, J) | | 4.3 | 2.29 min (a) | (M + H)$^+$ 501 |
| (3-Amino-pyrrolidin-1-yl)-(3-trifluoro-methyl-7,8-dihydro-5H-[1,6]naphthyridin-6-yl)-methanone (A, B, C, F) | 4-Phenyl-cyclohexanone | | 4.4 | 2.10 min (a) | (M + H)$^+$ 473 |
| (3-Amino-pyrrolidin-1-yl)-(3-trifluoro-methyl-7,8-dihydro-5H-[1,6]naphthyridin-6-yl)-methanone (A, B, C, F) | Tetrahydro-pyran-4-carbaldehyde | | 4.5 | 1.53 min (a) | (M + H)$^+$ 413 |
| (3-Amino-pyrrolidin-1-yl)-(3-trifluoro-methyl-7,8-dihydro-5H-[1,6]naphthyridin-6-yl)-methanone (A, B, C, F) | 4-Phenyl-butyraldehyde | | 4.6 | 2.00 min (a) | (M + H)$^+$ 447 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| (3-Amino-pyrrolidin-1-yl)-(3-trifluoro-methyl-7,8-dihydro-5H-[1,6]naphthyridin-6-yl)-methanone (A, B, C, F) | 2-Methyl-4-phenyl-pentanal | | 4.7 | 2.13 min (a) | (M + H)$^+$ 475 |
| (3-Amino-pyrrolidin-1-yl)-(3-trifluoro-methyl-7,8-dihydro-5H-[1,6]naphthyridin-6-yl)-methanone (A, B, C, F) | Benzo[b]-thiophene-3-carbaldehyde | | 4.8 | 1.98 min (a) | (M + H)$^+$ 461 |
| (3-Amino-pyrrolidin-1-yl)-(3-trifluoro-methyl-7,8-dihydro-5H-[1,6]naphthyridin-6-yl)-methanone (A, B, C, F) | 3-Phenyl-propion-aldehyde | | 4.9 | 1.91 min (a) | (M + H)$^+$ 433 |
| (3-Amino-pyrrolidin-1-yl)-(3-trifluoro-methyl-7,8-dihydro-5H-[1,6]naphthyridin-6-yl)-methanone (A, B, C, F) | 2,2-Dimethyl-3-p-tolyl-propion-aldehyde | | 4.10 | 2.22 min (a) | (M + H)$^+$ 475 |
| (3-Amino-pyrrolidin-1-yl)-(3-trifluoro-methyl-7,8-dihydro-5H-[1,6]naphthyridin-6-yl)-methanone (A, B, C, F) | 3-Phenyl-butyraldehyde | | 4.11 | 1.98 min (a) | (M + H)$^+$ 447 |

TABLE 4-continued

Examples synthesized using general procedure E

| Amine | Aldehyde or ketone | Product | Ex. # | HPLC R_t (Method) | m/z or ¹H NMR (d6 DMSO, 400 MHz) |
|---|---|---|---|---|---|
| (3-Amino-pyrrolidin-1-yl)-(3-trifluoro-methyl-7,8-dihydro-5H-[1,6]naphthyridin-6-yl)-methanone (A, B, C, F) | 3-(4-Isopropyl-phenyl)-2-methyl-propion-aldehyde | | 4.12 | 1.98 min (a) | (M + H)+ 489 |
| (3-Amino-pyrrolidin-1-yl)-(3-trifluoro-methyl-7,8-dihydro-5H-[1,6]naphthyridin-6-yl)-methanone (A, B, C, F) | 3-Benzo[1,3]dioxol-5-yl-2-methyl-propion-aldehyde | | 4.13 | 1.96 min (a) | (M + H)+ 491 |
| (3-Amino-pyrrolidin-1-yl)-(3-trifluoro-methyl-7,8-dihydro-5H-[1,6]naphthyridin-6-yl)-methanone (A, B, C, F) | Benzaldehyde | | 4.14 | 1.74 min (a) | (M + H)+ 405 |
| (3-Amino-pyrrolidin-1-yl)-(3-trifluoro-methyl-7,8-dihydro-5H-[1,6]naphthyridin-6-yl)-methanone (A, B, C, F) | Naphthalene-2-carbaldehyde | | 4.15 | 1.98 min (a) | (M + H)+ 455 |
| (3-Amino-pyrrolidin-1-yl)-(3-trifluoro-methyl-7,8-dihydro-5H-[1,6]naphthyridin-6-yl)-methanone (A, B, C, F) | Naphthalene-2-carbaldehyde | | 4.16 | 1.98 min (a) | (M + H)+ 455 |
| (3-Amino-pyrrolidin-1-yl)-(3-trifluoro-methyl-7,8-dihydro-5H-[1,6]naphthyridin-6-yl)-methanone (A, B, C, F) | 1-Phenyl-piperidin-4-one | | 4.17 | 1.89 min (a) | (M + H)+ 474 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| (3-Amino-pyrrolidin-1-yl)-(3-trifluoro-methyl-7,8-dihydro-5H-[1,6]naphthyridin-6-yl)-methanone (A, B, C, F) | Pyridine-4-carbaldehyde | | 4.18 | 1.55 min (a) | (M + H)$^+$ 406 |
| (3-Amino-pyrrolidin-1-yl)-(3-trifluoro-methyl-7,8-dihydro-5H-[1,6]naphthyridin-6-yl)-methanone (A, B, C, F) | Pyridine-3-carbaldehyde | | 4.19 | 1.54 min (a) | (M + H)$^+$ 406 |
| (3-Amino-pyrrolidin-1-yl)-(3-trifluoro-methyl-7,8-dihydro-5H-[1,6]naphthyridin-6-yl)-methanone (A, B, C, F) | Quinoline-3-carbaldehyde | | 4.20 | 1.74 min (a) | (M + H)$^+$ 456 |
| (3-Amino-pyrrolidin-1-yl)-(3-trifluoro-methyl-7,8-dihydro-5H-[1,6]naphthyridin-6-yl)-methanone (A, B, C, F) | 6-Morpholin-4-yl-pyridine-3-carbaldehyde | | 4.21 | 1.64 min (a) | (M + H)$^+$ 491 |
| (3-Amino-pyrrolidin-1-yl)-(3-trifluoro-methyl-7,8-dihydro-5H-[1,6]naphthyridin-6-yl)-methanone (A, B, C, F) | Pyridine-2-carbaldehyde | | 4.22 | 1.60 min (a) | (M + H)$^+$ 406 |
| (3-Amino-pyrrolidin-1-yl)-(3-trifluoro-methyl-7,8-dihydro-5H-[1,6]naphthyridin-6-yl)-methanone (A, B, C, F) | 6-Methyl-pyridine-2-carbaldehyde | | 4.23 | 1.68 min (a) | (M + H)$^+$ 420 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| (3-Amino-pyrrolidin-1-yl)-(3-trifluoro-methyl-7,8-dihydro-5H-[1,6]naphthyridin-6-yl)-methanone (A, B, C, F) | 1-Methyl-1H-indole-2-carbaldehyde | | 4.24 | 2.07 min (a) | (M + H)$^+$ 458 |
| (3-Amino-pyrrolidin-1-yl)-(3-trifluoro-methyl-7,8-dihydro-5H-[1,6]naphthyridin-6-yl)-methanone (A, B, C, F) | Benzofuran-2-carbaldehyde | | 4.25 | 2.04 min (a) | (M + H)$^+$ 445 |
| (3-Amino-pyrrolidin-1-yl)-(3-trifluoro-methyl-7,8-dihydro-5H-[1,6]naphthyridin-6-yl)-methanone (A, B, C, F) | 3-Methyl-benzo[b]-thiophene-2-carbaldehyde | | 4.26 | 2.29 min (a) | (M + H)$^+$ 475 |
| (3-Amino-pyrrolidin-1-yl)-(3-trifluoro-methyl-7,8-dihydro-5H-[1,6]naphthyridin-6-yl)-methanone (A, B, C, F) | Diphenyl-acetaldehyde | | 4.27 | 2.17 min (a) | (M + H)$^+$ 495 |
| (3-Amino-pyrrolidin-1-yl)-(3-trifluoro-methyl-7,8-dihydro-5H-[1,6]naphthyridin-6-yl)-methanone (A, B, C, F) | 2-Phenyl-propion-aldehyde | | 4.28 | 1.82 min (a) | (M + H)$^+$ 433 |
| (3-Amino-pyrrolidin-1-yl)-(3-trifluoro-methyl-7,8-dihydro-5H-[1,6]naphthyridin-6-yl)-methanone (A, B, C, F) | Phenylacet-aldehyde | | 4.29 | 1.70 min (a) | (M + H)$^+$ 419 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| [3-(3-Phenyl-propylamino)-pyrrolidin-1-yl]-(3-trifluoromethyl-7,8-dihydro-5H-[1,6]naphthyridin-6-yl)-methanone (A, B, C, F, E) | 3-Phenyl-propion-aldehyde | 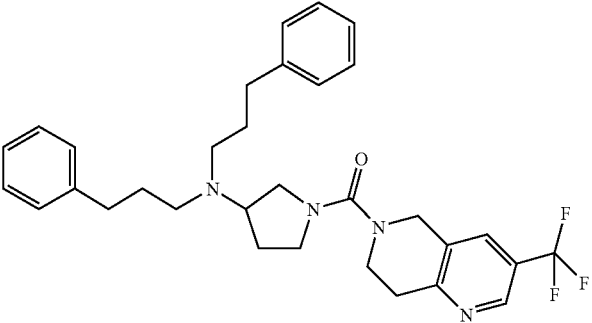 [SMILES: O=C(N1CCc2ncc(C(F)(F)F)cc2C1)N1CCC(N(CCCc2ccccc2)CCCc2ccccc2)C1] | 4.30 | 2.67 min (a) | (M + H)$^+$ 551 |
| [3-(3-Phenyl-butylamino)-pyrrolidin-1-yl]-(3-trifluoromethyl-7,8-dihydro-5H-[1,6]naphthyridin-6-yl)-methanone (A, B, C, F, E) | 3-Phenyl-butyraldehyde | 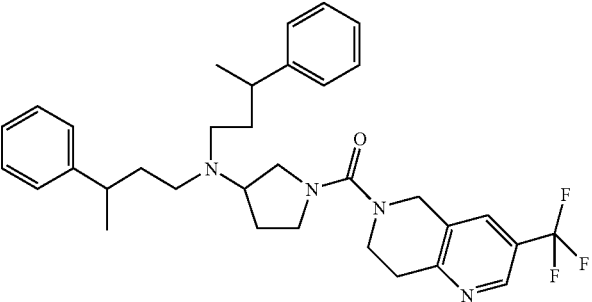 [SMILES: CC(CCN(CCC(C)c1ccccc1)C1CCN(C(=O)N2CCc3ncc(C(F)(F)F)cc3C2)C1)c1ccccc1] | 4.31 | 2.95 min (a) | (M + H)$^+$ 579 |
| {3-[(Naphthalen-2-ylmethyl)-amino]-pyrrolidin-1-yl}-(3-trifluoromethyl-7,8-dihydro-5H-[1,6]naphthyridin-6-yl)-methanone (A, B, C, F, E) | Naphthalene-2-carbaldehyde | 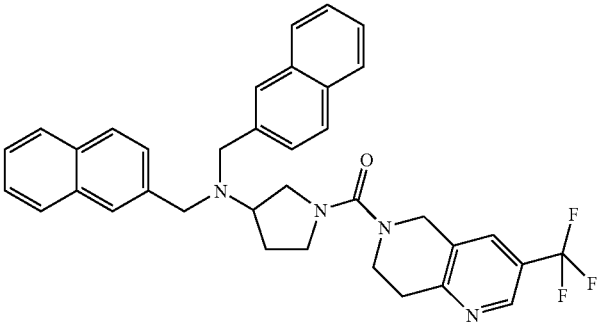 [SMILES: O=C(N1CCc2ncc(C(F)(F)F)cc2C1)N1CCC(N(Cc2ccc3ccccc3c2)Cc2ccc3ccccc3c2)C1] | 4.32 | 4.14 min (a) | (M + H)$^+$ 595 |
| {3-[(Pyridin-3-ylmethyl)-amino]-pyrrolidin-1-yl}-(3-trifluoromethyl-7,8-dihydro-5H-[1,6]naphthyridin-6-yl)-methanone (A, B, C, F, E) | Pyridine-3-carbaldehyde | 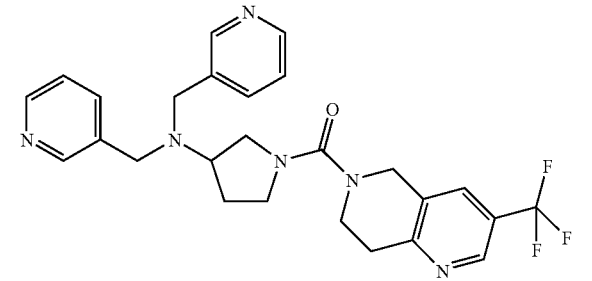 [SMILES: O=C(N1CCc2ncc(C(F)(F)F)cc2C1)N1CCC(N(Cc2cccnc2)Cc2cccnc2)C1] | 4.33 | 2.03 min (d) | (M + H)$^+$ 497 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| {3-[(1-Methyl-1H-indol-2-ylmethyl)-amino]-pyrrolidin-1-yl}-(3-trifluoro-methyl-7,8-dihydro-5H-[1,6]naphthyridin-6-yl)-methanone (A, B, C, F, E) | 1-Methyl-1H-indol-2-carbaldehyde | | 4.34 | 1.30 min (d) | (M + H)$^+$ 497 |
| {3-[(Benzofuran-2-ylmethyl)-amino]-pyrrolidin-1-yl}-(3-trifluoromethyl-7,8-dihydro-5H-[1,6]naphthyridin-6-yl)-methanone (A, B, C, F, E) | Benzofuran-2-carbaldehyde | | 4.35 | 1.37 min (d) | (M + H)$^+$ 525 |
| (3-Amino-pyrrolidin-1-yl)-(3-trifluoro-methyl-7,8-dihydro-5H-[1,6]naphthyridin-6-yl)-methanone (A, B, C, F) | 1-Pyridin-4-yl-ethanone | | 4.36 | 1.42 min (a) | (M + H)$^+$ 420 |
| (3-Amino-pyrrolidin-1-yl)-(3-trifluoro-methyl-7,8-dihydro-5H-[1,6]naphthyridin-6-yl)-methanone (A, B, C, F) | 1-Pyridin-3-yl-ethanone | | 4.37 | 1.39 min (a) | (M + H)$^+$ 420 |
| (3-Amino-pyrrolidin-1-yl)-(3-trifluoro-methyl-7,8-dihydro-5H-[1,6]naphthyridin-6-yl)-methanone (A, B, C, F) | Indan-1-one | | 4.38 | 1.61 min (a) | (M + H)$^+$ 431 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| (3-Amino-pyrrolidin-1-yl)-(3-trifluoro-methyl-7,8-dihydro-5H-[1,6]naphthyridin-6-yl)-methanone (A, B, C, F) | Indan-2-one | | 4.39 | 1.62 min (a) | (M + H)$^+$ 431 |
| (3-Amino-pyrrolidin-1-yl)-(3-trifluoro-methyl-7,8-dihydro-5H-[1,6]naphthyridin-6-yl)-methanone (A, B, C, F) | 6,7-Dihydro-5H-benzofuran-4-one | | 4.40 | 1.57 min (a) | (M + H)$^+$ 435 |
| (3-Amino-pyrrolidin-1-yl)-(3-trifluoro-methyl-7,8-dihydro-5H-[1,6]naphthyridin-6-yl)-methanone (A, B, C, F) | 1-Acetyl-piperidin-4-one | | 4.41 | 1.32 min (a) | (M + H)$^+$ 440 |
| (3-Amino-pyrrolidin-1-yl)-(3-trifluoro-methyl-7,8-dihydro-5H-[1,6]naphthyridin-6-yl)-methanone (A, B, C, F) | 3,4-Dihydro-2H-naphthalen-1-one | | 4.42 | 1.69 min (a) | (M + H)$^+$ 445 |
| (3-Amino-pyrrolidin-1-yl)-(3-trifluoro-methyl-7,8-dihydro-5H-[1,6]naphthyridin-6-yl)-methanone (A, B, C, F) | 6,7-Dihydro-5H-quinolin-8-one | | 4.43 | 1.53 min (a) | (M + H)$^+$ 446 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| (3-Amino-pyrrolidin-1-yl)-(3-trifluoro-methyl-7,8-dihydro-5H-[1,6]naphthyridin-6-yl)-methanone (A, B, C, F) | 4-Phenyl-cyclohexanone | | 4.44 | 2.20 min (e) | (M + H)$^+$ 473 |
| (3-Amino-pyrrolidin-1-yl)-(3-trifluoro-methyl-7,8-dihydro-5H-[1,6]naphthyridin-6-yl)-methanone (A, B, C, F) | 4-Methyl-cyclohexanone | | 4.45 | 1.92 min (e) | (M + H)$^+$ 411 |
| (3-Amino-pyrrolidin-1-yl)-(3-trifluoro-methyl-7,8-dihydro-5H-[1,6]naphthyridin-6-yl)-methanone (A, B, C, F) | 1-Pyridin-2-yl-ethanone | | 4.46 | 1.46 min (f) | (M + H)$^+$ 420 |
| (3-Amino-pyrrolidin-1-yl)-(3-trifluoro-methyl-7,8-dihydro-5H-[1,6]naphthyridin-6-yl)-methanone (A, B, C, F) | 1-Pyrazin-2-yl-ethanone | | 4.47 | 1.39 min (f) | (M + H)$^+$ 421 |
| (3-Amino-pyrrolidin-1-yl)-(3-trifluoro-methyl-7,8-dihydro-5H-[1,6]naphthyridin-6-yl)-methanone (A, B, C, F) | 2-Methoxy-cyclohexanone | | 4.48 | 1.79 min (e) | (M + H)$^+$ 427 |
| (3-Amino-pyrrolidin-1-yl)-(3-trifluoro-methyl-7,8-dihydro-5H-[1,6]naphthyridin-6-yl)-methanone (A, B, C, F) | 1-Pyridin-2-yl-propan-2-one | | 4.49 | 1.78 min (e) | (M + H)$^+$ 434 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| (3-Amino-pyrrolidin-1-yl)-(3-trifluoro-methyl-7,8-dihydro-5H-[1,6]naphthyridin-6-yl)-methanone (A, B, C, F) | 4-Pyrazol-1-yl-butan-2-one | 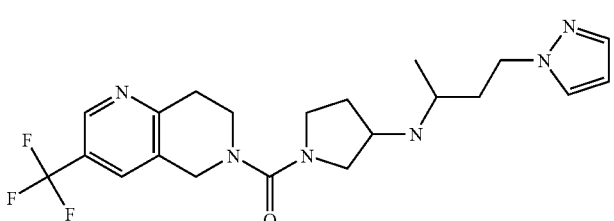 | 4.50 | 1.67 min (e) | (M + H)$^+$ 437 |
| (3-Amino-pyrrolidin-1-yl)-(3-trifluoro-methyl-7,8-dihydro-5H-[1,6]naphthyridin-6-yl)-methanone (A, B, C, F) | 5-Fluoro-indan-1-one | 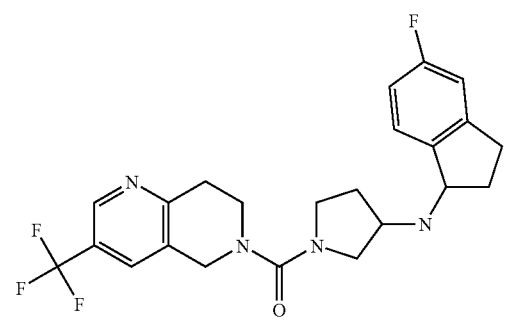 [SMILES: O=C(N1CCc2ncc(C(F)(F)F)cc2C1)N1CCC(NC2CCc3cc(F)ccc32)C1] | 4.51 | 1.61 min (f) | (M + H)$^+$ 449 |
| (3-Amino-pyrrolidin-1-yl)-(3-trifluoro-methyl-7,8-dihydro-5H-[1,6]naphthyridin-6-yl)-methanone (A, B, C, F) | 1-m-Tolyl-piperidin-4-one | 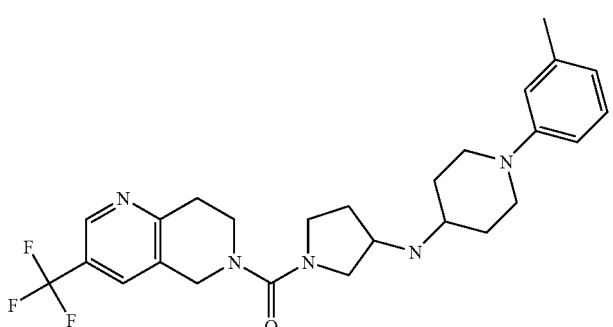 | 4.52 | 2.09 min (e) | (M + H)$^+$ 488 |
| (3-Amino-pyrrolidin-1-yl)-(3-trifluoro-methyl-7,8-dihydro-5H-[1,6]naphthyridin-6-yl)-methanone (A, B, C, F) | 1-Benzyl-piperidin-4-one | 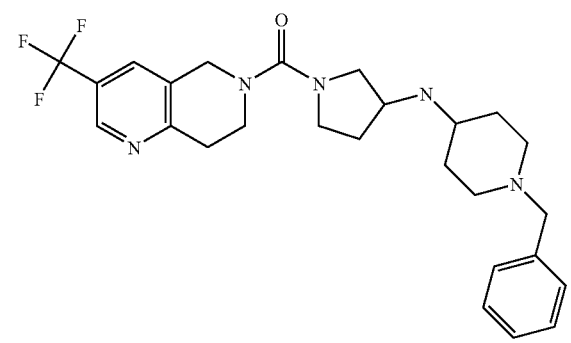 [SMILES: O=C(N1CCc2ncc(C(F)(F)F)cc2C1)N1CCC(NC2CCN(Cc3ccccc3)CC2)C1] | 4.53 | 1.39 min (f) | (M + H)$^+$ 488 |

TABLE 4-continued

Examples synthesized using general procedure E

| Amine | Aldehyde or ketone | Product | Ex. # | HPLC R_t (Method) | m/z or $^1$H NMR (d6 DMSO, 400 MHz) |
|---|---|---|---|---|---|
| (3-Amino-pyrrolidin-1-yl)-(3-trifluoro-methyl-7,8-dihydro-5H-[1,6]naphthyridin-6-yl)-methanone (A, B, C, F) | 1-Pyridin-2-ylmethyl-piperidin-4-one | | 4.54 | 1.28 min (f) | (M + H)$^+$ 489 |
| (3-Amino-pyrrolidin-1-yl)-(3-trifluoro-methyl-7,8-dihydro-5H-[1,6]naphthyridin-6-yl)-methanone (A, B, C, F) | 1-(4-Methoxy-phenyl)-piperidin-4-one | | 4.55 | 1.91 min (e) | (M + H)$^+$ 504 |
| (3-Amino-pyrrolidin-1-yl)-(3-trifluoro-methyl-7,8-dihydro-5H-[1,6]naphthyridin-6-yl)-methanone (A, B, C, F) | Benzofuran-3-one | | 4.56 | 2.01 min (e) | (M + H)$^+$ 433 |
| (3-Amino-pyrrolidin-1-yl)-(3-trifluoro-methyl-7,8-dihydro-5H-[1,6]naphthyridin-6-yl)-methanone (A, B, C, F) | 1-Methane-sulfonyl propan-2-one | | 4.57 | 1.44 min (f) | (M + H)$^+$ 435 |
| (3-Amino-pyrrolidin-1-yl)-(3-trifluoro-methyl-7,8-dihydro-5H-[1,6]naphthyridin-6-yl)-methanone (A, B, C, F) | (4-Oxo-piperidin-1-yl)-acetonitrile | | 4.58 | 1.39 min (f) | (M + H)$^+$ 437 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| (3-Amino-pyrrolidin-1-yl)-(3-trifluoro-methyl-7,8-dihydro-5H-[1,6]naphthyridin-6-yl)-methanone (A, B, C, F) | Chroman-4-one | | 4.59 | 1.71 min (f) | (M + H)$^+$ 447 |
| (3-Amino-pyrrolidin-1-yl)-(3-trifluoro-methyl-7,8-dihydro-5H-[1,6]naphthyridin-6-yl)-methanone (A, B, C, F) | 6-Fluoro-indan-1-one | | 4.60 | 1.69 min (f) | (M + H)$^+$ 449 |
| (3-Amino-pyrrolidin-1-yl)-(3-trifluoro-methyl-7,8-dihydro-5H-[1,6]naphthyridin-6-yl)-methanone (A, B, C, F) | 1-Pyrimidin-2-yl-piperidin-4-one | | 4.61 | 1.46 min (f) | (M + H)$^+$ 476 |
| (3-Amino-pyrrolidin-1-yl)-(3-trifluoro-methyl-7,8-dihydro-5H-[1,6]naphthyridin-6-yl)-methanone (A, B, C, F) | 1-Pyridin-4-ylmethyl-piperidin-4-one | | 4.62 | 1.34 min (f) | (M + H)$^+$ 489 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| (3-Amino-pyrrolidin-1-yl)-(3-trifluoro-methyl-7,8-dihydro-5H-[1,6]naphthyridin-6-yl)-methanone (A, B, C, F) | 6'-Fluoro-2,3,5,6-tetrahydro-[1,2']bipyridinyl-4-one | | 4.63 | 1.70 (f) | (M + H)$^+$ 493 |
| (3-Amino-pyrrolidin-1-yl)-(3-trifluoro-methyl-7,8-dihydro-5H-[1,6]naphthyridin-6-yl)-methanone (A, B, C, F) | 1-(2,6-Dichloro-benzyl)-piperidin-4-one | | 4.64 | 1.78 min (f) | (M + H)$^+$ 556 |
| (3-Amino-pyrrolidin-1-yl)-(3-trifluoro-methyl-7,8-dihydro-5H-[1,6]naphthyridin-6-yl)-methanone (A, B, C, F) | 1-(3,5-Dimethyl-phenyl)-piperidin-4-one | | 4.65 | 2.18 min (e) | (M + H)$^+$ 502 |
| (3-Amino-pyrrolidin-1-yl)-(3-trifluoro-methyl-7,8-dihydro-5H-[1,6]naphthyridin-6-yl)-methanone (A, B, C, F) | 4-tert-Butyl-cyclohexanone | | 4.66 | 2.23 min (e) | (M + H)$^+$ 453 |
| 2-Amino-1-[3-(4-phenyl-piperidin-1-yl)-pyrrolidin-1-yl]-ethanone (E, F, G, F) | 3,4-Dichloro-benzaldehyde | | 4.67 | 1.60 min (b) | (M + H)$^+$ 446 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| N-(2-(3-aminopyrrolidin-1-yl)-2-oxoethyl)-3,4-dichlorobenzamide (G, F) | dihydro-2H-pyran-4(3H)-one | | 4.68 | 1.64 min (a) | (M + H)$^+$ 400/402 |
| N-(2-(3-aminopyrrolidin-1-yl)-2-oxoethyl)-3,4-dichlorobenzamide (G, F) | 3-methyldihydro-2H-pyran-4(3H)-one | | 4.69 | 1.67 min (a) | (M + H)$^+$ 414/416 |
| N-(2-(3-aminopyrrolidin-1-yl)-2-oxoethyl)-3,4-dichlorobenzamide (G, F) | (R)-3-methoxydihydro-2H-pyran-4(3H)-one | | 4.70 | 1.64 min (a) | (M + H)$^+$ 430/432 |
| N-(2-(3-aminopyrrolidin-1-yl)-2-oxoethyl)-3,4-dichlorobenzamide (G, F) | 4-hydroxy-4-(6-methoxy-pyridin-3-yl)cyclohexanone | | 4.71 | 1.79 min (a) | (M + H)$^+$ 521/523 |
| 1-Piperazin-1-yl-ethanone | 3,4-Dichloro-N-[2-oxo-2-(3-oxo-pyrrolidin-1-yl)-ethyl]-benzamide (F, G) | | 4.72 | 1.46 min (a) | (M + H)$^+$ 428 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| Phenyl-piperazin-1-yl-methanone | 3,4-Dichloro-N-[2-oxo-2-(3-oxo-pyrrolidin-1-yl)-ethyl]-benzamide (F, G) | | 4.73 | 1.68 min (a) | (M + H)$^+$ 490 |
| 3H-spiro[isobenzo-furan-1,4'-piperidine] | 3,4-Dichloro-N-[2-oxo-2-(3-oxo-pyrrolidin-1-yl)-ethyl]-benzamide (F, G) | | 4.74 | 1.76 min (a) | (M + H)$^+$ 489 |
| spiro[indene-1,4'-piperidin]-3(2H)-one | 3,4-Dichloro-N-[2-oxo-2-(3-oxo-pyrrolidin-1-yl)-ethyl]-benzamide (F, G) | | 4.75 | 1.65 min (a) | (M + H)$^+$ 501 |
| 2,8-diazaspiro[4.5]-decan-1-one | 3,4-Dichloro-N-[2-oxo-2-(3-oxo-pyrrolidin-1-yl)-ethyl]-benzamide (F, G) | | 4.76 | 1.42 min (a) | (M + H)$^+$ 454 |
| 2-methyl-2,8-diazaspiro[4.5]-decan-1-one | 3,4-Dichloro-N-[2-oxo-2-(3-oxo-pyrrolidin-1-yl)-ethyl]-benzamide (F, G) | | 4.77 | 1.46 min (a) | (M + H)$^+$ 468 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| thiomorpholine | 3,4-Dichloro-N-[2-oxo-2-(3-oxo-pyrrolidin-1-yl)-ethyl]-benzamide (F, G) | | 4.78 | 1.52 min (a) | (M + H)$^+$ 403 |
| Thiomorpholine 1,1-dioxide | 3,4-Dichloro-N-[2-oxo-2-(3-oxo-pyrrolidin-1-yl)-ethyl]-benzamide (F, G) | | 4.78 | 1.59 min (a) | (M + H)$^+$ 435 |
| 2-methylmorpholine | 3,4-Dichloro-N-[2-oxo-2-(3-oxo-pyrrolidin-1-yl)-ethyl]-benzamide (F, G) | | 4.80 | 1.51 min (a) | (M + H)$^+$ 401 |
| 1-phenylpiperazin-2-one | 3,4-Dichloro-N-[2-oxo-2-(3-oxo-pyrrolidin-1-yl)-ethyl]-benzamide (F, G) | | 4.81 | 1.70 min (a) | (M + H)$^+$ 476 |
| spiro[chroman-4,4'-piperidine] | 3,4-Dichloro-N-[2-oxo-2-(3-oxo-pyrrolidin-1-yl)-ethyl]-benzamide (F, G) | | 4.82 | 1.91 min (a) | (M + H)$^+$ 503 |

TABLE 4-continued

Examples synthesized using general procedure E

| Amine | Aldehyde or ketone | Product | Ex. # | HPLC R$_t$ (Method) | m/z or ¹H NMR (d6 DMSO, 400 MHz) |
|---|---|---|---|---|---|
| 3,3-difluoropiperidine | 3,4-dichloro-N-(2-oxo-2-(3-oxopyrrolidin-1-yl)ethyl)-benzamide (K, L, G) | | 4.83 | 2.34 min (b) | (M + H)⁺ 420 |
| ((3S,4R)-4-(4-fluorophenyl)-piperidin-3-yl)methanol | 3,4-dichloro-N-(2-oxo-2-(3-oxopyrrolidin-1-yl)ethyl)-benzamide (K, L, G) | Chiral | 4.84 | 1.99 min (b) | (M + H)⁺ 508 |
| 4,4-difluoropiperidine | 3,4-dichloro-N-(2-oxo-2-(3-oxopyrrolidin-1-yl)ethyl)-benzamide (K, L, G) | | 4.85 | 2.19 min (b) | (M + H)⁺ 420 |
| 4-(1H-pyrazol-1-yloxy)piperidine (H, I, F) | 3,4-dichloro-N-(2-oxo-2-(3-oxopyrrolidin-1-yl)ethyl)-benzamide (K, L, G) | | 4.86 | 1.77 min. (b) | (M + H)⁺ 466 |
| 4-fluoro-4-phenylpiperidine | 3,4-dichloro-N-(2-oxo-2-(3-oxopyrrolidin-1-yl)ethyl)-benzamide (K, L, G) | | 4.87 | 2.4 min. (b) | (M + H)⁺ 478 |
| 1-(Piperidin-4-yl)-1H-indole | 1-(2-(6,7-Dichloro-quinazolin-4-ylamino)-acetyl)-pyrrolidin-3-one (Preparation #32) | | 4.88 | 2.51 min (a) | (M + H)⁺ 523/525 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| 4-(Pyridin-2-yl)piperidin-4-ol | 1-(2-(6,7-Dichloro-quinazolin-4-ylamino)-acetyl)-pyrrolidin-3-one (Preparation #32) | | 4.89 | 1.73 min (a) | (M + H)$^+$ 501/503 |
| 2,2,2-Trifluoro-N-(piperidin-4-ylmethyl)-acetamide | 1-(2-(6,7-Dichloro-quinazolin-4-ylamino)-acetyl)-pyrrolidin-3-one (Preparation #32) | | 4.90 | 1.93 min (a) | (M + H)$^+$ 533/535 |
| 3-(Piperidin-4-yl)-1H-pyrrolo[2,3-b]pyridine | 1-(2-(6,7-Dichloro-quinazolin-4-ylamino)-acetyl)-pyrrolidin-3-one (Preparation #32) | | 4.91 | 1.86 min (a) | (M + H)$^+$ 524/526 |
| 6-Fluoro-3-(piperidin-4-yl)-1H-indole | 1-(2-(6,7-Dichloro-quinazolin-4-ylamino)-acetyl)-pyrrolidin-3-one (Preparation #32) | | 4.92 | 2.21 min (a) | (M + H)$^+$ 541/543 |
| 2-(Piperidin-4-yloxy)pyridine | 1-(2-(6,7-Dichloro-quinazolin-4-ylamino)-acetyl)-pyrrolidin-3-one (Preparation #32) | | 4.93 | 1.92 min (a) | (M + H)$^+$ 501/503 |
| 4-(2H-1,2,3-Triazol-2-yl)piperidine (H, I, F) | 1-(2-(6,7-Dichloro-quinazolin-4-ylamino)-acetyl)-pyrrolidin-3-one (Preparation #32) | | 4.94 | 1.79 min (a) | (M + H)$^+$ 475/477 |
| 4-(1H-1,2,4-Triazol-1-yl)piperidine (H, I, F) | 1-(2-(6,7-Dichloro-quinazolin-4-ylamino)-acetyl)-pyrrolidin-3-one (Preparation #32) | | 4.95 | 1.76 min (a) | (M + H)$^+$ 475/477 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| 1-(Piperidin-4-yl)pyridin-2(1H)-one (H, I, F) | 1-(2-(6,7-Dichloro-quinazolin-4-ylamino)-acetyl)-pyrrolidin-3-one (Preparation #31) | | 4.96 | 1.79 min (a) | (M − H)$^-$ 499/501 |
| 2-methylpiperidine | 3,4-dichloro-N-(2-oxo-2-(3-oxopyrrolidin-1-yl)ethyl)-benzamide (K) | | 4.97 | 1.72 min (a) | (M + H)$^+$ 398 |
| 2-(piperidin-4-yl)pyridine (U, V, F) | 3,4-dichloro-N-(2-oxo-2-(3-oxopyrrolidin-1-yl)ethyl)-benzamide (K) | | 4.98 | 1.79 min (a) | (M + H)$^+$ 461 |
| 4-(4-fluorophenyl)-1,2,3,6-tetrahydropyridine | 3,4-dichloro-N-(2-oxo-2-(3-oxopyrrolidin-1-yl)ethyl)-benzamide (K) | | 4.99 | 2.29 min (a) | (M + H)$^+$ 476 |
| 2-(piperidin-4-yl)pyridine 1-oxide | 3,4-dichloro-N-(2-oxo-2-(3-oxopyrrolidin-1-yl)ethyl)-benzamide (K) | | 4.100 | 1.61 min (a) | (M + H)$^+$ 477 |
| 7-Piperidine-4-yl-1H-indole (U, V) | 3,4-dichloro-N-(2-oxo-2-(3-oxopyrrolidin-1-yl)ethyl)-benzamide (K) | | 4.101 | 2.20 min (a) | (M + H)$^+$ 499 |
| 2-methoxy-5-(piperidin-4-yl)pyrimidine (U, V) | 3,4-dichloro-N-(2-oxo-2-(3-oxopyrrolidin-1-yl)ethyl)-benzamide (K) | | 4.102 | 1.75 min (a) | (M + H)$^+$ 492 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| 8-(piperidin-4-yl)-1,2,3,4-tetrahydro-quinoline (U, V, F) | 3,4-dichloro-N-(2-oxo-2-(3-oxopyrrolidin-1-yl)ethyl)-benzamide (K) | | 4.103 | 2.18 min (a) | (M + H)$^+$ 515 |
| 3-methoxy-6-(piperidin-4-yl)pyridazine (U, V, F) | 3,4-dichloro-N-(2-oxo-2-(3-oxopyrrolidin-1-yl)ethyl)-benzamide (K) | | 4.104 | 1.79 min (a) | (M + H)$^+$ 492 |
| 2-(1,2,3,6-tetrahydro-pyridin-4-yl)benzonitrile (U, F) | 3,4-dichloro-N-(2-oxo-2-(3-oxopyrrolidin-1-yl)ethyl)-benzamide (K) | | 4.105 | 2.22 min (a) | (M + H)$^+$ 483 |
| 4-(1,2,3,6-tetrahydro-pyridin-4-yl)benzo[d]-thiazol-2-amine (U, V, F) | 3,4-dichloro-N-(2-oxo-2-(3-oxopyrrolidin-1-yl)ethyl)-benzamide (K) | | 4.106 | 2.04 min (a) | (M + H)$^+$ 530 |
| 2-(piperidin-4-yl)pyrimidine (U, V, F) | 3,4-dichloro-N-(2-oxo-2-(3-oxopyrrolidin-1-yl)ethyl)-benzamide (K) | | 4.107 | 1.70 min (a) | (M + H)$^+$ 462 |
| 5-(1,2,3,6-tetrahydro-pyridin-4-yl)picolinonitrile (U, V, F) | 3,4-dichloro-N-(2-oxo-2-(3-oxopyrrolidin-1-yl)ethyl)-benzamide (K) | | 4.108 | 2.03 min (a) | (M + H)$^+$ 484 |
| 2-methoxy-6-(piperidin-4-yl)pyridine (U, V, F) | 3,4-dichloro-N-(2-oxo-2-(3-oxopyrrolidin-1-yl)ethyl)-benzamide (K) | | 4.109 | 2.08 min (a) | (M + H)$^+$ 491 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| 2-methoxy-5-(piperidin-4-yl)pyridine (U, V, F) | 3,4-dichloro-N-(2-oxo-2-(3-oxopyrrolidin-1-yl)ethyl)-benzamide (K) | | 4.110 | 2.13 min (a) | (M + H)$^+$ 491 |
| 4-(1,3,5-trimethyl-1H-pyrazol-4-yl)piperidine (U, V, F) | 3,4-dichloro-N-(2-oxo-2-(3-oxopyrrolidin-1-yl)ethyl)-benzamide (K) | | 4.111 | 2.20 min (a) | (M + H)$^+$ 492 |
| 3-methoxy-5-(piperidin-4-yl)pyridine (U, V, F) | 3,4-dichloro-N-(2-oxo-2-(3-oxopyrrolidin-1-yl)ethyl)-benzamide (K) | | 4.112 | 2.11 min (a) | (M + H)$^+$ 491 |
| 2,4-dimethoxy-5-(piperidin-4-yl)pyrimidine (U, V, F) | 3,4-dichloro-N-(2-oxo-2-(3-oxopyrrolidin-1-yl)ethyl)-benzamide (K) | | 4.113 | 1.83 min (a) | (M + H)$^+$ 522 |
| (4-phenylpiperidin-4-yl)methanol (preparation #31) | 3,4-dichloro-N-(2-oxo-2-(3-oxopyrrolidin-1-yl)ethyl)-benzamide (K) | | 4.114 | 1.83 min (a) | (M + H)$^+$ 490 |
| 3-phenyl-8-azabicyclo[3.2.1]-octan-3-ol (O, F) | 3,4-dichloro-N-(2-oxo-2-(3-oxopyrrolidin-1-yl)ethyl)-benzamide (K) | | 4.115 | 1.86 min (a) | (M + H)$^+$ 502 |
| 3-phenyl-9-azabicyclo[3.3.1]-nonan-3-ol (O, F) | 3,4-dichloro-N-(2-oxo-2-(3-oxopyrrolidin-1-yl)ethyl)-benzamide (K) | | 4.116 | 1.72 min (a) | (M + H)$^+$ 516 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| 9-phenyl-3-oxa-7-azabicyclo[3.3.1]-nonan-9-ol (O, F) | 3,4-dichloro-N-(2-oxo-2-(3-oxopyrrolidin-1-yl)ethyl)-benzamide (K) | 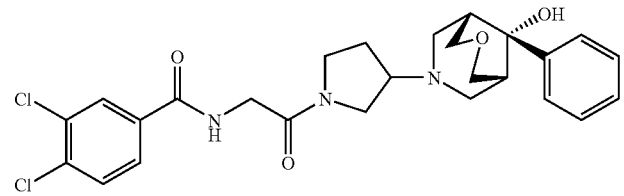 [SMILES: O=C(NCC(=O)N1CCC(N2C[C@H]3COC[C@@H](C2)[C@]3(O)c2ccccc2)C1)c1ccc(Cl)c(Cl)c1] | 4.117 | 1.85 min (a) | (M + H)$^+$ 518 |
| 9-phenyl-3-oxa-7-azabicyclo[3.3.1]-nonan-9-ol (O, F) | 3,4-dichloro-N-(2-oxo-2-(3-oxopyrrolidin-1-yl)ethyl)-benzamide (K) | 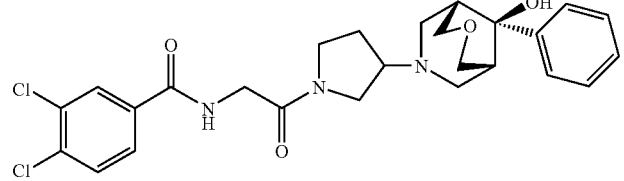 | 4.118 | 1.78 min (a) | (M + H)$^+$ 518 |
| 4-(1H-indol-7-yl)piperidin-4-ol (O, AA) | 1-(2-(6,7-Dichloro-quinazolin-4-ylamino)-acetyl)-pyrrolidin-3-one (Preparation #32) | 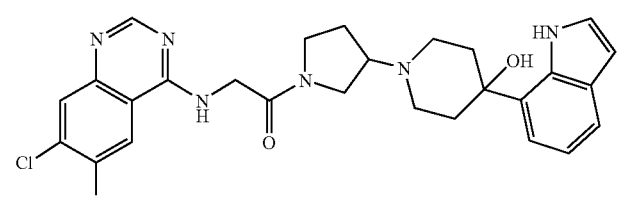 | 4.119 | 1.94 min (a) | (M + H)$^+$ 539 |
| (R)-1-(3-aminopyrrolidin-1-yl)-2-(6,7-dichloro-quinazolin-4-ylamino)ethanone (M, F) | dihydro-2H-pyran-4(3H)-one | 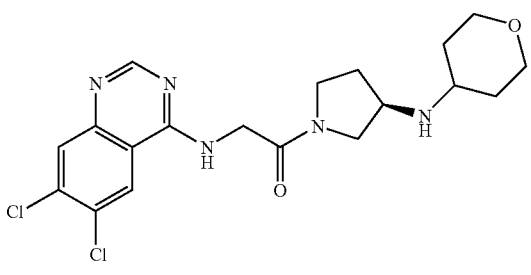 [SMILES: O=C(CNc1ncnc2cc(Cl)c(Cl)cc12)N1CC[C@@H](NC2CCOCC2)C1] | 4.120 | 1.50 min (b) | (M + H)$^+$ 424 |
| (R)-1-(3-aminopyrrolidin-1-yl)-2-(6,7-dichloro-quinazolin-4-ylamino)ethanone (M, F) | dihydrofuran-3(2H)-one | 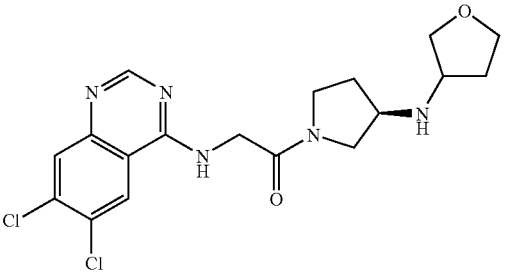 [SMILES: O=C(CNc1ncnc2cc(Cl)c(Cl)cc12)N1CC[C@@H](NC2CCOC2)C1] | 4.121 | 1.43 min (b) | (M + H)$^+$ 410 |
| (R)-1-(3-aminopyrrolidin-1-yl)-2-(6,7-dichloro-quinazolin-4-ylamino)ethanone (M, F) | 2-methyldihydrofuran-3(2H)-one | 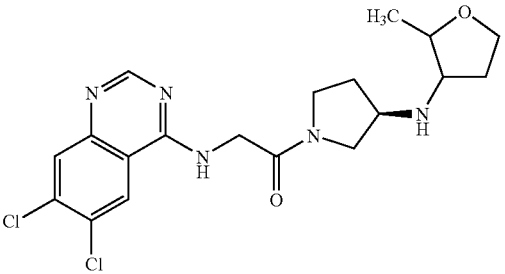 [SMILES: CC1OCCC1N[C@@H]1CCN(C(=O)CNc2ncnc3cc(Cl)c(Cl)cc23)C1] | 4.122 | 1.52 min (b) | (M + H)$^+$ 424 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| (R)-1-(3-aminopyrrolidin-1-yl)-2-(6,7-dichloro-quinazolin-4-ylamino)ethanone (M, F) | dihydro-2H-pyran-3(4H)-one | 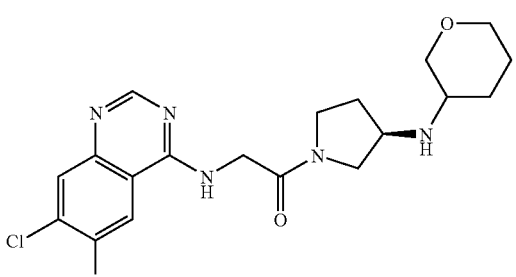 | 4.123 | 1.52 min (b) | (M + H)$^+$ 424 |
| (R)-1-(3-aminopyrrolidin-1-yl)-2-(6,7-dichloro-quinazolin-4-ylamino)ethanone (M, F) | 2,2-dimethyldi-hydro-2H-pyran-4(3H)-one | 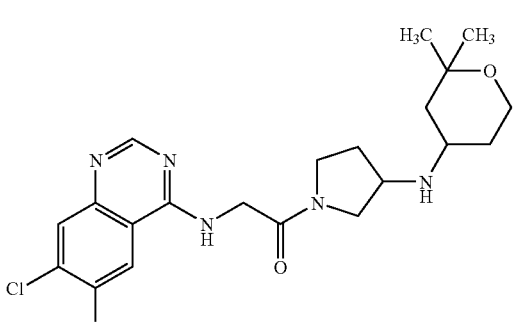 | 4.124 | 1.55 min (b) | (M + H)$^+$ 452 |
| (R)-1-(3-aminopyrrolidin-1-yl)-2-(6,7-dichloro-quinazolin-4-ylamino)ethanone (M, F) | 2,2-dimethyl-tetrahydro-2H-pyran-4-carbaldehyde | 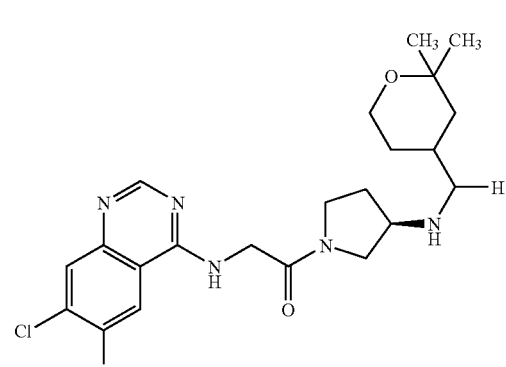 | 4.125 | 1.55 min (b) | (M + H)$^+$ 452 |
| (R)-1-(3-aminopyrrolidin-1-yl)-2-(6,7-dichloro-quinazolin-4-ylamino)ethanone (M, F) | dihydro-thiophen-3(2H)-one | 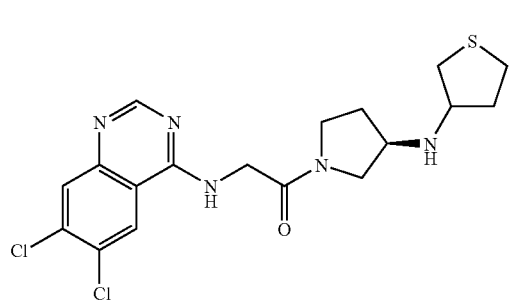 | 4.126 | 1.52 min (b) | (M + H)$^+$ 426 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| (R)-1-(3-aminopyrrolidin-1-yl)-2-(6,7-dichloro-quinazolin-4-ylamino)ethanone (M, F) | dihydro-2H-thiopyran-4(3H)-one | | 4.127 | 1.57 min (b) | (M + H)$^+$ 440 |
| (R)-1-(3-aminopyrrolidin-1-yl)-2-(6,7-dichloro-quinazolin-4-ylamino)ethanone (M, F) | 2-methyldi-hydrothiophen-3(2H)-one | | 4.128 | 1.65 min (b) | (M + H)$^+$ 440 |
| (R)-1-(3-aminopyrrolidin-1-yl)-2-(6,7-dichloro-quinazolin-4-ylamino)ethanone (M, F) | 4-oxotetra-hydrothiophene-3-carbonitrile | | 4.129 | 1.97 min (b) | (M + H)$^+$ 451 |
| (R)-1-(3-aminopyrrolidin-1-yl)-2-(6,7-dichloro-quinazolin-4-ylamino)ethanone (M, F) | cyclohexanone | | 4.130 | 1.63 min (b) | (M + H)$^+$ 422 |
| (R)-1-(3-aminopyrrolidin-1-yl)-2-(6,7-dichloro-quinazolin-4-ylamino)ethanone (M, F) | (R)-3-methylcyclo-hexanone | | 4.131 | 1.68 min (b) | (M + H)$^+$ 436 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| (R)-1-(3-aminopyrrolidin-1-yl)-2-(6,7-dichloroquinazolin-4-ylamino)ethanone (M, F) | 2,6-diphenyl-dihydro-2H-thiopyran-4(3H)-one | | 4.132 | 2.26 min (b) | (M + H)$^+$ 592 |
| (R)-1-(3-aminopyrrolidin-1-yl)-2-(6,7-dichloroquinazolin-4-ylamino)ethanone (M, F) | 2,6-diphenyl-dihydro-2H-thiopyran-4(3H)-one | | 4.133 | 2.41 min (b) | (M + H)$^+$ 592 |
| (R)-1-(3-aminopyrrolidin-1-yl)-2-(6,7-dichloroquinazolin-4-ylamino)ethanone (M, F) | (R)-3-phenylcyclohexanone | | 4.134 | 1.86 min (b) | (M + H)$^+$ 498 |
| (R)-1-(3-aminopyrrolidin-1-yl)-2-(6,7-dichloroquinazolin-4-ylamino)ethanone (M, F) | (S)-3-phenylcyclohexanone | | 4.135 | 1.84 min (b) | (M + H)$^+$ 498 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| (R)-1-(3-aminopyrrolidin-1-yl)-2-(6,7-dichloro-quinazolin-4-ylamino)ethanone (M, F) | cyclopenta-none | | 4.136 | 1.56 min (b) | (M + H)$^+$ 408 |
| (R)-1-(3-aminopyrrolidin-1-yl)-2-(6,7-dichloro-quinazolin-4-ylamino)ethanone (M, F) | (S)-3-methylcyclo-pentanone | | 4.137 | 1.64 min (b) | (M + H)$^+$ 422 |
| (R)-1-(3-aminopyrrolidin-1-yl)-2-(6,7-dichloro-quinazolin-4-ylamino)ethanone (M, F) | (S)-3-phenylcyclo-pentanone | | 4.138 | 1.80 min (b) | (M + H)$^+$ 484 |
| (R)-1-(3-aminopyrrolidin-1-yl)-2-(6,7-dichloro-quinazolin-4-ylamino)ethanone (M, F) | 4-phenylcyclo-hexanone | | 4.139 | 1.83 min (b) | (M + H)$^+$ 498 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| (R)-1-(3-aminopyrrolidin-1-yl)-2-(6,7-dichloro-quinazolin-4-ylamino)ethanone (M, F) | 1-phenyl-piperidin-4-one | | 4.140 | 1.72 min (b) | (M + H)$^+$ 499 |
| (R)-1-(3-aminopyrrolidin-1-yl)-2-(6,7-dichloro-quinazolin-4-ylamino)ethanone (M, F) | 1-(6-fluoropyridin-2-yl)piperidin-4-one | | 4.141 | 1.74 min (b) | (M + H)$^+$ 518 |
| (R)-1-(3-aminopyrrolidin-1-yl)-2-(6,7-dichloro-quinazolin-4-ylamino)ethanone (M, F) | 1,1-Dioxo-tetrahydro-λ6-thiopyran-4-one | | 4.142 | 1.53 min (b) | (M + H)$^+$ 472 |
| (R)-1-(3-aminopyrrolidin-1-yl)-2-(6,7-dichloro-quinazolin-4-ylamino)ethanone (M, F) | 4-methylcyclo-hexanone | | 4.143 | 1.70 min (b) | (M + H)$^+$ 436 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| (R)-1-(3-aminopyrrolidin-1-yl)-2-(6,7-dichloro-quinazolin-4-ylamino)ethanone (M, F) | 3-methylcyclo-hexanone | | 4.144 | 1.70 min (b) | (M + H)$^+$ 436 |
| (R)-1-(3-aminopyrrolidin-1-yl)-2-(6,7-dichloro-quinazolin-4-ylamino)ethanone (M, F) | 2,2-dimethyl-5-phenyldi-hydrofuran-3(2H)-one | | 4.145 | 1.95 min (b) | (M + H)$^+$ 514 |
| (R)-1-(3-aminopyrrolidin-1-yl)-2-(6,7-dichloro-quinazolin-4-ylamino)ethanone (M, F) | | | 4.146 | 1.95 min (a) | (M + H)$^+$ 458 |
| 4-(2-aminobenzo[d]-thiazol-4-yl)piperidin-4-ol (O, F) | 3,4-dichloro-N-(2-oxo-2-(3-oxopyrrolidin-1-yl)ethyl)-benzamide (K) | | 4.147 | 2.05 min (a) | (M + H)$^+$ 572 |

TABLE 4-continued

Examples synthesized using general procedure E

| Amine | Aldehyde or ketone | Product | Ex. # | HPLC R$_t$ (Method) | m/z or $^1$H NMR (d6 DMSO, 400 MHz) |
|---|---|---|---|---|---|
| (R)-1-(3-aminopyrrolidin-1-yl)-2-(6,7-dichloro-quinazolin-4-ylamino)ethanone (M, F) | dihydro-2H-pyran-4(3H)-one | | 4.148 | 1.86 min (a) | (M + H)$^+$ 425 |
| 2-Piperidin-4-yl-phenylamine | 3,4-Dichloro-N-[2-oxo-2-(3-oxo-pyrrolidin-1-yl)-ethyl]-benzamide (K, G) | | 4.149 | 1.65 min (a) | (M + H)$^+$ 475 |
| 2-Piperidin-4-yl-benzoic acid (F) | 3,4-Dichloro-N-[2-oxo-2-(3-oxo-pyrrolidin-1-yl)-ethyl]-benzamide (K, G) | | 4.150 | 1.46 min. (a) | (M + H)$^+$ 504 |
| spiro[indoline-3,4'-piperidine] | 1-(2-(6,7-Dichloro-quinazolin-4-ylamino)-acetyl)-pyrrolidin-3-one (Preparation #32) | | 4.151 | 1.71 min. (a) | (M + H)$^+$ 512 |
| 5-fluorospiro-[indoline-3,4'-piperidine] | 1-(2-(6,7-Dichloro-quinazolin-4-ylamino)-acetyl)-pyrrolidin-3-one (Preparation #32) | | 4.152 | 1.79 min. (a) | (M + H)$^+$ 531 |

EXAMPLE 4.1.53

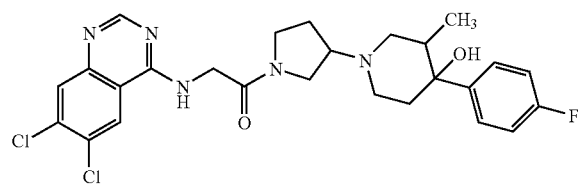 [SMILES: CC1CN(C2CCN(C(=O)CNc3ncnc4cc(Cl)c(Cl)cc34)C2)CCC1(O)c1ccc(F)cc1]

2-(6,7-dichloroquinazolin-4-ylamino)-1-(3-(4-(4-fluorophenyl)-4-hydroxy-3-methylpiperidin-1-yl)pyrrolidin-1-yl)ethanone was prepared as a mixture of 4 isomers from (3S,4R)-4-(4-fluorophenyl)-3-methylpiperidin-4-ol (prepared via general procedure O, AA) and 1-(2-(6,7-Dichloroquinazolin-4-ylamino)acetyl)pyrrolidin-3-one (Preparation #32) according to general procedure E then purified via chiral preparative NP-HPLC (isocratic 2.5% methanol:2.5% ethanol:95% heptane:0.1% diethylamine modifier at 16 mL/min, room temperature; UV detection monitored at 265 nm; Daicel AD-H column, 20×250 mm, 5 um particle) to yield two products. Product A eluted at $R_t$ 7.5-11 min. Product B eluted at $R_t$ 11-15 min. Product A has a positive optical rotation and product B has a negative optical rotation. Product A was further separated via chiral preparative NP-HPLC (isocratic 10% methanol:10% ethanol:80% heptane:0.1% diethylamine modifier at 14 mL/min, room temperature; UV detection monitored at 265 nm; Daicel OD-H column, 20×250 mm, 5 um particle) to yield two isomers. Isomer 1 eluted at $R_t$ 14-16.3 min. Isomer 2 eluted at $R_t$ 16.3-19 min. Both isomers have positive optical rotation. The absolute stereochemistry of the isomers was not assigned. Isomers 1 & 2: RP-HPLC (Table 1, Method a) $R_t$ 1.99 min; m/z: (M+H)$^+$ 532. Product B was further separated via chiral preparative NP-HPLC (isocratic 10% methanol:10% ethanol:80% heptane:0.1% diethylamine modifier at 14 mL/min, room temperature; UV detection monitored at 265 nm; Daicel OD-H column, 20×250 mm, 5 um particle) to yield two isomers. Isomer 3 eluted at $R_t$ 13.3-16 min. Isomer 4 eluted at $R_t$ 16.3-19 min. Both isomers have negative optical rotation. The absolute stereochemistry of the isomers was not assigned. Isomers 3 & 4: RP-HPLC (Table 1, Method a) $R_t$ 1.92 min; m/z: (M+H)$^+$ 532.

General Procedure F: Deprotection of a Boc-amine.

A mixture of the Boc-amine (preferably 1 equivalent) in an organic solvent (preferably dioxane when HCl is used, DCM when TFA is used) and an acid (TFA or HCl$_3$) is stirred at about 20-100° C. (preferably about 20° C.) for about 0.5 to 60 hours (preferably about 16 hours). The product can then be isolated by filtration and further purified by crystallization, trituration or chromatography.

Illustration of General Procedure F

Preparation #7:
4-Phenyl-1-pyrrolidin-3-yl-piperidine dihydrochloride

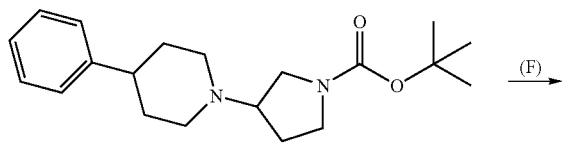

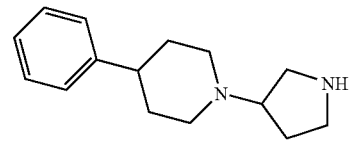

A solution of 3-(4-phenyl-piperidin-1-yl)-pyrrolidine-1-carboxylic acid tert-butyl ester (preparation #5) (4.3 g, 13.1 mmol) in 4N HCl/dioxane (7 mL) was stirred at ambient temperature for about 16 h. The precipitate was collected by filtration, rinsed with Et$_2$O (20 mL) and dried in vacuo to afford 4-phenyl-1-pyrrolidin-3-yl-piperidine dihydrochloride (2.4 g, 61%) as a hygroscopic beige solid that was used in subsequent reaction without further purification. RP-HPLC (Table 1, Method d) $R_t$ 1.67 min; m/z: (M+H)$^+$ 231.

Illustration of General Procedure F

Preparation #8: (3-Amino-pyrrolidin-1-yl)-(3-trifluoromethyl-7,8-dihydro-5H-[1,6]naphthyridin-6-yl)-methanone hydrochloride

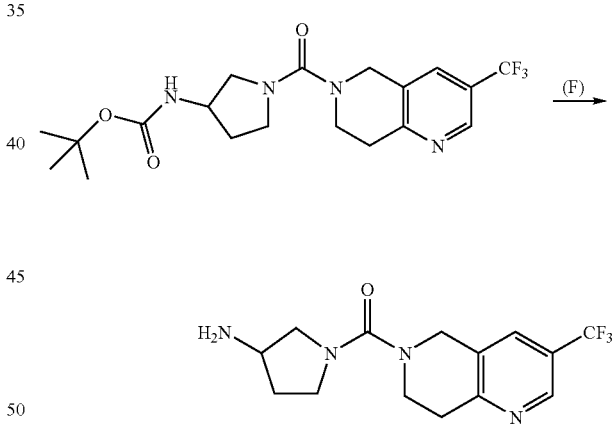

A solution of [1-(3-trifluoromethyl-7,8-dihydro-5H-[1,6]naphthyridine-6-carbonyl)-pyrrolidin-3-yl]-carbamic acid tert-butyl ester (preparation #5) (4.91 g, 11.8 mmol) in 4NHCl/dioxane (16 mL) was stirred at ambient temperature for about 16 h. The liquid was decanted and the residue was triturated with isopropyl acetate. The precipitate was collected by filtration and dried (high vacuum) to afford (3-amino-pyrrolidin-1-yl)-(3-trifluoromethyl-7,8-dihydro-5H-[1,6]naphthyridin-6-yl)-methanone hydrochloride (4.42 g, 100%) as a peach solid; RP-HPLC (Table 1, Method a) $R_t$ 1.40 min; m/z: (M+H)$^+$ 315.

Illustration of General Procedure F

Preparation #9: 2-Amino-1-[3-(4-phenyl-piperidin-1-yl)-pyrrolidin-1-yl]-ethanone

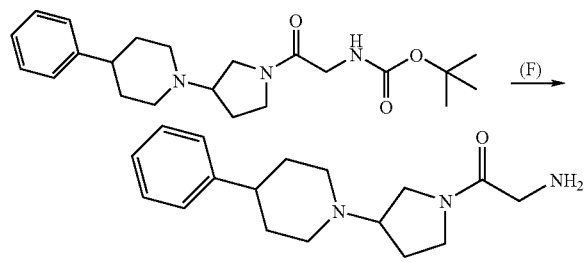

To a solution of {2-oxo-2-[3-(4-phenyl-piperidin-1-yl)-pyrrolidin-1-yl]-ethyl}-carbamic acid tert-butyl ester (preparation #10) (3.25 g, 8.39 mmol) in DCM (200 mL) was added TFA (15 mL). The reaction mixture was stirred at ambient temperature for about 5 h. Toluene (100 mL) was added and the solvents were removed in vacuo. The residue was dissolved in DCM (400 mL) and the organic was washed with saturated NaHCO$_3$, 1.0N NaOH, brine, dried over MgSO$_4$, filtered and concentrated in vacuo to give 2-amino-1-[3-(4-phenyl-piperidin-1-yl)-pyrrolidin-1-yl]-ethanone (2.34 g, 97%) as a light tan solid; RP-HPLC (Table 1, Method a) R$_t$ 1.09 min; m/z: (M+H)$^+$ 288.

General Procedure G: Formation of an Amide by Peptide Coupling.

To a mixture of PS-carbodiimide resin (1 to 10 equivalents, preferably 3 equivalents) or a coupling reagent (EDC, DCC, preferably EDC), an acid (1 to 10 equivalents, preferably 1 equivalent), HOBT (1 to 10 equivalents, preferably 1 equivalent) and an amine (1 to 10 equivalents, preferably 1.25 equivalents) in an organic solvent (preferably DMA when PS-carbodiimide was used, DCM when coupling reagent was used) is added a base (preferably DIEA, 1 to 10 equivalents, preferably 4 equivalents). The reaction mixture is stirred at about 20° C. to 100° C. (preferably about 65° C. when PS-carbodiimide was used, about 20° C. when coupling reagent was used) for about 2 to 24 hours (preferably about 12 hours) or at about 20° C. to 150° C. (preferably about 100° C.) in the microwave (CEM Explorer, maximum power) for about 1 to 30 minutes (preferably about 7 minutes). The reaction mixture is concentrated in vacuo. The residue can be purified by chromatography or crystallization.

Illustration of General Procedure G:

EXAMPLE #3

3,4-Dichloro-N-(2-oxo-2-(3-(4-phenylpiperidin-1-yl)pyrrolidin-1-yl)benzamide

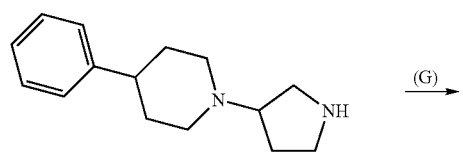

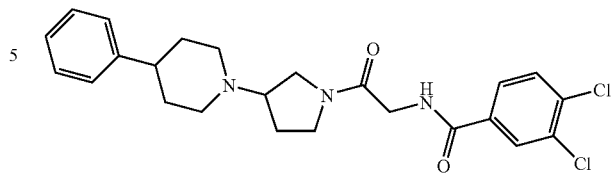

To a mixture of PS-carbodiimide resin (0.153 g, 0.243 mmol), 2-(3,4-dichlorobenzamido)acetic acid (preparation #14) (0.02 g, 0.081 mmol), HOBT (0.011 g, 0.081 mmol) and 4-phenyl-1-(pyrrolidin-3-yl)piperidine (preparation #7) (0.023 g, 1.01 mmol) in DMA (1.5 mL) was added DIEA (0.057 mL, 0.324 mmol). The reaction mixture was heated at about 100° C. in the microwave (CEM Explorer, maximum power 300 W) for about 7 minutes. The reaction mixture was concentrated in vacuo and the crude residue purified by RP-HPLC (10% acetonitrile/0.05M aqueous ammonium acetate, buffered to pH 4.5 for 3 min., 5% to 60% acetonitrile/0.05M aqueous ammonium acetate over 6 min at 22.5 mL/min with 2.5 mL/min. acetonitrile at-column dilution; APCI positive mode detection; Xterra prep. MS C18. 19×50 mm column) to afford 3,4-dichloro-N-(2-oxo-2-(3-(4-phenylpiperidin-1-yl)pyrrolidin-1-yl)benzamide (0.015 g, 40%). RP-HPLC (Table 1, Method b) R$_t$ 1.72 min; m/z: (M+H)$^+$ 460.

Illustration of General Procedure G

Preparation #10: {2-Oxo-2-[3-(4-phenyl-piperidin-1-yl)-pyrrolidin-1-yl]-ethyl}-carbamic acid tert-butyl ester

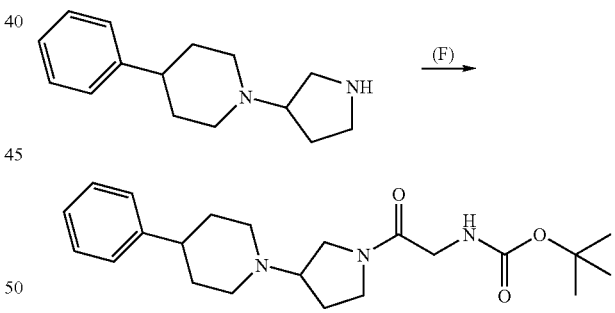

To a mixture of 4-phenyl-1-pyrrolidin-3-yl-piperidine dihydrochloride (preparation #7) (3.0 g, 9.90 mmol), tert-butoxycarbonylamino-acetic acid (1.73 g, 9.90 mmol) and EDC (1.90, 9.90 mmol) in DCM (60 mL) was added Et$_3$N (5.5 mL, 39.6 mmol). The reaction mixture was stirred at ambient temperature for about 16 h. DCM was added and the organic layer was washed with water and saturated NaHCO$_3$, dried over MgSO$_4$, filtered and concentrated in vacuo. The crude product was purified by silica gel chromatography using 5% MeOH/EtOAc as the mobile phase to afford {2-oxo-2-[3-(4-phenyl-piperidin-1-yl)-pyrrolidin-1-yl]-ethyl}-carbamic acid tert-butyl ester (1.47 g, 38% yield). RP-HPLC (Table 1, Method b) R$_t$ 1.54 min; m/z: (M+H)$^+$ 388.

TABLE 5

Examples synthesized using general procedure G

| Amine | Acid | Product | Ex. # | HPLC $R_t$ (Method) | m/z or $^1$H NMR (d6 DMSO, 400 MHz) |
|---|---|---|---|---|---|
| 2-Amino-1-[3-(4-phenyl-piperidin-1-yl)-pyrrolidin-1-yl]-ethanone (E, F, G, F) | 3,5-Bis-trifluoromethyl-benzoic acid | 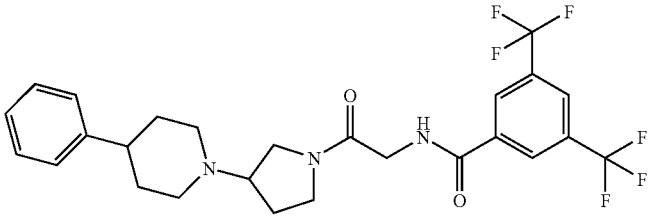 [SMILES: O=C(NCC(=O)N1CCC(N2CCC(c3ccccc3)CC2)C1)c1cc(C(F)(F)F)cc(C(F)(F)F)c1] | 5.1 | 2.01 min (b) | (M + H)⁺ 528 |
| 4-phenyl-1-(pyrrolidin-3-yl)piperidine (E, F) | 2-(3,4-dichlorobenz-amido)acetic acid (K) | 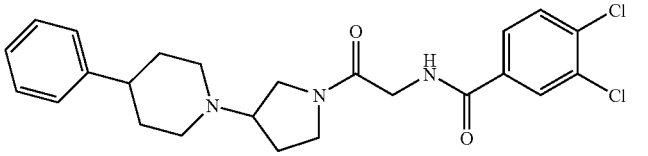 [SMILES: O=C(NCC(=O)N1CCC(N2CCC(c3ccccc3)CC2)C1)c1ccc(Cl)c(Cl)c1] | 5.2 | 1.72 min (b) | (M + H)⁺ 461 |
| N-methyl-N-(tetrahydro-2H-pyran-4-yl)pyrrolidin-3-amine (E, F) | 2-(3,4-dichlorobenz-amido)acetic acid (K) | 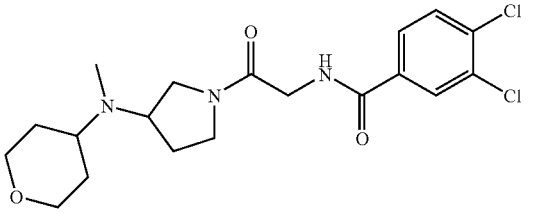 [SMILES: CN(C1CCOCC1)C1CCN(C(=O)CNC(=O)c2ccc(Cl)c(Cl)c2)C1] | 5.3 | 1.38 min (b) | (M + H)⁺ 415 |
| 4-phenyl-1-(pyrrolidin-3-yl)piperidine (E, F) | 2-(3-trifluoromethyl)benzamido)-acetic acid (K) | 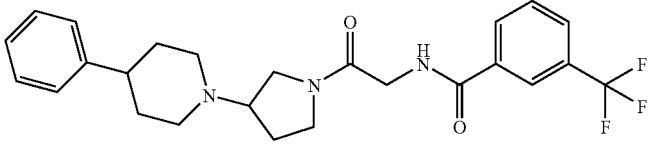 [SMILES: O=C(NCC(=O)N1CCC(N2CCC(c3ccccc3)CC2)C1)c1cccc(C(F)(F)F)c1] | 5.4 | 1.70 min (b) | (M + H)⁺ 461 |
| N-methyl-N-(tetrahydro-2H-pyran-4-yl)pyrrolidin-3-amine (E, F) | 2-(3-trifluoromethyl)benzamido)-acetic acid (K) | 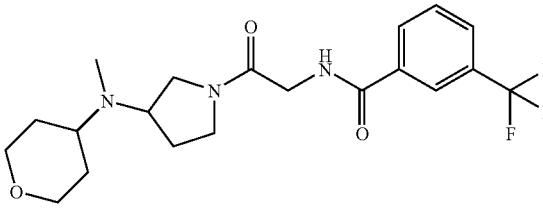 | 5.5 | 1.35 min (b) | (M + H)⁺ 414 |
| 4-phenyl-1-(pyrrolidin-3-yl)piperidine (E, F) | 2-(3,4-dichlorobenz-amido)-3-methyl butanoic acid (K) | 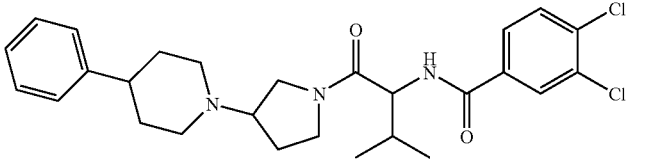 [SMILES: CC(C)C(NC(=O)c1ccc(Cl)c(Cl)c1)C(=O)N1CCC(N2CCC(c3ccccc3)CC2)C1] | 5.6 | 2.00 min (b) | (M + H)⁺ 502 |
| 4-phenyl-1-(pyrrolidin-3-yl)piperidine (E, F) | 2-(3,4-dichlorobenz-amido)-3,3-dimethyl butanoic acid (K) | 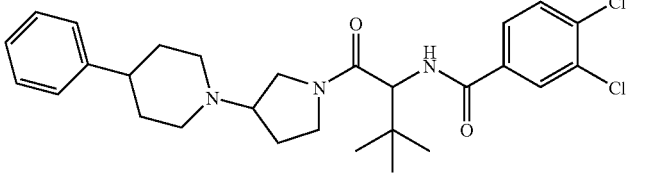 | 5.7 | 1.83 min (b) | (M + H)⁺ 517 |

TABLE 5-continued

Examples synthesized using general procedure G

| Amine | Acid | Product | Ex. # | HPLC $R_t$ (Method) | m/z or $^1$H NMR (d6 DMSO, 400 MHz) |
|---|---|---|---|---|---|
| 4-phenyl-1-(pyrrolidin-3-yl)piperidine (E, F) | 2-(benzo[d][1,3]dioxole-5-carboxamido)acetic acid (K) | | 5.8 | 1.46 min (b) | (M + H)$^+$ 436 |
| 4-phenyl-1-(pyrrolidin-3-yl)piperidine (E, F) | 2-(benzo[d][1,3]dioxole-5-carboxamido)-3-methylbutanoic acid (K) | | 5.9 | 1.62 min (b) | (M + H)$^+$ 478 |
| 4-Phenyl-1-pyrrolidin-3-yl-piperidine (E, F) | 3'-Fluor-biphenyl-4-carboxylic acid | | 5.10 | 2.32 min (e) | (M + H)$^+$ 429 |
| 4-Phenyl-1-pyrrolidin-3-yl-piperidine (E, F) | 3',4'-Dichloro-biphenyl-4-carboxylic acid | | 5.11 | 2.99 min (e) | (M + H)$^+$ 479 |
| 4-Phenyl-1-pyrrolidin-3-yl-piperidine (E, F) | [(3,4-Dichloro-benzoyl)-methyl-amino]-acetic acid (K) | | 5.12 | 2.01 min (a) | (M + H)$^+$ 474 |
| 4-Phenyl-1-pyrrolidin-3-yl-piperidine (E, F) | 4-(3,4-Dichloro-phenyl)-4-oxo-butyric acid | | 5.13 | 2.42 min (e) | (M + H)$^+$ 459 |

TABLE 5-continued

Examples synthesized using general procedure G

| Amine | Acid | Product | Ex. # | HPLC R$_t$ (Method) | m/z or $^1$H NMR (d6 DMSO, 400 MHz) |
|---|---|---|---|---|---|
| 4-Phenyl-1-pyrrolidin-3-yl-piperidine (E, F) | (3,4-Dichloro-benzene-sulfonylamino)-acetic acid (K) | | 5.14 | 2.23 min (e) | (M + H)$^+$ 496 |
| 4-Phenyl-1-pyrrolidin-3-yl-piperidine (E, F) | (R)-Cyclohexyl-(3,4-dichloro-benzoylamino)-acetic acid (K) | | 5.15 | 3.01 min (e) | (M + H)$^+$ 542 |
| 4-Phenyl-1-pyrrolidin-3-yl-piperidine (E, F) | 2-(3,4-Dichloro-benzoylamino)-propionic acid (K) | | 5.16 | 2.21 min (e) | (M + H)$^+$ 474 |
| 4-Phenyl-1-pyrrolidin-3-yl-piperidine (E, F) | (R)-(3,4-Dichloro-benzoylamino)-(4-fluoro-phenyl)-acetic acid (K) | | 5.17 | 2.12 min (e) | (M + H)$^+$ 554 |

TABLE 5-continued

Examples synthesized using general procedure G

| Amine | Acid | Product | Ex. # | HPLC R$_t$ (Method) | m/z or $^1$H NMR (d6 DMSO, 400 MHz) |
|---|---|---|---|---|---|
| 4-Phenyl-1-pyrrolidin-3-yl-piperidine (E, F) | (S)-(3,4-Dichloro-benzoylamino)-(4-fluoro-phenyl)-acetic acid (K) | 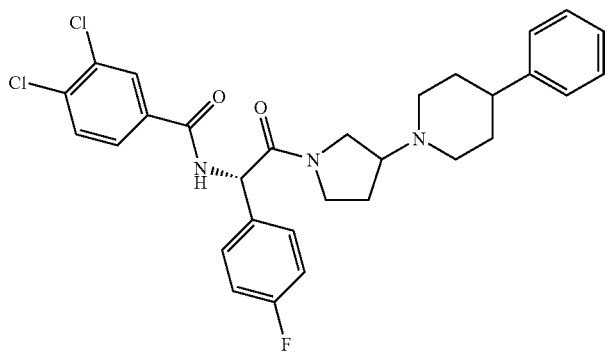 [SMILES: O=C(N[C@H](C(=O)N1CCC(N2CCC(c3ccccc3)CC2)C1)c1ccc(F)cc1)c1ccc(Cl)c(Cl)c1] | 5.18 | 2.12 min (e) | (M + H)$^+$ 554 |
| 4-Phenyl-1-pyrrolidin-3-yl-piperidine (E, F) | (1-Oxo-3,4-dihydro-1H-isoquinolin-2-yl)-acetic acid (Q, L) | 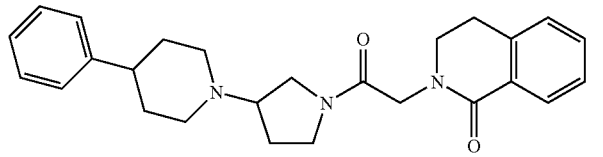 [SMILES: O=C(CN1CCc2ccccc2C1=O)N1CCC(N2CCC(c3ccccc3)CC2)C1] | 5.19 | 1.59 min (a) | (M + H)$^+$ 418 |
| 4-Phenyl-1-pyrrolidin-3-yl-piperidine (E, F) | (5-Chloro-1-oxo-3,4-dihydro-1H-isoquinolin-2-yl)-acetic acid (Q, L) | 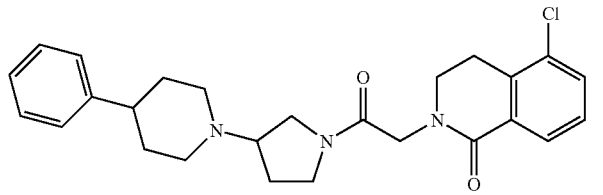 [SMILES: O=C(CN1CCc2c(Cl)cccc2C1=O)N1CCC(N2CCC(c3ccccc3)CC2)C1] | 5.20 | 1.72 min (a) | (M + H)$^+$ 452/454 |
| 4-Phenyl-1-pyrrolidin-3-yl-piperidine (E, F) | (6-Chloro-1-oxo-3,4-dihydro-1H-isoquinolin-2-yl)-acetic acid (Q, L) | 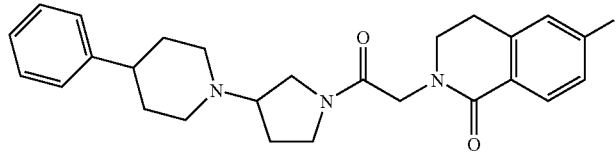 | 5.21 | 1.72 min (a) | (M + H)$^+$ 452/454 |
| 4-Phenyl-1-pyrrolidin-3-yl-piperidine (E, F) | (7-Chloro-1-oxo-3,4-dihydro-1H-isoquinolin-2-yl)-acetic acid (Q, L) | 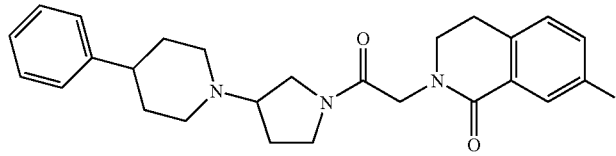 | 5.22 | 1.72 min (a) | (M + H)$^+$ 452/454 |
| 4-Phenyl-1-pyrrolidin-3-yl-piperidine (E, F) | (E)-3-(3,4-Dichloro-phenyl)-acrylic acid | 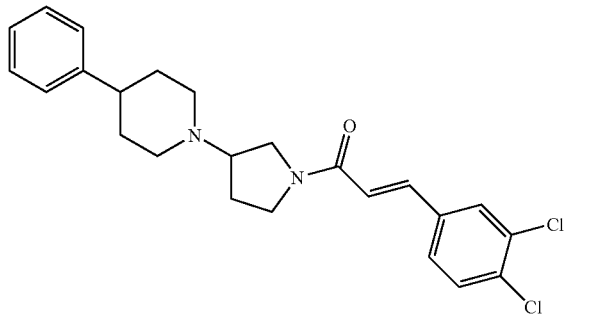 [SMILES: O=C(/C=C/c1ccc(Cl)c(Cl)c1)N1CCC(N2CCC(c3ccccc3)CC2)C1] | 5.23 | 2.53 min (a) | (M + H)$^+$ 429/431 |

TABLE 5-continued

Examples synthesized using general procedure G

| Amine | Acid | Product | Ex. # | HPLC $R_t$ (Method) | m/z or $^1$H NMR (d6 DMSO, 400 MHz) |
|---|---|---|---|---|---|
| (R)-N-(tetrahydro-2H-pyran-4-yl)pyrrolidin-3-amine (E, F) | 2-(3,4-dichlorophenylamino)acetic acid (Preparation #28) | 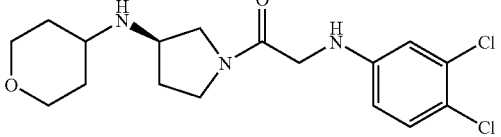 | 5.24 | 2.00 min (a) | (M + H)$^+$ 372/374 |
| (R)-N-(tetrahydro-2H-pyran-4-yl)pyrrolidin-3-amine (E, F) | 3-(3,4-dichlorophenyl)propanoic acid | 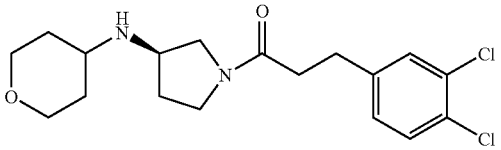 [SMILES: O=C(CCc1ccc(Cl)c(Cl)c1)N1CC[C@@H](NC2CCOCC2)C1] | 5.25 | 1.94 min (a) | (M + H)$^+$ 371/373 |
| 1'-(pyrrolidin-3-yl)-2H-spiro[benzofuran-3,4'-piperidine] (E, F) | 2-(3,4-dichlorobenzamido)acetic acid (K) | 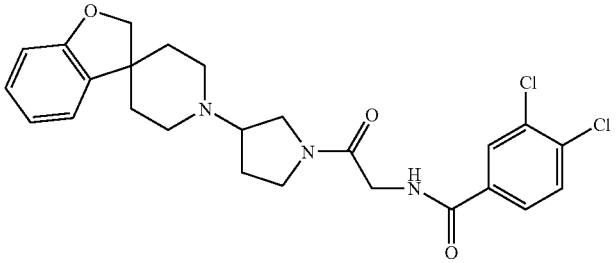 [SMILES: O=C(NCC(=O)N1CCC(N2CCC3(CC2)COc2ccccc23)C1)c1ccc(Cl)c(Cl)c1] | 5.26 | 1.91 min (a) | (M + H)$^+$ 489 |
| 2-Amino-1-[3-(4-phenyl-piperidin-1-yl)-pyrrolidin-1-yl]-ethanone (E, F, G, F) | 5,6-dichloronicotinic acid | 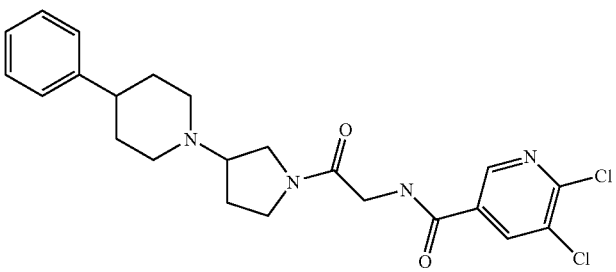 [SMILES: O=C(NCC(=O)N1CCC(N2CCC(c3ccccc3)CC2)C1)c1cnc(Cl)c(Cl)c1] | 5.27 | 1.87 min (b) | (M + H)$^+$ 461 |
| 2-Amino-1-(3-(4-phenylpiperidin-1-yl)pyrrolidin-1-yl)ethanone (E, F, G, F) | 4-(Trifluoromethyl)nicotinic acid | 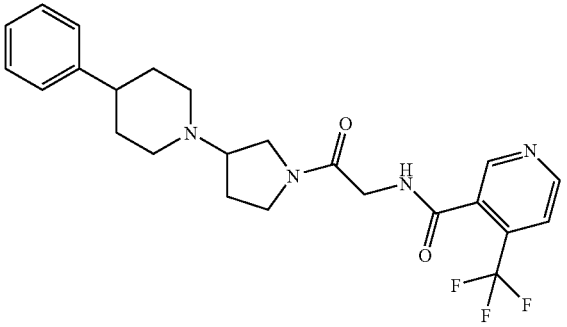 [SMILES: O=C(NCC(=O)N1CCC(N2CCC(c3ccccc3)CC2)C1)c1cnccc1C(F)(F)F] | 5.28 | 1.70 min (a) | (M − H)$^-$ 459 |
| 2-Amino-1-(3-(4-phenylpiperidin-1-yl)pyrrolidin-1-yl)ethanone (E, F, G, F) | 5-Methyl-2-(trifluoromethyl)furan-3-carboxylic acid | 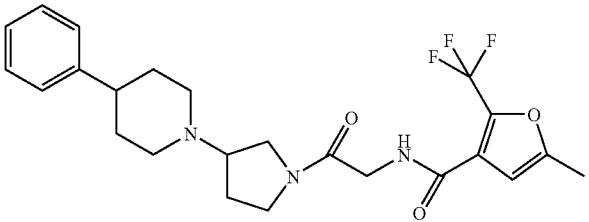 [SMILES: Cc1cc(C(=O)NCC(=O)N2CCC(N3CCC(c4ccccc4)CC3)C2)c(C(F)(F)F)o1] | 5.29 | 2.08 min (a) | (M + H)$^+$ 464 |

TABLE 5-continued

Examples synthesized using general procedure G

| Amine | Acid | Product | Ex. # | HPLC R$_t$ (Method) | m/z or $^1$H NMR (d6 DMSO, 400 MHz) |
|---|---|---|---|---|---|
| 2-Amino-1-(3-(4-phenylpiperidin-1-yl)pyrrolidin-1-yl)ethanone (E, F, G, F) | 6-(Trifluoromethyl)nicotinic acid | | 5.30 | 2.02 min (a) | (M + H)$^+$ 461 |
| 2-Amino-1-(3-(4-phenylpiperidin-1-yl)pyrrolidin-1-yl)ethanone (E, F, G, F) | 2-(Trifluoromethyl)-1H-benzo[d]imidazole-5-carboxylic acid | | 5.31 | 1.88 min (a) | (M + H)$^+$ 500 |
| 2-Amino-1-(3-(4-phenylpiperidin-1-yl)pyrrolidin-1-yl)ethanone (E, F, G, F) | 2-Methyl-5-(trifluoromethyl)oxazole-4-carboxylic acid | | 5.32 | 2.15 min (a) | (M + H)$^+$ 465 |
| 2-Amino-1-(3-(4-phenylpiperidin-1-yl)pyrrolidin-1-yl)ethanone (E, F, G, F) | 1-Methyl-3-(trifluoromethyl)-1H-pyrazole-5-carboxylic acid | | 5.33 | 2.05 min (a) | (M − H)$^-$ 462 |
| 2-Amino-1-(3-(4-phenylpiperidin-1-yl)pyrrolidin-1-yl)ethanone (E, F, G, F) | 7-(Trifluoromethyl)-1H-indole-2-carboxylic acid | | 5.34 | 2.12 min (a) | (M + H)$^+$ 499 |

TABLE 5-continued

Examples synthesized using general procedure G

| Amine | Acid | Product | Ex. # | HPLC R$_t$ (Method) | m/z or $^1$H NMR (d6 DMSO, 400 MHz) |
|---|---|---|---|---|---|
| 2-Amino-1-(3-(4-phenylpiperidin-1-yl)pyrrolidin-1-yl)ethanone (E, F, G, F) | 5-Methyl-7-(trifluoromethyl)pyrazolo[1,5-a]pyrimidine-2-carboxylic acid | | 5.35 | 1.94 min (a) | (M − H)$^-$ 513 |
| 2-Amino-1-(3-(4-phenylpiperidin-1-yl)pyrrolidin-1-yl)ethanone (E, F, G, F) | 5-Methyl-7-(trifluoromethyl)-4,5,6,7-tetrahydropyrazolo[1,5-a]pyrimidine-2-carboxylic acid | | 5.36 | 2.03 min (a) | (M + H)$^+$ 519 |
| 2-Amino-1-(3-(4-phenylpiperidin-1-yl)pyrrolidin-1-yl)ethanone (E, F, G, F) | 1-Methyl-5-(trifluoromethyl)-1H-pyrazole-3-carboxylic acid | | 5.37 | 1.97 min (a) | (M + H)$^+$ 464 |
| 2-Amino-1-(3-(4-phenylpiperidin-1-yl)pyrrolidin-1-yl)ethanone (E, F, G, F) | 4-(Trifluoromethyl)picolinic acid | | 5.38 | 2.10 min (a) | (M + H)$^+$ 461 |
| 2-Amino-1-(3-(4-phenylpiperidin-1-yl)pyrrolidin-1-yl)ethanone (E, F, G, F) | 5-Chloronicotinic acid | | 5.39 | 1.60 min (a) | (M + H)$^+$ 427/429 |

TABLE 5-continued

Examples synthesized using general procedure G

| Amine | Acid | Product | Ex. # | HPLC R$_t$ (Method) | m/z or $^1$H NMR (d6 DMSO, 400 MHz) |
|---|---|---|---|---|---|
| 2-Amino-1-(3-(4-phenylpiperidin-1-yl)pyrrolidin-1-yl)ethanone (E, F, G, F) | 5-Chloropicolinic acid | 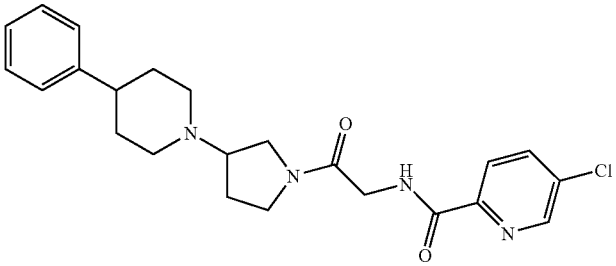 [SMILES: O=C(NCC(=O)N1CCC(N2CCC(c3ccccc3)CC2)C1)c1ccc(Cl)cn1] | 5.40 | 1.81 min (a) | (M + H)$^+$ 427/429 |
| 2-Amino-1-(3-(4-phenylpiperidin-1-yl)pyrrolidin-1-yl)ethanone (E, F, G, F) | 6-Chloronicotinic acid | 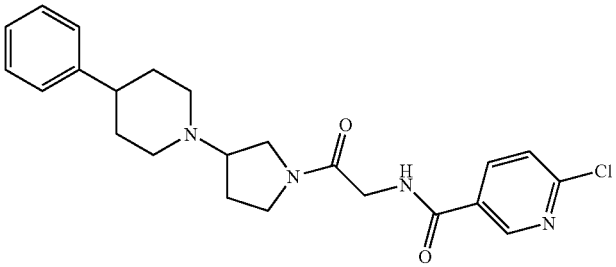 [SMILES: O=C(NCC(=O)N1CCC(N2CCC(c3ccccc3)CC2)C1)c1ccc(Cl)nc1] | 5.41 | 1.64 min (a) | (M + H)$^+$ 427/429 |
| 2-Amino-1-(3-(4-phenylpiperidin-1-yl)pyrrolidin-1-yl)ethanone (E, F, G, F) | 4-Chloropicolinic acid | 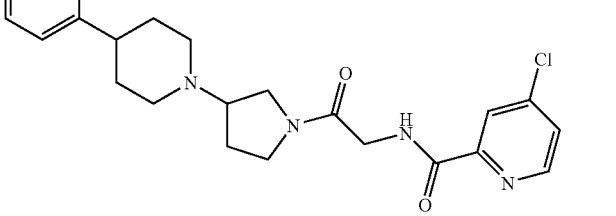 | 5.42 | 1.84 min (a) | (M + H)$^+$ 427/429 |
| 2-Amino-1-(3-(4-phenylpiperidin-1-yl)pyrrolidin-1-yl)ethanone (E, F, G, F) | 2-Chloroisonicotinic acid | 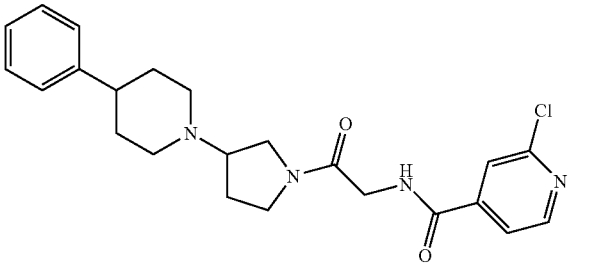 [SMILES: O=C(NCC(=O)N1CCC(N2CCC(c3ccccc3)CC2)C1)c1ccnc(Cl)c1] | 5.43 | 1.79 min (a) | (M + H)$^+$ 427/429 |
| 2-Amino-1-(3-(4-phenylpiperidin-1-yl)pyrrolidin-1-yl)ethanone (E, F, G, F) | 6-Chloropicolinic acid | 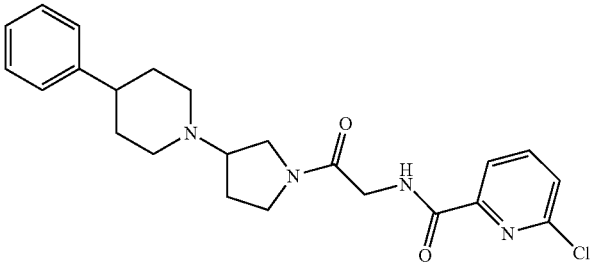 [SMILES: O=C(NCC(=O)N1CCC(N2CCC(c3ccccc3)CC2)C1)c1cccc(Cl)n1] | 5.44 | 1.72 min (a) | (M + H)$^+$ 427/429 |

TABLE 5-continued

Examples synthesized using general procedure G

| Amine | Acid | Product | Ex. # | HPLC R$_t$ (Method) | m/z or $^1$H NMR (d6 DMSO, 400 MHz) |
|---|---|---|---|---|---|
| 2-Amino-1-(3-(4-phenylpiperidin-1-yl)pyrrolidin-1-yl)ethanone (E, F, G, F) | 2-(2-(Trifluoromethyl)-1H-benzo[d]imidazol-1-yl)acetic acid | | 5.45 | 1.98 min. (a) | (M + H)$^+$ 514 |
| 1-((3S)-2-methylpyrrolidin-3-yl)-4-phenylpiperidine (Y, Z, AA) | 2-(3,4-dichlorobenzamido)acetic acid (K) | | 5.46 | 1.81 min. (a) | (M + H)$^+$ 474 |
| 1-((3S)-2-methylpyrrolidin-3-yl)-4-phenylpiperidine (Y, Z, AA) | 2-(3,4-dichlorobenzamido)acetic acid (K) | | 5.47 | 1.88 min. (a) | (M + H)$^+$ 474 |
| 1-((3S)-2-methylpyrrolidin-3-yl)-4-phenylpiperidine (Y, Z, AA) | 2-(3,4-dichlorobenzamido)acetic acid (K) | | 5.48 | 1.79 min. (a) | (M + H)$^+$ 474 |

TABLE 5-continued

Examples synthesized using general procedure G

| Amine | Acid | Product | Ex. # | HPLC R$_t$ (Method) | m/z or $^1$H NMR (d6 DMSO, 400 MHz) |
|---|---|---|---|---|---|
| 1-((3R)-2-methylpyrrolidin-3-yl)-4-2-methoxyphenyl)-piperidine (Y, Z, AA) | 2-(3,4-dichlorobenz-amido)acetic acid (K) | | 5.49 | 1.93 min. (a) | (M + H)$^+$ 504 |
| 1-((3R)-2-methylpyrrolidin-3-yl)-4-2-methoxyphenyl)-piperidine (Y, Z, AA) | 2-(3,4-dichlorobenz-amido)acetic acid (K) | | 5.50 | 1.79 min. (a) | (M + H)$^+$ 504 |
| 1-((3R)-2-cyclopropylpyrrolidin-3-yl)-4-(2-methoxyphenyl)-piperidine (Preparation #27) | 2-(3,4-dichlorobenz-amido)acetic acid (K) | | 5.51 | 2.26 min. (a) | (M + H)$^+$ 530 |
| 1-((3R)-2-cyclopropylpyrrolidin-3-yl)-4-(2-methoxyphenyl)-piperidine (Preparation #27) | 2-(3,4-dichlorobenz-amido)acetic acid (K) | | 5.52 | 2.35 min. (a) | (M + H)$^+$ 530 |

TABLE 5-continued

Examples synthesized using general procedure G

| Amine | Acid | Product | Ex. # | HPLC R$_t$ (Method) | m/z or $^1$H NMR (d6 DMSO, 400 MHz) |
|---|---|---|---|---|---|
| 1-((3R)-2-cyclopropylpyrrolidin-3-yl)-4-(2-methoxyphenyl)-piperidine (Preparation #27) | 2-(tert-butoxycarbonylamino)acetic acid (K) | | 5.53 | 1.94 min. (a) | (M + H)$^+$ 485 |
| (1S,3'R)-1'-((3R)-2-cyclopropylpyrrolidin-3-yl)-3'-methyl-2,3-dihydrospiro[indene-1,4'-piperidine] | 2-(3,4-dichlorobenzamido)acetic acid (K) | | 5.54 | 4.99 min. (d) | (M + H)$^+$ 514 |

(R)- and (S)-3,4-dichloro-N-(2-oxo-2-(3-(4-phenylpiperidin-1-yl)pyrrolidin-1-yl)ethyl)benzamide were prepared as a mixture of isomers, as described in Example 5.2, then separated via chiral preparative NP-HPLC (isocratic 35% isopropanol:65% heptane:0.2% diethylamine modifier at 16 mL/min, column temperature 45° C.; UV detection monitored at 254 nm; Daicel OD-H column, 20×250 mm, 5 um particle). Isomer 1 eluted at R$_t$ 12-16 min. Isomer 2 eluted at R$_t$ 20-27 min. The absolute stereochemistry of the isomers was not assigned.

General Procedure H: Formation of a Mesylate from an Alcohol.

A suspension of an alcohol (preferably 1 equivalent) in a polar solvent (preferably pyridine) is stirred at about 20-100° C. (preferably about 50° C.) until the suspension becomes homogenous. The reaction mixture is cooled to about −20° C. to 15° C. (preferably about 0° C.). Methanesulfonyl chloride (1 to 20 equivalents, preferably 3.0 equivalents) is added to the solution dropwise. The reaction mixture is allowed to warm to ambient temperature then concentrated in vacuo. The residue is dissolved in DCM, washed with brine, and dried in vacuo. The product is used without further purification.

Illustration of General Procedure H

Preparation #11: Methanesulfonic acid 1-[2-(3,4-dichloro-benzoylamino)-acetyl]-pyrrolidin-3-yl ester a) 3,4-Dichloro-N-[2-(3-hydroxy-pyrrolidin-1-yl)-2-oxo-ethyl]-benzamide

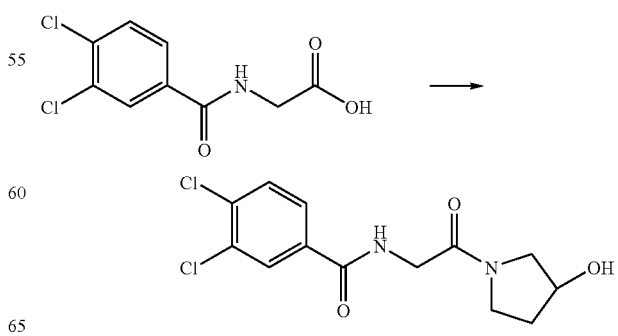

The titled compound was prepared from (3,4-dichloro-benzoylamino)-acetic acid (preparation #14) and pyrrolidin-3-ol according to the general procedure G. m/z: (M+H)+ 317.

b) Methanesulfonic acid 1-[2-(3,4-dichloro-benzoy-lamino)-acetyl]-pyrrolidin-3-yl ester

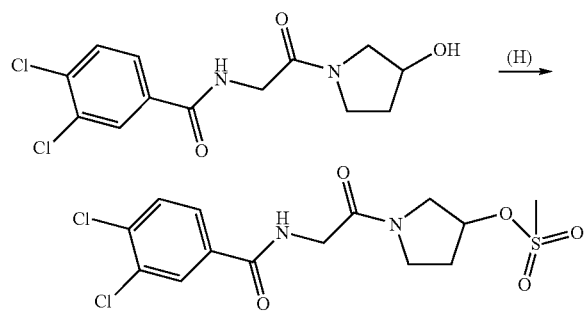

A suspension of 3,4-dichloro-N-[2-(3-hydroxy-pyrrolidin-1-yl)-2-oxo-ethyl]-benzamide (2.00 g, 6.30 mol) in pyridine (40 mL) was heated at about 50° C. until the solution became homogenous and then cooled to about 0° C. Methanesulfonyl chloride (1.46 mL, 18.9 mol) was added to the reaction mixture dropwise. The reaction mixture was allowed to warm to room temperature and then concentrated in vacuo. The residue was dissolved in DCM (50 mL), washed with brine (2×50 mL), and the organic portion was separated, dried over MgSO4, filtered, and concentrated in vacuo to give methanesulfonic acid 1-[2-(3,4-dichloro-benzoylamino)-acetyl]-pyrrolidin-3-yl ester (2.46 g, 98%) as a brown oil which was used in subsequent reactions without further purification. RP-HPLC (Table 1, Method n) $R_t$ 1.76 min; m/z: (M+H)+ 395.

General Procedure I: Formation of an Amine by Mesylate Displacement.

A mixture of a mesylate (1.0 equivalent), an amine (1 to 20 equivalents, preferably 4 equivalents), sodium iodide (1 to 20 equivalents, preferably 1.5 equivalents), potassium carbonate (0.5 to 20 equivalents, preferably 1 equivalent) in an organic solvent (preferably MeCN) is stirred at about 50-100° C. (preferably about 75° C.) for about 1-10 days (preferably about 2 days). The reaction mixture is dissolved in DCM, washed with brine and dried in vacuo. The product can then be further purified by crystallization or chromatography.

Illustration of General Procedure I

EXAMPLE #4

3,4-Dichloro-N-{2-oxo-2-[3-(4-phenyl-piperazin-1-yl)-pyrrolidin-1-yl]-ethyl}-benzamide

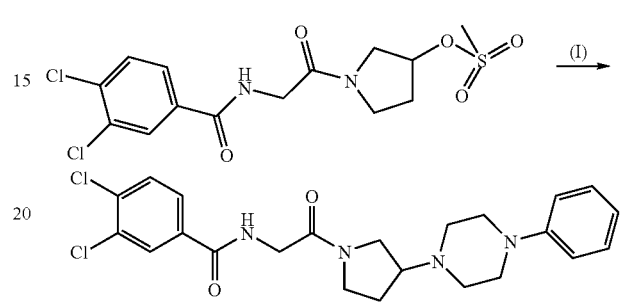

A mixture of methanesulfonic acid 1-[2-(3,4-dichloro-benzoylamino)-acetyl]-pyrrolidin-3-yl ester (preparation #11) (0.025 g, 0.063 mmol), 1-phenyl-piperazine (0.041 g, 0.25 mmol), sodium iodide (0.014 g, 0.093 mmol) and potassium carbonate (0.005 g, 0.04 mmol) in MeCN (1 mL) was stirred at about 75° C. for about 2 days. The reaction mixture was cooled to ambient temperature and concentrated in vacuo. The residue was dissolved in DCM (5 mL) and washed with brine (2×5 mL). The organic portion was separated, concentrated in vacuo, and the residue purified by RP-HPLC (10% acetonitrile/0.05M aqueous ammonium acetate, buffered to pH 4.5 for 3 min., 10% to 60% acetonitrile/0.05M aqueous ammonium acetate over 6 min at 22.5 mL/min with 2.5 mL/min. acetonitrile at-column dilution; APCI positive mode detection; Xterra prep. MS C18. 19×50 mm column) to give 3,4-dichloro-N-{2-oxo-2-[3-(4-phenyl-piperazin-1-yl)-pyrrolidin-1-yl]-ethyl}-benzamide (0.014 g, 48%). RP-HPLC (Table 1, Method m) $R_t$ 2.35 min; m/z: (M+H)+ 461.

TABLE 6

Examples synthesized using general procedure I

| Amine | Mesylate | Product | Ex. # | HPLC $R_t$ (Method) | m/z or $^1$H NMR (d6 DMSO, 400 MHz) |
|---|---|---|---|---|---|
| 1-Phenyl-piperazine | Methanesulfonic acid 1-[2-(3,4-dichloro-benzoylamino)-acetyl]-pyrrolidin-3-yl ester (K, H) | | 6.1 | 2.35 min (e) | (M + H)+ 462 |
| Dimethyl-amine | Methanesulfonic acid 1-[2-(3,4-dichloro-benzoylamino)-acetyl]-pyrrolidin-3-yl ester (K, H) | | 6.2 | 1.41 min (f) | (M + H)+ 344 |

TABLE 6-continued

Examples synthesized using general procedure I

| Amine | Mesylate | Product | Ex. # | HPLC R<sub>t</sub> (Method) | m/z or $^1$H NMR (d6 DMSO, 400 MHz) |
|---|---|---|---|---|---|
| Pyrrolidine | Methanesulfonic acid 1-[2-(3,4-dichlorobenzoylamino)-acetyl]-pyrrolidin-3-yl ester (K, H) | (structure) | 6.3 | 1.44 min (f) | (M + H)$^+$ 370 |
| Diethylamine | Methanesulfonic acid 1-[2-(3,4-dichlorobenzoylamino)-acetyl]-pyrrolidin-3-yl ester (K, H) | (structure) | 6.4 | 1.47 min (f) | (M + H)$^+$ 372 |
| Morpholine | Methanesulfonic acid 1-[2-(3,4-dichlorobenzoylamino)-acetyl]-pyrrolidin-3-yl ester (K, H) | (structure) | 6.5 | 1.50 min (f) | (M + H)$^+$ 386 |
| 1-Methylpiperazine | Methanesulfonic acid 1-[2-(3,4-dichlorobenzoylamino)-acetyl]-pyrrolidin-3-yl ester (K, H) | (structure) | 6.6 | 1.41 min (f) | (M + H)$^+$ 399 |
| Piperidin-4-ol | Methanesulfonic acid 1-[2-(3,4-dichlorobenzoylamino)-acetyl]-pyrrolidin-3-yl ester (K, H) | (structure) | 6.7 | 1.34 min (f) | (M + H)$^+$ 400 |
| Piperidine-4-carbonitrile | Methanesulfonic acid 1-[2-(3,4-dichlorobenzoylamino)-acetyl]-pyrrolidin-3-yl ester (K, H) | (structure) | 6.8 | 1.52 min (f) | (M + H)$^+$ 409 |
| Piperidin-4-yl-methanol | Methanesulfonic acid 1-[2-(3,4-dichlorobenzoylamino)-acetyl]-pyrrolidin-3-yl ester (K, H) | (structure) | 6.9 | 1.38 min (f) | (M + H)$^+$ 414 |

TABLE 6-continued

Examples synthesized using general procedure I

| Amine | Mesylate | Product | Ex. # | HPLC R$_t$ (Method) | m/z or $^1$H NMR (d6 DMSO, 400 MHz) |
|---|---|---|---|---|---|
| Piperidine-4-carboxylic acid amide | Methanesulfonic acid 1-[2-(3,4-dichloro-benzoylamino)-acetyl]-pyrrolidin-3-yl ester (K, H) | | 6.10 | 1.34 min (f) | (M + H)$^+$ 426 |
| Dimethyl-piperidin-4-yl-amine | Methanesulfonic acid 1-[2-(3,4-dichloro-benzoylamino)-acetyl]-pyrrolidin-3-yl ester (K, H) | | 6.11 | 1.36 min (f) | (M + H)$^+$ 427 |
| 4-Methoxy methyl-piperidine | Methanesulfonic acid 1-[2-(3,4-dichloro-benzoylamino)-acetyl]-pyrrolidin-3-yl ester (K, H) | | 6.12 | 1.45 min (f) | (M + H)$^+$ 428 |
| 2-Piperidin-4-yl-ethanol | Methanesulfonic acid 1-[2-(3,4-dichloro-benzoylamino)-acetyl]-pyrrolidin-3-yl ester (K, H) | | 6.13 | 1.30 min (f) | (M + H)$^+$ 428 |
| 2,4-Dimethyl-benzylamine | Methanesulfonic acid 1-[2-(3,4-dichloro-benzoylamino)-acetyl]-pyrrolidin-3-yl ester (K, H) | | 6.14 | 1.82 min (f) | (M + H)$^+$ 434 |
| N-Piperidin-4-yl-methyl-acetamide | Methanesulfonic acid 1-[2-(3,4-dichloro-benzoylamino)-acetyl]-pyrrolidin-3-yl ester (K, H) | | 6.15 | 1.25 min (f) | (M + H)$^+$ 455 |
| 3-Piperidin-4-yl-propion-amide | Methanesulfonic acid 1-[2-(3,4-dichloro-benzoylamino)-acetyl]-pyrrolidin-3-yl ester (K, H) | | 6.16 | 1.42 min (f) | (M + H)$^+$ 455 |
| Dimethyl-(2-piperidin-4-yl-ethyl)-amine | Methanesulfonic acid 1-[2-(3,4-dichloro-benzoylamino)-acetyl]-pyrrolidin-3-yl ester (K, H) | | 6.17 | 1.35 min (f) | (M + H)$^+$ 455 |

TABLE 6-continued

Examples synthesized using general procedure I

| Amine | Mesylate | Product | Ex. # | HPLC R$_t$ (Method) | m/z or $^1$H NMR (d6 DMSO, 400 MHz) |
|---|---|---|---|---|---|
| Piperidine-4-carboxylic acid ethyl ester | Methanesulfonic acid 1-[2-(3,4-dichloro-benzoylamino)-acetyl]-pyrrolidin-3-yl ester (K, H) | | 6.18 | 1.43 min (f) | (M + H)$^+$ 422 |
| 1,2,3,4,5,6-Hexahydro-[4,4']bi-pyridinyl | Methanesulfonic acid 1-[2-(3,4-dichloro-benzoylamino)-acetyl]-pyrrolidin-3-yl ester (K, H) | | 6.19 | 1.34 min (f) | (M + H)$^+$ 461 |
| 3-Phenyl-pyrrolidin-3-ol | Methanesulfonic acid 1-[2-(3,4-dichloro-benzoylamino)-acetyl]-pyrrolidin-3-yl ester (K, H) | | 6.20 | 1.65 min (f) | (M + H)$^+$ 462 |
| 4-Piperidin-4-yl-morpholine | Methanesulfonic acid 1-[2-(3,4-dichloro-benzoylamino)-acetyl]-pyrrolidin-3-yl ester (K, H) | | 6.21 | 1.35 min (f) | (M + H)$^+$ 468 |
| Piperidin-4-yl-acetic acid ethyl ester | Methanesulfonic acid 1-[2-(3,4-dichloro-benzoylamino)-acetyl]-pyrrolidin-3-yl ester (K, H) | | 6.22 | 1.33 min (f) | (M + H)$^+$ 456 |
| 4-p-Tolyl-piperidine | Methanesulfonic acid 1-[2-(3,4-dichloro-benzoylamino)-acetyl]-pyrrolidin-3-yl ester (K, H) | | 6.23 | 2.26 min (e) | (M + H)$^+$ 474 |
| 2-Methyl-1-phenyl-piperazine | Methanesulfonic acid 1-[2-(3,4-dichloro-benzoylamino)-acetyl]-pyrrolidin-3-yl ester (K, H) | | 6.24 | 1.97 min (f) | (M + H)$^+$ 475 |

TABLE 6-continued

Examples synthesized using general procedure I

| Amine | Mesylate | Product | Ex. # | HPLC R$_t$ (Method) | m/z or $^1$H NMR (d6 DMSO, 400 MHz) |
|---|---|---|---|---|---|
| 4-Phenyl-piperidin-4-ol | Methanesulfonic acid 1-[2-(3,4-dichloro-benzoylamino)-acetyl]-pyrrolidin-3-yl ester (K, H) | | 6.25 | 1.65 min (f) | (M + H)$^+$ 476 |
| Phenyl-piperidin-4-yl-methanol | Methanesulfonic acid 1-[2-(3,4-dichloro-benzoylamino)-acetyl]-pyrrolidin-3-yl ester (K, H) | | 6.26 | 1.62 min (f) | (M + H)$^+$ 490 |
| 3-Piperidin-4-yl-phenol | Methanesulfonic acid 1-[2-(3,4-dichloro-benzoylamino)-acetyl]-pyrrolidin-3-yl ester (K, H) | | 6.27 | 1.54 min (f) | (M + H)$^+$ 476 |
| 2,3,5,6-Tetrahydro-1H-[4,4']bi-pyridinyl-4-ol | Methanesulfonic acid 1-[2-(3,4-dichloro-benzoylamino)-acetyl]-pyrrolidin-3-yl ester (K, H) | | 6.28 | 1.39 min (f) | (M + H)$^+$ 477 |
| 2',3',5',6'-Tetrahydro-1'H-[2,4']bi-pyridinyl-4'-ol | Methanesulfonic acid 1-[2-(3,4-dichloro-benzoylamino)-acetyl]-pyrrolidin-3-yl ester (K, H) | | 6.29 | 1.51 min (f) | (M + H)$^+$ 477 |
| 3-(Piperidin-4-yloxy)-pyridine | Methanesulfonic acid 1-[2-(3,4-dichloro-benzoylamino)-acetyl]-pyrrolidin-3-yl ester (K, H) | | 6.30 | 1.49 min (f) | (M + H)$^+$ 477 |
| 2-(Piperidin-4-yloxy)-pyrimidine | Methanesulfonic acid 1-[2-(3,4-dichloro-benzoylamino)-acetyl]-pyrrolidin-3-yl ester (K, H) | | 6.31 | 1.50 min (f) | (M + H)$^+$ 478 |

TABLE 6-continued

Examples synthesized using general procedure I

| Amine | Mesylate | Product | Ex. # | HPLC $R_t$ (Method) | m/z or $^1$H NMR (d6 DMSO, 400 MHz) |
|---|---|---|---|---|---|
| 4-(3-Fluor-phenyl)-piperidine | Methanesulfonic acid 1-[2-(3,4-dichloro-benzoylamino)-acetyl]-pyrrolidin-3-yl ester (K, H) | | 6.32 | 2.16 min (f) | $(M + H)^+$ 478 |
| 4-(1-Methyl-1H-imidazol-2-yl)-piperidin-3-ol | Methanesulfonic acid 1-[2-(3,4-dichloro-benzoylamino)-acetyl]-pyrrolidin-3-yl ester (K, H) | | 6.33 | 1.65 min (e) | $(M + H)^+$ 480 |
| 4-(4-Methoxy-phenyl)-piperidine | Methanesulfonic acid 1-[2-(3,4-dichloro-benzoylamino)-acetyl]-pyrrolidin-3-yl ester (K, H) | | 6.34 | 1.80 min (f) | $(M + H)^+$ 490 |
| 4-Benzyl-piperidin-4-ol | Methanesulfonic acid 1-[2-(3,4-dichloro-benzoylamino)-acetyl]-pyrrolidin-3-yl ester (K, H) | | 6.35 | 1.66 min (f) | $(M + H)^+$ 490 |
| 4-o-Tolyl-piperidin-4-ol | Methanesulfonic acid 1-[2-(3,4-dichloro-benzoylamino)-acetyl]-pyrrolidin-3-yl ester (K, H) | | 6.36 | 1.72 min (f) | $(M + H)^+$ 490 |
| 4-p-Tolyl-piperidin-4-ol | Methanesulfonic acid 1-[2-(3,4-dichloro-benzoylamino)-acetyl]-pyrrolidin-3-yl ester (K, H) | | 6.37 | 1.65 min (f) | $(M + H)^+$ 490 |
| 4-(2-Fluoro-phenyl)-piperidin-4-ol | Methanesulfonic acid 1-[2-(3,4-dichloro-benzoylamino)-acetyl]-pyrrolidin-3-yl ester (K, H) | | 6.38 | 1.57 min (f) | $(M + H)^+$ 494 |

TABLE 6-continued

Examples synthesized using general procedure I

| Amine | Mesylate | Product | Ex. # | HPLC R$_t$ (Method) | m/z or $^1$H NMR (d6 DMSO, 400 MHz) |
|---|---|---|---|---|---|
| 4-(4-Fluoro-phenyl)-piperidin-4-ol | Methanesulfonic acid 1-[2-(3,4-dichloro-benzoylamino)-acetyl]-pyrrolidin-3-yl ester (K, H) | | 6.39 | 1.70 min (f) | (M + H)$^+$ 494 |
| 4-(4-Chloro-phenyl)-piperidin-4-ol | Methanesulfonic acid 1-[2-(3,4-dichloro-benzoylamino)-acetyl]-pyrrolidin-3-yl ester (K, H) | | 6.40 | 1.74 min (f) | (M + H)$^+$ 510 |
| 4-Phenyl-piperidine-4-carbonitrile | Methanesulfonic acid 1-[2-(3,4-dichloro-benzoylamino)-acetyl]-pyrrolidin-3-yl ester (K, H) | | 6.41 | 1.99 min (f) | (M + H)$^+$ 485 |
| 3-Methyl-piperidine | Methanesulfonic acid 1-[2-(3,4-dichloro-benzoylamino)-acetyl]-pyrrolidin-3-yl ester (K, H) | | 6.42 | 1.55 min (f) | (M + H)$^+$ 398 |
| 4-Phenyl-1-pyrrolidin-3-yl-piperidine | Methanesulfonic acid 2-(3,4-dichloro-benzoylamino)-ethyl ester (K, H) | | 6.43 | 2.30 min (e) | (M + H)$^+$ 466 |
| 4-Benzyl-piperidine | Methanesulfonic acid 1-[2-(3,4-dichloro-benzoylamino)-acetyl]-pyrrolidin-3-yl ester (K, H) | | 6.44 | 2.17 min (e) | (M + H)$^+$ 474 |
| 4-(2-Methoxy-phenyl)-piperidine | Methanesulfonic acid 1-[2-(3,4-dichloro-benzoylamino)-acetyl]-pyrrolidin-3-yl ester (K, H) | | 6.45 | 2.13 min (e) | (M + H)$^+$ 490 |

TABLE 6-continued

Examples synthesized using general procedure I

| Amine | Mesylate | Product | Ex. # | HPLC R$_t$ (Method) | m/z or $^1$H NMR (d6 DMSO, 400 MHz) |
|---|---|---|---|---|---|
| 4-Phenoxy-piperidine | Methanesulfonic acid 1-[2-(3,4-dichloro-benzoylamino)-acetyl]-pyrrolidin-3-yl ester (K, H) | | 6.46 | 2.67 min (e) | (M + H)$^+$ 476 |
| 3-(Piperidin-4-yl-benzonitrile | Methanesulfonic acid 1-[2-(3,4-dichloro-benzoylamino)-acetyl]-pyrrolidin-3-yl ester (K, H) | | 6.47 | 2.58 min (e) | (M + H)$^+$ 485 |
| 4-Piperidin-4-yl-benzonitrile | Methanesulfonic acid 1-[2-(3,4-dichloro-benzoylamino)-acetyl]-pyrrolidin-3-yl ester (K, H) | | 6.48 | 2.58 min (e) | (M + H)$^+$ 485 |
| 1-Piperidin-3-yl-1H-indole | Methanesulfonic acid 1-[2-(3,4-dichloro-benzoylamino)-acetyl]-pyrrolidin-3-yl ester (K, H) | | 6.49 | 2.13 min (b) | (M + H)$^+$ 501 |
| 1-Piperidin-4-yl-1H-indole | Methanesulfonic acid 1-[2-(3,4-dichloro-benzoylamino)-acetyl]-pyrrolidin-3-yl ester (K, H) | | 6.50 | 1.99 min (b) | (M + H)$^+$ 501 |
| 4-(3-Chloro-phenyl)-piperidine | Methanesulfonic acid 1-[2-(3,4-dichloro-benzoylamino)-acetyl]-pyrrolidin-3-yl ester (K, H) | | 6.51 | 1.92 min (b) | (M + H)$^+$ 494 |

TABLE 6-continued

Examples synthesized using general procedure I

| Amine | Mesylate | Product | Ex. # | HPLC $R_t$ (Method) | m/z or $^1$H NMR (d6 DMSO, 400 MHz) |
|---|---|---|---|---|---|
| 2,3-Dihydro-spiro[indene-1,3'-piperidine] | Methanesulfonic acid 1-[2-(3,4-dichloro-benzoylamino)-acetyl]-pyrrolidin-3-yl ester (K, H) | | 6.52 | 1.96 min (b) | $(M + H)^+$ 486 |
| Spiro[indene-1,4'-piperidine] | Methanesulfonic acid 1-[2-(3,4-dichloro-benzoylamino)-acetyl]-pyrrolidin-3-yl ester (K, H) | | 6.53 | 1.90 min (b) | $(M + H)^+$ 484 |
| 2,3-Dihydro-spiro[indene-1,4'-piperidine] | Methanesulfonic acid 1-[2-(3,4-dichloro-benzoylamino)-acetyl]-pyrrolidin-3-yl ester (K, H) | | 6.54 | 1.87 min (b) | $(M + H)^+$ 486 |
| (1R,3'R)-3'-Methyl-spiro[indene-1,4'-piperidine] | Methanesulfonic acid 1-[2-(3,4-dichloro-benzoylamino)-acetyl]-pyrrolidin-3-yl ester (K, H) | Chiral | 6.55 | 1.96 min (b) | $(M + H)^+$ 498 |
| 3-(4-(Trifluoro-methyl)phenyl)pyrrolidine | Methanesulfonic acid 1-[2-(3,4-dichloro-benzoylamino)-acetyl]-pyrrolidin-3-yl ester (K, H) | | 6.56 | 2.00 min (b) | $(M + H)^+$ 514 |
| 7-Chloro-1,2,3,4-tetrahydro-isoquinoline | Methanesulfonic acid 1-[2-(3,4-dichloro-benzoylamino)-acetyl]-pyrrolidin-3-yl ester (K, H) | | 6.57 | 2.02 min (b) | $(M + H)^+$ 466 |

TABLE 6-continued

Examples synthesized using general procedure I

| Amine | Mesylate | Product | Ex. # | HPLC R$_t$ (Method) | m/z or $^1$H NMR (d6 DMSO, 400 MHz) |
|---|---|---|---|---|---|
| 3-(4-Fluoro-phenyl)piperidine | Methanesulfonic acid 1-[2-(3,4-dichloro-benzoylamino)-acetyl]-pyrrolidin-3-yl ester (K, H) | | 6.58 | 1.86 min (b) | (M + H)$^+$ 478 |
| 4-(4-Chloro-phenyl)-piperidine | Methanesulfonic acid 1-[2-(3,4-dichloro-benzoylamino)-acetyl]-pyrrolidin-3-yl ester (K, H) | | 6.58 | 1.96 min (b) | (M + H)$^+$ 494 |
| 4-(4-Trifluoro methyl-phenyl)-piperidine | Methanesulfonic acid 1-[2-(3,4-dichloro-benzoylamino)-acetyl]-pyrrolidin-3-yl ester (K, H) | | 6.60 | 2.02 min (b) | (M + H)$^+$ 528 |
| 3-(3-Fluoro-phenyl)-pyrrolidine | Methanesulfonic acid 1-[2-(3,4-dichloro-benzoylamino)-acetyl]-pyrrolidin-3-yl ester (K, H) | | 6.61 | 1.81 min (b) | (M + H)$^+$ 464 |
| 3-(4-Fluoro-phenyl)-pyrrolidine | Methanesulfonic acid 1-[2-(3,4-dichloro-benzoylamino)-acetyl]-pyrrolidin-3-yl ester (K, H) | | 6.62 | 1.81 min (b) | (M + H)$^+$ 464 |
| 3-(3-Fluoro-phenyl)-piperidine | Methanesulfonic acid 1-[2-(3,4-dichloro-benzoylamino)-acetyl]-pyrrolidin-3-yl ester (K, H) | | 6.63 | 1.82 min (b) | (M + H)$^+$ 458 |

TABLE 6-continued

Examples synthesized using general procedure I

| Amine | Mesylate | Product | Ex. # | HPLC R$_t$ (Method) | m/z or $^1$H NMR (d6 DMSO, 400 MHz) |
|---|---|---|---|---|---|
| 3-(4-Methoxy-phenyl)-pyrrolidine | Methanesulfonic acid 1-[2-(3,4-dichloro-benzoylamino)-acetyl]-pyrrolidin-3-yl ester (K, H) | | 6.64 | 1.76 min (b) | (M + H)$^+$ 476 |
| 4-Trifluoromethyl-piperidine | Methanesulfonic acid 1-[2-(3,4-dichloro-benzoylamino)-acetyl]-pyrrolidin-3-yl ester (K, H) | | 6.65 | 2.11 min (e) | (M + H)$^+$ 452 |
| Piperidine | Methanesulfonic acid 1-[2-(3,4-dichloro-benzoylamino)-acetyl]-pyrrolidin-3-yl ester (K, H) | | 6.66 | 1.39 min (e) | (M + H)$^+$ 384 |
| 4-Methyl-piperidine | Methanesulfonic acid 1-[2-(3,4-dichloro-benzoylamino)-acetyl]-pyrrolidin-3-yl ester (K, H) | | 6.67 | 1.72 min (e) | (M + H)$^+$ 398 |
| Piperidin-3-ol | Methanesulfonic acid 1-[2-(3,4-dichloro-benzoylamino)-acetyl]-pyrrolidin-3-yl ester (K, H) | | 6.68 | 1.40 min (f) | (M + H)$^+$ 400 |
| 3-Fluoro-piperidine | Methanesulfonic acid 1-[2-(3,4-dichloro-benzoylamino)-acetyl]-pyrrolidin-3-yl ester (K, H) | | 6.69 | 1.50 min (f) | (M + H)$^+$ 402 |
| Piperidine-3-carbonitrile | Methanesulfonic acid 1-[2-(3,4-dichloro-benzoylamino)-acetyl]-pyrrolidin-3-yl ester (K, H) | | 6.70 | 2.15 min (f) | (M + H)$^+$ 409 |

TABLE 6-continued

Examples synthesized using general procedure I

| Amine | Mesylate | Product | Ex. # | HPLC $R_t$ (Method) | m/z or $^1$H NMR (d6 DMSO, 400 MHz) |
|---|---|---|---|---|---|
| 3,5-Dimethyl-piperidine | Methanesulfonic acid 1-[2-(3,4-dichloro-benzoylamino)-acetyl]-pyrrolidin-3-yl ester (K, H) | 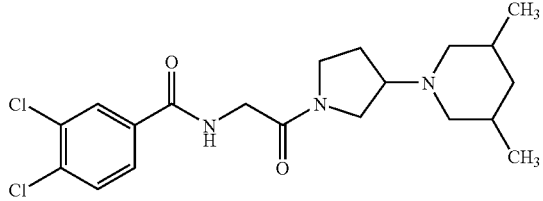 [SMILES: CC1CC(C)CN(C2CCN(C(=O)CNC(=O)c3ccc(Cl)c(Cl)c3)C2)C1] | 6.71 | 1.61 min (f) | $(M + H)^+$ 412 |
| 3,3-Dimethyl-piperidine | Methanesulfonic acid 1-[2-(3,4-dichloro-benzoylamino)-acetyl]-pyrrolidin-3-yl ester (K, H) | 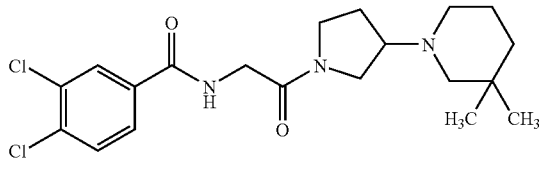 [SMILES: CC1(C)CCCN(C2CCN(C(=O)CNC(=O)c3ccc(Cl)c(Cl)c3)C2)C1] | 6.72 | 1.58 min (f) | $(M + H)^+$ 412 |
| 3-Methoxy-piperidine | Methanesulfonic acid 1-[2-(3,4-dichloro-benzoylamino)-acetyl]-pyrrolidin-3-yl ester (K, H) | 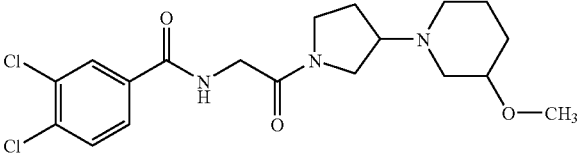 [SMILES: COC1CCCN(C2CCN(C(=O)CNC(=O)c3ccc(Cl)c(Cl)c3)C2)C1] | 6.73 | 1.47 min (f) | $(M + H)^+$ 414 |
| Piperidin-3-yl-methanol | Methanesulfonic acid 1-[2-(3,4-dichloro-benzoylamino)-acetyl]-pyrrolidin-3-yl ester (K, H) | 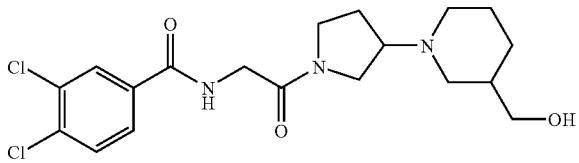 [SMILES: O=C(NCC(=O)N1CCC(N2CCCC(CO)C2)C1)c1ccc(Cl)c(Cl)c1] | 6.74 | 1.41 min (f) | $(M + H)^+$ 414 |
| Piperidine-3-carboxylic acid amide | Methanesulfonic acid 1-[2-(3,4-dichloro-benzoylamino)-acetyl]-pyrrolidin-3-yl ester (K, H) | 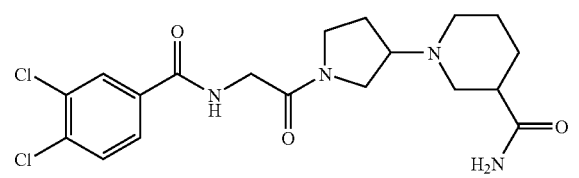 [SMILES: NC(=O)C1CCCN(C2CCN(C(=O)CNC(=O)c3ccc(Cl)c(Cl)c3)C2)C1] | 6.75 | 1.40 min (f) | $(M + H)^+$ 427 |
| 3-Methoxymethyl-1-methyl-piperidine | Methanesulfonic acid 1-[2-(3,4-dichloro-benzoylamino)-acetyl]-pyrrolidin-3-yl ester (K, H) | 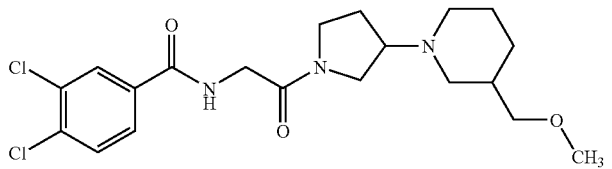 [SMILES: COCC1CCCN(C2CCN(C(=O)CNC(=O)c3ccc(Cl)c(Cl)c3)C2)C1] | 6.76 | 1.49 min (f) | $(M + H)^+$ 428 |
| Decahydro-isoquinoline | Methanesulfonic acid 1-[2-(3,4-dichloro-benzoylamino)-acetyl]-pyrrolidin-3-yl ester (K, H) | 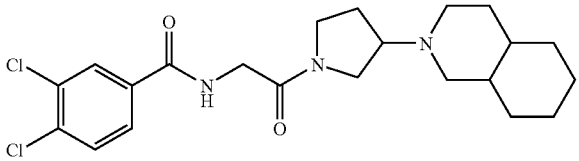 [SMILES: O=C(NCC(=O)N1CCC(N2CCC3CCCCC3C2)C1)c1ccc(Cl)c(Cl)c1] | 6.77 | 1.67 min (f) | $(M + H)^+$ 438 |
| 3-Trifluoromethyl-piperidine | Methanesulfonic acid 1-[2-(3,4-dichloro-benzoylamino)-acetyl]-pyrrolidin-3-yl ester (K, H) | 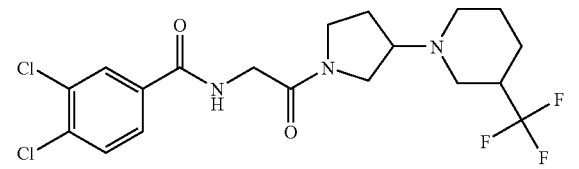 [SMILES: O=C(NCC(=O)N1CCC(N2CCCC(C(F)(F)F)C2)C1)c1ccc(Cl)c(Cl)c1] | 6.78 | 1.94 min (f) | $(M + H)^+$ 452 |

TABLE 6-continued

Examples synthesized using general procedure I

| Amine | Mesylate | Product | Ex. # | HPLC $R_t$ (Method) | m/z or $^1$H NMR (d6 DMSO, 400 MHz) |
|---|---|---|---|---|---|
| 3-Phenoxy-piperidine | Methanesulfonic acid 1-[2-(3,4-dichloro-benzoylamino)-acetyl]-pyrrolidin-3-yl ester (K, H) | | 6.79 | 2.32 min (e) | (M + H)$^+$ 476 |
| 4-(4-Fluoro-phenyl)-3-methyl-piperidin-4-ol (O) | Methanesulfonic acid 1-[2-(3,4-dichloro-benzoylamino)-acetyl]-pyrrolidin-3-yl ester (K, H) | | 6.80 | 2.04 min (e) | (M + H)$^+$ 508 |
| 4-(4-Fluoro-phenyl)-piperidine | Methanesulfonic acid 1-[2-(3,4-dichloro-benzoylamino)-acetyl]-pyrrolidin-3-yl ester (K, H) | | 6.81 | 2.17 min (e) | (M + H)$^+$ 478 |
| 3-Phenyl-piperidine | Methanesulfonic acid 1-[2-(3,4-dichloro-benzoylamino)-acetyl]-pyrrolidin-3-yl ester (K, H) | | 6.82 | 2.16 min (f) | (M + H)$^+$ 460 |
| 4-(4-Fluoro-phenyl)-3-methyl-piperidine (O, P) | Methanesulfonic acid 1-[2-(3,4-dichloro-benzoylamino)-acetyl]-pyrrolidin-3-yl ester (K, H) | | 6.83 | 2.24 min (f) | (M + H)$^+$ 492 |
| 3-Methyl-4-phenyl-piperidine (O, P) | Methanesulfonic acid 1-[2-(3,4-dichloro-benzoylamino)-acetyl]-pyrrolidin-3-yl ester (K, H) | | 6.84 | 2.27 min (f) | (M + H)$^+$ 474 |
| Phenyl-piperidin-3-yl-amine | Methanesulfonic acid 1-[2-(3,4-dichloro-benzoylamino)-acetyl]-pyrrolidin-3-yl ester (K, H) | | 6.85 | 1.82 min (f) | (M + H)$^+$ 474 |

TABLE 6-continued

Examples synthesized using general procedure I

| Amine | Mesylate | Product | Ex. # | HPLC R$_t$ (Method) | m/z or $^1$H NMR (d6 DMSO, 400 MHz) |
|---|---|---|---|---|---|
| 1-(piperidin-4-yl)pyridin-2(1H)-one (U, V, F) | 1-(2-(3,4-dichlorobenzamido)acetyl)pyrrolidin-3-yl methanesulfonate (K, H) | | 6.86 | 1.66 min (f) | (M + H)$^+$ 477 |
| 2,3,4,4a,9,9a-hexahydro-1H-pyrido[3,4-b]indole (Preparation #29) | 1-(2-(3,4-dichlorobenzamido)acetyl)pyrrolidin-3-yl methanesulfonate (K, H) | | 6.87 | 2.00 min (f) | (M + H)$^+$ 473 |
| 7-(piperidin-4-yl)-1H-indazole (U, V, F) | 1-(2-(3,4-dichlorobenzamido)acetyl)pyrrolidin-3-yl methanesulfonate (K, H) | | 6.88 | 1.98 min (f) | (M + H)$^+$ 500 |
| 4-o-tolylpiperidine | 1-(2-(3,4-dichlorobenzamido)acetyl)pyrrolidin-3-yl methanesulfonate (K, H) | | 6.89 | 2.20 min (f) | (M + H)$^+$ 474 |
| 4-(2-(trifluoromethyl)phenyl)piperidine | 1-(2-(3,4-dichlorobenzamido)acetyl)pyrrolidin-3-yl methanesulfonate (K, H) | | 6.90 | 2.42 min (f) | (M + H)$^+$ 528 |
| 4-(2-fluorophenyl)piperidine | 1-(2-(3,4-dichlorobenzamido)acetyl)pyrrolidin-3-yl methanesulfonate (K, H) | | 6.91 | 2.14 min (f) | (M + H)$^+$ 478 |
| 2,3,4,9-tetrahydro-1H-pyrido[3,4-b]indole | 1-(2-(3,4-dichlorobenzamido)acetyl)pyrrolidin-3-yl methanesulfonate (K, H) | | 6.92 | 2.26 min (f) | (M + H)$^+$ 471 |

3,4-Dichloro-N-(2-((R)-3-((1R,3'R)-3'-methylspiro[indene-1,4'-piperidine]-1'-yl)pyrrolidin-1-yl)-2-oxoethyl)benzamide and 3,4-dichloro-N-(2-((S)-3-((1R,3'R)-3'-methylspiro[indene-1,4'-piperidine]-1'-yl)pyrrolidin-1-yl)-2-oxoethyl)benzamide were prepared as a mixture, as described in Example 6.55, then separated via chiral preparative RP-HPLC (isocratic 10% methanol:10% ethanol:80% heptane: 0.2% diethylamine modifier at 10 mL/min, column temperature 45° C.; UV detection monitored at 254 nm; Daicel OD-H column, 20×250 mm, 5 um particle) to yield 3,4-dichloro-N-(2-((R)-3-((1R,3'R)-3'-methylspiro[indene-1,4'-piperidine]-1'-yl)pyrrolidin-1-yl)-2-oxoethyl)benzamide and 3,4- dichloro-N-(2-((S)-3-((1R,3'R)-3'-methylspiro[indene-1,4'-piperidine]-1'-yl)pyrrolidin-1-yl)-2-oxoethyl)benzamide. Isomer 1 eluted at R$_t$ 26-30 min. Isomer 2 eluted at R$_t$ 3843 min. The absolute stereochemistry of the isomers was not assigned.

General Procedure J: Oxidation of an Alcohol to a Ketone.

To a mixture of an alcohol in an organic solvent (preferably DCM) is added an oxidizing agent (preferably Dess-Martin periodinane 1 to 3 equivalents, preferably 2 equivalents). The reaction mixture is stirred at about 20-100° C. (preferably about 20° C.) for about 0.5 to 60 hours (preferably about 16 hours). The product can then be isolated by filtration and further purified by crystallization or chromatography.

Illustration of General Procedure J

Preparation #12: (S)-5-isopropyl-1-(3-trifluoromethyl-7,8-dihydro-5H-[1,6]naphthyridine-6-carbonyl)-pyrrolidin-3-one

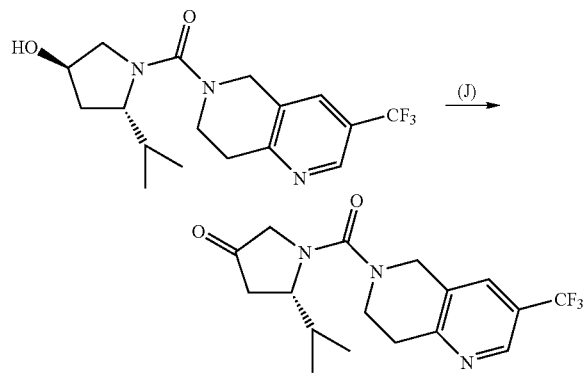

To a solution of ((2S,4R)-4-hydroxy-2-isopropyl-pyrrolidin-1-yl)-(3-trifluoromethyl-7,8-dihydro-5H-[1,6]naphthyridin-6-yl)-methanone (prepared as in example #1) (0.118 g, 0.330 mmol) in DCM (4 mL) was added Dess-Martin periodinane (0.210 g, 0.495 mmol). The reaction mixture was stirred at ambient temperature for about 40 min. Additional Dess-Martin reagent (0.303 g, 0.714 mmol) was added in portions over about 4 h and the reaction mixture was stirred for about 16 h. Saturated aqueous sodium bicarbonate (4 mL) was added and the organic portion was separated, dried over MgSO$_4$, filtered, and concentrated to afford (S)-5-isopropyl-1-(3-trifluoromethyl-7,8-dihydro-5H-[1,6]naphthyridine-6-carbonyl)-pyrrolidin-3-one as a sticky yellow solid that was used in subsequent reactions without further purification. RP-HPLC (Table 1, Method d) R$_t$ 2.49 min; m/z: (M+H)$^+$ 356.

General Procedure K: Formation of an Amide by an Acid Chloride Acylation.

To a mixture of an amine (preferably 1 equivalent) and a base (preferably Et$_3$N, 2-4 equivalents, preferably 2 equivalents or 2.0N aqueous NaOH, 24 equivalent, preferably 2 equivalent) in an organic solvent (preferably DCM or acetonitrile) at about 0-25° C. (preferably at about 0° C.) is added a solution of an acid chloride (1 to 3 equivalents, preferably 1 equivalent, if not commercially available, generated from the acid an oxalyl chloride using procedures familiar to those skilled in the art) in an organic solvent (preferably DCM). The reaction mixture is stirred at about 0-20° C. (preferably about 20° C.) for about 0.5 to 60 hours (preferably about 3 hours). The reaction mixture is concentrated in vacuo and the product can then be further purified by chromatography or crystallization.

Illustration of General Procedure K

EXAMPLE #5

3,5-Difluoro-N-{2-oxo-2-[3-(4-phenyl-piperidin-1-yl)-pyrrolidin-1-yl]-ethyl}-benzamide

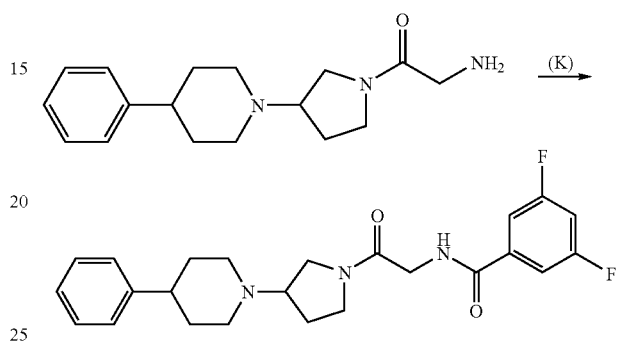

To a solution of 2-amino-1-[3-(4-phenyl-piperidin-1-yl)-pyrrolidin-1-yl]-ethanone (preparation #9) (0.026 g, 0.09 mmol) and triethylamine (0.025 mL, 0.18 mmol) in DCM (0.7 mL) was added a solution of 3,5-difluoro-benzoyl chloride (0.016 g, 0.09 mmol) in dichloromethane (0.2 mL). The reaction mixture was stirred at ambient temperature for about 3 h then concentrated in vacuo. The residue was purified by flash chromatography on silica gel using 10% MeOH/EtOAc as the mobile phase to give 3,5-difluoro-N-{2-oxo-2-[3-(4-phenyl-piperidin-1-yl)-pyrrolidin-1-yl]-ethyl}-benzamide (0.021 g, 55%). RP-HPLC (Table 1, Method b) R$_t$ 1.51 min; m/z: (M+H)$^+$ 428.

Illustration of General Procedure K

Preparation #13: 2-(3,4-Dichlorobenzamido)acetic acid

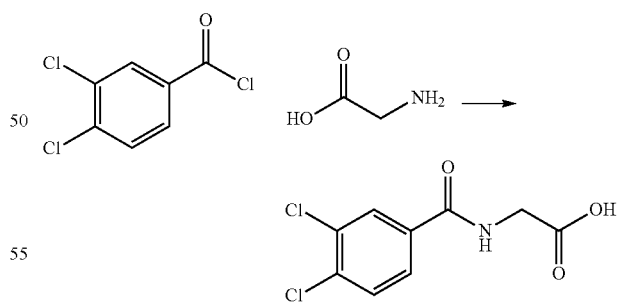

To glycine (3.6 g, 47.7 mmol) in acetonitrile (100 mL) at ambient temperature was added 2N aqueous sodium hydroxide (60 mL, 120 mmol). The reaction mixture was cooled to about 0° C. and 3,4-dichlorobenzoyl chloride (10 g, 47.7 mmol) in acetonitrile (20 mL) was added slowly over about 5 minutes. The reaction mixture was stirred for about 30 minutes at 0° C. then the pH of the reaction mixture was adjusted to 3 by addition of 3N aqueous hydrochloric acid. The organic solvent was removed in vacuo and the aqueous layer extracted with ethyl acetate. The combined organic layers were washed with brine (30 mL), dried over MgSO$_4$ and concentrated in vacuo to afford a light yellow solid. The crude material was triturated with toluene (100 mL) and washed with cold toluene (3×100 mL). The resulting white solid was recrystallized from ethyl acetate to afford 2-(3,4-dichlorobenzamido)acetic acid (4.9 g, 42%) as a white solid. RP-HPLC (table 1, Method b) R$_t$ 1.45 min; m/z: (M+H)$^+$ 246.

TABLE 7

Examples synthesized using general procedure K

| Amine | Acid chloride | Product | Ex. # | HPLC R$_t$ (Method) | m/z or $^1$H NMR (d6 DMSO, 400 MHz) |
|---|---|---|---|---|---|
| 2-Amino-1-[3-(4-phenyl-piperidin-1-yl)-pyrrolidin-1-yl]-ethanone (E, F, G, F) | 3,4-Difluoro-benzoyl chloride | | 7.1 | 1.63 min (a) | (M + H)$^+$ 428 |
| 2-Amino-1-[3-(4-phenyl-piperidin-1-yl)-pyrrolidin-1-yl]-ethanone (E, F, G, F) | 3,5-Difluoro-benzoyl chloride | | 7.2 | 1.51 min (a) | (M + H)$^+$ 428 |
| 2-Amino-1-[3-(4-phenyl-piperidin-1-yl)-pyrrolidin-1-yl]-ethanone (E, F, G, F) | 2-Hydroxy-benzoyl chloride | | 7.3 | 1.61 min (a) | (M + H)$^+$ 408 |
| 2-Amino-1-[3-(4-phenyl-piperidin-1-yl)-pyrrolidin-1-yl]-ethanone (E, F, G, F) | 4-Chloro-carbonyl-benzoic acid methyl ester | | 7.4 | 1.57 min (a) | (M + H)$^+$ 450 |
| 2-Amino-1-[3-(4-phenyl-piperidin-1-yl)-pyrrolidin-1-yl]-ethanone (E, F, G, F) | 3,5-Dimethoxy-benzoyl chloride | | 7.5 | 1.65 min (a) | (M + H)$^+$ 1.65 |
| 2-Amino-1-[3-(4-phenyl-piperidin-1-yl)-pyrrolidin-1-yl]-ethanone (E, F, G, F) | 2,4-Difluoro-benzoyl chloride | | 7.6 | 1.61 min (a) | (M + H)$^+$ 428 |
| 2-Amino-1-[3-(4-phenyl-piperidin-1-yl)-pyrrolidin-1-yl]-ethanone (E, F, G, F) | 2,3-Dichloro-benzoyl chloride | | 7.7 | 1.70 min (a) | (M + H)$^+$ 460 |

TABLE 7-continued

Examples synthesized using general procedure K

| Amine | Acid chloride | Product | Ex. # | HPLC R$_t$ (Method) | m/z or $^1$H NMR (d6 DMSO, 400 MHz) |
|---|---|---|---|---|---|
| 2-Amino-1-[3-(4-phenyl-piperidin-1-yl)-pyrrolidin-1-yl]-ethanone (E, F, G, F) | 2,6-Difluoro-benzoyl chloride | 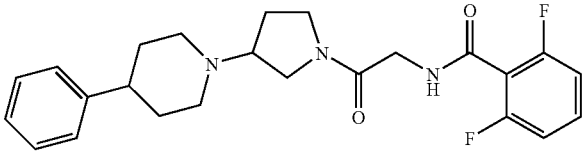 [SMILES: O=C(NCC(=O)N1CCC(N2CCC(c3ccccc3)CC2)C1)c1c(F)cccc1F] | 7.8 | 1.53 min (a) | (M + H)$^+$ 428 |
| 2-Amino-1-[3-(4-phenyl-piperidin-1-yl)-pyrrolidin-1-yl]-ethanone (E, F, G, F) | 3-Fluoro-benzoyl chloride | 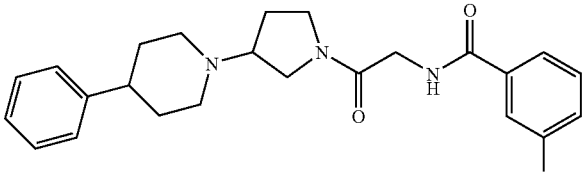 | 7.9 | 1.57 min (a) | (M + H)$^+$ 410 |
| 2-Amino-1-[3-(4-phenyl-piperidin-1-yl)-pyrrolidin-1-yl]-ethanone (E, F, G, F) | 4-Fluoro-benzoyl chloride | 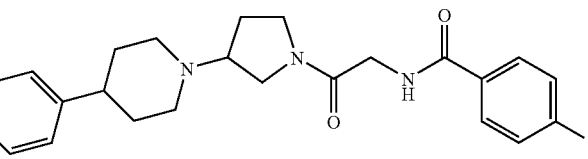 | 7.10 | 1.56 min (a) | (M + H)$^+$ 410 |
| 2-Amino-1-[3-(4-phenyl-piperidin-1-yl)-pyrrolidin-1-yl]-ethanone (E, F, G, F) | 2,5-Difluoro-benzoyl chloride | 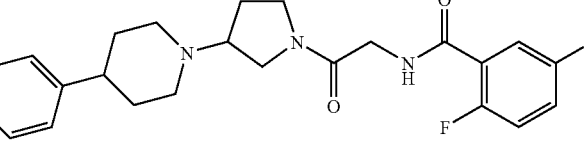 | 7.11 | 1.62 min (a) | (M + H)$^+$ 428 |
| 2-Amino-1-[3-(4-phenyl-piperidin-1-yl)-pyrrolidin-1-yl]-ethanone (E, F, G, F) | 3-Cyano-benzoyl chloride | 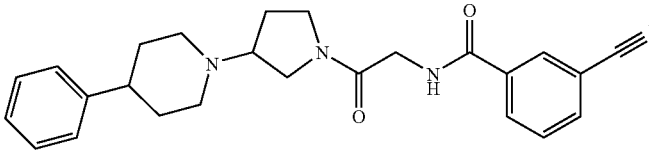 | 7.12 | 1.51 min (a) | (M + H)$^+$ 417 |
| 2-Amino-1-[3-(4-phenyl-piperidin-1-yl)-pyrrolidin-1-yl]-ethanone (E, F, G, F) | 2,3-Difluoro-benzoyl chloride | 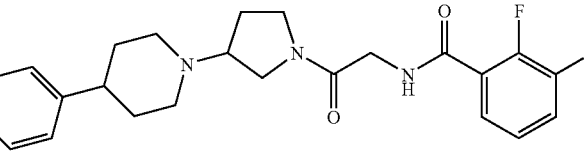 | 7.13 | 1.61 min (a) | (M + H)$^+$ 428 |
| 2-Amino-1-[3-(4-phenyl-piperidin-1-yl)-pyrrolidin-1-yl]-ethanone (E, F, G, F) | 3-Trifluoro-methoxy-benzoyl chloride | 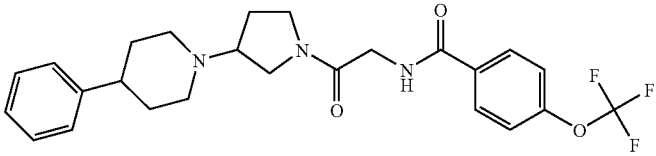 [SMILES: O=C(NCC(=O)N1CCC(N2CCC(c3ccccc3)CC2)C1)c1ccc(OC(F)(F)F)cc1] | 7.14 | 1.84 min (a) | (M + H)$^+$ 476 |
| 2-Amino-1-[3-(4-phenyl-piperidin-1-yl)-pyrrolidin-1-yl]-ethanone (E, F, G, F) | 2,4,6-Trifluoro-benzoyl chloride | 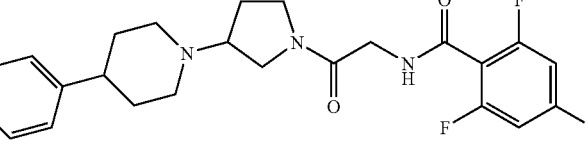 | 7.15 | 1.59 min (a) | (M + H)$^+$ 446 |

TABLE 7-continued

Examples synthesized using general procedure K

| Amine | Acid chloride | Product | Ex. # | HPLC R$_t$ (Method) | m/z or $^1$H NMR (d6 DMSO, 400 MHz) |
|---|---|---|---|---|---|
| 2-Amino-1-[3-(4-phenyl-piperidin-1-yl)-pyrrolidin-1-yl]-ethanone (E, F, G, F) | 2-Chloro-4-fluoro-benzoyl chloride | 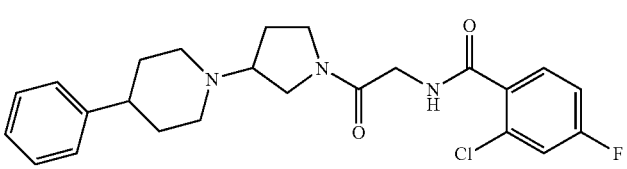 [SMILES: O=C(NCC(=O)N1CCC(N2CCC(c3ccccc3)CC2)C1)c1ccc(F)cc1Cl] | 7.16 | 1.64 min (a) | (M + H)$^+$ 444 |
| 2-Amino-1-[3-(4-phenyl-piperidin-1-yl)-pyrrolidin-1-yl]-ethanone (E, F, G, F) | 2-Trifluoro-methyl-benzoyl chloride | 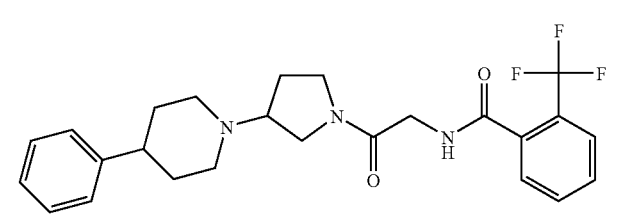 [SMILES: O=C(NCC(=O)N1CCC(N2CCC(c3ccccc3)CC2)C1)c1ccccc1C(F)(F)F] | 7.17 | 1.66 min (a) | (M + H)$^+$ 460 |
| 2-Amino-1-[3-(4-phenyl-piperidin-1-yl)-pyrrolidin-1-yl]-ethanone (E, F, G, F) | 2-Fluoro-4-trifluoro-methyl-benzoyl chloride | 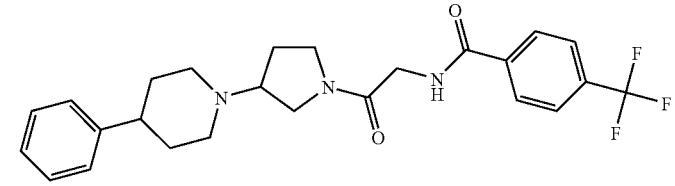 [SMILES: O=C(NCC(=O)N1CCC(N2CCC(c3ccccc3)CC2)C1)c1ccc(C(F)(F)F)cc1] | 7.18 | 1.82 min (a) | (M + H)$^+$ 478 |
| 2-Amino-1-[3-(4-phenyl-piperidin-1-yl)-pyrrolidin-1-yl]-ethanone (E, F, G, F) | 3-Fluoro-4-trifluoro-methyl-benzoyl chloride | 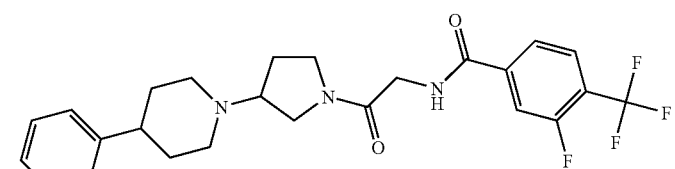 | 7.19 | 1.85 min (a) | (M + H)$^+$ 478 |
| 2-Amino-1-[3-(4-phenyl-piperidin-1-yl)-pyrrolidin-1-yl]-ethanone (E, F, G, F) | 2,4-Dichloro-benzoyl chloride | 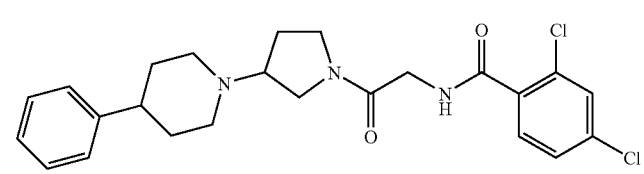 [SMILES: O=C(NCC(=O)N1CCC(N2CCC(c3ccccc3)CC2)C1)c1ccc(Cl)cc1Cl] | 7.20 | 1.73 min (a) | (M + H)$^+$ 460 |
| 2-Amino-1-[3-(4-phenyl-piperidin-1-yl)-pyrrolidin-1-yl]-ethanone (E, F, G, F) | 2-chloro-benzoyl chloride | 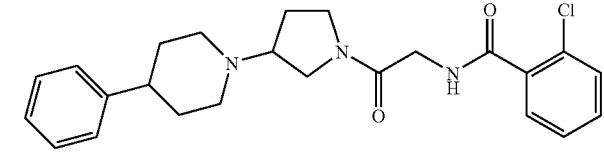 [SMILES: O=C(NCC(=O)N1CCC(N2CCC(c3ccccc3)CC2)C1)c1ccccc1Cl] | 7.21 | 1.56 min (a) | (M + H)$^+$ 426 |
| 2-Amino-1-[3-(4-phenyl-piperidin-1-yl)-pyrrolidin-1-yl]-ethanone (E, F, G, F) | 3,5-Dichloro-benzoyl chloride | 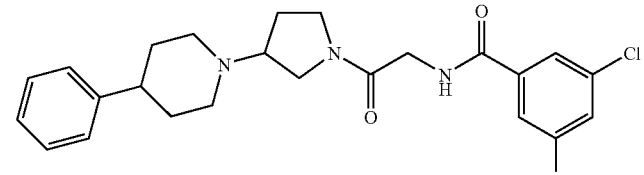 | 7.22 | 1.81 min (a) | (M + H)$^+$ 460 |

TABLE 7-continued

Examples synthesized using general procedure K

| Amine | Acid chloride | Product | Ex. # | HPLC R$_t$ (Method) | m/z or $^1$H NMR (d6 DMSO, 400 MHz) |
|---|---|---|---|---|---|
| 2-Amino-1-[3-(4-phenyl-piperidin-1-yl)-pyrrolidin-1-yl]-ethanone (E, F, G, F) | 2-Fluoro-benzoyl chloride | | 7.23 | 1.49 min (a) | (M + H)$^+$ 410 |
| 2-Amino-1-[3-(4-phenyl-piperidin-1-yl)-pyrrolidin-1-yl]-ethanone (E, F, G, F) | 4-Fluoro-3-methyl-benzoyl chloride | | 7.24 | 1.65 min (a) | (M + H)$^+$ 424 |
| 2-Amino-1-[3-(4-phenyl-piperidin-1-yl)-pyrrolidin-1-yl]-ethanone (E, F, G, F) | 3-dimethyl-amino-benzoyl chloride | | 7.25 | 1.63 min (a) | (M + H)$^+$ 435 |
| 2-Amino-1-[3-(4-phenyl-piperidin-1-yl)-pyrrolidin-1-yl]-ethanone (E, F, G, F) | 2-Fluoro-6-tri-fluormethyl-benzoyl chloride | | 7.26 | 1.68 min (a) | (M + H)$^+$ 478 |
| 2-Amino-1-[3-(4-phenyl-piperidin-1-yl)-pyrrolidin-1-yl]-ethanone (E, F, G, F) | 2-Fluoro-5-tri-fluormethyl-benzoyl chloride | | 7.27 | 1.83 min (a) | (M + H)$^+$ 478 |
| 2-Amino-1-[3-(4-phenyl-piperidin-1-yl)-pyrrolidin-1-yl]-ethanone (E, F, G, F) | 3,4-Dimethoxy-benzoyl chloride | | 7.28 | 1.47 min (a) | (M + H)$^+$ 452 |
| 2-Amino-1-[3-(4-phenyl-piperidin-1-yl)-pyrrolidin-1-yl]-ethanone (E, F, G, F) | Naphthalene-2-carbonyl chloride | | 7.29 | 1.73 min (a) | (M + H)$^+$ 442 |

TABLE 7-continued

Examples synthesized using general procedure K

| Amine | Acid chloride | Product | Ex. # | HPLC R$_t$ (Method) | m/z or $^1$H NMR (d6 DMSO, 400 MHz) |
|---|---|---|---|---|---|
| 2-Amino-1-[3-(4-phenyl-piperidin-1-yl)-pyrrolidin-1-yl]-ethanone (E, F, G, F) | 4-Chloro-2-fluoro-benzoyl chloride | | 7.30 | 1.7 min (a) | (M + H)$^+$ 444 |
| 2-Amino-1-[3-(4-phenyl-piperidin-1-yl)-pyrrolidin-1-yl]-ethanone (E, F, G, F) | 2-Methoxy-benzoyl chloride | | 7.31 | 1.54 min (b) | (M + H)$^+$ 422 |
| 2-Amino-1-[3-(4-phenyl-piperidin-1-yl)-pyrrolidin-1-yl]-ethanone (E, F, G, F) | 2-Trifluoro-methoxy-benzoic acid | | 7.32 | 1.70 min (b) | (M + H)$^+$ 476 |
| 2-Amino-1-[3-(4-phenyl-piperidin-1-yl)-pyrrolidin-1-yl]-ethanone (E, F, G, F) | 4-Chloro-2-hydroxy-benzoyl chloride | | 7.33 | 1.73 min (b) | (M + H)$^+$ 442 |

General Procedure L: Hydrolysis of an Ester to a Carboxylic Acid.

A mixture of an ester (preferably 1 equivalent) and an inorganic hydroxide base (preferably potassium hydroxide; 1 to 10 equivalents, preferably 5 equivalents) in an organic solvent (preferably EtOH) is stirred at about 20-60° C. (preferably about 20° C.) for about 0.5 to 60 hours (preferably about 16 hours). The reaction mixture is concentrated in vacuo and the residue partitioned between water and Et$_2$O. The aqueous portion is separated, acidified by the addition of aqueous acid (preferably 1N aqueous HCl), and extracted with an organic solvent (preferably Et$_2$O). The combined organic portions are washed with brine, dried over an inorganic drying agent (preferably MgSO$_4$), filtered, and dried in vacuo. The product can then be further purified by trituration, crystallization or chromatography.

Illustration of General Procedure L

Preparation #14: 4-Methoxy-1H-indole-2-carboxylic acid

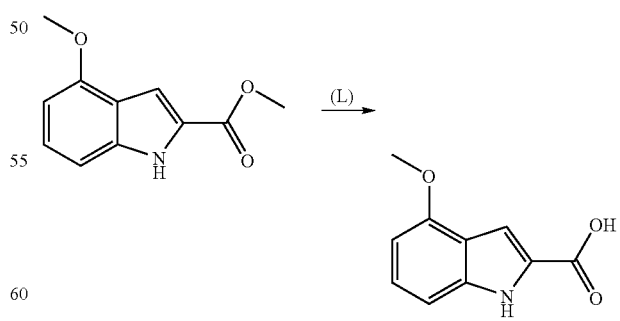

A mixture of 4-methoxy-1H-indole-2-carboxylic acid methyl ester (0.448 g, 2.18 mmol) in potassium hydroxide (0.612 g, 10.9 mmol) and EtOH (111 mL) was stirred at ambient temperature for about 16 h. The reaction mixture was concentrated in vacuo and the residue portioned between water (10 mL) and Et$_2$O (10 mL). The aqueous portion was separated and acidified by the addition of 1N aqueous HCl, then extracted with Et$_2$O (2×10 mL). The combined organic extracts were washed with brine (10 mL), dried over MgSO$_4$, filtered, and concentrated in vacuo to give 4-methoxy-1H-indole-2-carboxylic acid (0.371 g, 89%) as a white solid which was used in subsequent reactions without further purification. $^1$H NMR (d$_6$ DMSO, 400 MHz) 12.84 (1H, s), 11.74 (1H, s), 7.15 (1H, t), 7.00-7.03 (2H, m), 6.52 (1H, d), and 3.87 (3H, s).

General Procedure M: Amine Displacement of a Heterocyclic Halide.

A mixture of an amine (preferably 1 equivalent), a heterocyclic halide (preferably 1 equivalent), and an organic base (preferably DIEA, 1-5 equivalents, preferably 2 equivalents) in an organic solvent (preferably n-butanol) is heated (preferably in a microwave) at about 80-200° C. (preferably about 120° C.) for about 5 min to 12 h (preferably about 20 min). The product can then be further purified by trituration, crystallization, or chromatography.

Illustration of General Procedure M

EXAMPLE #6

2-(7-Chloroquinazolin-4-ylamino)-1-[3-(4-phenylpiperidin-1-yl)pyrrolidin-1-yl]ethanone

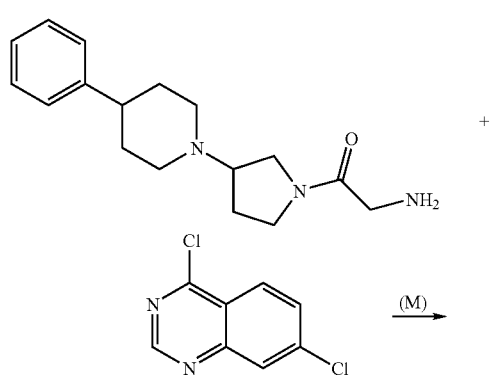

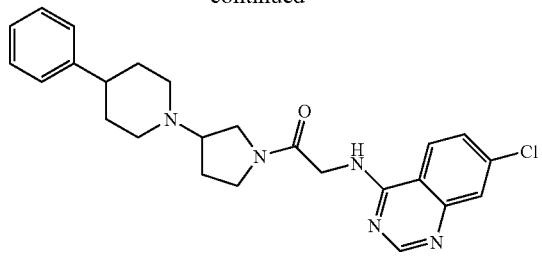

A solution of 2-amino-1-[3-(4-phenylpiperidin-1-yl)pyrrolidin-1-yl]ethanone (preparation #9) (0.108 g, 0.377 mmol), 4,7-dichloroquinazoline (0.075 g, 0.377 mmol) and DIEA (0.1 mL, 0.565 mmol) in n-butanol was heated in a microwave (CEM Explorer, maximum power 300 W) at about 120° C. for about 20 min. The solvent was removed in vacuo and the residue was purified by preparative RP-HPLC (20% to 50% acetonitrile/0.05M aqueous ammonium acetate, buffered to pH 4.5, over 30 min at 81 mL/min; λ=254 nm; Microsorb C18, 100 Å, 5 µm, 250×46 mm column) to yield 2-(7-chloroquinazolin-4-ylamino)-1-[3-(4-phenylpiperidin-1-yl)pyrrolidin-1-yl]ethanone (0.100 g, 0.222 mmol) as a yellow solid. RP-HPLC (Table 1, Method a) R$_t$ 1.77 min; m/z: (M+H)$^+$ 450.

Preparation #15: 4,7,8-Trichloroquinazoline

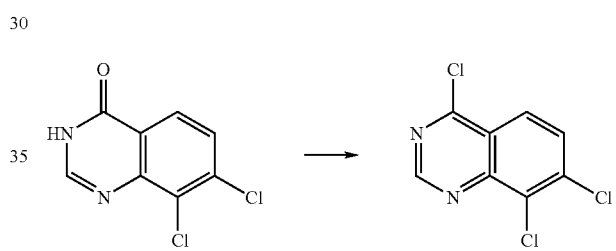

A mixture of 7,8-dichloro-3H-quinazolin-4-one (0.72 g, 3.35 mmol) in phosphorus oxychloride (6.6 g, 12.8 mmol) was heated at reflux for about 4 hours. The reaction mixture was cooled at ambient temperature then added dropwise to ice-cold water. The precipitate was collected by filtration and dried in vacuo to give 4,7,8-trichloroquinazoline as a brown solid (0.64 g, 2.74 mmol, 82%).

TABLE 8

Examples synthesized using general procedure M

| Amine | Chloroquinazoline | Product | Ex. # | HPLC R$_t$ (Method) | m/z or $^1$H NMR (d6 DMSO, 400 MHz) |
|---|---|---|---|---|---|
| 2-amino-1-[3-(4-phenylpiperidin-1-yl)pyrrolidin-1-yl]ethanone (preparation #9) | 4,7,8-Trichloroquinazoline (Preparation #15) | | 8.1 | 1.88 min (a) | (M + H)$^+$ 484 |

TABLE 8-continued

Examples synthesized using general procedure M

| Amine | Chloro-quinazoline | Product | Ex. # | HPLC $R_t$ (Method) | m/z or $^1$H NMR (d6 DMSO, 400 MHz) |
|---|---|---|---|---|---|
| 2-amino-1-[3-(4-phenylpiperidin-1-yl)pyrrolidin-1-yl]ethanone (preparation #9) | 4,6,7-Trichloro-quinazoline | 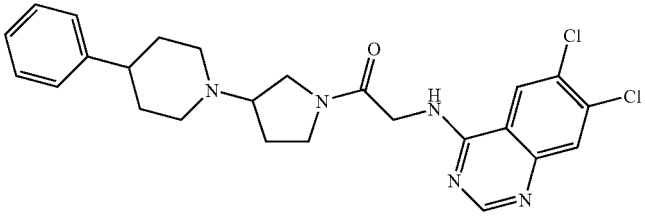 [SMILES: O=C(CNc1ncnc2cc(Cl)c(Cl)cc12)N1CCC(N2CCC(c3ccccc3)CC2)C1] | 8.2 | 2.00 min (a) | (M + H)$^+$ 484 |
| 2-Amino-1-[3-(3-methyl-piperidin-1-yl)-pyrrolidin-1-yl]-ethanone (E, F, G, F) | 4,6,7-Trichloro-quinazoline | 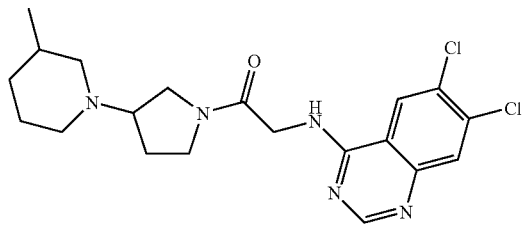 [SMILES: CC1CCCN(C2CCN(C(=O)CNc3ncnc4cc(Cl)c(Cl)cc34)C2)C1] | 8.3 | 2.02 min (a) | (M + H)$^+$ 423 |
| 2-Amino-1-{3-[4-(4-fluoro-phenyl)-4-hydroxy-piperidin-1-yl]-pyrrolidin-1-yl}-ethanone (E, F, G, F) | 4,6,7-Trichloro-quinazoline | 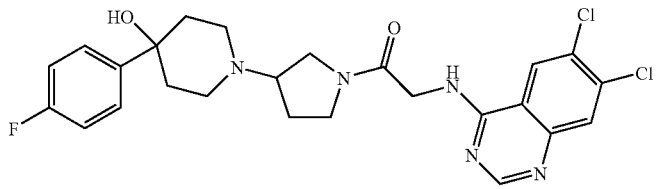 [SMILES: O=C(CNc1ncnc2cc(Cl)c(Cl)cc12)N1CCC(N2CCC(O)(c3ccc(F)cc3)CC2)C1] | 8.4 | 2.28 min (a) | (M + H)$^+$ 519 |
| 2-Amino-1-{3-[4-(2-methoxy-phenyl)-piperidin-1-yl]-pyrrolidin-1-yl-ethanone (E, F, G, F) | 4,6,7-Trichloro-quinazoline | 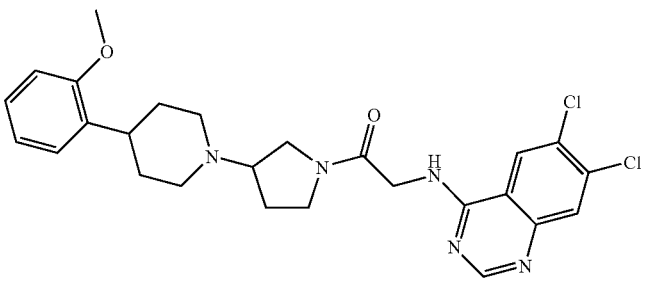 [SMILES: COc1ccccc1C1CCN(C2CCN(C(=O)CNc3ncnc4cc(Cl)c(Cl)cc34)C2)CC1] | 8.5 | 2.13 min (a) | (M + H)$^+$ 515 |
| 2-Amino-1-[3-(4-phenyl-piperidin-1-yl)-pyrrolidin-1-yl]-ethanone (E, F, G, F) | 4,6,7-Trichloro-quinazoline | 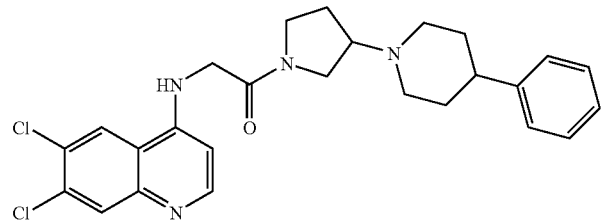 [SMILES: O=C(CNc1ccnc2cc(Cl)c(Cl)cc12)N1CCC(N2CCC(c3ccccc3)CC2)C1] | 8.6 | 1.53 min (a) | (M + H)$^+$ 483 |
| 2-Amino-1-[3-(3-methyl-piperidin-1-yl)-pyrrolidin-1-yl]-ethanone (E, F, G, F) | 4,6,7-Trichloro-quinazoline | 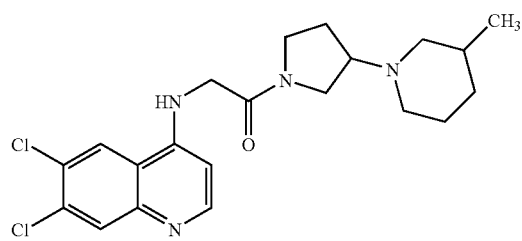 [SMILES: CC1CCCN(C2CCN(C(=O)CNc3ccnc4cc(Cl)c(Cl)cc34)C2)C1] | 8.7 | 1.27 min (a) | (M + H)$^+$ 421 |

TABLE 8-continued

Examples synthesized using general procedure M

| Amine | Chloro-quinazoline | Product | Ex. # | HPLC R$_t$ (Method) | m/z or $^1$H NMR (d6 DMSO, 400 MHz) |
|---|---|---|---|---|---|
| 1-(3-(3H-spiro[isobenzofuran-1,4'-piperidine]-1'-yl)pyrrolidin-1-yl)-2-aminoethanone (E, F, G, F) | 4,6,7-Trichloro-quinazoline | | 8.8 | 1.69 min (a) | (M + H)$^+$ 513 |
| 2-amino-1-(3-(spiro[isochroman-1,4'-piperidine]-1'-yl)pyrrolidin-1-yl)ethanone (E, F, G, F) | 4,6,7-Trichloro-quinazoline | | 8.9 | 1.83 min (a) | (M + H)$^+$ 527 |
| 1-(3-(2H-spiro[benzofuran-3,4'-piperidine]-1'-yl)pyrrolidin-1-yl)-2-aminoethanone (E, F, G, F) | 4,6,7-Trichloro-quinazoline | | 8.10 | 1.80 min (a) | (M + H)$^+$ 513 |
| 2-amino-1-(3-((1R,3'R)-3'-methylspiro[indene-1,4'-piperidine]-1'-yl)pyrrolidin-1-yl)ethanone (E, F, G, F) | 4,6,7-Trichloro-quinazoline | Chiral | 8.11 | 2.36 min (a) | (M + H)$^+$ 522 |

TABLE 8-continued

Examples synthesized using general procedure M

| Amine | Chloro-quinazoline | Product | Ex. # | HPLC R_t (Method) | m/z or ¹H NMR (d6 DMSO, 400 MHz) |
|---|---|---|---|---|---|
| 2-amino-1-[3-(4-phenylpiperidin-1-yl)pyrrolidin-1-yl]ethanone (Preparation #9) | 4,6,7-trichloro-quinazoline | | 8.12 | 1.53 min (b) | (M + H)⁺ 483 |
| 2-amino-1-(3-(3-methylpiperidin-1-yl)pyrrolidin-1-yl)ethanone (E, F, G, F) | 4,6,7-Trichloro-quinazoline | | 8.13 | 1.27 min (b) | (M + H)⁺ 421 |
| 1-((3R)-2-cyclopropyl-pyrrolidin-3-yl)-4-(2-methoxy-phenyl)piperidine (Preparation #27) | 4,7,8-Trichloro-quinazoline | | 8.14 | 1.98 min (a) | (M + H)⁺ 554 |

General Procedure N: Demethylation of a Methoxy Group to a Phenol.

A mixture of a methoxyphenyl piperidine (preferably 1 equivalent) is treated with boron tribromide (1-20 equivalents, preferably about 5 equivalents) in an organic solvent (preferably DCM) at about −20 to 0° C. (preferably about 0° C.) and stirred for about 0.5-24 h (preferably about 1 h). The precipitate is collected by filtration and can be further purified by trituration, crystallization, or chromatography.

Illustration of General Procedure N

EXAMPLE #7

3,4-Dichloro-N-(2-(3-(4-(2-hydroxyphenyl)piperidin-1-yl)pyrrolidin-1-yl)-2-oxoethyl)benzamide

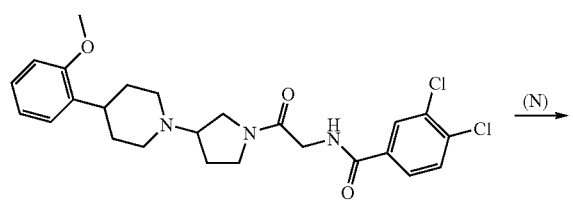

(N) →

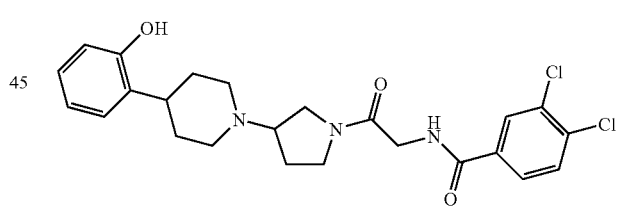

3,4-Dichloro-N-(2-(3-(4-(2-methoxyphenyl)piperidin-1-yl)pyrrolidin-1-yl)-2-oxoethyl)benzamide (0.035 g, 0.071 mmol) and boron tribromide (1M solution in DCM, 0.357 mL, 0.357 mmol) was stirred at about 0° C. for about 1 hour. The precipitate was collected by filtration, rinsed with DCM. The residue was purified by preparative RP-HPLC (15% acetonitrile/0.05M aqueous ammonium acetate buffered to pH 4.5 for 3 min then 15% to 60% acetonitrile/0.05M aqueous ammonium acetate buffered to pH 4.5 over 6 min at 25 mL/min; APCI positive mode detection; Xterra prep. MS C18 19×50 mm column) to yield 3,4-dichloro-N-(2-(3-(4-(2-hydroxyphenyl)piperidin-1-yl)pyrrolidin-1-yl)-2-oxoethyl)benzamide (0.029 g, 0.061 mmol). RP-HPLC (Table 1, Method a) R_t 1.91 min; m/z: (M+H)⁺ 476.

TABLE 9

Examples synthesized using general procedure N

| Starting Material | Product | Ex. # | HPLC R$_t$ (Method) | m/z or $^1$H NMR (d6 DMSO, 400 MHz) |
|---|---|---|---|---|
| 2-(6,7-Dichloro-quinazolin-4-ylamino)-1-{3-[4-(2-methoxy-phenyl)-piperidin-1-yl]-pyrrolidin-1-yl}-ethanone (Ex. 8.5) | | 9.1 | 1.98 min (a) | (M + H)$^+$ 501 |
| 3,4-Dichloro-N-(2-{3-[4-(4-methoxy-phenyl)-piperidin-1-yl]-pyrrolidin-1-yl}-2-oxo-ethyl)-benzamide (K, H, I) | | 9.2 | 1.82 min (a) | (M + H)$^+$ 476 |
| 3,4-Dichloro-N-(2-{3-[4-(2-methoxy-phenyl)-piperidin-1-yl]-pyrrolidin-1-yl}-2-oxo-ethyl)-benzamide (K, H, I) | | 9.3 | 1.89 min (a) | (M + H)$^+$ 476 |
| ((2S,3R)-3-(4-(2-methoxyphenyl)piperidin-1-yl)-2-methylpyrrolidin-1-yl)(3-(trifluoromethyl)-7,8-dihydro-1,6-naphthyridin-6(5H)-yl)methanone (A, B, Y, Z, AA) | | 9.4 | 1.60 min (a) | (M + H)$^+$ 489 |
| 3,4-dichloro-N-(2-((2R,3R)-3-(4-(2-methoxyphenyl)piperidin-1-yl)-2-methylpyrrolidin-1-yl)-2-oxoethyl)benzamide (K, Y, Z, AA) | | 9.5 | 1.62 min (a) | (M + H)$^+$ 490 |
| 3,4-dichloro-N-(2-((2S,3R)-3-(4-(2-methoxyphenyl)piperidin-1-yl)-2-methylpyrrolidin-1-yl)-2-oxoethyl)benzamide (K, Y, Z, AA) | | 9.6 | 1.63 min (a) | (M + H)$^+$ 490 |

TABLE 9-continued

Examples synthesized using general procedure N

| Starting Material | Product | Ex. # | HPLC R_t (Method) | m/z or ¹H NMR (d6 DMSO, 400 MHz) |
|---|---|---|---|---|
| 3,4-dichloro-N-(2-((2R,3R)-2-cyclopropyl-3-(4-(2-methoxyphenyl)piperidin-1-yl)pyrrolidin-1-yl)-2-oxoethyl)benzamide (K, W, X, Y, Z, AA) | [structure] | 9.7 | 1.93 min (a) | (M + H)+ 516 |
| 3,4-dichloro-N-(2-((2S,3R)-2-cyclopropyl-3-(4-(2-methoxyphenyl)piperidin-1-yl)pyrrolidin-1-yl)-2-oxoethyl)benzamide (K, W, X, Y, Z, AA) | [structure] | 9.8 | 1.95 min (a) | (M + H)+ 516 |
| ((2S,3R)-2-cyclopropyl-3-(4-(2-methoxyphenyl)piperidin-1-yl)pyrrolidin-1-yl)(3-(trifluoromethyl)-7,8-dihydro-1,6-naphthyridin-6(5H)-yl)methanone (Y, Z, AA, A, B, C, N) | [structure] | 9.9 | 1.60 min (a) | (M + H)+ 489 |
| 1-((2S,3R)-2-cyclopropyl-3-(4-(2-methoxyphenyl)piperidin-1-yl)pyrrolidin-1-yl)-2-(6,7-dichloroquinazolin-4-ylamino)ethanone (W, X, Y, Z, AA, G, F, M) | [structure] | 9.10 | 4.40 min (d) | (M + H)+ 541 |

(R)-3,4-dichloro-N-(2-(3-(4-(2-hydroxyphenyl)piperidin-1-yl)pyrrolidin-1-yl)-2-oxoethyl)benzamide and (S)-3,4-dichloro-N-(2-(3-(4-(2-hydroxyphenyl)piperidin-1-yl)pyrrolidin-1-yl)-2-oxoethyl)benzamide were prepared as a mixture as described in Example 9.3, then separated via chiral preparative NP-HPLC (isocratic 10% methanol:10% ethanol:80% heptane:0.2% diethylamine modifier at 12 mL/min, column temperature 45° C.; UV detection monitored at 254 nm; Daicel OD-H column, 20×250 mm, 5 um particle) to yield two isomers. Isomer 1 eluted at R_t 20-24 min. Isomer 2 eluted at R_t 29-37 min. The absolute stereochemistry of the isomers was not assigned.

General Procedure O: Formation of an Aryl Piperidinol.

To a solution of n-butyllithium in an organic solvent (preferably hexane) is added an aryl halide (preferably 1 equivalent) in an organic solvent (preferably Et$_2$O) at about −78° C. to −50° C. (preferably about −50° C.). The reaction mixture is stirred at about −78° C. to −50° C. (preferably about −50° C.) for about 0.5 to 4 hours (preferably about 40 minutes). A solution of ketone (1 to 5 equivalents, preferably 1 equivalent) in an organic solvent (preferably Et$_2$O) is added to the reaction mixture dropwise. The mixture is allowed to warm up to about −10° C. 1 M hydrochloric acid is added and the aqueous phase is diluted with an organic solvent (preferably Et$_2$O). Aqueous NH$_4$OH is added to adjust the pH to >9. The residue is dissolved in DCM, washed with brine, and dried in vacuo to yield the arylpiperidin-4-ol that can be used crude in subsequent reactions or further purified by crystallization or chromatography.

Illustration of General Procedure O

Preparation #16:
1-Benzyl-4-(4-fluorophenyl)-3-methylpiperidin-4-ol

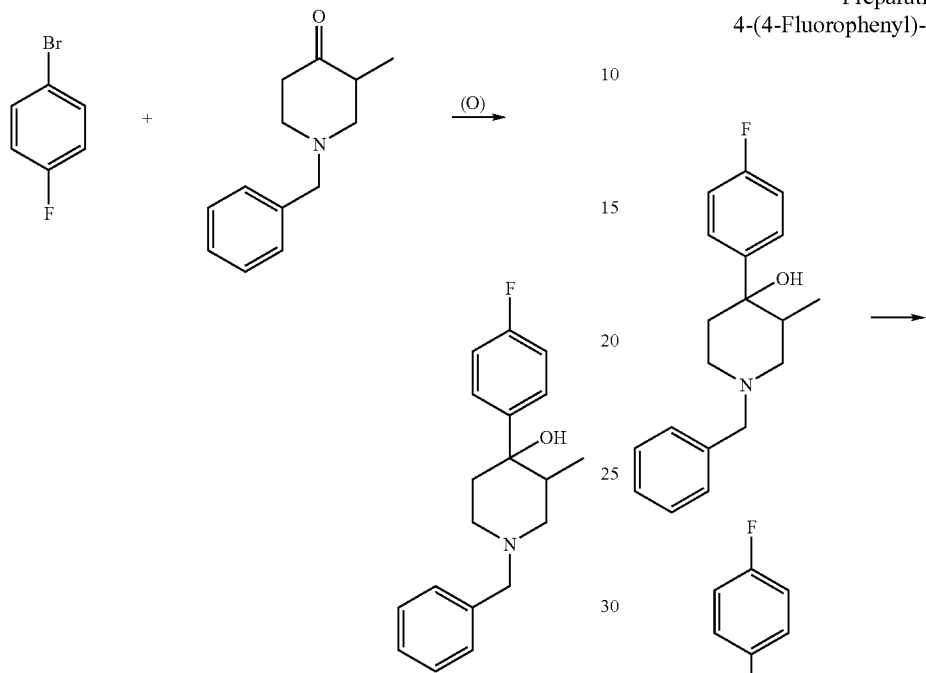

To a solution of n-butyllithium (1-2 equivalents, preferably 1.1 equivalents) (1.6 M in hexane, 8.6 ml, 13.76 mmol) in Et$_2$O (10.32 mL) was added a solution of 1-bromo-4-fluorobenzene (2.21 g, 12.63 mmol) in Et$_2$O (5 ml) at about −50° C. After the reaction mixture was stirred at about −50° C. for about 40 min, a solution of 1-benzyl-3-methylpiperidin-4-one (2.00 g, 9.84 mmol) in Et$_2$O (7 mL) was added dropwise. The mixture was allowed to warm up to about −20° C. to 0° C. (preferably −10° C.). 1M hydrochloric acid (20 mL) was added and the organic phase was discarded. Et$_2$O (20 mL) was added to the aqueous solution and aqueous NH$_4$OH was added to the solution until pH>9. The organic layer was separated and the aqueous layer was extracted with DCM (20 mL). The combined organic portions were washed with brine (2×10 mL), dried over MgSO$_4$, filtered, and concentrated in vacuo to give 1-benzyl-4-(4-fluorophenyl)-3-methylpiperidin-4-ol (2.48 g, 84%) as an oil which was used in subsequent reactions without further purification. RP-HPLC (Table 1, Method a) R$_t$ 1.63 min; m/z: (M+H)$^+$ 300.

General Procedure P: Dehydration and Hydrogenation of an Aryl Piperidinol.

To an aryl piperidinol (preferably 1 equivalent) in an organic solvent (preferably ethanol) at about 70-85° C. (preferably about 80° C.) is added concentrated HCl (50 to 500 equivalents, preferably 175 equivalents). The reaction mixture is refluxed for about 0.5 to 4 hours (preferably about 2 hours). The organic solvent is removed in vacuo after cooling to ambient temperature. The aqueous solution is basified by the addition of base (preferably concentrated NaOH) to pH>9 and then extracted with DCM. The organic phase is washed with brine and dried in vacuo. The residue is hydrogenated at about 40-80° C. (preferably about 60° C.) in the presence of a catalyst (preferably 10% Pd on carbon), with or without a catalytic amount of HOAc, in an organic solvent (preferably EtOH or EtOAc). The solvent is removed in vacuo to afford the product that can be further purified by chromatography or crystallization.

Illustration of General Procedure P

Preparation #17:
4-(4-Fluorophenyl)-3-methylpiperidine

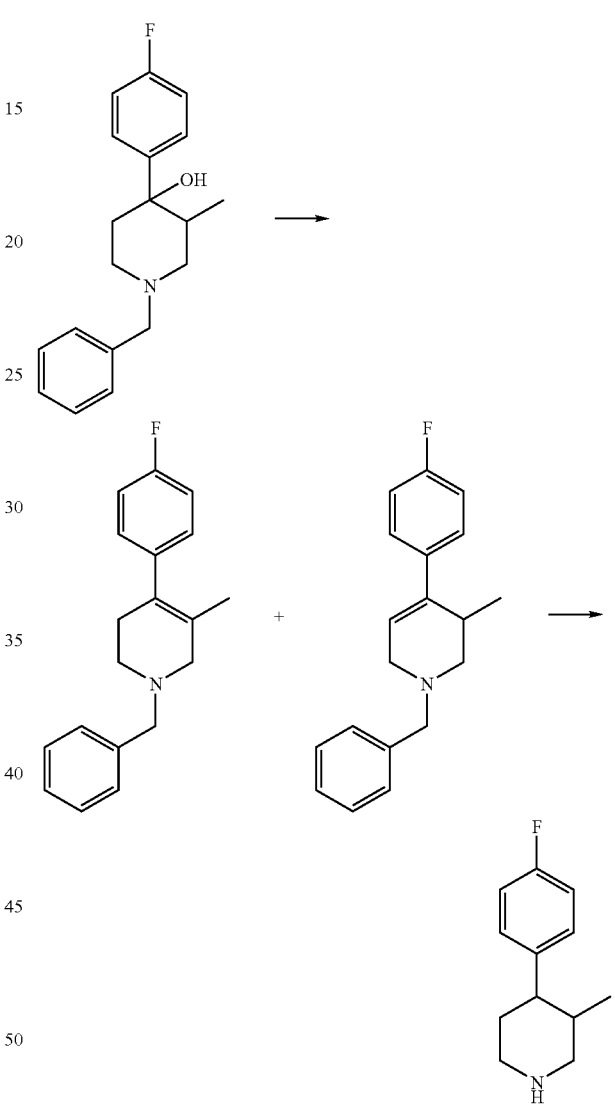

To a solution of 1-benzyl-4-(4-fluorophenyl)-3-methylpiperidin-4-ol (1.02 g, 3.41 mmol) in ethanol (18 mL) at 80° C. was added concentrated HCl (18 mL, 592 mmol). The reaction mixture was refluxed for 2 hour and then cooled to ambient temperature. The organic solvent was removed in vacuo. The aqueous solution was basified with concentrated NaOH to pH>9 then extracted with DCM (50 mL). The organic layer was washed with brine (2×10 mL), dried over MgSO$_4$, filtered, and concentrated in vacuo. The residue was dissolved in EtOH (2 mL) and acetic acid (0.2 mL). The reaction mixture was hydrogenated with Pd/C (10%) in an H-cube™ apparatus at 60° C. for 3 minutes. The solvent was removed in vacuo and the residue was purified by preparative RP-HPLC (10% acetonitrile/0.05M aqueous ammonium acetate buffered to pH 4.5 for 2.5 min then 10% to 15% acetonitrile/0.05M aqueous ammonium acetate buffered to pH 4.5 over 4.0 min then 15% to 45% acetonitrile/0.05M aqueous ammonium acetate buffered to pH 4.5 over 4.0 min at 25 mL/min; APCI positive mode detection; Xterra prep. MS C18 19×50 mm column) to afford 4-(4-fluorophenyl)-3-the mixture was again heated at about reflux for about 12 h. The reaction mixture was cooled at room temperature and filtered, rinsed with toluene. The filtrate was concentrated in vacuo to provide (1-oxo-3,4-dihydro-1H-isoquinolin-2-yl)-acetic acid ethyl ester as a peach oil (0.336 g, 1.44 mmol). The crude material was used in subsequent reactions without further purification.

TABLE 10

Examples synthesized using general procedure Q

| Starting Material | Product | Ex. # | HPLC R_t (Method) | m/z or $^1$H NMR (d6 DMSO, 400 MHz) |
|---|---|---|---|---|
| 2-Bromo-1-[3-(4-phenyl-piperidin-1-yl)-pyrrolidin-1-yl]-ethanone (Preparation #20) | | 10.1 | 2.43 min (a) | (M + H)$^+$ 473 | methylpiperidine (0.438 g, 66%). RP-HPLC (Table 1, Method a) R_t 1.43 min; m/z: (M+H)$^+$ 194.

General Procedure Q: Alkylation of an Amine or Amide with an Alkyl Halide.

To a solution of an amine or amide (preferably 1 equivalent) in an anhydrous solvent (preferably toluene) is added an inorganic base (preferably sodium hydride, 1-20 equivalents, preferably about 1.2 equivalents) and heated at about 20 to 150° C. (preferably about 110° C.) for about 0.5 to 24 h (preferably about 2 h). An alkyl halide (1-5 equivalents, preferably about 1 equivalent) is added and the reaction mixture heated at about 20 to 150° C. (preferably about 110° C.) for about 0.5-24 h (preferably about 12 h). The reaction mixture is filtered and the filtrate concentrated in vacuo to give the crude product that can be further purified by trituration, crystallization, or chromatography.

Illustration of General Procedure Q

Preparation #18:
(1-Oxo-3,4-dihydro-1H-isoquinolin-2-yl)-acetic acid ethyl ester

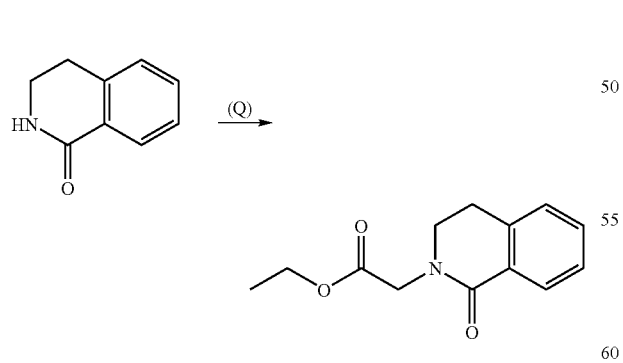

To a solution of 3,4-dihydro-2H-isoquinolin-1-one (0.250 g, 1.70 mmol) in toluene (5 mL) was added sodium hydride (60% in mineral oil, 0.049 g, 2.04 mmol) and the resulting suspension was heated at about reflux for about 1 h. The reaction mixture was cooled at room temperature and ethyl 2-iodoacetate (0.364 g, 1.70 mmol) was added dropwise and General Procedure R: Addition of an Amine to a bis-Benzotriazolyl Ethanedione.

To a suspension of 1,2-bis-benzotriazol-1-yl-ethane-1,2-dione (preferably 1 equivalent) in an organic solvent (preferably THF) is added an amine (1-5 equivalents, preferably 1 equivalent) with or without additional organic base (preferably Et$_3$N, 1-5 equivalents, preferably 1 equivalent) and the reaction mixture is stirred at about 0-50° C. (preferably about 25° C.) for about 1 to 24 h (preferably about 4 h). The reaction mixture is concentrated in vacuo and triturated with iPrOAc. The filtrate is concentrated in vacuo then dissolved in EtOAc, washed with aqueous NaOH and aqueous NaHCO$_3$, and dried in vacuo. The residue can be used crude in subsequent reactions or be further purified by crystallization or chromatography.

Illustration of General Procedure R

Preparation #19: 1-Benzotriazol-1-yl-2-(3-trifluoromethyl-7,8-dihydro-5H-[1,6]naphthyridin-6-yl)-ethane-1,2-dione

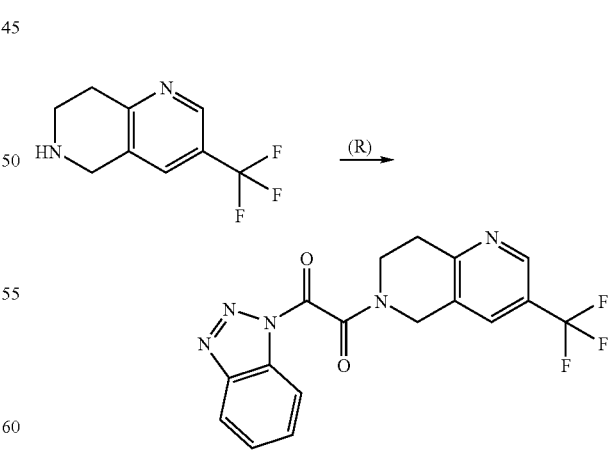

To a suspension of 1,2-bis-benzotriazol-1-yl-ethane-1,2-dione (0.100 g, 0.342 mmol) in THF (3.4 mL) was added 3-trifluoromethyl-5,6,7,8-tetrahydro-[1,6]naphthyridine monohydrochloride (0.082 g, 0.342 mmol) and the reaction mixture was stirred at ambient temperature for about 4 h.

Et₃N (0.05 mL, 0.34 mmol) was added and stirring was resumed for about 1 hour. The reaction mixture was concentrated in vacuo and the residue triturated from hot iPrOAc. The solid was removed by filtration and the filtrate concentrated in vacuo then dissolved in EtOAc (10 mL), washed with 1N aq NaOH (2×5 mL), and saturated aqueous NaHCO₃ (10 mL). The organic portion was separated, dried over MgSO₄, filtered, and concentrated in vacuo to provide 1-benzotriazol-1-yl-2-(3-trifluoromethyl-7,8-dihydro-5H-[1,6]naphthyridin-6-yl)-ethane-1,2-dione as an orange oil (0.056 g, 0.15 mmol). The crude material was used without further purification.

General Procedure S: Formation of an Oxamide from a Benzotriazolyl Ethanedione.

To a mixture of amine (1-5 equivalents, preferably 1 equivalent) in an organic solvent (preferably THF) is added sodium hydride (1-5 equivalents, preferably about 3 equivalents) and the reaction mixture is stirred for about 0.5 h. This mixture is added to a solution of benzotriazole dione (preferably 1 equivalent) in an organic solvent (preferably THF) and stirred at about 0-50° C. (preferably about 25° C.) for about 1-24 h (preferably about 2 h). The reaction mixture is quenched by the addition of saturated aqueous NaHCO₃ and the organic portion separated, dried, filtered, and concentrated to afford the product that can be further purified by crystallization or chromatography.

Illustration of General Procedure S

EXAMPLE #8

1-[3-(4-Phenyl-piperidin-1-yl)-pyrrolidin-1-yl]-2-(3-trifluoromethyl-7,8-dihydro-5H-[1,6]naphthyridin-6-yl)-ethane-1,2-dione

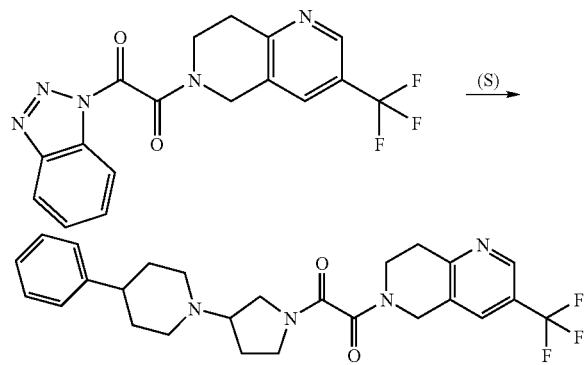

To a suspension of 4-phenyl-1-pyrrolidin-3-yl-piperidine dihydrochloride (Preparation #7, 0.041 g, 0.135 mmol) in THF (1.3 mL) was added sodium hydride (60% in mineral oil, 0.016 g, 0.405 mmol) and the reaction mixture was stirred at ambient temperature for about 0.5 h then added to a solution of 1-benzotriazol-1-yl-2-(3-trifluoromethyl-7,8-dihydro-5H-[1,6]naphthyridin-6-yl)-ethane-1,2-dione (0.051 g, 0.135 mmol) in THF (1.3 mL). The reaction mixture was stirred at ambient temperature for about 2 hour then quenched by the addition of saturated aqueous NaHCO₃. The organic phase was separated and the aqueous portion extracted with EtOAc (15 mL). The combined organic extracts were dried over MgSO₄, filtered, and concentrated in vacuo to give the product as a red oil that solidified upon standing (0.063 g, 0.129 mmol). The residue was purified by preparative RP-HPLC (10% acetonitrile/0.05M aqueous ammonium acetate buffered to pH 4.5 for 3 min then 10% to 50% acetonitrile/0.05M aqueous ammonium acetate buffered to pH 4.5 over 6 min at 25 mL/min; APCI positive mode detection; Xterra prep. MS C18 19×50 mm column) to 1-[3-(4-phenyl-piperidin-1-yl)-pyrrolidin-1-yl]-2-(3-trifluoromethyl-7,8-dihydro-5H-[1,6]naphthyridin-6-yl)-ethane-1,2-dione. RP-HPLC (Table 1, Method a) $R_t$ 2.02 min; m/z: (M+H)⁺ 487.

General Procedure T: Formation of an α-bromo Amide.

To a mixture of an amine (1-5 equivalents, preferably 1 equivalent) and an organic base (preferably Et₃N, 1-5 equivalents, preferably 2 equivalents) in an organic solvent (preferably THF) is added bromoacetyl bromide (1-5 equivalents, preferably about 1 equivalent) and the reaction mixture is stirred for about 0.5 to 24 h (preferably about 12 h). The reaction mixture is concentrated in vacuo to afford the product that can be further purified by crystallization or chromatography or used without further purification.

Illustration of General Procedure T

Preparation #20: 2-Bromo-1-[3-(4-phenyl-piperidin-1-yl)-pyrrolidin-1-yl]-ethanone

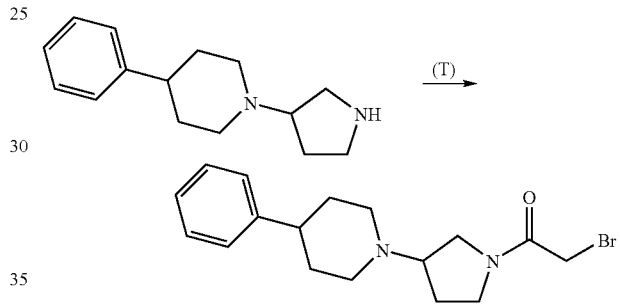

To a solution of 4-phenyl-1-pyrrolidin-3-yl-piperidine dihydrochloride (prepared using general procedures E, F, 0.051 g, 0.17 mmol) and Et₃N (0.05 mL, 0.34 mmol) in THF (1.7 mL) was added bromoacetylbromide (0.015 mL, 0.17 mmol). The reaction mixture was stirred at ambient temperature for about 12 h then concentrated in vacuo to give 2-bromo-1-[3-(4-phenyl-piperidin-1-yl)-pyrrolidin-1-yl]-ethanone that was used without further purification.

General Procedure U: Suzuki Coupling of a Halide with a Boronate Ester or Boronic Acid A mixture of a boronate ester or a boronic acid (1-5 equivalents, preferably 1.0 equivalents), a halide (for example a bromide or an iodide, preferably an iodide) (preferably 1 equivalent) and a base (for example, sodium carbonate or sodium bicarbonate, preferably sodium carbonate) (1-10 equivalents, preferably 4 equivalents), a palladium catalyst (for example, palladium (II) acetate, tris(dibenzylideneacetone)dipalladium(0), tetrakis(triphenylphosphine)palladium(0), preferably tetrakis(triphenylphosphine)-palladium (0)) (0.01-0.2 equivalents, preferably 0.10 equivalents) in a mixture of an organic solvent (for example, ethylene glycol dimethyl ether, N,N-dimethylformamide, or toluene, preferably ethylene glycol dimethyl ether) and water is either heated at about 130-180° C. (preferably 150° C.) for about 5-10 minutes (preferably about 8 minutes) in a microwave or heated under stirring at about 60-90° C. (preferably about 85° C.) for about 10-20 hours (preferably about 12 hours). The mixture is allowed to cool to ambient temperature and the solvents are removed under reduced pressure. The residue is partitioned between water and an organic solvent (DCM, ether or ethylacetate, preferably DCM), the organic layer is separated and the aqueous layer is further extracted with organic solvent. The combined organic extracts are dried over a desiccant. The solvents are evaporated under reduced pressure to afford the product that can be further purified by crystallization or chromatography.

Illustration of General Procedure U

Preparation #21: tert-butyl 4-(pyridin-2-yl)-5,6-dihydropyridine-1(2H)-carboxylate

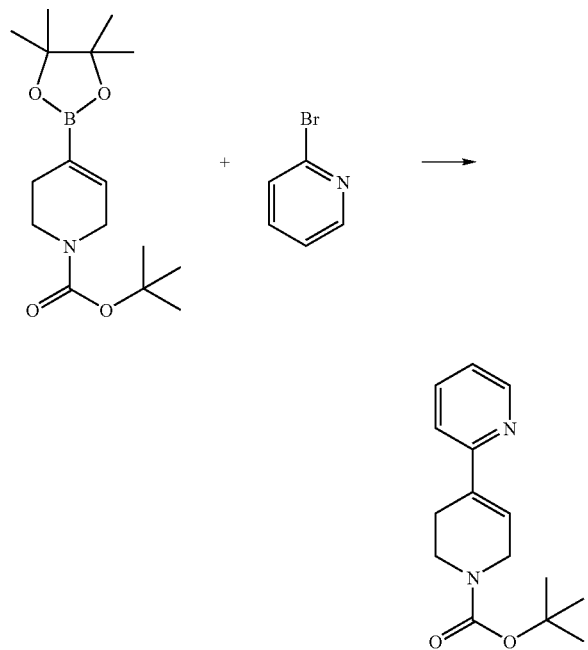 [SMILES: CC(C)(C)OC(=O)N1CC=C(B2OC(C)(C)C(C)(C)O2)CC1 ; Brc1ccccn1 ; CC(C)(C)OC(=O)N1CC=C(c2ccccn2)CC1]

A mixture of tert-butyl 4-(4,4,5,5-tetramethyl-1,3,2-dioxaborolan-2-yl)-5,6-dihydropyridine-1(2H)-carboxylate (0.500 g, 1.04 mmol), 2-bromopyridine (0.164 g, 1.04 mmol), sodium carbonate (0.439 g, 4.14 mmol), tetrakis(triphenylphosphine)palladium(0) (0.120 g, 0.103 mmol) in ethylene glycol dimethyl ether (20 mL) and water (10 mL) was heated at about 85° C. for about 12 hours. The reaction mixture was allowed to cool to ambient temperature and the solvent was removed under reduced pressure. The residue was partitioned between water (25 mL) and dichloromethane (50 mL). The organic layer was separated and the aqueous layer was further extracted with dichloromethane (2×50 mL). The combined organic extracts were dried over magnesium sulfate and evaporated under reduced pressure. The residue was purified by using preparative RP-HPLC (Rainin C18, 8 mm, 300 Å, 35 cm; 5-100% acetonitrile—0.1M ammonium acetate over 20 min, 100% acetonitrile hold 10 minutes, 21 mL/min) to give tert-butyl 4-(pyridin-2-yl)-5,6-dihydropyridine-1(2H)-carboxylate (0.202 g, 0.776 mmol) as a white solid; RP-HPLC (Table 1, Method b) $R_t$ 2.78 min; m/z: (M+H)$^+$ 261.

General Procedure V: Hydrogenation to Reduce a Double Bond in a Tetrahydropyridine.

A tetrahydro-pyridine is hydrogenated at about 40-80° C. (preferably about 60° C.) in the presence of a catalyst (preferably 10% Pd on carbon), with or without a catalytic amount of acid (preferably HOAc) in an organic solvent (preferably EtOH or EtOAc). The solvent is removed in vacuo to afford the product that can be further purified by chromatography or crystallization.

Illustration of General Procedure V

Preparation #22: tert-Butyl 4-(pyridin-2-yl)piperidine-1-carboxylate

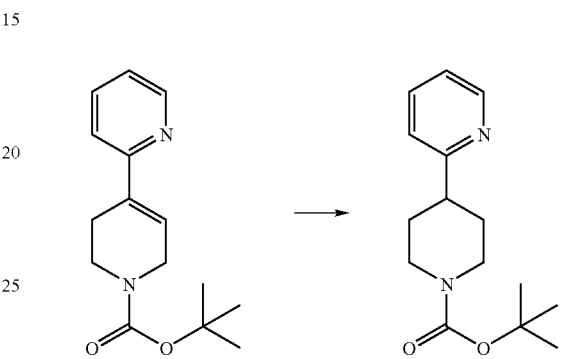

Tert-butyl 4-(pyridin-2-yl)-5,6-dihydropyridine-1(2H)-carboxylate (0.150 g, 0.576 mmol) was dissolved in ethanol (2 mL) and acetic acid (0.2 mL). The reaction mixture was hydrogenated with Pd/C (10%) in an H-cubemapparatus at about 60° C. for about 3 minutes. The solvent was removed in vacuo to give tert-butyl 4-(pyridin-2-yl)piperidine-1-carboxylate (0.151 g, 0.576 mmol) as white solid which was used in subsequent reactions without further purification. RP-HPLC (Table 1, Method b) $R_t$ 1.97 min; m/z: (M+H)$^+$ 263.

General Procedure W: Formation of a Saturated Chiral Bicyclic Lactam

A mixture of an 2-amino-2-phenylethanol (1-2 equivalents, preferably 1.2 equivalents) and a γ-ketoacid (preferably 1 equivalent) in an organic solvent (preferably toluene) is heated at reflux for about 6-24 hours (preferably 6 hours). The reaction mixture is diluted with an organic solvent (preferably EtOAc) and washed with dilute aqueous acid (preferably aqueous HCl), saturated NaHCO$_3$, brine, dried, filtered and concentrated in vacuo. The residue can then be further purified by crystallization or chromatography.

Illustration of General Procedure W

Preparation #23: (3S,7aS)-7a-cyclopropyl-3-phenyltetrahydropyrrolo[2,1-b]oxazol-5(6H)-one

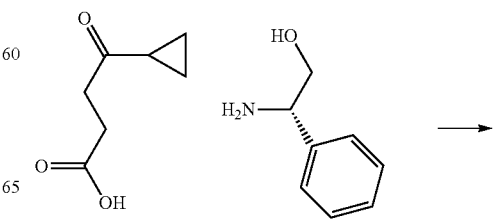

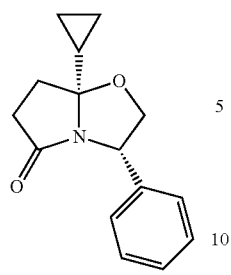

A mixture of (S)-2-amino-2-phenylethanol (2.28 g, 16.6 mmol) and 4-cyclopropyl-4-oxobutanoic acid (1.97 g, 13.8 mmol) in toluene (35 mL) was heated at reflux for about 6 h. The reaction mixture was cooled to room temperature and diluted with EtOAc, washed with aqueous HCl (1.0 N), saturated NaHCO$_3$, brine, dried over MgSO$_4$, filtered and concentrated in vacuo. The residue was purified on a Biotage silica gel column eluting with heptane/EtOAc (3:2) to afford (3S,7aS)-7a-cyclopropyl-3-phenyltetrahydropyrrolo[2,1-b]oxazol-5(6H)-one (2.54 g, 10.4 mmol) as a bright yellow needle-like solid. RP-HPLC (Table 1, Method a) R$_t$ 1.77 min; m/z: (M+H)$^+$ 244.

General Procedure X: Formation of an Unsaturated Chiral Bicyclic Lactam

To an inorganic base (preferably potassium hydride, 2-5 equivalents, preferably 2.5 equivalents) in an organic solvent (preferably THF) is added a solution of a chiral lactam (preferably 1 equivalent) in an organic solvent (preferably THF) slowly, followed by a solution of methyl benzenesulfinate (1-3 equivalents, preferably 1.2 equivalents) in an organic solvent (preferably THF). The reaction mixture is stirred at room temperature for about 1.5-60 hours (preferably about 16 hours). The reaction is quenched with water and concentrated in vacuo. The residue is partitioned between dilute H$_3$PO$_4$ and DCM. The layers are separated and the aqueous layer is extracted with DCM. The combined organic layers are washed with brine, dried over a dessicant, filtered and concentrated. Toluene is added to the residue, followed by an inorganic base (preferably solid Na$_2$CO$_3$). The reaction mixture is heated at about reflux for about 0.5 to 60 hours (preferably about 16 hours). After cooling to room temperature, the reaction mixture is filtered and concentrated in vacuo. The residue can be further purified by recrystallization or chromatography.

Illustration of General Procedure X

Preparation #24: (3S,7aR)-7a-cyclopropyl-3-phenyl-2,3-dihydropyrrolo[2,1-b]oxazol-5(7aH)-one

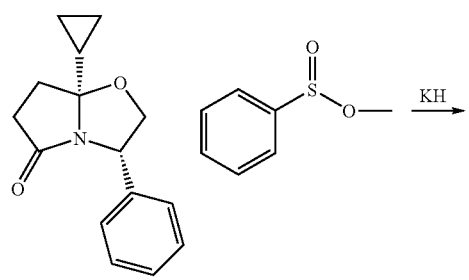

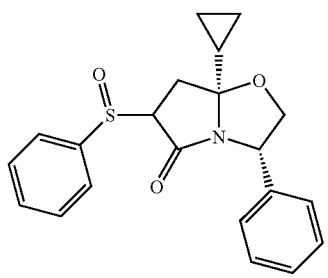

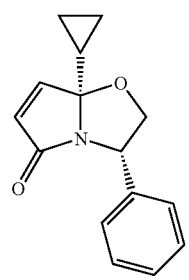

To potassium hydride (35 weight % in oil, washed with heptane (×3), 3.01 g, 26.3 mmol), in THF (20 mL) was added a solution of (3S,7aS)-7a-cyclopropyl-3-phenyltetrahydropyrrolo[2,1-b]oxazol-5(6H)-one (preparation #23) (2.56 g, 10.5 mmol) in THF (20 mL) dropwise via an addition funnel. A solution of methyl benzenesulfinate (1.97 g, 12.6 mmol) in THF (20 mL) was then added dropwise via an addition funnel. The reaction mixture was stirred at ambient temperature for about 16 hours. The reaction was quenched by the addition of water (4.2 mL). The mixture was concentrated and the residue was partitioned between 0.5 M H$_3$PO$_4$ (100 mL) and DCM (200 mL). The layers were separated and the aqueous layer was extracted with DCM (3×100 mL). The combined organic extracts were washed with brine, dried over MgSO$_4$, filtered and concentrated to yield a light brown solid. Toluene (83 mL) was added followed by solid Na$_2$CO$_3$ (10.35 g). The reaction mixture was refluxed for about 16 hours and then filtered and concentrated in vacuo. The residue was purified on a Biotage silica gel column eluting with heptane/EtOAc (4:1). A second purification on silica gel eluting DCM/EtOAc (1:0 to 4:1) afforded (3S,7aR)-7a-cyclopropyl-3-phenyl-2,3-dihydropyrrolo[2,1-b]oxazol-5(7aH)-one (1.82 g, 7.57 mmol). $^1$H NMR (CDCl$_3$-d) δ 7.34 (m, 4H), 7.28 (m, 1H), 7.11 (d, 1H), 6.08 (d, 1H), 5.06 (t, 1H), 4.69 (t, 1H), 4.43 (dd, 1H), 1.14 (m, 1H), 0.45 (m, 2H), 0.32 (m, 1H), 0.21 (m, 1H).

General Procedure Y: Michael Addition of an Amine to a Bicyclic Lactam

To a mixture of an amine (1-2 equivalents, preferably 1.2 equivalents) and an unsaturated bicyclic lactam (preferably 1 equivalent) is added water (10-20 equivalents, preferably 10 equivalents). After about 5 minutes, DCM is added until the solid dissolves. The reaction mixture is stirred at room temperature for about 0.5-60 hours (preferably about 16 hours). The product can be purified by crystallization or chromatography.

Illustration of General Procedure Y

Preparation #25: (3S,7R,7aR)-7a-cyclopropyl-7-(4-(2-methoxyphenyl)piperidin-1-yl)-3-phenyltetrahydropyrrolo[2,1-b]oxazol-5(6H)-one

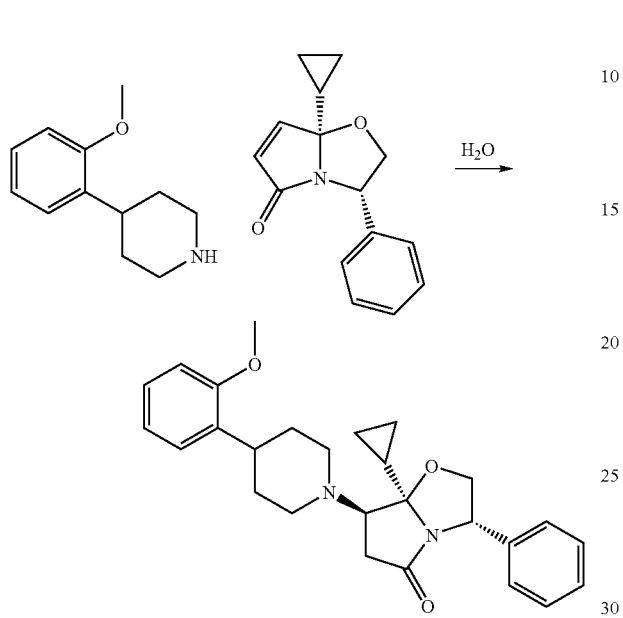

To a mixture of 4-(2-methoxyphenyl)piperidine (0.951 g, 4.97 mmol) and (3S,7aR)-7a-cyclopropyl-3-phenyl-2,3-dihydropyrrolo[2,1-b]oxazol-5(7aH)-one (preparation #24) (1.0 g, 4.1 mmol) was added water (0.8 mL, 44 mmol). After about 5 minutes, DCM (5 mL) was added. All the solids dissolved. The reaction mixture was stirred at room temperature for about 16 hours. Purification on a Biotage silica gel column eluting with DCM/EtOAc (1:0 to 1:1) afforded (3S,7R,7aR)-7a-cyclopropyl-7-(4-(2-methoxyphenyl)piperidin-1-yl)-3-phenyltetrahydropyrrolo[2,1-b]oxazol-5(6H)-one (1.29 g, 2.98 mmol) as a white solid. RP-HPLC (Table 1, Method a) $R_t$ 2.14 min; m/z: $(M+H)^+$ 433.

General Procedure Z: Reduction and Ring Opening of a Bicyclic Lactam

To aluminum chloride (1-2 equivalent, preferably 1 equivalent) at 0° C. is added in an organic solvent (preferably THF). A reducing agent (preferably lithium aluminum hydride, 3-5 equivalents, preferably 3.5 equivalents) in an organic solvent (preferably THF) is added dropwise and the reaction mixture is allowed to warm to room temperature. After about 10-60 minutes (preferably 20 minutes), the reaction mixture is cooled to about −50 to −100° C. (preferably −78° C.) and a solution of a bicyclic lactam (preferably 1 equivalent) in an organic solvent (preferably THF) is added. After about 1.5 to 5 hours (preferably 1 hour) the reaction mixture is allowed to warm to room temperature and stirred at room temperature for about 0.5 to 5 hours (preferably about 3 hours). After cooling to about 0° C., water is added dropwise followed by a solution of aqueous base (preferably aqueous NaOH). More water is added followed by an organic solvent (preferably ether). After about 10-50 minutes (preferably 30 minutes), the organic portion is decanted, dried over MgSO$_4$, and concentrated in vacuo. The product can be used as is or further purified by recrystallization or chromatography.

Illustration of General Procedure Z

Preparation #26: (2S)-2-((3R)-3-(4-(2-methoxyphenyl)piperidin-1-yl)-2-cyclopropylpyrrolidin-1-yl)-2-phenylethanol

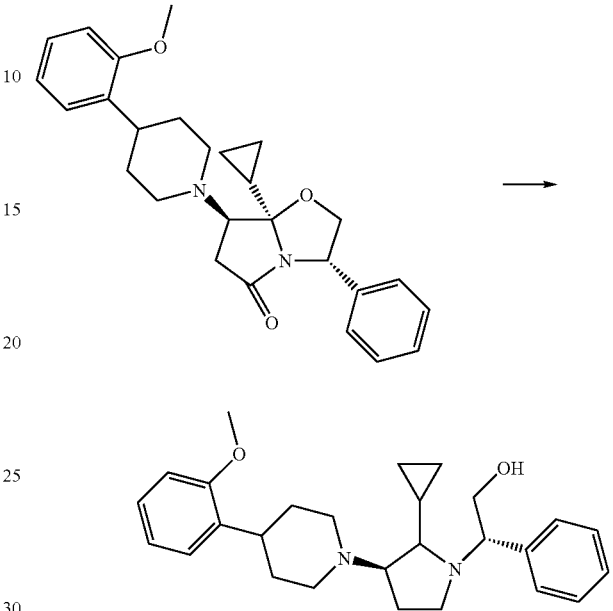

To solid aluminum chloride (0.422 g, 3.16 mmol) at 0° C. was added anhydrous THF (23 mL). The mixture was stirred until all solid went into solution. Lithium aluminum hydride (1.0 N in THF, 8.95 mL, 8.95 mmol) was added dropwise and the reaction mixture was allowed to warm to room temperature. After about 20 minutes, the reaction mixture was cooled to about −78° C. and a solution of (3S,7R,7aR)-7a-cyclopropyl-7-(4-(2-methoxyphenyl)piperidin-1-yl)-3-phenyltetrahydropyrrolo[2,1-b]oxazol-5(6H)-one (preparation #25) (1.29 g, 2.98 mmol) in THF (16 mL) was added. The reaction mixture was stirred for about 1 h then allowed to warm up to room temperature and stirred for an additional 3 h. The reaction mixture was cooled to about 0° C. and water (2.7 mL) was added dropwise followed by aqueous NaOH (2.0N, 4 mL). More water (9 mL) was added, then ether (70 mL) and the mixture was stirred for about 30 min. The ether solution was decanted, dried over MgSO$_4$ and concentrated in vacuo to afford (2S)-2-((3R)-3-(4-(2-methoxyphenyl)piperidin-1-yl)-2-cyclopropylpyrrolidin-1-yl)-2-phenylethanol (1.25 g, 2.98 mmol) as a pair of diastereomers as a white solid. RP-HPLC (Table 1, Method a) $R_t$ 1.79 and 1.96 min; m/z: $(M+H)^+$ 421.

General Procedure AA: Removal of a Benzyl Group by Hydrogenation

A solution of a benzyl amine in an organic solvent (preferably EtOH) is hydrogenated under hydrogen at about 50-70 bar (preferably 60 bar) at about 25-80° C. (preferably at about 60° C.) in a H-cubemapparatus with a palladium catalyst (preferably palladium hydroxide on carbon) for about 5 min-2 h (preferably about 30 min). The solvent is removed in vacuo to afford the desired 2-substituted 3-aminopyrrolidines that can be further purified by crystallization or chromatography.

Illustration of General Procedure AA

Preparation #27: 1-((3R)-2-cyclopropylpyrrolidin-3-yl)-4-(2-methoxyphenyl)piperidine

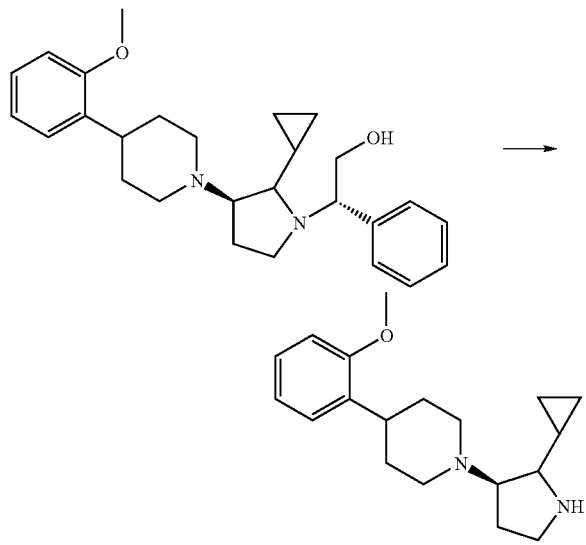

A solution of (2S)-2-((3R)-3-(4-(2-methoxyphenyl)piperidin-1-yl)-2-cyclopropylpyrrolidin-1-yl)-2-phenylethanol (preparation #26) (1.708 g, 4.06 mmol) in EtOH (25 mL) was hydrogenated under hydrogen at about 60 bar at about 60° C. in a H-cube™ apparatus using palladium hydroxide on carbon (20%) as a catalyst until all starting material was converted to product. The solvent was removed in vacuo to afford 1-((3R)-2-cyclopropylpyrrolidin-3-yl)-4-(2-methoxyphenyl)piperidine (1.23 g, 4.09 mmol) as an orange oil. RP-HPLC (Table 1, Method a) $R_t$ 1.48 min; m/z: (M+H)$^+$ 301.

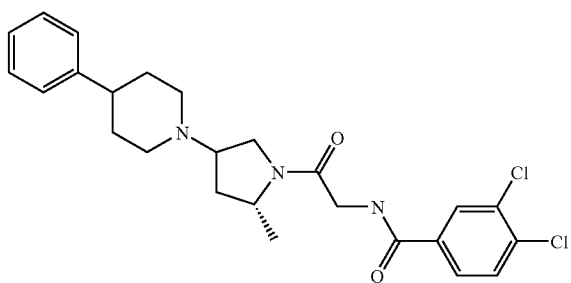 [SMILES: C[C@@H]1CC(N2CCC(c3ccccc3)CC2)CN1C(=O)CNC(=O)c1ccc(Cl)c(Cl)c1]

EXAMPLE #9

3,4-dichloro-N-(2-((2R)-2-methyl-4-(4-phenylpiperidin-1-yl)pyrrolidin-1-yl)-2-oxoethyl)benzamide a) (2S,4R)-1-tert-butyl 2-methyl 4-(tert-butyldimethylsilyloxy)pyrrolidine-1,2-dicarboxylate To a solution of (2S,4R)-1-tert-butyl 2-methyl 4-hydroxypyrrolidine-1,2-dicarboxylate (5.12 g, 20.8 mmol) in DMF (40 mL), imidazole (2.84 g, 41.7 mmol) and tert-butyldimethylchlorosilane (3.46 g, 22.9 mmol) were added sequentially and the mixture was stirred at ambient temperature for about 2 hours. The DMF was removed under reduced pressure and the residue partitioned between water (150 mL) and ether (150 mL). The organic phase was washed with 1N aqueous phosphoric acid (3×100 mL), water (2×100 mL), sodium bicarbonate saturated solution (2×100 mL) and brine (100 mL). The organic phase was dried with magnesium sulfate and concentrated to yield (2S,4R)-1-tert-butyl 2-methyl 4-(tert-butyldimethylsilyloxy)pyrrolidine-1,2-dicarboxylate (5.44 g, 15.1 mmol) as a colorless oil. RP-HPLC (Table 1, Method f) $R_t$ 6.49 min.

b) (2S,4R)-tert-butyl 4-(tert-butyldimethylsilyloxy)-2-(hydroxymethyl)pyrrolidine-1-carboxylate A solution of (2S,4R)-1-tert-butyl 2-methyl 4-(tert-butyldimethylsilyloxy)pyrrolidine-1,2-dicarboxylate (5.34 g, 14.8 mmol) in THF (20 mL) was cooled to 0° C. and lithium borohydride (0.485 g, 22.2 mmol) in THF (10 mL) was added dropwise. The mixture was stirred for about 16 hours while the ice-salt bath gradually melted. Ethyl acetate (30 mL) was added followed by the addition of ice. The organic portion was separated and quenched by a dropwise addition of 1N aqueous phosphoric acid. The organic portion was separated and washed with water (120 mL), saturated sodium bicarbonate solution (2×120 mL), and brine (100 mL) and dried over magnesium sulfate. The filtrate was concentrated under reduced pressure to yield (2S,4R)-tert-butyl 4-(tert-butyldimethylsilyloxy)-2-(hydroxymethyl)pyrrolidine-1-carboxylate (4.8 g, 14.4 mmol) as a colorless oil. RP-HPLC (Table 1, Method f) $R_t$ 6.25 min; m/z: (M−H)$^−$ 390.

c) (2S,4R)-tert-butyl 4-(tert-butyldimethylsilyloxy)-2-(methylsulfonyloxy)methyl)pyrrolidine-1-carboxylate To a solution of (2S,4R)-tert-butyl 4-(tert-butyldimethylsilyloxy)-2-(hydroxymethyl)pyrrolidine-1-carboxylate (4.72 g, 14.2 mmol) and triethylamine (3.97 mL, 28.5 mmol) in DCM (30 mL) cooled to 0° C. was added methanesulfonyl chloride (1.66 mL, 21.9 mmol). The reaction mixture was stirred overnight while the ice bath was allowed to warm to room temperature. The solvent was removed under reduced pressure and the residue partitioned between EtOAc and water. The organic phase was washed with 1N phosphoric acid (100 mL), water (100 mL), saturated sodium bicarbonate solution (100 mL) and brine (100 mL) and then was dried over magnesium sulfate and concentrated to yield (2S,4R)-tert-butyl-4-(tert-butyldimethylsilyloxy)-2-((methylsulfonyloxy)methyl)pyrrolidine-1-carboxylate (5.34 g, 13.0 mmol) as a colorless oil. RP-HPLC (Table 1, Method f) $R_t$ 6.25 min; m/z: (M−H)$^−$ 468.

d) (2R,4R)-tert-butyl 4-(tert-butyldimethylsilyloxy)-2-methylpyrrolidine-1-carboxylate A solution of (2S,4R)-tert-butyl-4-(tert-butyldimethylsilyloxy)-2-((methylsulfonyloxy)methyl)pyrrolidine-1-carboxylate (5.34 g, 13.0 mmol) in THF (30 mL) was cooled to about 0° C. and a solution of lithium triethylborohydride (1M in THF, 52 mL) was added dropwise. The ice-bath was removed and the reaction mixture was stirred at ambient temperature for about 2 hours. The reaction mixture was cooled to about 0° C. and additional lithium triethylborohydride solution (10 mL) was added. The reaction mixture was stirred at ambient temperature for about 1 h and then the reaction was quenched by a dropwise addition of water. EtOAc (100 mL) was added and the layers were separated. The organic phase was washed with water (75 mL), 1N phosphoric acid (2×100 mL), water (100 mL), aqueous sodium bicarbonate (100 mL) and brine (100 mL) then dried over magnesium sulfate and concentrated to give (2R,4R)-tert-butyl 4-(tert-butyldimethylsilyloxy)-2-methylpyrrolidine-1-carboxylate that was used without further purification.

e) (2R)-tert-butyl-4-hydroxy-2-methylpyrrolidine-1-carboxylate

A solution of tetrabutylammonium fluoride (1M in THF, 28 mL) was added to a solution of (2R,4R)-tert-butyl 4-(tert-butyldimethylsilyloxy)-2-methylpyrrolidine-1-carboxylate (3.87 g, 12.27 mmol) in THF (10 mL). The reaction mixture was stirred at ambient temperature for about 3 hours. The solvent was removed in vacuo and the residue partitioned between EtOAc and water. The aqueous phase was further extracted with EtOAc (3×100 mL). The combined organic extracts were dried over magnesium sulfate, filtered and concentrated in vacuo. Purification by silica gel flash chromatography eluting with 40% EtOAc:heptane yielded (2R)-tert-butyl 4-hydroxy-2-methylpyrrolidine-1-carboxylate (2.3 g, 11.4 mmol) as a colorless oil. $^1$H NMR ($d_6$ DMSO, 400 MHz) 4.41 (1H, br), 4.00 (1H, br), 3.48 (2H, br), 2.3-2.0 (2H, m), 1.72 (1H, m), 1.46 (9H, s) and 1.22 (3H, d).

f) (R)-tert-butyl 2-methyl-4-oxopyrrolidine-1-carboxylate

The title compound was prepared from (2R)-tert-butyl 4-hydroxy-2-methylpyrrolidine-1-carboxylate according to the general procedure J.

g) (2R)-tert-butyl 2-methyl-4-(4-phenylpiperidin-1-yl)pyrrolidine-1-carboxylate

The title compound was prepared from (R)-tert-butyl 2-methyl-4-oxopyrrolidine-1-carboxylate and 4-phenylpiperidine according to the general procedure E.

h) 1-((5R)-5-methylpyrrolidin-3-yl)-4-phenylpiperidine

The title compound was prepared from (2R)-tert-butyl 2-methyl-4-(4-phenylpiperidin-1-yl)pyrrolidine-1-carboxylate according to the general procedure F.

i) 3,4-dichloro-N-(2-((2R)-2-methyl-4-(4-phenylpiperidin-1-yl)pyrrolidin-1-yl)-2-oxoethyl)benzamide The title compound was prepared from (2R)-2-methyl-4-(4-phenylcyclohexyl)pyrrolidine and 2-(3,4-dichlorobenzamido)acetic acid according to the general procedure G. RP-HPLC (Table 1, Method b) R$_t$ 2.25 min; m/z: (M+H)$^+$ 474.

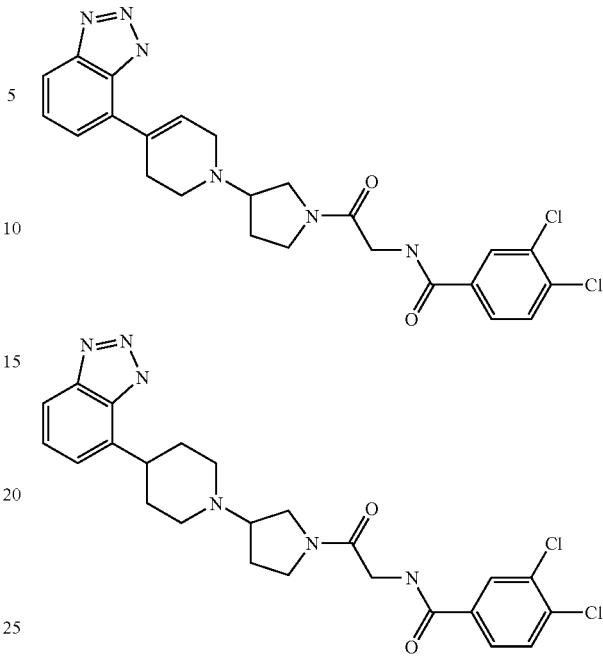

EXAMPLE #10

N-(2-(3-(4-(1H-benzo[d][1,2,3]triazol-7-yl)piperidin-1-yl)pyrrolidin-1-yl)-2-oxoethyl)-3,4-dichlorobenzamide and N-(2-(3-(4-(1H-benzo[d][1,2,3]triazol-7-yl)-5,6-dihydropyridin-1(2H)-yl)pyrrolidin-1-yl)-2-oxoethyl)-3,4-dichlorobenzamide a) tert-butyl 4-(2-amino-3-nitrophenyl)-5,6-dihydropyridine-1(2H)-carboxylate A solution containing 2-chloro-6-nitroaniline (0.83 g, 4.8 mmol), tert-butyl 4-(4,4,5,5-tetramethyl-1,3,2-dioxaborolan-2-yl)-5,6-dihydropyridine-1(2H)-carboxylate (2.97 g, 9.6 mmol), and cesium carbonate (3.13 g, 9.6 mmol) in dioxane (32 mL) and water (6 mL) was degassed with nitrogen and tris(dibenzylideneacetone)palladium(0) (0.22 g, 0.24 mmol) was added followed by the addition of tri-t-butylphosphine tetrafluoroborate (0.139 g, 0.48 mmol). The mixture was stirred at room temperature for about 20 min then heated at about 80° C. for about 18 h. The solvent was removed in vacuo and the residue was partitioned between water (40 mL) and EtOAc (50 mL). The organic phase was washed with brine (40 mL), dried over magnesium sulfate, filtered and concentrated in vacuo. The residue was purified by silica gel chromatography eluting with 12% EtOAc:heptane to yield the desired product as a yellow solid (0.87 g, 2.7 mmol). R$_f$ (25% EtOAc:heptane) 0.68.

b) tert-butyl 4-(2,3-diaminophenyl)piperidine-1-carboxylate and tert-butyl 4-(2,3-diaminophenyl)-5,6-dihydropyridine-1(2H)-carboxylate A solution of tert-butyl 4-(2-amino-3-nitrophenyl)-5,6-dihydropyridine-1(2H)-carboxylate (0.303 g, 0.949 mmol) in ethanol (15 mL) and acetic acid (1 mL) was hydrogenated in an H-cubes apparatus at about 40° C. with a Pd/C as a catalyst. The solvents were removed in vacuo to yield a mixture of tert-butyl 4-(2,3-diaminophenyl)piperidine-1-carboxylate and tert-butyl 4-(2,3-diaminophenyl)-5,6-dihydropyridine-1 (2H)-carboxylate (0.27 g) that was used without further purification.

c) 7-(piperidin-4-yl)-1H-benzo[d][1,2,3]triazole and 4-(1,2,3,6-tetrahydropyridin-4-yl)-2,3-dihydro-1H-benzo[d][1,2,3]triazole To a solution of tert-butyl 4-(2,3-diaminophenyl)piperidine-1-carboxylate and tert-butyl 4-(2,3-diaminophenyl)-5,6-dihydropyridine-1(2H)-carboxylate (0.21 g) in concentrated hydrochloric acid (3 mL), sodium nitrite (0.059 g, 0.85 mmol) solution in water (5 mL) was added and the reaction mixture was stirred at room temperature for about 1 h. The solvent was removed in vacuo to provide a mixture of 7-(piperidin-4-yl)-1H-benzo[d][1,2,3]triazole and 4-(1,2,3,6-tetrahydropyridin-4-yl)-2,3-dihydro-1H-benzo[d][1,2,3]triazole that was used directly in the next step without further characterization or purification.

d) N-(2-(3-(4-(1H-benzo[d][1,2,3]triazol-7-yl)piperidin-1-yl)pyrrolidin-1-yl)-2-oxoethyl)-3,4-dichlorobenzamide and N-(2-(3-(4-(1H-benzo[d][1,2,3]triazol-7-yl)-5,6-dihydropyridin-1(2H)-yl)pyrrolidin-1-yl)-2-oxoethyl)-3,4-dichlorobenzamide The title compounds were prepared from 7-(piperidin-4-yl)-1H-benzo[d][1,2,3]triazole and 4-(1,2,3,6-tetrahydropyridin-4-yl)-2,3-dihydro-1H-benzo[d][1,2,3]triazole and 3,4-dichloro-N-(2-oxo-2-(3-oxopyrrolidin-1-yl)ethyl) benzamide according to general procedure E. N-(2-(3-(4-(1H-benzo[d][1,2,3]triazol-7-yl)piperidin-1-yl)pyrrolidin-1-yl)-2-oxoethyl)-3,4-dichlorobenzamide. HPLC (Table 1, Method b) R$_t$ 1.82 min; m/z: (M+H)$^+$ 501. N-(2-(3-(4-(1H-benzo[d][1,2,3]triazol-7-yl)-5,6-dihydropyridin-1(2H)-yl)pyrrolidin-1-yl)-2-oxoethyl)-3,4-dichlorobenzamide. HPLC (Table 1, Method b) R$_t$ 1.95 min; m/z: (M+H)$^+$ 499.

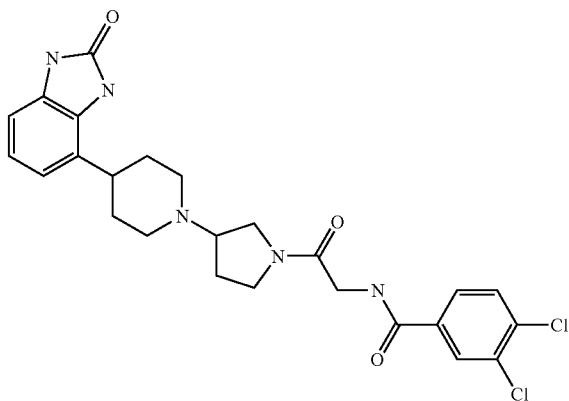 [SMILES: O=C(NCC(=O)N1CCC(N2CCC(c3cccc4[nH]c(=O)[nH]c34)CC2)C1)c1ccc(Cl)c(Cl)c1]

EXAMPLE #11

3,4-dichloro-N-(2-oxo-2-(3-(4-(2-oxo-2,3-dihydro-1H-benzo[d]imidazol-4-yl)piperidin-1-yl)pyrrolidin-1-yl)ethyl)benzamide a) tert-butyl 4-(1-(tert-butoxycarbonyl)piperidin-4-yl)-2-oxo-2,3-dihydro-1H-benzo[d]imidazole-1-carboxylate To a solution of tert-butyl 4-(2,3-diaminophenyl)piperidine-1-carboxylate (0.265 g, 0.91 mmol) and 4-dimethylaminopyridine (0.11 g, 0.91 mmol) in acetonitrile (6 mL) was added a solution of BOC anhydride (0.218 g, 0.99 mmol) in acetonitrile (4 mL) and the mixture was stirred at ambient temperature for about 2 hours. The precipitate was collected by filtration and dried under reduced pressure to yield tert-butyl 4-(1-(tert-butoxycarbonyl)piperidin-4-yl)-2-oxo-2,3-dihydro-1H-benzo[d]imidazole-1-carboxylate (0.212 g, 0.51 mmol) as a white solid. HPLC (Table 1, Method b) R$_t$ 3.21 min; m/z: (M+H)$^+$ 418.

b) 4-(piperidin-4-yl)-1H-benzo[d]imidazol-2(3H)-one

The title compound was prepared from tert-butyl 4-(1-(tert-butoxycarbonyl)piperidin-4-yl)-2-oxo-2,3-dihydro-1H-benzo[d]imidazole-1-carboxylate using general procedure F.

c) 3,4-dichloro-N-(2-oxo-2-(3-(4-(2-oxo-2,3-dihydro-1H-benzo[d]imidazol-4-yl)piperidin-1-yl)pyrrolidin-1-yl)ethyl)benzamide The title compound was prepared from 4-(piperidin-4-yl)-1H-benzo[d]imidazol-2(3H)-one and 3,4-dichloro-N-(2-oxo-2-(3-oxopyrrolidin-1-yl)ethyl)benzamide using general procedure E. HPLC (Table 1, Method b) R$_t$ 1.73 min; m/z: (M+H)$^+$ 516.

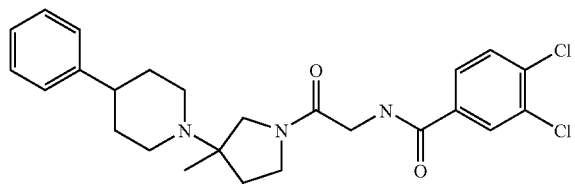 [SMILES: CC1(N2CCC(c3ccccc3)CC2)CCN(C(=O)CNC(=O)c2ccc(Cl)c(Cl)c2)C1]

EXAMPLE #12

3,4-dichloro-N-(2-(3-methyl-3-(4-phenylpiperidin-1-yl)pyrrolidin-1-yl)-2-oxoethyl)benzamide a) tert-butyl 3-cyano-3-(4-phenylpiperidin-1-yl)pyrrolidine-1-carboxylate A mixture of tert-butyl 3-oxopyrrolidine-1-carboxylate (0.91 g, 4.9 mmol), 4-phenylpiperidine (0.792 g, 4.91 mmol) and titanium (IV) isopropoxide (1.39 g, 4.91 mmol) was stirred at room temperature for about 16 h. Diethylaluminum cyanide solution (1M in DCE, 9.82 mL) was added and the reaction mixture was stirred for about 4 hours then quenched by the dropwise addition of saturated aqueous sodium bicarbonate solution. The reaction mixture was filtered and the layers separated. The organic phase was washed with saturated aqueous sodium bicarbonate (50 mL) and brine (50 mL), dried over magnesium sulfate and concentrated under reduced pressure to yield tert-butyl 3-cyano-3-(4-phenylpiperidin-1-yl)pyrrolidine-1-carboxylate (1.2 g, 3.38 mmol) as a yellow oil. HPLC (Table 1, Method f) R$_t$ 6.03 min; m/z: (M+H)$^+$ 356.

b) tert-butyl 3-methyl-3-(4-phenylpiperidin-1-yl)pyrrolidine-1-carboxylate

To a 0° C. solution of tert-butyl 3-cyano-3-(4-phenylpiperidin-1-yl)pyrrolidine-1-carboxylate (1.2 g, 3.38 mmol) in THF (16 mL) was added a solution of methylmagnesium bromide (1.4M in THF, 12.06 mL) dropwise. The mixture was stirred at ambient temperature for about 2.5 h, cooled to about 0° C. and quenched by the dropwise addition of saturated ammonium chloride solution. The organic phase was separated, washed with water (2×75 mL) and brine (50 mL), dried over magnesium sulfate and concentrated under reduced pressure to yield tert-butyl 3-methyl-3-(4-phenylpiperidin-1-yl)pyrrolidine-1-carboxylate (1.12 g, 3.25 mmol) as a yellow solid. HPLC (Table 1, Method f) $R_t$ 5.01 min; m/z: (M+H)$^+$ 345.

c) 1-(3-methylpyrrolidin-3-yl)-4-phenylpiperidine

The title compound was prepared from tert-butyl 3-methyl-3-(4-phenylpiperidin-1-yl)pyrrolidine-1-carboxylate according to the general procedure F.

d) 3,4-dichloro-N-(2-(3-methyl-3-(4-phenylpiperidin-1-yl)pyrrolidin-1-yl)-2-oxoethyl)benzamide The title compound was prepared (as a mixture of two enantiomers) from 1-(3-methylpyrrolidin-3-yl)-4-phenylpiperidine and 2-(3,4-dichlorobenzamido)acetic acid using general procedure G. HPLC (Table 1, Method b) $R_t$ 2.13 min; m/z: (M+H)$^+$ 474. From the mixture, the enantiomers were isolated via chiral preparative RP-HPLC (isocratic 10% methanol:10% ethanol:80% heptane:0.2% diethylamine modifier at 15 mL/min, column temperature 50° C.; UV detection monitored at 254 nm; Daicel OD-H column, 20×250 mm, 5 um particle) to yield two isomers, (S)- and (R)-3,4-dichloro-N-(2-(3-methyl-3-(4-phenylpiperidin-1-yl)pyrrolidin-1-yl)-2-oxoethyl)benzamide. The absolute stereochemistry of the isomers was not assigned. Isomer 1 eluted at $R_t$ 11.5-14 min. Isomer 2 eluted at $R_t$ 14.8-18 min.

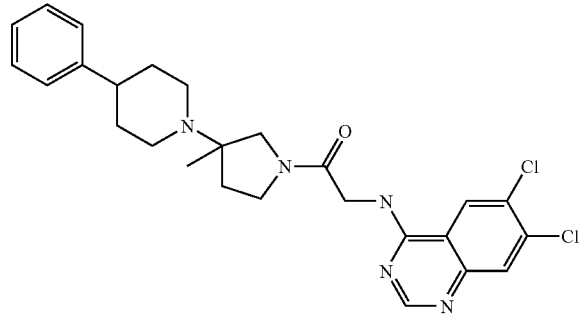 [SMILES: CC1(N2CCC(c3ccccc3)CC2)CCN(C(=O)CNc2ncnc3cc(Cl)c(Cl)cc23)C1]

EXAMPLE #13

2-(6,7-dichloroquinazolin-4-ylamino)-1-(3-methyl-3-(4-phenylpiperidin-1-yl)pyrrolidin-1-yl)ethanone a) 2-amino-1-(3-methyl-3-(4-phenylpiperidin-1-yl)pyrrolidin-1-yl)ethanone The title compound was prepared from 1-(3-methylpyrrolidin-3-yl)-4-phenylpiperidine and 2-(tert-butoxycarbonylamino)acetic acid using general procedures G, F.

b) 2-(6,7-dichloroquinazolin-4-ylamino)-1-(3-methyl-3-(4-phenylpiperidin-1-yl)pyrrolidin-1-yl)ethanone The title compound was prepared from 2-amino-1-(3-methyl-3-(4-phenylpiperidin-1-yl)pyrrolidin-1-yl)ethanone and 2,4,6-trichloroquinazoline according to general procedure M. HPLC (Table 1, Method b) $R_t$ 2.2 min; m/z: (M+H)$^+$ 498.

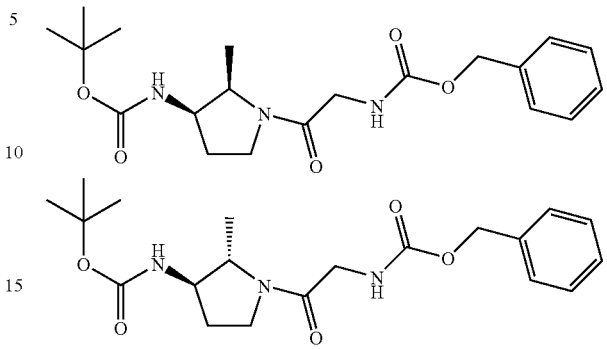

EXAMPLE #14

[(2R,3R)-1-(2-Benzyloxycarbonylamino-acetyl)-2-methyl-pyrrolidin-3-yl]-carbamic acid tert-butyl ester and [(2S,3R)-1-(2-Benzyloxycarbonylamino-acetyl)-2-methyl-pyrrolidin-3-yl]-carbamic acid tert-butyl ester a) (3S,7R,7aR)-7-(Benzylamino)-7a-methyl-3-phenyltetrahydropyrrolo[2,1-b]oxazol-5(6H)-one (3S,7R,7aR)-7-(Benzylamino)-7a-methyl-3-phenyltetrahydropyrrolo[2,1-b]oxazol-5(6H)-one was synthesized from (3S,7aR)-7a-methyl-3-phenyl-2,3-dihydropyrrolo[2,1-b]oxazol-5(7aH)-one and benzyl amine using general procedure Y. RP-HPLC (Table 1, Method a) $R_t$ 1.73; m/z: (M+H)$^+$ 323.

b) (3S,7R,7aR)-7-Amino-7a-methyl-3-phenyltetrahydropyrrolo[2,1-b]oxazol-5(6H)-one (3S,7R,7aR)-7-Amino-7a-methyl-3-phenyltetrahydropyrrolo[2,1-b]oxazol-5(6H)-one was synthesized from (3S,7R,7aR)-7-(benzylamino)-7a-methyl-3-phenyltetrahydropyrrolo[2,1-b]oxazol-5(6H)-one using general procedure V. RP-HPLC (Table 1, Method a) $R_t$ 1.25; m/z: (M+H)$^+$ 233.

c) (2S)-2-((3R)-3-Amino-2-methylpyrrolidin-1-yl)-2-phenylethanol (2S)-2-((3R)-3-Amino-2-methylpyrrolidin-1-yl)-2-phenylethanol was synthesized from (3S,7R,7aR)-7-amino-7a-methyl-3-phenyltetrahydropyrrolo[2,1-b]oxazol-5(6H)-one using general procedure Z. RP-HPLC (Table 1, Method a) $R_t$ 1.24 min; m/z: (M+H)$^+$ 221.

d) tert-Butyl (3R)-1-((S)-2-hydroxy-1-phenylethyl)-2-methylpyrrolidin-3-ylcarbamate To (2S)-2-((3R)-3-amino-2-methylpyrrolidin-1-yl)-2-phenylethanol (3.14 g, 14.25 mmol) in THF (30 mL) was added BOC anhydride (3.31 mL, 14.2 mmol) and triethylamine (3.97 mL, 28.5 mmol). After stirring at room temperature for about 4 hours the solvent was removed in vacuo. The residue was purified on by silica gel column chromatography eluting with 0-5% MeOH/EtOAc to afford tert-butyl (3R)-1-((S)-2-hydroxy-1-phenylethyl)-2-methylpyrrolidin-3-ylcarbamate (1.75 g, 5.46 mmol) as a mixture of diastereomers. RP-HPLC (Table 1, Method a) $R_t$ 1.50 min; m/z: (M+H)⁺ 321.

e) tert-Butyl (3R)-2-methylpyrrolidin-3-ylcarbamate tert-Butyl (3R)-2-methylpyrrolidin-3-ylcarbamate was synthesized from tert-Butyl (3R)-1-((S)-2-hydroxy-1-phenylethyl)-2-methylpyrrolidin-3-ylcarbamate using general procedure V. RP-HPLC (Table 1, Method d) $R_t$ 1.98; nm/z: (M+H)⁺ 201.

f) [(2R,3R)-1-(2-Benzyloxycarbonylamino-acetyl)-2-methyl-pyrrolidin-3-yl]-carbamic acid tert-butyl ester and [(2S,3R)-1-(2-Benzyloxycarbonylamino-acetyl)-2-methyl-pyrrolidin-3-yl]-carbamic acid tert-butyl ester

[(2R,3R)-1-(2-Benzyloxycarbonylamino-acetyl)-2-methyl-pyrrolidin-3-yl]-carbamic acid tert-butyl ester and [(2S,3R)-1-(2-benzyloxycarbonylamino-acetyl)-2-methyl-pyrrolidin-3-yl]-carbamic acid tert-butyl ester were synthesized from tert-butyl (3R)-2-methylpyrrolidin-3-ylcarbamate and 2-(benzyloxycarbonylamino)acetic acid using general procedure G. RP-HPLC (Table 1, Method d) $R_t$ 5.57 min. (trans) and 5.53 min. (cis); m/z: (M+H)⁺ 392.

ylpyrrolidin-3-ylcarbamate and 4,6,7-trichloroquinazoline using general procedure M. RP-HPLC (Table 1, Method d) $R_t$ 5.67; m/z: (M+H)⁺ 454.

c) 1-((2S,3R)-3-Amino-2-methylpyrrolidin-1-yl)-2-(6,7-dichloroquinazolin-4-ylamino)ethanone 1-((2S,3R)-3-Amino-2-methylpyrrolidin-1-yl)-2-(6,7-dichloroquinazolin-4-ylamino)ethanone was synthesized from tert-Butyl (2S,3R)-1-(2-(6,7-dichloroquinazolin-4-ylamino)acetyl)-2-methylpyrrolidin-3-ylcarbamate using general procedure F. RP-HPLC (Table 1, Method d) $R_t$ 3.81; m/z: (M+H)⁺ 354.

d) 2-(6,7-Dichloroquinazolin-4-ylamino)-1-((2S,3R)-2-methyl-3-(tetrahydro-2H-pyran-4-ylamino)pyrrolidin-1-yl)ethanone 2-(6,7-Dichloroquinazolin-4-ylamino)-1-((2S,3R)-2-methyl-3-(tetrahydro-2H-pyran-4-ylamino)pyrrolidin-1-yl)ethanone was synthesized from 1-((2S,3R)-3-Amino-2-methylpyrrolidin-1-yl)-2-(6,7-dichloroquinazolin-4-ylamino)ethanone and dihydro-2H-pyran-4(3H)-one using general procedure E. RP-HPLC (Table 1, Method a) $R_t$ 1.52; m/z: (M+H)⁺ 438.

EXAMPLE #16

N-(2-(3-(4-(2-acetamidophenyl)piperidin-1-yl)pyrrolidin-1-yl)-2-oxoethyl)-3,4-dichlorobenzamide

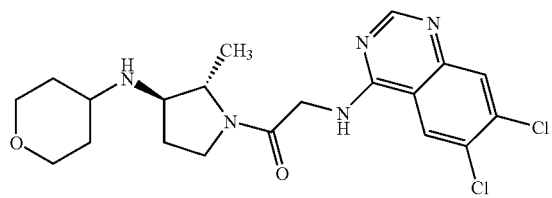 [SMILES: C[C@H]1[C@H](NC2CCOCC2)CCN1C(=O)CNc1ncnc2cc(Cl)c(Cl)cc12]

EXAMPLE #15

2-(6,7-dichloroquinazolin-4-ylamino)-1-((2S,3R)-2-methyl-3-(tetrahydro-2H-pyran-4-ylamino)pyrrolidin-1-yl)ethanone a) tert-Butyl (2S,3R)-1-(2-aminoacetyl)-2-methylpyrrolidin-3-ylcarbamate To [(2S,3R)-1-(2-benzyloxycarbonylamino-acetyl)-2-methyl-pyrrolidin-3-yl]-carbamic acid tert-butyl ester (example #14) (0.75 g, 1.916 mmol) in ethanol (101 mL) was added 10% palladium on carbon (0.020 g, 0.19 mmol). The flask was fitted with a hydrogen balloon and hydrogenated for about 16 h. The reaction mixture was filtered, washing with EtOH. The filtrate was concentrated under reduced pressure to afford tert-butyl (2S,3R)-1-(2-aminoacetyl)-2-methylpyrrolidin-3-ylcarbamate (0.50 g, 1.9 mmol). RP-HPLC (Table 1, Method d) $R_t$ 3.05; m/z: (M+H)⁺ 258.

b) tert-Butyl (2S,3R)-1-(2-(6,7-dichloroquinazolin-4-ylamino)acetyl)-2-methylpyrrolidin-3-ylcarbamate tert-Butyl (2S,3R)-1-(2-(6,7-dichloroquinazolin-4-ylamino)acetyl)-2-methylpyrrolidin-3-ylcarbamate was synthesized from tert-butyl (2S,3R)-1-(2-aminoacetyl)-2-meth-

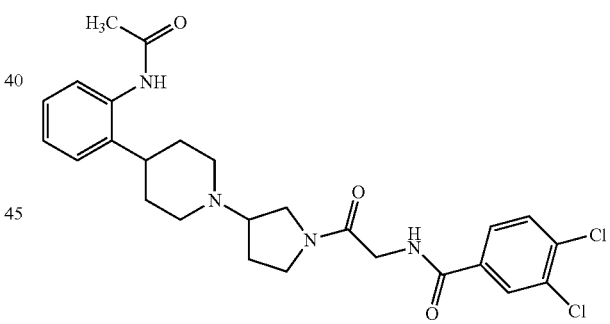

To N-(2-(3-(4-(2-aminophenyl)piperidin-1-yl)pyrrolidin-1-yl)-2-oxoethyl)-3,4-dichlorobenzamide (Example #4.149, 0.050 g, 0.10 mmol) in DCM (1 mL) was sequentially added triethylamine (0.044 mL, 0.32 mmol) and acetic anhydride (10.9 μL, 0.116 mmol). The reaction mixture was stirred at room temperature for about 16 h. The solvent was removed in vacuo and the residue purified by RP-HPLC (10% acetonitrile/0.05M aqueous ammonium acetate, buffered to pH 4.5 for 3 min., 5% to 60% acetonitrile/0.05M aqueous ammonium acetate over 6 min at 22.5 mL/min with 2.5 mL/min. acetonitrile at-column dilution; APCI positive mode detection; Xterra prep. MS C18. 19×50 mm column) to afford N-(2-(3-(4-(2-acetamidophenyl)piperidin-1-yl)pyrrolidin-1-yl)-2-oxoethyl)-3,4-dichlorobenzamide (0.0075 g, 0.014 mmol). RP-HPLC (Table 1, Method a) $R_t$ 1.92 min; nm/z: (M+H)⁺ 517.

EXAMPLE #17

3,4-dichloro-N-(2-(3-(4-(2-(methylsulfonamido)phenyl)piperidin-1-yl)pyrrolidin-1-yl)-2-oxoethyl)benzamide

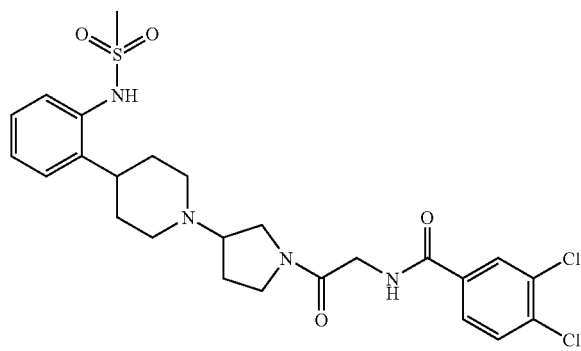 [SMILES: CS(=O)(=O)Nc1ccccc1C1CCN(C2CCN(C(=O)CNC(=O)c3ccc(Cl)c(Cl)c3)C2)CC1]

To N-(2-(3-(4-(2-aminophenyl)piperidin-1-yl)pyrrolidin-1-yl)-2-oxoethyl)-3,4-dichlorobenzamide (Example #4.149, 0.063 g, 0.13 mmol) in DCM (1 mL) was added triethylamine (0.037 mL, 0.26 mmol) and methanesulfonyl chloride (0.011 mL, 0.14 mmol). The reaction mixture was stirred at room temperature for about 16 h. The solvent was removed in vacuo and the residue was purified by RP-HPLC (10% acetonitrile/0.05M aqueous ammonium acetate, buffered to pH 4.5 for 3 min., 5% to 60% acetonitrile/0.05M aqueous ammonium acetate over 6 min at 22.5 mL/min with 2.5 mL/min. acetonitrile at-column dilution; APCI positive mode detection; Xterra prep. MS C18. 19×50 mm column) to afford 3,4-dichloro-N-(2-(3-(4-(2-(methylsulfonamido)phenyl)piperidin-1-yl)pyrrolidin-1-yl)-2-oxoethyl)benzamide (0.0052 g, 0.009 mmol). RP-HPLC (Table 1, Method a) $R_t$ 2.07 min; m/z: (M+H)$^+$ 553.

Preparation #28: 2-(3,4-dichlorophenylamino)acetic acid

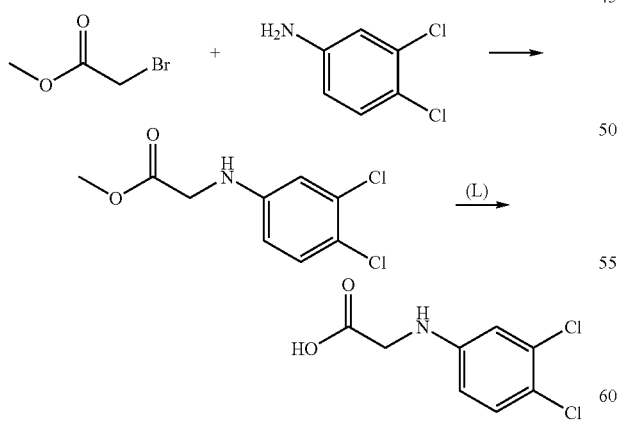

To a solution of 3,4-dichloroaniline (1.059 g, 6.54 mmol) in acetonitrile (20 mL) was added potassium carbonate (0.903 g, 6.54 mmol) and the mixture was heated at about 80° C. for about 1 h. Methyl 2-bromoacetate (0.619 mL, 6.54 mmol) was added and the reaction mixture was heated at about 80° C. for about 2 h. Sodium iodide (0.980 g, 6.54 mmol) was added and the reaction mixture was heated at about 80° C. for about 2 h. iPr$_2$EtN (1.14 ml, 6.54 mmol) was added and the reaction mixture was heated at about 80° C. for about 16 h. The reaction mixture was cooled at ambient temperature then filtered to remove solids. The filtrate was concentrated in vacuo and the residue taken up in EtOAc (50 mL) then washed with water (30 mL), sodium thiosulfate (30 mL) and brine (30 mL). The organic portion was separated, dried over MgSO$_4$, filtered, and concentrated in vacuo to provide a light orange solid (1.39 g). The crude material was purified via silica gel chromatography eluting with 10-20% EtOAc/heptane to afford methyl 2-(3,4-dichlorophenylamino)acetate as a white solid (0.732 g, 48%). RP-HPLC (Table 1, Method a) $R_t$ 2.67 min; m/z: (M+H)$^+$ 235/237. This material was hydrolyzed to the acid according to General Procedure L, to give 2-(3,4-dichlorophenylamino)acetic acid (0.600 g, 87%). RP-HPLC (Table 1, Method a) $R_t$ 1.94 min; m/z: (M+H)$^-$ 218/220.

Preparation #29:
2,3,4,4a,9,9a-Hexahydro-1H-beta-carboline

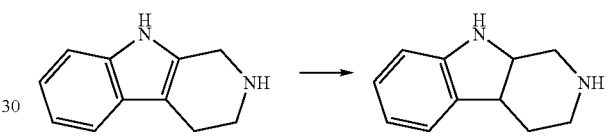

To a solution of 2,3,4,9-tetrahydro-1H-beta-carboline (0.100 g, 0.581 mmol) in TFA (1 mL) was added sodium cyanoborohydride (0.109 g, 1.74 mmol) and the reaction mixture was stirred at ambient temperature for about 16 h. The reaction mixture was concentrated in vacuo and the residue was partitioned between water (25 mL) and dichloromethane (50 mL). The organic layer was separated and the aqueous layer was further extracted with dichloromethane (2×50 mL). The combined organic extracts were dried over magnesium sulfate, and evaporated under reduced pressure. The residue was purified by using preparative RP-HPLC (Rainin C18, 8 mm, 300 Å, 35 cm; 5-100% acetonitrile—0.1M ammonium acetate over 20 min, 100% acetonitrile hold 10 minutes, 21 mL/min) to give 2,3,4,4a,9,9a-hexahydro-1H-beta-carboline (0.073 g, 0.42 mmol) as a brown oil; RP-HPLC (Table 1, Method a) $R_t$ 1.35 min; m/z: (M+H)$^+$ 175.

Preparation #30:1-Oxy-3',4',5',6'-tetrahydro-2'H-[2,4']bipyridinyl-1'-carboxylic acid tert-butyl ester

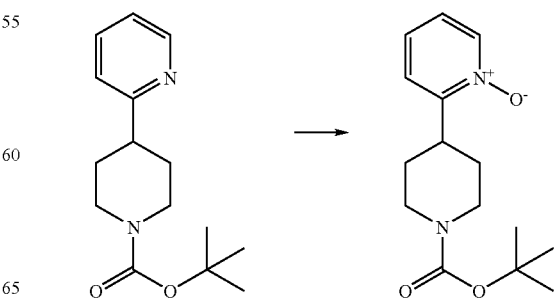

To a solution of 4-(1-{(Z)-[(E)-propenyl]imino}-allyl)-piperidine-1-carboxylic acid tert-butyl ester (0.151 g, 0.576 mmol) (prepared via the route detailed in Journal of Organic Chemistry (2004), 69(15), 5120-5123) in DCM (1 mL) was added m-CPBA (0.165 g, 0.623 mmol) at about 0° C. The reaction mixture was allowed to warm to room temperature and stirred for about 2 hours. The reaction mixture was partitioned between 1N NaOH (25 mL) and dichloromethane (50 mL). The organic layer was separated and the aqueous layer was further extracted with dichloromethane (2×50 mL). The combined organic extracts were dried over magnesium sulfate, filtered and evaporated under reduced pressure to give 1-oxy-3',4',5',6'-tetrahydro-2'H-[2,4']bipyridinyl-1'-carboxylic acid tert-butyl ester (0.123 g, 0.443 mmol) as a brown oil which was used in subsequent reactions without further purification. RP-HPLC (Table 1, Method b) $R_t$ 1.61 min; m/z: $(M+H)^+$ 279.

Preparation #31: (4-Phenyl-piperidin-4-yl)-methanol

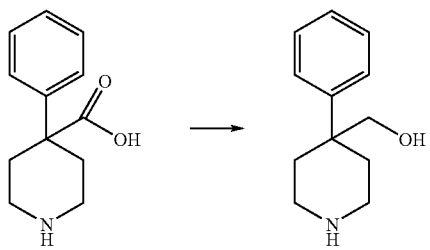 [SMILES: O=C(O)C1(c2ccccc2)CCNCC1 ; OCC1(c2ccccc2)CCNCC1]

A solution of 4-phenyl-piperidine-4-carboxylic acid (0.168 g, 0.819 mmol) in THF (2 mL) was added dropwise to a 0° C. solution of lithium aluminum hydride (1.0N in THF, 1.63 mL, 1.64 mmol). The reaction was stirred at room temperature for about 16 h. Water (1 mL) was added to the reaction mixture, followed by 2 N NaOH (1 mL). The solution was stirred for about 1 h then filtered. The filtrate was extracted with DCM (25 mL) and the organic layer was separated. The aqueous layer was further extracted with dichloromethane (2×25 mL). The combined organic extracts were dried over magnesium sulfate, filtered and evaporated under reduced pressure to give (4-phenyl-piperidin-4-yl)-methanol (0.078 g, 0.41 mmol) as brown oil, which was used in subsequent reactions without further purification. RP-HPLC (Table 1, Method b) $R_t$ 1.24 min; m/z: $(M+H)^+$ 192.

Preparation #32: 1-(2-(6,7-dichloroquinazolin-4-ylamino)acetyl)pyrrolidin-3-one

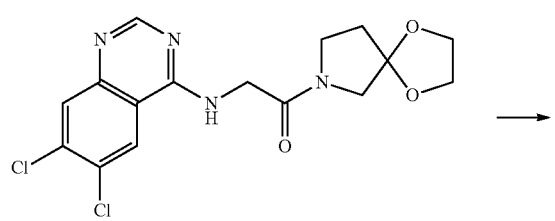

-continued

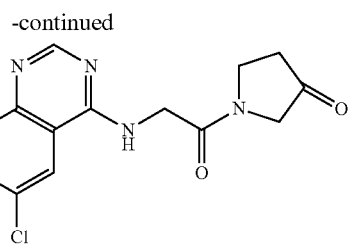

To a stirring 0° C. solution of 2-(6,7-dichloroquinazolin-4-ylamino)-1-(1,4-dioxa-7-azaspiro[4.4]nonan-7-yl)ethanone (0.603 g, 1.57 mmol) (prepared by general procedures G, F, M) in DCM (15 mL) was slowly added perchloric acid (0.406 mL, 4.72 mmol). The mixture was allowed to warm to room temperature and stirred for about 1 hour. The solvent was decanted and discarded. The remaining solid was washed with aqueous sodium carbonate (10 mL) and water (10 mL) and then dried over magnesium sulfate, filtered and concentrated under reduced pressure to give 1-(2-(6,7-dichloroquinazolin-4-ylamino)acetyl)pyrrolidin-3-one (0.493 g, 1.45 mmol) as white solid which was used in subsequent reactions without further purification. RP-HPLC (Table 1, Method b) $R_t$ 1.62 min; m/z: $(M+H)^+$ 339.

What is claimed is:

1. A compound of formula I

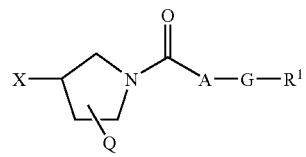

I or a stereoisomer thereof, or a pharmaceutically acceptable salt of the compound or stereoisomer, wherein X is

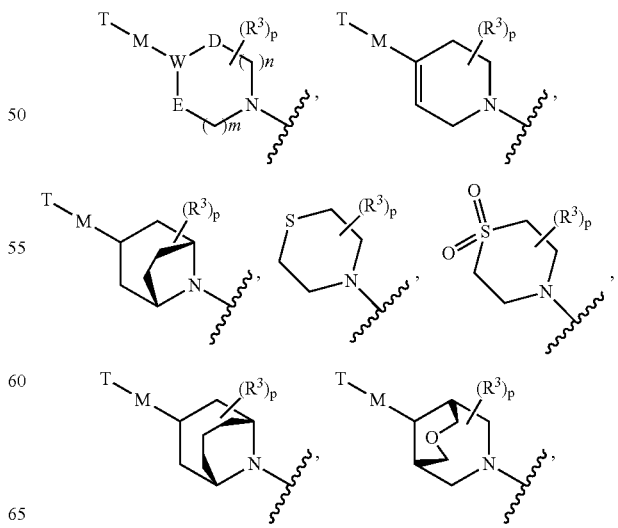

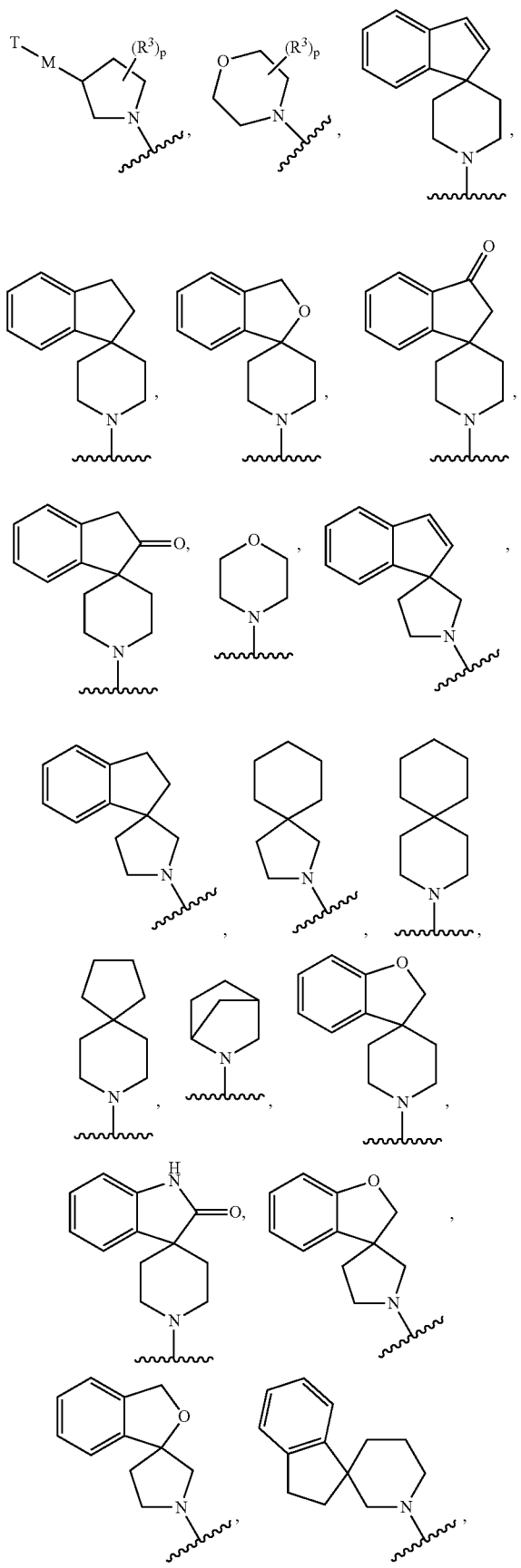
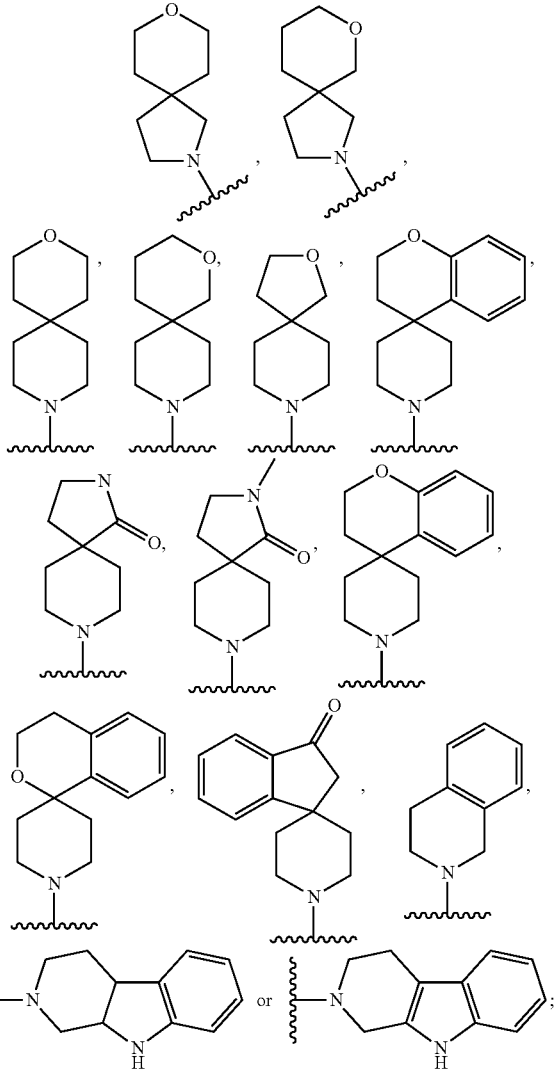

optionally substituted with one or more substituents selected from the group consisting of $(C_1-C_5)$alkyl, $-O(C_1-C_3)$alkyl, CN, Cl, F, $CF_3$ and OH;

D is $C(R^5)_2$;
E is $C(R^5)_2$;
W is $C(R^4)$;
M is a bond or C(O); or
M is selected from the optionally substituted group consisting of $-(C_1-C_4)$alkyl, $-C(O)N(R^2)$, $-N(R^2)C(O)$, $-N(R^2)$, -aryl, -heterocyclyl and -heteroaryl; or
M is selected from the optionally substituted group consisting of $-(C_1-C_4)$alkyl-heterocyclyl, $-(C_1-C_4)$alkyl-C(O)$, $-(C_1-C_4)$alkyl-C(O)N(R^2)$, $-(C_1-C_4)$alkyl-C(O)O, $-(C_1-C_4)$alkyl-N(R^2)C(O)O, $-(C_1-C_4))$alkyl-N(R^2)C(O)$ and $-CH_2-NH-C(O)$ wherein the alkyl portion of the moiety is connected to W;
T is H or is selected from the optionally substituted group consisting of indanyl, indenyl and phenyl;
A is a bond or $CH_2$;
G is NH, NH—$CH_2$, or NH—C(O), wherein the N is attached to A;
Q is H or is selected from the optionally substituted group consisting of $(C_1-C_5)$alkyl, $(C_3-C_7)$cycloalkyl, $-O-(C_3-C_7)$cycloalkyl and $-(C_1-C_3)$alkyl-O—$(C_1-C_3)$alkyl;

R[1] is selected from the optionally substituted group consisting of 5,6,7,8-tetrahydro-[1,6]naphthyridinyl, phenyl, piperidinyl and quinazolinyl;

R[2] is independently selected from the optionally substituted group consisting of H, $(C_1-C_4)$alkyl and $(C_3-C_5)$ cycloalkyl;

R[3] is independently H, OH, CN, F, $CF_3$, $C(O)N(R^2)_2$, $N(R^2)_2$, or oxo; or R[3] is independently selected from the optionally substituted group consisting of $(C_1-C_3)$alkyl, $(C_3-C_7)$cycloalkyl, $(C_1-C_3)$alkyl-O—$(C_1-C_3)$alkyl, —$(C_1-C_3)$alkyl-C(O)—O—$(C_1-C_3)$alkyl, aryl, -D-aryl, heteroaryl, heterocyclyl, —$(C_1-C_3)$alkyl-aryl, —$N(R^2)$aryl, —O-aryl, —C(O)—O—$(C_1-C_3)$alkyl, —NH-phenyl and phenyl;

R[4] is H, OH, CN or F or R[4] is selected from the optionally substituted group consisting of —O—$(C_1-C_3)$alkyl, —O—$(C_3-C_7)$cycloalkyl, aryl and heteroaryl;

R[5] is H or $CH_3$;

m and n are independently 0, 1, or 2;

p is 1 or 2;

x is 1 or 2; and y is 0, 1 or 2.

2. The compound or stereoisomer of claim 1, or a salt of the compound or stereoisomer, wherein X is

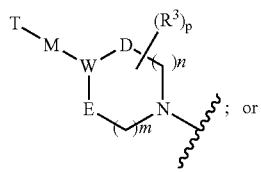

; or

X is:

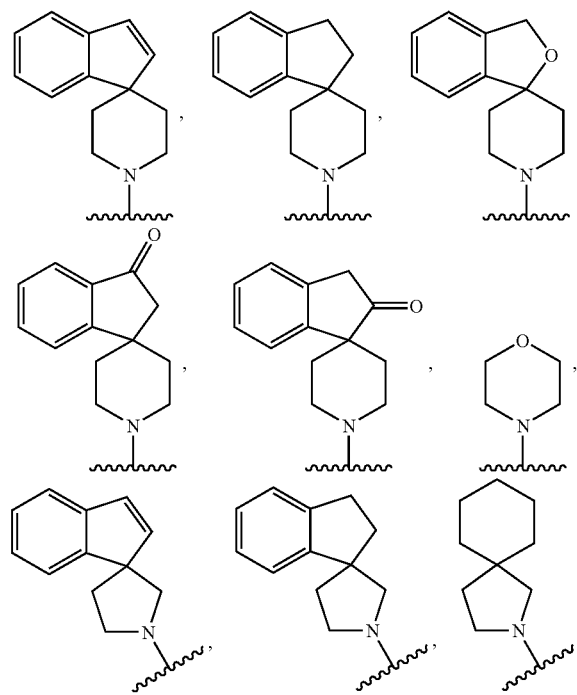

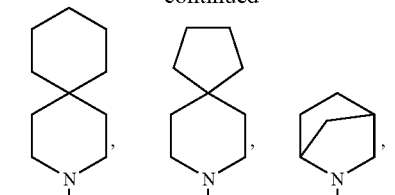

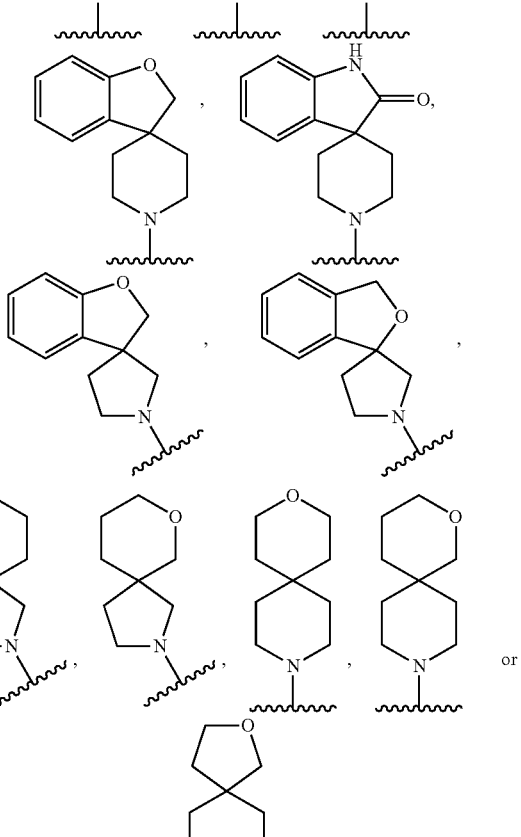

optionally substituted with one or more substituents selected from the group consisting of $(C_1-C_5)$alkyl, —$O(C_1-C_3)$alkyl, CN, Cl, F, $CF_3$ and OH;

D is $C(R^5)_2$;

E is $C(R^5)_2$;

W is $C(R^4)$;

M is a bond or C(O); or

M is selected from the optionally substituted group consisting of —$(C_1-C_4)$alkyl, —$C(O)N(R^2)$, —$N(R^2)C(O)$, —$N(R^2)$, -aryl, -heterocyclyl and -heteroaryl; or M is selected from the optionally substituted group consisting of —$(C_1-C_4)$alkyl-heterocyclyl, —$(C_1-C_4)$alkyl-C(O), —$(C_1-C_4)$alkyl-$C(O)N(R^2)$, —$(C_1-C_4)$alkyl-C(O)O, —$(C_1-C_4)$alkyl-$N(R^2)C(O)O$, —$(C_1-C_4)$alkyl-$N(R^2)C(O)$ and —$CH_2$—NH—C(O) wherein the alkyl portion of the moiety is connected to W;

T is H or is selected from the optionally substituted group consisting of indanyl, indenyl and phenyl;

A is a bond or $CH_2$;

G is NH, NH—$CH_2$, or NH—C(O), wherein the N is attached to A;

Q is H or is selected from the optionally substituted group consisting of $(C_1-C_5)$alkyl, $(C_3-C_7)$cycloalkyl, —O—$(C_3-C_7)$cycloalkyl and —$(C_1-C_3)$alkyl-O—$(C_1-C_3)$alkyl;

$R^1$ is selected from the optionally substituted group consisting of 5,6,7,8-tetrahydro[1,6]naphthyridinyl, phenyl, piperidinyl and quinazolinyl; and $R^2$ is independently selected from the optionally substituted group consisting of H, $(C_1-C_4)$alkyl and $(C_3-C_5)$cycloalkyl;

$R^3$ is H, OH, CN, F, $CF_3$, $C(O)N(R^2)_2$, $N(R^2)_2$, or $R^3$ is selected from the optionally substituted group consisting of $(C_1-C_3)$alkyl, $(C_3-C_7)$cycloalkyl, —O—$(C_1-C_3)$alkyl, $(C_1-C_3)$alkyl-O—$(C_1-C_3)$alkyl, —$(C_1-C_3)$alkyl-C(O)—O—$(C_1-C_3)$alkyl, aryl, —O-aryl, heteroaryl, heterocyclyl, —$(C_1-C_3)$alkyl-aryl, —$N(R^2)$aryl, —O-aryl, —C(O)—O—$(C_1-C_3)$alkyl, —NH-phenyl and phenyl;

$R^5$ is H or $CH_3$;

$R^4$ is H, OH, CN or F or $R^4$ is selected from the optionally substituted group consisting of —O—$(C_1-C_3)$alkyl, —O—$(C_3-C_7)$cycloalkyl, aryl and heteroaryl;

m and n are independently 0, 1, or 2;

p is 1 or 2;

x is 1 or 2; and y is 0, 1 or 2.

3. The compound or stereoisomer of claim 2, or a salt of the compound or stereoisomer, wherein X is

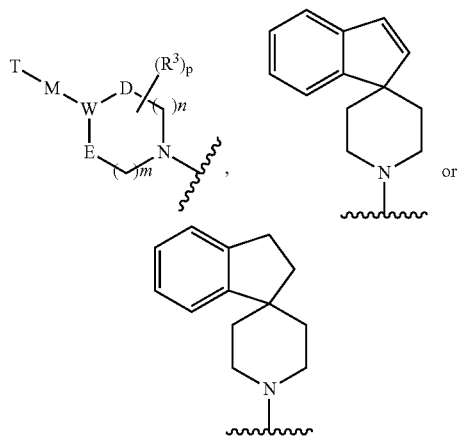

optionally substituted with one or more substituents selected from the group consisting of $(C_1-C_5)$alkyl, —$O(C_1-C_3)$alkyl, CN, Cl, F, $CF_3$ and OH.

4. The compound or stereoisomer of claim 3, or a salt of the compound or stereoisomer, wherein M is a bond, C(O), optionally substituted pyrrolidinyl, optionally substituted $(C_1-C_4)$alkyl, —$CH_2$—NH—C(O) or $(C_1)$alkyl-C(O)O; wherein the alkyl portion of the moiety is connected to W;

T is H or is selected from the optionally substituted group consisting of indanyl, indenyl and phenyl;

A is a bond or $CH_2$;

G is NH, NH—$CH_2$, or NH—C(O), wherein the N is attached to A;

Q is H, methyl, isopropyl or cyclopropyl;

$R^1$ is selected from the optionally substituted group consisting of 5,6,7,8-tetrahydro-[1,6]naphthyridinyl, phenyl, piperidinyl and quinazolinyl;

$R^2$ is H or $(C_1)$alkyl;

$R^3$ is H, OH, F, $CH_3$, $OCH_3$, $CF_3$, CN, —$CH_2$—O—$CH_3$, —$CH_2$—C(O)—O—$CH_3$, —C(O)—$OCH_3$, —NH-phenyl, —O-phenyl, indolyl, optionally substituted phenyl, phenoxy or $C(O)NH_2$;

$R^4$ is H, CN or OH;

m is 0 or 1; and n is 1.

5. The compound or stereoisomer of claim 4, or a salt of the compound or stereoisomer, wherein M is a bond, C(O), optionally substituted $(C_1-C_4)$alkyl, —$CH_2$—NH—C(O) or $(C_1)$alkyl-C(O)O; wherein the alkyl portion of the moiety is connected to W;

T is H or is selected from the optionally substituted group consisting of indanyl, indenyl and phenyl;

A is a bond or $CH_2$;

G is NH, NH—$CH_2$, or NH—C(O), wherein the N is attached to A;

Q is H or isopropyl;

$R^1$ is selected from the optionally substituted group consisting of 5,6,7,8-tetrahydro-[1,6]naphthyridinyl, phenyl, piperidinyl and quinazolinyl;

$R^2$ is H or $(C_1)$alkyl;

$R^3$ is H, OH, F, $CH_3$, $OCH_3$, $CF_3$, CN, —$CH_2$—O—$CH_3$, —$CH_2$—C(O)—O—$CH_3$, —C(O)—$OCH_3$, —NH-phenyl, indolyl, optionally substituted phenyl, phenoxy or $C(O)NH_2$;

$R^4$ is H, CN or OH;

m is 0 or 1; and n is 1.

6. The compound or stereoisomer of claim 5, or a salt of the compound or stereoisomer, wherein M is a bond, C(O), optionally substituted $(C_1-C_4)$alkyl, —$CH_2$—NH—C(O) or $(C_1)$alkyl-C(O)O;

T is H or is selected from the optionally substituted group consisting of indanyl, indenyl and phenyl;

G is NH, NH—$CH_2$, or NH—C(O), wherein the N is attached to A;

$R^1$ is selected from the optionally substituted group consisting of 5,6,7,8-tetrahydro-[1,6]naphthyridinyl, phenyl, piperidinyl and quinazolinyl; and $R^3$ is H, OH, F, $CH_3$, $OCH_3$, $CF_3$, —$CH_2$—O—$CH_3$, —$CH_2$—C(O)—O—$CH_3$, —C(O)—$OCH_3$, —NH-phenyl, phenyl, phenoxy or $C(O)NH_2$.

7. The compound or stereoisomer of claim 6, or a salt of the compound or stereoisomer, wherein M is a bond, C(O), optionally substituted $(C_1-C_4)$alkyl, —$CH_2$—NH—C(O) or $(C_1)$alkyl-C(O)O;

T is H or is selected from the optionally substituted group consisting of indanyl, indenyl and phenyl;

G is NH, NH—$CH_2$, or NH—C(O), wherein the N is attached to A;

$R^1$ is selected from the optionally substituted group consisting of 5,6,7,8-tetrahydro-[1,6]naphthyridinyl, phenyl, piperidinyl and quinazolinyl; and W is CH.

8. The compound or stereoisomer of claim 7, or a salt of the compound or stereoisomer, wherein M is a bond, C(O), $(C_1-C_2)$alkyl or $(C_1)$alkyl-C(O)O;

T is H or is selected from the optionally substituted group consisting of indanyl, indenyl and phenyl;

G is NH, NH—$CH_2$, or NH—C(O), wherein the N is attached to A;

Q is H;

$R^1$ is selected from the optionally substituted group consisting of 5,6,7,8-tetrahydro-[1,6]naphthyridinyl, phenyl, piperidinyl and quinazolinyl;

$R^3$ is H, OH, CH$_3$, —CH$_2$—O—CH$_3$, —CH$_2$—C(O)—O—CH$_3$, —C(O)—OCH$_3$ or —NH-phenyl; and m is 1.

9. The compound or stereoisomer of claim 8, or a salt of the compound or stereoisomer, wherein M is bond or (C$_1$)alkyl;

T is H or is selected from the optionally substituted group consisting of indanyl, indenyl and phenyl;

R$^1$ is selected from the optionally substituted group consisting of 5,6,7,8-tetrahydro-[1,6]naphthyridinyl, phenyl, piperidinyl and quinazolinyl; and R$^2$ is H.

10. The compound or stereoisomer of claim 9, or a salt of the compound or stereoisomer, wherein W is CH;

M is a bond;

T is H or is selected from the optionally substituted group consisting of indanyl, indenyl and phenyl;

R$^3$ is H, OH or CH$_3$;

m is 1; and n is 1.

11. The compound or stereoisomer of claim 10, or a salt of the compound or stereoisomer, wherein E is CH$_2$;

W is CH;

T is H or is selected from the optionally substituted group consisting of indanyl, indenyl and phenyl and is optionally substituted with one or more substituents selected from the group consisting of Cl, F, OH CN, CH$_3$ and OCH$_3$;

A is CH$_2$;

D is CH$_2$; and

R$^1$ is selected from the optionally substituted group consisting of phenyl and quinazolinyl; wherein R$^1$ is optionally substituted with one or more substitutents selected from the group consisting of Cl, F, CH$_3$ and CF$_3$.

12. The compound or stereoisomer of claim 10, or a salt of the compound or stereoisomer, wherein X is optionally substituted with one or more substituents selected from the group consisting of (C$_1$-C$_5$)alkyl, —O(C$_1$-C$_3$)alkyl, CN, Cl, F, CF$_3$ and OH.

13. The compound or stereoisomer of claim 12, or a salt of the compound or stereoisomer, wherein G is NH or —NH—C(O), wherein the N is attached to A;

R$^1$ is phenyl or quinazolinyl and R$^1$ is optionally substituted with one or more Cl;

R$^3$ is H, OH or CH$_3$; and p is 1.

14. A method of treating a CCR2 dependent disease or condition, wherein the CCR2 dependent disease or condition is an autoimmune disease selected from rheumatoid arthritis, osteoarthritis, asthma, chronic obstructive pulmonary disease (COPD), sepsis, psoriasis, psoriatic arthritis, inflammatory bowel disease, Crohn's disease, lupus, multiple sclerosis, juvenile chronic arthritis, Lyme arthritis, reactive arthritis, septic arthritis, spondyloarthropathy and systemic lupus erythematosus, comprising administering a therapeutically effective amount of a compound of formula I or a stereoisomer thereof, or a pharmaceutically acceptable salt of the compound or stereoisomer to a subject in need thereof, wherein X is -continued

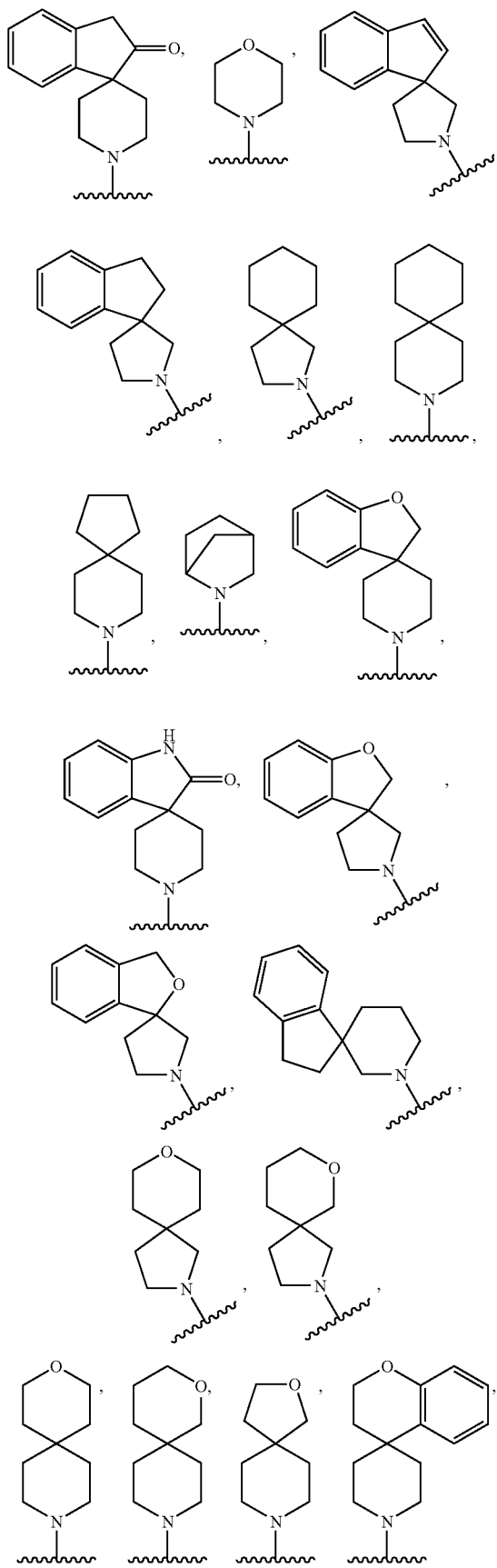

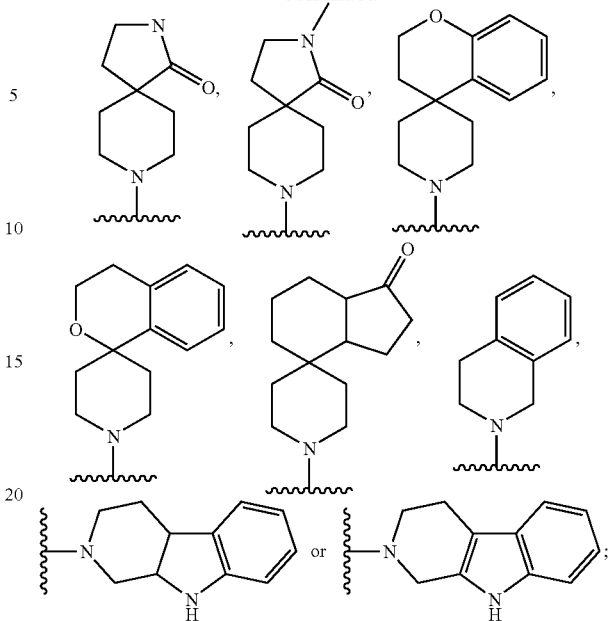

optionally substituted with one or more substituents selected from the group consisting of $(C_1-C_5)$alkyl, $-O(C_1-C_3)$alkyl, CN, Cl, F, $CF_3$ and OH;

D is $C(R^5)_2$;

E is $C(R^5)_2$;

W is $C(R^4)$;

M is a bond or C(O); or

M is selected from the optionally substituted group consisting of —$(C_1-C_4)$alkyl, —$C(O)N(R^2)$, —$N(R^2)C(O)$, —$N(R^2)$, -aryl, -heterocyclyl and -heteroaryl; or M is selected from the optionally substituted group consisting of —$(C_1-C_4)$alkyl-heterocyclyl, —$(C_1-C_4)$alkyl-C(O), —$(C_1-C_4)$alkyl-C(O)N(R^2)$, —$(C_1-C_4)$alkyl-C(O)O, —$(C_1-C_4)$alkyl-N$(R^2)$C(O)O, —$(C_1-C_4)$)alkyl-N$(R^2)$C(O) and —$CH_2$—NH—C(O) wherein the alkyl portion of the moiety is connected to W;

T is H or is selected from the optionally substituted group consisting of indanyl, indenyl and phenyl;

A is a bond or $CH_2$;

G is NH, NH—$CH_2$, or NH—C(O), wherein the N is attached to A;

Q is H or is selected from the optionally substituted group consisting of $(C_1-C_5)$alkyl, $(C_3-C_7)$cycloalkyl, —O—$(C_3-C_7)$cycloalkyl and —$(C_1-C_3)$alkyl-O—$(C_1-C_3)$alkyl;

$R^1$ is selected from the optionally substituted group consisting of 5,6,7,8-tetrahydro-[1,6]naphthyridinyl, phenyl, piperidinyl and quinazolinyl;

$R^2$ is independently selected from the optionally substituted group consisting of H, $(C_1-C_4)$alkyl and $(C_3-C_5)$cycloalkyl;

$R^3$ is independently H, OH, CN, F, $CF_3$, $C(O)N(R^2)_2$, $N(R^2)_2$, and oxo or $R^3$ is independently selected from the optionally substituted group consisting of $(C_1-C_3)$alkyl, $(C_3-C_7)$cycloalkyl, —O—$(C_1-C_3)$alkyl, $(C_1-C_3)$alkyl-O—$(C_1-C_3)$alkyl, —$(C_1-C_3)$alkyl-C(O)—O—$(C_1-C_3)$alkyl, aryl, —O-aryl, heteroaryl, heterocyclyl, —$(C_1-C_3)$alkyl-aryl, —$N(R^2)$aryl, —O-aryl, —C(O)—O—$(C_1-C_3)$alkyl, —NH-phenyl and phenyl;

$R^5$ is H or $CH_3$;

$R^4$ is H, OH, CN or F or $R^4$ is selected from the optionally substituted group consisting of —O—$(C_1$-$C_3)$alkyl, —O—$(C_3$-$C_7)$cycloalkyl, aryl and heteroaryl;

m and n are independently 0, 1, or 2;

p is 1 or 2;

x is 1 or 2; and y is 0, 1 or 2.

15. The method of claim 14 wherein the autoimmune disease is multiple sclerosis.

16. A pharmaceutical composition comprising a compound of formula I

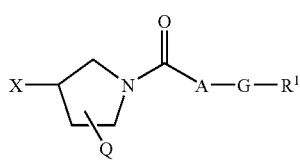
          I or a stereoisomer thereof, or a pharmaceutically acceptable salt of the compound or stereoisomer, wherein X is

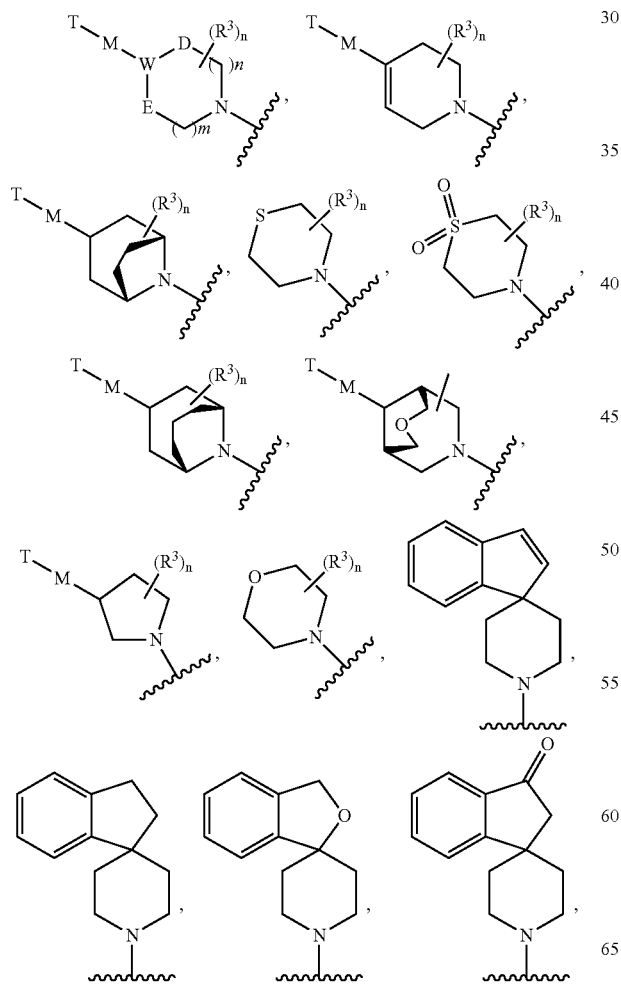

-continued

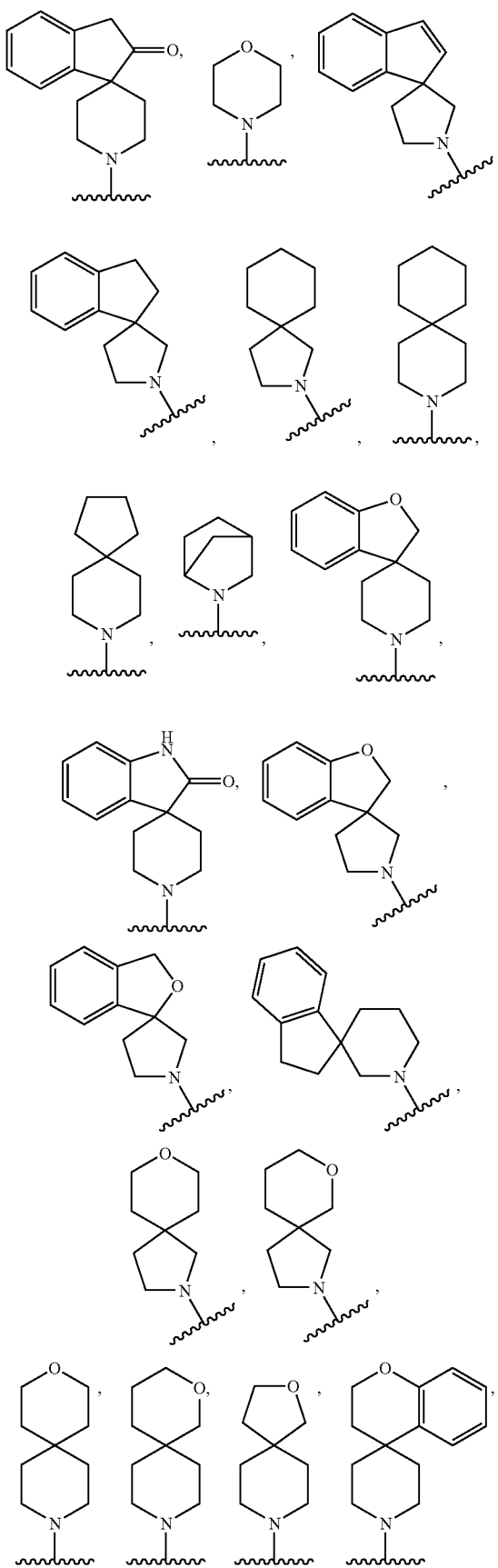

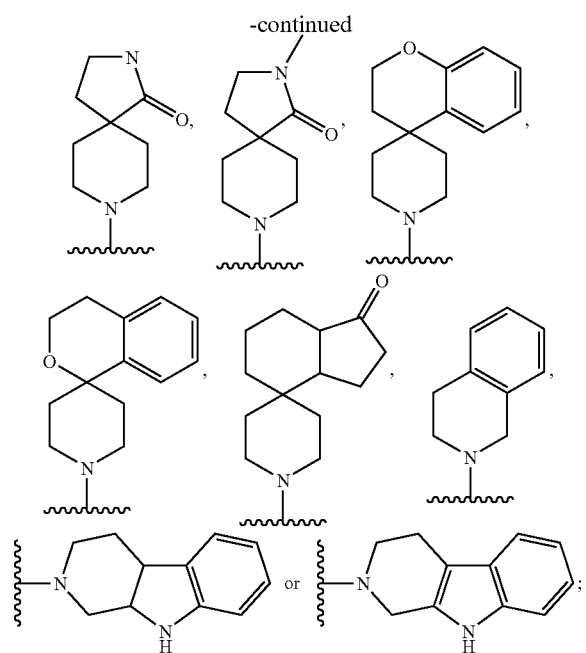

optionally substituted with one or more substituents selected from the group consisting of $(C_1-C_5)$alkyl, $-O(C_1-C_3)$alkyl, CN, Cl, F, $CF_3$ and OH;

D is $C(R^5)_2$;
E is $C(R^5)_2$;
W is $C(R^4)$;
M is a bond or C(O); or
M is selected from the optionally substituted group consisting of $-(C_1-C_4)$alkyl, $-C(O)N(R^2)$, $-N(R^2)C(O)$, $-N(R^2)$, -aryl, -heterocyclyl and -heteroaryl; or
M is selected from the optionally substituted group consisting of $-(C_1-C_4)$alkyl-heterocyclyl, $-(C_1-C_4)$alkyl-C(O)$, $-(C_1-C_4)$alkyl-C(O)N(R^2)$, $-(C_1-C_4)$alkyl-C(O)O$, $-(C_1-C_4)$alkyl-N(R^2)C(O)O$, $-(C_1-C_4))$alkyl-N(R^2)C(O)$ and $-CH_2-NH-C(O)$ wherein the alkyl portion of the moiety is connected to W;
T is H or is selected from the optionally substituted group consisting of indanyl, indenyl and phenyl;
A is a bond or $CH_2$;
G is NH, NH—$CH_2$, or NH—C(O), wherein the N is attached to A;
Q is H or is selected from the optionally substituted group consisting of $(C_1-C_5)$alkyl, $(C_3-C_7)$cycloalkyl, $-O-(C_3-C_7)$cycloalkyl and $-(C_1-C_3)$alkyl-O-$(C_1-C_3)$alkyl;
$R^1$ is selected from the optionally substituted group consisting of 5,6,7,8-tetrahydro-[1,6]naphthyridinyl, phenyl, piperidinyl and quinazolinyl;
$R^2$ is independently selected from the optionally substituted group consisting of H, $(C_1-C_4)$alkyl and $(C_3-C_5)$cycloalkyl;
$R^3$ is independently H, OH, CN, F, $CF_3$, $C(O)N(R^2)_2$, $N(R^2)_2$, and oxo or $R^3$ is independently selected from the optionally substituted group consisting of $(C_1-C_3)$alkyl, $(C_3-C_7)$cycloalkyl, $-O-(C_1-C_3)$alkyl, $(C_1-C_3)$alkyl-O-$(C_1-C_3)$alkyl, $-(C_1-C_3)$alkyl-C(O)-O-$(C_1-C_3)$alkyl, aryl, $-O$-aryl, heteroaryl, heterocyclyl, $-(C_1-C_3)$alkyl-aryl, $-N(R^2)$aryl, $-O$-aryl, $-C(O)-O-(C_1-C_3)$alkyl, $-NH$-phenyl and phenyl;
$R^5$ is H or $CH_3$;
$R^4$ is H, OH, CN or F or $R^4$ is selected from the optionally substituted group consisting of $-O-(C_1-C_3)$alkyl, $-O-(C_3-C_7)$cycloalkyl, aryl and heteroaryl;
m and n are independently 0, 1, or 2;
p is 1 or 2;
x is 1 or 2; and
y is 0, 1 or 2;
and a pharmaceutically acceptable carrier or excipient.

17. A compound, or a pharmaceutically acceptable salt thereof, wherein the compound is selected from the group consisting of

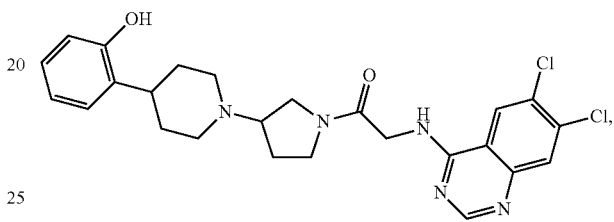

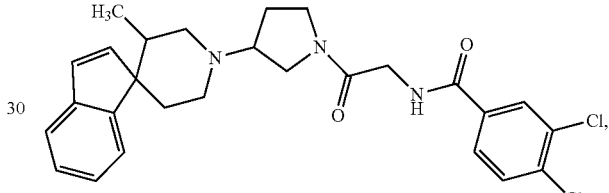

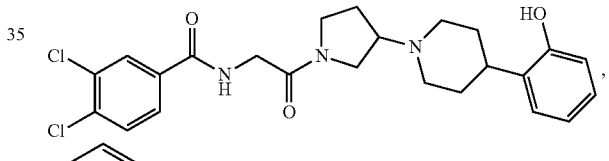

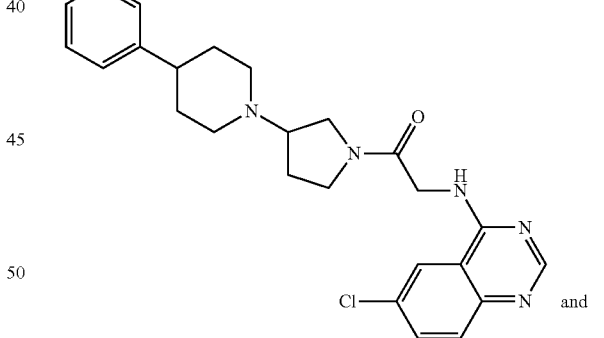

and

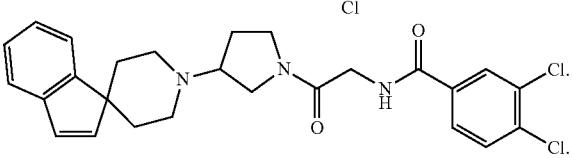

* * * * *